United States Patent
Mete et al.

(10) Patent No.: US 12,030,856 B2
(45) Date of Patent: Jul. 9, 2024

(54) POTASSIUM CHANNEL INHIBITORS

(71) Applicant: ACESION PHARMA APS, Copenhagen N (DK)

(72) Inventors: Antonio Mete, Loughborough (GB); Ulrik Sørensen, Copenhagen N (DK)

(73) Assignee: ACESION PHARMA APS, Copenhagen N (DK)

( * ) Notice: Subject to any disclaimer, the term of this patent is extended or adjusted under 35 U.S.C. 154(b) by 0 days.

(21) Appl. No.: 18/238,732

(22) Filed: Aug. 28, 2023

(65) Prior Publication Data
US 2023/0399301 A1 Dec. 14, 2023

Related U.S. Application Data

(63) Continuation of application No. PCT/EP2023/056277, filed on Mar. 13, 2023.

(30) Foreign Application Priority Data

Mar. 17, 2022 (EP) ..................................... 22162647

(51) Int. Cl.
*C07D 233/88* (2006.01)

(52) U.S. Cl.
CPC ................................. *C07D 233/88* (2013.01)

(58) Field of Classification Search
None
See application file for complete search history.

(56) References Cited

FOREIGN PATENT DOCUMENTS

| | | |
|---|---|---|
| WO | 2013104577 A1 | 7/2013 |
| WO | 2019034603 A1 | 2/2019 |

OTHER PUBLICATIONS

International Search Report and Written Opinion issued on May 23, 2023, in corresponding International Application No. PCT/EP2023/056277, 9 pages.

*Primary Examiner* — Samantha L Shterengarts
(74) *Attorney, Agent, or Firm* — Maier & Maier, PLLC

(57) ABSTRACT

A compound of the general formula (I), and the pharmaceutical composition including a compound of formula (I) and optionally a pharmaceutically acceptable additive. Also, the treatment of a cardiac disease, disorder or condition in a mammal, which includes the administration to the mammal a therapeutically effective amount of at least one compound of formula (I), or the pharmaceutically acceptable salt thereof.

14 Claims, No Drawings

US 12,030,856 B2

POTASSIUM CHANNEL INHIBITORS

FIELD

The present invention relates to novel compounds, the use of said compounds as medicament and for the manufacture of a medicament for the treatment of a cardiac disease, disorder or condition in mammals. The invention also relates to pharmaceutical compositions comprising said novel compounds.

BACKGROUND

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment, or electrolyte imbalances. Such disturbances in the impulse are called arrhythmia or dysrythmia and they may lead to unease, emboli, syncope or sudden death. In its simplest form, an arrhythmia covers everything different from a normal cardiac sinus rhythm. Disturbances can cover anything from simple palpitations to devastating ventricular fibrillation including bradycardia and tachycardia.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore evident targets for anti-arrhythmic cardiac drugs, and many anti-arrhythmic drugs on the market do exert their effect by interacting with ion channels.

Anti-arrhythmic drugs are usually divided into four main classes according to the so-called Singh Vaughan Williams classification: Class I compounds all inhibit the cardiac voltage-dependent sodium channel. Some Class I compounds do have additional effects influencing the cardiac action potential being the basis for a further subdivision into three subclasses:

Class IA compounds are sodium channel inhibitors such as Quinidine, Procainamide or Disopyramid, which prolong the action potential;

Class IB compounds are sodium channel inhibitors such as Lidocaine, Mexiletine, Tocainide or Phenytoine, which shorten the action potential; and Class IC compounds are sodium channel inhibitors such as Flecainide, Moricizine or Propafenone, which do not change the action potential duration.

Class I compounds interact with the sodium channel during its open or inactivated state and are dissociated from the channels during its closed state (during diastole). The rate of dissociation determines whether they show a frequency-dependent channel inhibition. Some of the class I compounds also inhibit subtypes of potassium or calcium permeable channels in addition to their sodium channel inhibiting effect.

Class II compounds are β-adrenoceptor inhibitors and include drugs like Atenolol, Metoprolol, Timolol or Propranolol. β-adrenoceptor inhibitors can be selective for cardiac β1-receptors or have affinity for β1-as well as β2-receptors. Some of the compounds also have an intrinsic β-stimulating effect.

Class III compounds are potassium channel inhibitors such as Amiodarone, Dronedarone, Sotalol, Ibutilide and Dofetilide, which prolong the action potential.

Class IV compounds are inhibitors of L-type calcium channels such as Verapamil.

Small-conductance calcium-activated potassium (SK) channels belongs to the family of $Ca^{2+}$-activated $K^+$ channels. Three SK channel subtypes have been cloned: SK1, SK2 and SK3 (corresponding to KCNN1-3 using the genomic nomenclature). The activity of these channels is determined by the concentration of free intracellular calcium ($[Ca^{2+}]i$) via calmodulin that is constitutively bound to the channels. SK channels are tightly regulated by $[Ca^{2+}]i$ in the physiological range being closed at $[Ca^{2+}]i$ up to around 0.1 µM but fully activated at a $[Ca^{2+}]i$ of 1 µM. Being selective for potassium, open or active SK channels have a hyperpolarizing influence on the membrane potential of the cell. SK channels are widely expressed in the central nervous system (CNS) and in peripheral tissue, including the heart.

The hyperpolarizing action of active SK channels plays an important role in the control of firing pattern and excitability of excitable cells. SK channel inhibitors such as apamin and N-methyl bicuculline, have been demonstrated to increase excitability, whereas the SK channel opener 1-EBIO is able to reduce electrical activity. In non-excitable cells, where the amount of $Ca^{2+}$ influx via voltage-independent pathways is highly sensitive to the membrane potential, an activation of SK channels will increase the driving force, whereas an inhibitor of SK channels will have a depolarizing effect, and thus diminish the driving force for calcium.

An SK channel inhibitor is a pharmaceutical agent that impairs the conduction of potassium ions ($K^*$) through $Ca^{2+}$-activated small conductance $K^+$ channels. The impairment can be obtained by any reduction in current resulting from e.g. a direct inhibition of ion conduction to a prevention of $Ca^{2+}$ binding, that is an obligate request for channel activation, or a reduction in calcium sensitivity.

A review of SK channels and SK channel modulators may be found in Wulff H et al.: "Modulators of Small- and Intermediate-Conductance Calcium-Activated Potassium Channels and their Therapeutic Indications", Currrent Medicinal Chemistry 2007 14 1437-1457; and in Liegeois J-F et al.: "Modulation of small conductance calcium-activated potassium (SK) channels: a new challenge in medicinal chemistry", Current Medicinal Chemistry 2003 10 625-647.

Based on the important role of SK channels in linking $[Ca^{2+}]i$ and membrane potential, SK channels are interesting targets for developing novel therapeutic agents, and the potential of inhibitors of SK channels for use in anti-arrhythmic treatment has recently been established, see e.g. Nattel S; J. Physiol. 2009 587 1385-1386; Diness J G, Sørensen U S, Nissen J D, Al-Shahib B, Jespersen T, Grunnet M, Hansen R S; Circ. Arrhythm. Electrophysiol. 2010 3 380-90; and Diness et al; Hypertension 2011 57 1129-1135.

WO 2006/013210 describes certain 2-amino benzimidazole derivatives and their use as modulators of small-conductance calcium-activated potassium channels.

SUMMARY

The compounds of the present invention are inhibitors or negative modulators of the small-conductance calcium activated potassium (SK) channel and have an IC50 value of below 30 µM as demonstrated in the Automated patch clamping system described herein, and are considered potent drug candidates. A certain selection of these compounds has a strongly improved IC50 value of below 1 µM. Some of these compounds also have physicochemical properties suitable for a drug substance and important for making pharmaceutical formulations and may have beneficial properties with respect to pharmacological selectivity profile, in vivo absorption/bioavailability, toxicity and safety profile, and manufacturability. Further, some of these compounds have pharmacokinetic properties making them suitable for use as pharmaceutical drugs.

In a broad aspect the present invention relates to a compound of formula (I)

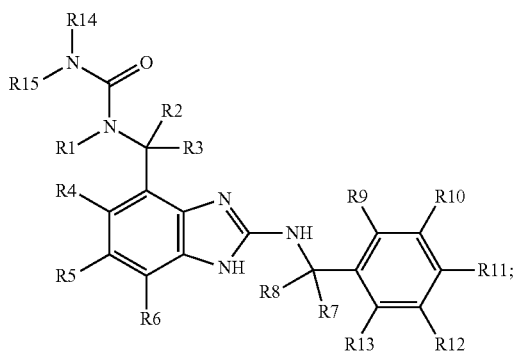

Wherein

R1 is selected from hydrogen and $C_{1-6}$ alkyl;

R2-R3 are independently a group selected from hydrogen and $C_{1-6}$ alkyl; or R2 and R3 taken together with the carbon atom to which they are linked form a $C_{3-4}$ cycloalkyl;

R4-R6 are independently a group selected from hydrogen, halogen, and $C_{1-4}$ alkyl;

R7 is selected from the group consisting of hydrogen and $C_{1-4}$ alkyl,

R8 is selected from the group consisting of $C_{1-6}$ alkyl, $C_{1-6}$ alkyl substituted with one OH, and $C_{1-6}$ alkyl substituted with one $OC_{1-3}$ alkyl, or R7 and R8 taken together with the carbon atom to which they are linked form a $C_{3-4}$ cycloalkyl;

R9-R13 are independently a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano;

R14 is selected from H, $C_{1-6}$ alkyl, or $C_{1-6}$ alkoxy;

R15 is selected from H, $C_{1-6}$ alkyl, $C_{1-6}$ alkyl substituted with at least one halogen, $C_{1-6}$ alkoxy, $C_{1-6}$ alkoxy substituted with at least one halogen, or $C_{3-4}$ cycloalkyl;

or R14 and R15 taken together with the nitrogen atom to which they are linked form a 4-6 membered non-aromatic heterocycle containing 1-2 nitrogen atoms, optionally 1 oxygen atom, and optionally 1 sulphur atom, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen; or a pharmaceutically acceptable salt thereof.

In an embodiment R1 is selected from hydrogen (H) and methyl. In another embodiment R1 is H.

In a further embodiment R2-R3 are independently a group selected from H and $C_{1-3}$ alkyl. In a still further embodiment R2 and R3 are independently a group selected from H and Methyl. In a further embodiment R2-R3 are both H.

In a still further embodiment R4-R6 are independently a group selected from H, F, and methyl.

In a further embodiment R7 is a group selected from H and $C_{1-3}$ alkyl. Typically, R7 is methyl or ethyl.

In a still further embodiment R8 is a group selected from $C_{1-4}$ alkyl substituted with one OH, and $C_{1-4}$ alkyl substituted with one $OC_{1-3}$ alkyl. Typically, R8 is selected from $CH_2OH$, $CH_2CH_2OH$, $CH_2OCH_3$ and $CH_2CH_2O—CH_3$.

In a further embodiment R9-R13 are independently a group selected from H, halogen, $C_{1-6}$ alkyl substituted with at least one halogen, and $C_{1-6}$ alkoxy substituted with at least one halogen.

In a still further embodiment R9, R12 and R13 are all H, and R10-R11 are independently a group selected from H, halogen, $C_{1-6}$ alkyl substituted with at least one halogen, and $C_{1-6}$ alkoxy substituted with at least one halogen; provided that R10 and R11 are not both H.

In a further embodiment R14 is selected from H and $C_{1-6}$ alkyl. Typically R14 is H, methyl or ethyl.

In a still further embodiment R15 is selected from H, $C_{1-6}$ alkyl, $C_{1-6}$ alkyl substituted with at least one halogen, $C_{1-6}$ alkoxy, $C_{1-6}$ alkoxy substituted with at least one halogen, or $C_{3-4}$ cycloalkyl. Typically, R15 is methyl, ethyl, methoxy, cyclopropyl, $CH_2CH_2CF_3$, or $CH_2CH_2OCF_3$.

In another embodiment R14 and R15 taken together with the nitrogen atom to which they are linked form a 4-6 membered non-aromatic heterocycle containing 1 nitrogen atom and optionally 1 oxygen atom, optionally substituted with at least one halogen, such as azetidinyl, piperidinyl, morpholinyl, and isoxazolidinyl, optionally substituted with at least one F.

In still further embodiments the compound of formula (I) is selected from any one of the exemplified compounds of examples 1-21b; or a pharmaceutically acceptable salt thereof.

In a further aspect the present invention relates to a compound of formula (I) as defined above for use as a medicine.

In a still further aspect the present invention relates to a pharmaceutical composition comprising a compound of formula (I) as defined above and optionally a pharmaceutically acceptable additive, such as carrier or excipient.

In a further aspect the present invention relates to a compound of formula (I) as defined above for use in a method for treating a cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

According to a further aspect of the specification there is provided a pharmaceutical composition, which comprises a compound of Formula (I), or a pharmaceutically acceptable salt thereof, as defined herein, in association with a pharmaceutically acceptable excipient.

According to a further aspect of the specification there is provided a pharmaceutical composition, which comprises a compound of Formula (I), or a pharmaceutically acceptable salt thereof, as defined herein, for use in the treatment of cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

According to a further aspect of the specification, there is provided a compound of Formula (I), or a pharmaceutically acceptable salt thereof, as defined herein, for use as a medicament.

According to a further aspect of the specification, there is provided a compound of Formula (I), or a pharmaceutically acceptable salt thereof, as defined herein, for use in therapy.

According to a further aspect of the specification, there is provided a compound of Formula (I), or a pharmaceutically acceptable salt thereof, as defined herein, for use in a method of treatment of the human or animal body by therapy.

According to a further aspect of the specification, there is provided a compound of Formula (I), or a pharmaceutically acceptable salt thereof, as defined herein, for use in the prevention or treatment of mammals, such as humans.

According to a further aspect of the specification there is provided the use of a compound of Formula (I), or a pharmaceutically acceptable salt thereof, as defined herein, for the manufacture of a medicament for the prevention or treatment of mammals, such as humans.

According to a further aspect of the specification there is provided a method for the prevention or treatment of cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure, in a mammal such as humans, in need of such treatment, which comprises administering to said animal an effective amount of a compound of Formula (I), or a pharmaceutically acceptable salt thereof, as defined herein.

In a further aspect the present invention relates to a method for treatment of a cardiac disease, disorder or condition in a mammal, such as a human, wherein a therapeutically effective amount of at least one compound of formula (I) as defined above is administered to a mammal in need of said treatment. In an embodiment the cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

In a still further aspect the present invention relates to a process of preparing a compound of formula I or a pharmaceutically acceptable salt or solvate thereof, as well as the intermediates, comprising the steps described in connection with reaction schemes 1-9.

DETAILED DESCRIPTION

In a broad aspect the present invention relates to a compound of formula (I)

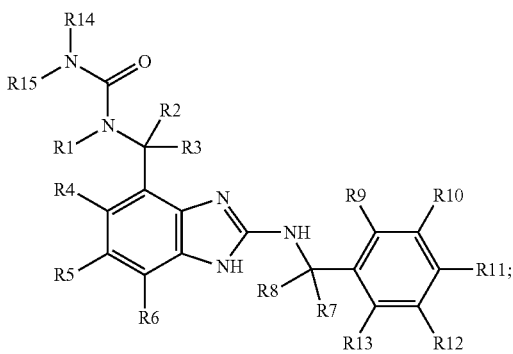

Wherein R1, R2, R3, R4, R5, R6, R7, R8, R9, R10, R11, R12, R13, R14 and R15 are as defined above.

In certain embodiments whenever $C_{1-6}$ alkyl or $C_{1-6}$ alkoxy is substituted with at least one halogen, it is preferred that such $C_{1-6}$ alkyl or $C_{1-6}$ alkoxy is substituted with 1 to 3 halogens, such as 1 to 3 F atoms, preferred are $CF_3$ and $OCF_3$.

In an embodiment R1 is H. In another embodiment R1 is $C_{1-6}$ alkyl.

In a further embodiment R2 is a group selected from hydrogen and $C_{1-6}$ alkyl. Typically, R2 is H. In another embodiment R2 is methyl.

In a still further embodiment R3 is a group selected from hydrogen and $C_{1-6}$ alkyl. Typically, R3 is H. In another embodiment R3 is methyl.

In a further embodiment R2 and R3 taken together with the carbon atom to which they are linked form a $C_{3-4}$ cycloalkyl, such as a cyclopropyl.

In a still further embodiment R4 is a group selected from hydrogen, halogen, and $C_{1-4}$ alkyl. Typically, R4 is H. in another embodiment R4 is halogen, such as Cl or F.

In a further embodiment R5 is a group selected from hydrogen, halogen, and $C_{1-4}$ alkyl. Typically, R5 is H.

In a still further embodiment R6 is a group selected from hydrogen, halogen, and $C_{1-4}$ alkyl. Typically, R6 is H.

In a further embodiment R7 is H. In a still further embodiment R7 is $C_{1-4}$ alkyl.

In a further embodiment R7 is methyl. In a still further embodiment R7 is ethyl.

In a still further embodiment R8 is $C_{1-6}$ alkyl.

In a further embodiment R8 is $C_{1-6}$ alkyl substituted with one OH. In a still further embodiment R8 is $CH_2OH$. In a further embodiment R8 is $CH_2CH_2OH$.

In a still further embodiment R8 is $C_{1-6}$ alkyl substituted with one $OC_{1-3}$ alkyl. In a further embodiment R8 is $C_{1-4}$ alkyl substituted with one $OC_{1-3}$ alkyl. In a still further embodiment R8 is $CH_2OCH_3$. In a further embodiment R8 is $CH_2CH_2OCH_3$.

In a still further embodiment R7 and R8 taken together with the carbon atom to which they are linked form a $C_{3-4}$ cycloalkyl. Typically, R7 and R8 taken together with the carbon atom to which they are linked form a cyclopropyl.

In a further embodiment R9 is a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano. In a still further embodiment R9 is selected from H, halogen, $C_{1-6}$ alkyl substituted with at least one halogen, and $C_{1-6}$ alkoxy substituted with at least one halogen. Typically, R9 is H.

In a further embodiment R10 is a group selected from hydrogen, halogen, $C_1$-6 alkyl substituted with at least one halogen, $C_{1-6}$ alkoxy, $C_{1-6}$ alkoxy substituted with at least one halogen, $C_{1-6}$ alkylthio, and cyano. In a still further embodiment R10 is a group selected from H, halogen, $C_{1-6}$ alkyl substituted with at least one halogen, and $C_{1-6}$ alkoxy substituted with at least one halogen. In a further embodiment R10 is H provided that R11 is not H. In a still further embodiment R10 is a halogen, such as Cl. In a further embodiment R10 is a $C_{1-6}$ alkyl substituted with at least one halogen, such as $CF_3$. In a still further embodiment R10 is a $C_{1-6}$ alkoxy substituted with at least one halogen, such as $OCF_3$.

In a further embodiment R11 is a group selected from hydrogen, halogen, Cl-6 alkyl substituted with at least one halogen, $C_{1-6}$ alkoxy, $C_{1-6}$ alkoxy substituted with at least one halogen, $C_{1-6}$ alkylthio, and cyano. In a still further embodiment R11 is a group selected from H, halogen, $C_{1-6}$ alkyl substituted with at least one halogen, and $C_{1-6}$ alkoxy substituted with at least one halogen. In a further embodiment R11 is H provided that R10 is not H. In a still further embodiment R11 is a halogen, such as F or Cl.

In a further embodiment R12 is a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano. In a still further embodiment R12 is selected from H, halogen, $C_{1-6}$ alkyl substituted with at least one halogen, and $C_{1-6}$ alkoxy substituted with at least one halogen. Typically, R12 is H.

In a further embodiment R13 is a group selected from hydrogen, halogen, $C_1$-6 alkyl substituted with at least one halogen, $C_{1-6}$ alkoxy, $C_{1-6}$ alkoxy substituted with a halogen, $C_{1-6}$ alkylthio, and cyano. In a still further embodiment R13 is selected from H, halogen, $C_{1-6}$ alkyl substituted with at least one halogen, and $C_{1-6}$ alkoxy substituted with at least one halogen. Typically, R13 is H.

In a further embodiment R14 is H. In a still further embodiment R14 is $C_{1-6}$ alkyl, such as methyl or ethyl.

In a further embodiment R15 is H. In a still further embodiment R15 is selected from $C_{1-6}$ alkyl, such as methyl or ethyl. In a further embodiment R15 is Cl-6 alkyl substituted with at least one halogen. In a still further embodiment R15 is $C_1$-4 alkyl substituted with at least one F, such as $CH_2CH_2CF_3$. In a still further embodiment R15 is $C_{1-6}$ alkoxy, such as methoxy. In a further embodiment R15 is $C_{1-6}$ alkoxy substituted with at least one halogen. In a still further embodiment R15 is $C_{1-3}$ alkoxy substituted with at least one F, such as $CH_2CH_2OCF_3$. In a further embodiment R15 is $C_{3-4}$ cycloalkyl, such as cyclopropyl.

In another embodiment R14 and R15 taken together with the nitrogen atom to which they are linked form a 4-6 membered non-aromatic heterocycle containing 1 nitrogen atom and optionally 1 oxygen atom, optionally substituted with a group selected from halogen, $C_{1-6}$ alkyl, $C_{1-6}$ alkyl substituted with at least one halogen, $C_{1-6}$ alkoxy, $C_{1-6}$ alkoxy substituted with at least one halogen. In a further embodiment R14 and R15 taken together with the nitrogen atom to which they are linked form a 4-6 membered non-aromatic heterocycle containing 1 nitrogen atom and optionally 1 oxygen atom, optionally substituted with at least one halogen, such as azetidinyl, piperidinyl, morpholinyl, and isoxazolidinyl, optionally substituted with at least one F.

In still further embodiments the compound of formula (I) is selected from any one of the exemplified compounds of examples 1-21b; or a pharmaceutically acceptable salt thereof.

In certain embodiments whenever $C_{1-6}$ alkyl or $C_{1-6}$ alkoxy is substituted with a halogen, it is preferred that such $C_{1-6}$ alkyl or $C_{1-6}$ alkoxy is substituted with 1 to 3 halogens, such as 1 to 3 F atoms, preferred are $CF_3$ and $OCF_3$.

Each of the compounds as described in the experimental part constitutes an embodiment of the present invention in any form, such as a salt or free base, and may be subject to a claim to such compound, or a salt thereof.

In a still further embodiment the compound of formula (I) is selected from a pharmaceutically acceptable acid salt of any one of the compounds of examples 1-21b Cardiac Diseases In the context of this invention a cardiac disease, disorder or condition is any cardiac disease, disorder or condition, including, but not limited to, an abnormal rhythm of the heart or variant and exercise induced angina.

In a more specific embodiment the cardiac disease, disorder or condition is any disease, disorder or condition associated with an abnormal rhythm of the heart or variant and exercise induced angina.

In a more specific embodiment the cardiac disease, disorder or condition is any disease, disorder or condition associated with an abnormal rhythm of the heart.

In a more specific embodiment the cardiac disease, disorder or condition associated with an abnormal rhythm of the heart is selected from cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In another embodiment a cardiac disease, disorder or condition of the invention is an abnormal rhythm caused by myocardial ischaemia, myocardial infarction, cardiac hypertrophy, or cardiomyopathy.

In another embodiment a cardiac disease, disorder or condition of the invention is an abnormal rhythm arising after cardiac surgery or a cardiac ablation procedure.

In a further specific embodiment, the cardiac disease, disorder or condition associated with an abnormal rhythm of the heart is a cardiac arrhythmia caused by a genetic disease.

In a still further preferred embodiment the cardiac disease, disorder or condition associated with an abnormal rhythm of the heart is cardiac arrhythmia.

In a preferred embodiment the cardiac disease, disorder or condition associated with an abnormal rhythm of the heart is atrial fibrillation.

In a particular embodiment the compound of formula (I) of the present invention is useful for treatment of atrial fibrillation by acute cardioversion to normal sinus rhythm.

In another particular embodiment the compound of formula (I) of the present invention is useful for treatment of atrial fibrillation by maintaining normal sinus rhythm and avoiding or reducing the occurrence of new episodes of atrial fibrillation.

Pharmacological Treatment of Atrial Fibrillation

In the context of this invention, and as understood by a person skilled in the art, treatment of atrial fibrillation is acute cardioversion or maintenance of sinus rhythm or both.

Acute conversion is defined as application of compound that has the ability to convert atrial fibrillation to a normal cardiac sinus rhythm. Normal sinus rhythm is defined as regular stable heart beating at frequencies between 40 and 100 beats at rest in adults with normal regular β-wave on a standard 12-lead electrocardiogram. Maintenance of sinus rhythm is defined as the ability for a compound to preserve a normal stable sinus rhythm over time with no relapse to atrial fibrillation or the ability of a compound to significantly reduced the incidence of relapse from atrial fibrillation to normal sinus rhythm compared to non-treated controls.

Description of General Process

Schemes 1-9 summarise one of the synthetic approaches that can be used to prepare compounds of general formula (I).

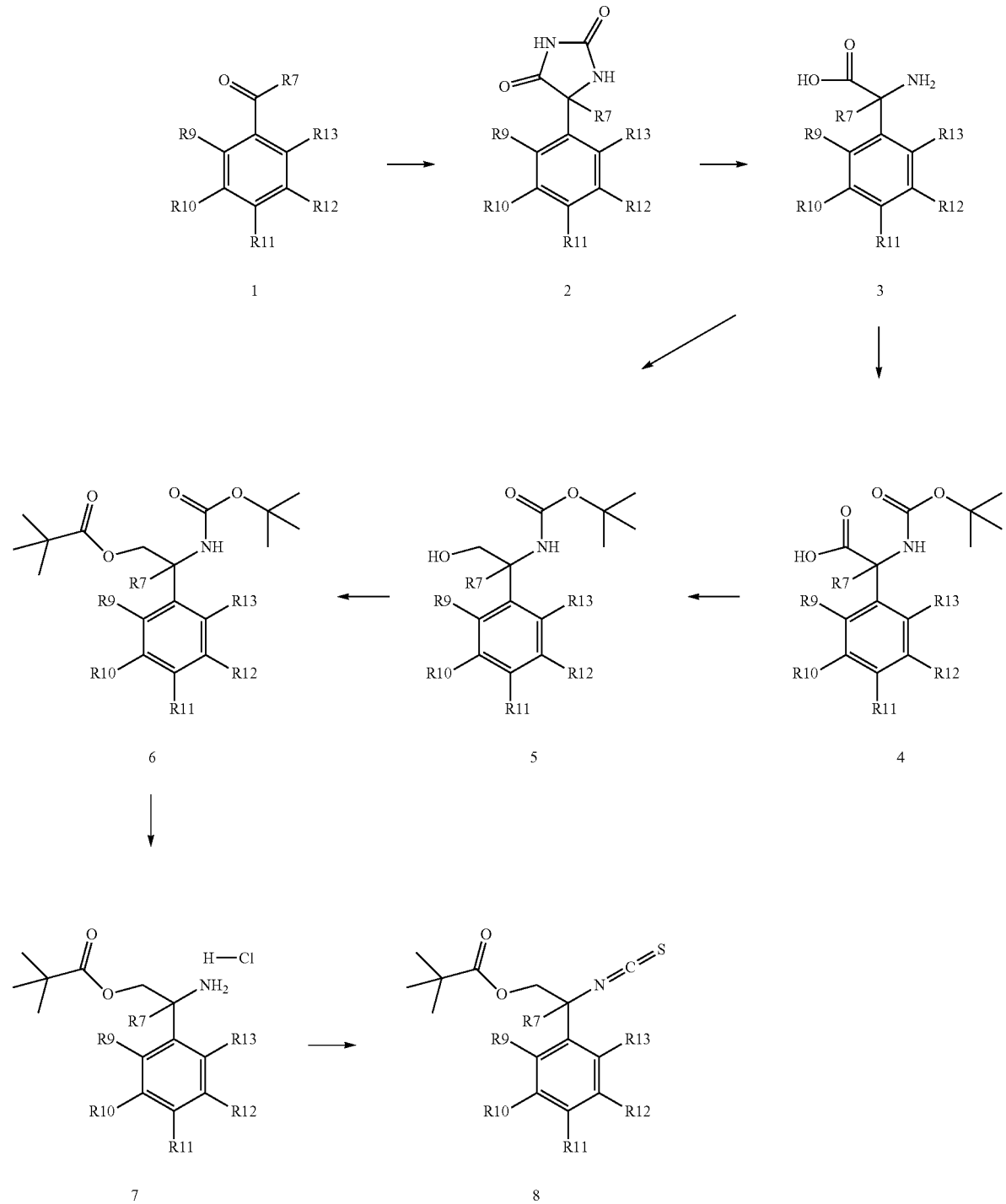

A large number of ketones and aldehydes (1) are commercially available or can be readily prepared by many routes described in the literature. The ketones and aldehydes (1) can be converted to the hydantoin derivatives (2) by a wide range of methods, such as reaction of (1) with potassium cyanide under the influence of ammonium salts (e.g. ammonium carbonate) upon heating is solvents such as water and alcohols (e.g. ethanol). The hydantoin derivatives (2) can be converted to the amino acid derivatives (3) by hydrolysis under the influence of a strong base (e.g. sodium hydroxide) and heat in water. There are many other well-established methods for the preparation of amino acids described in the literature. Many amino acid derivatives are also readily available commercially. Amino acids (3) can be protected as the N-(tert-butoxy)carbonyl derivatives (4) by treatment with di-tert-butyl dicarbonate and a base (e.g. sodium bicarbonate) in a suitable solvent (e.g. tetrahydrofuran, water). Intermediates (4) can be reduced to the alcohol derivatives (5) by a variety of methods, including by hydride reducing agents (e.g. sodium borohydride or lithium aluminium hydride). This can be achieved by direct reduction of the acid group (e.g. with lithium aluminium hydride in tetrahydrofuran) or by first activation of the acid group in (4) by converting it to a mixed anhydride (e.g. with isobutyl chloroformate and triethylamine in tetrahydrofuran), followed by reduction with sodium borohydride (e.g. in water). The alcohol derivative (5) may require protection such as converting it to an ester (e.g. 2,2-dimethylpropanoate ester) by reacting with 2,2-dimethylpropanoyl chloride and a base (such as triethylamine) in a solvent (such as dichloromethane). Intermediate (6) can be deprotected to the amine derivative (7) by treatment with an acid (e.g. hydrochloric acid or trifluoroacetic acid) in a suitable solvent (e.g. dioxane or dichloromethane). The intermediates (7) can be converted to the isothiocyanate derivatives (8) by reaction with thiophosgene in a suitable solvent (e.g. dichloromethane) under the influence of a base (e.g. sodium hydrogen carbonate).

Scheme 2: Route to Intermediates 14 & 16

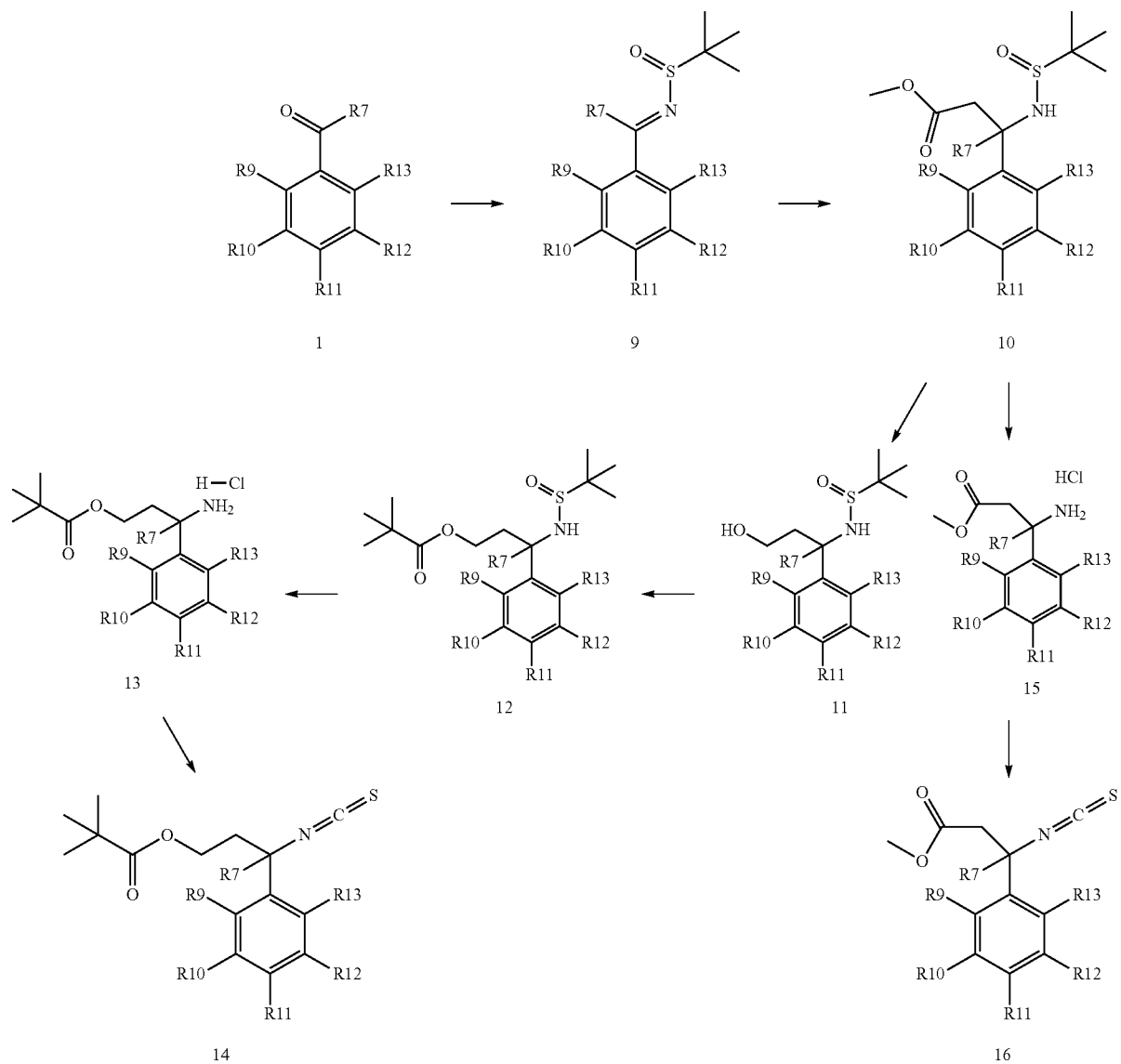

The ketones and aldehydes (1) can be converted to the sulfinamide derivatives (9) by reaction of (1) with 2-methylpropane-2-sulfinamide under the influence of a Lewis acid (e.g. titanium (IV) ethoxide) and heating in a suitable solvent (e.g. tetrahydrofuran). The sulfinamide derivatives (9) can be converted to the □-amino acid esters (10) by reaction with methyl 2-bromoacetate under the influence of zinc with heating in a solvent (e.g. tetrahydrofuran). There are many other well-established methods for the preparation of □-amino acids described in the literature. Some amino acid derivatives are also readily available commercially. The □-amino acid esters (10) can be reduced to the alcohol derivatives (11) by a variety of methods, including by hydride reducing agents (e.g. sodium borohydride, lithium aluminium hydride) in a suitable solvent (e.g. tetrahydrofuran). The alcohol derivative (11) may require protection such as converting it to an ester (e.g. 2,2-dimethylpropanoate ester) by reacting with 2,2-dimethylpropanoyl chloride and a base (such as triethylamine) in a solvent (e.g. dichloromethane). Intermediate (12) can be deprotected to the amine derivative (13) by treatment with an acid (e.g. hydrochloric acid or trifluoroacetic acid) in a suitable solvent (e.g. dioxane or dichloromethane). The intermediates (13) can be converted to the isothiocyanate derivatives (14) by reaction with thiophosgene in a suitable solvent (e.g. dichloromethane) under the influence of a base (e.g. sodium hydrogen carbonate).

Intermediate (10) can be deprotected to the amine derivative (15) by treatment with an acid (e.g. hydrochloric acid or trifluoroacetic acid) in a suitable solvent (e.g. dioxane or dichloromethane). The intermediates (15) can be converted to the isothiocyanate derivatives (16) by reaction with thiophosgene in a suitable solvent (e.g. dichloromethane) under the influence of a base (e.g. sodium hydrogen carbonate).

Scheme 3: Route to Intermediate 19

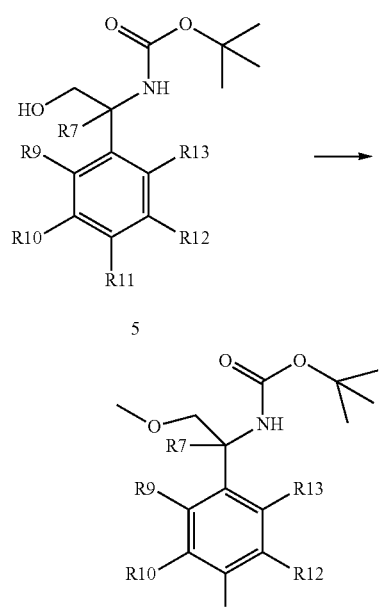

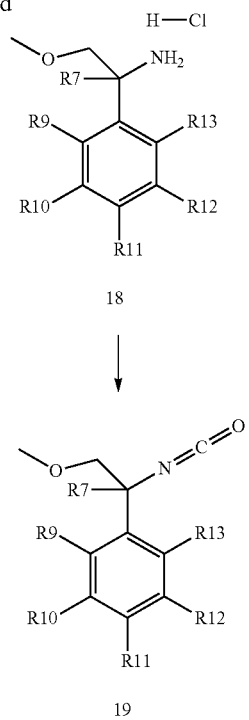

The alcohol derivatives (5) can be alkylated on the alcohol oxygen atom by reacting with methyl iodide under the influence of a metal oxide (e.g. silver oxide) in a solvent (e.g. acetonitrile) and converted to intermediates (17). Intermediate (17) can be deprotected to the amine derivative (18) by treatment with an acid (e.g. hydrochloric acid or trifluoroacetic acid) in a suitable solvent (e.g. dioxane or dichloromethane). The intermediates (18) can be converted to the isothiocyanate derivatives (19) by reaction with thiophosgene in a suitable solvent (e.g. dichloromethane) under the influence of a base (e.g. sodium hydrogen carbonate).

Scheme 4: Route to Intermediate 21

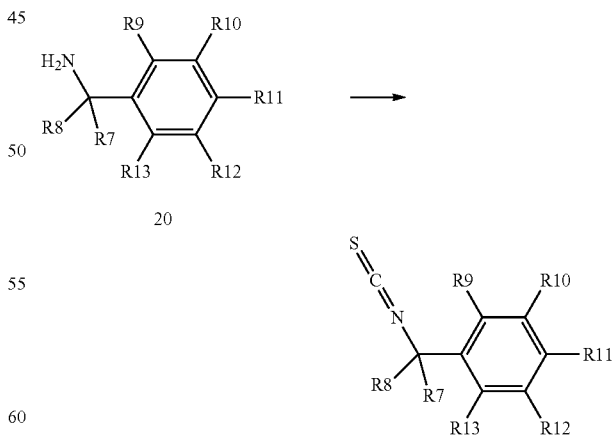

Where R7 and R8 together form a small ring

There are a wide range of intermediates (20) that are readily available commercially or can be prepared by methods described in the literature. The intermediates (20) can be converted to the isothiocyanate derivatives (21) by reaction with thiophosgene in a suitable solvent (e.g. dichloromethane) under the influence of a base (e.g. sodium hydrogen carbonate).

nyl carbamate, under the influence of a base (e.g. potassium carbonate) upon heating in a solvent (e.g. acetonitrile) to afford intermediates (25). Intermediates (25) can be deprotected to the amine derivatives (26) by treatment with an acid (e.g. hydrochloric acid or trifluoroacetic acid) in a Scheme 5: Route to Intermediate 28

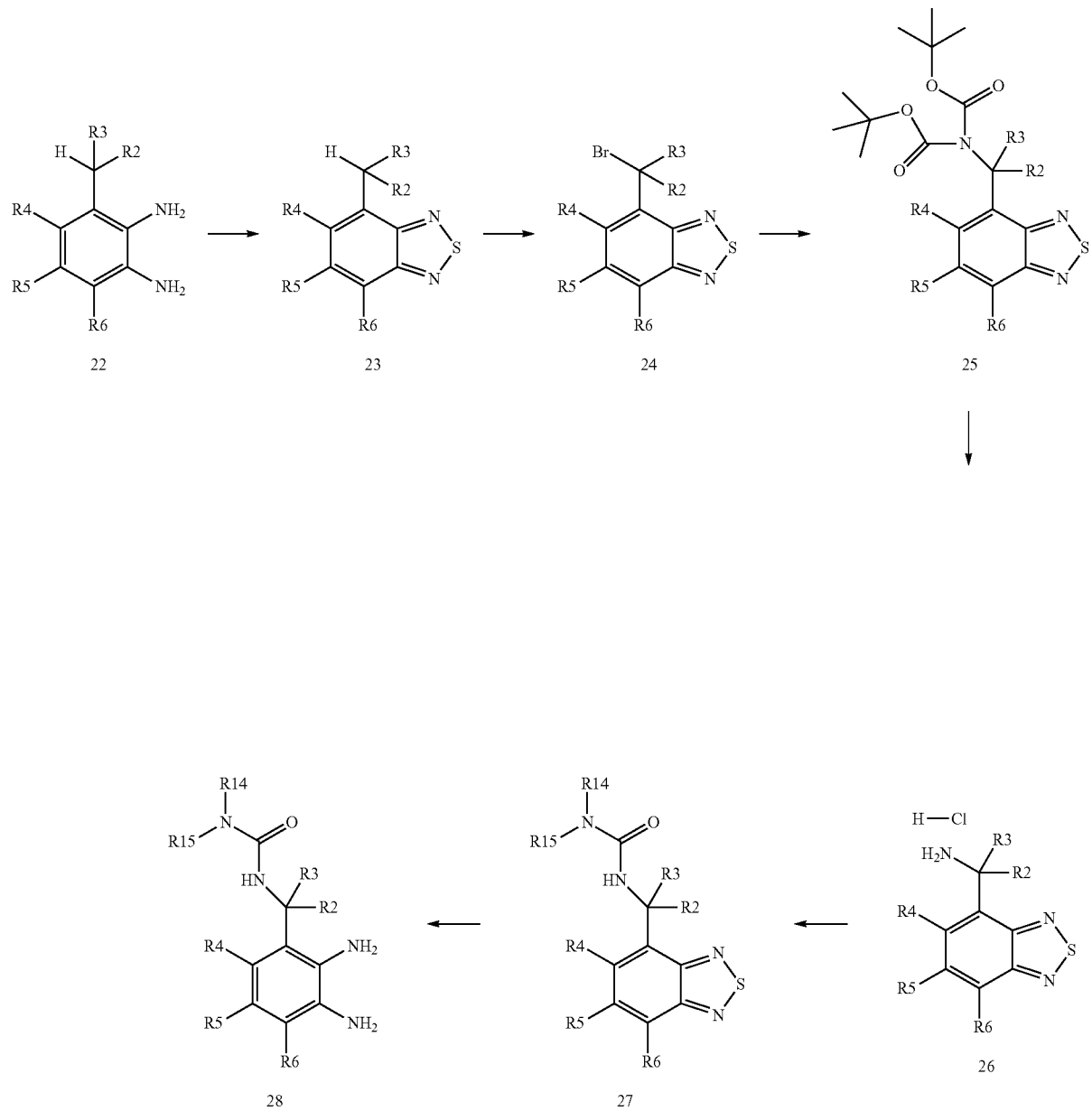

There are a wide range of benzene-1,2-diamine intermediates (22) that are readily available commercially or can be prepared by methods described in the literature. The intermediates (22) can be converted to the 2,1,3-benzothiadiazole derivatives (23) by reaction with thionyl chloride in pyridine. The intermediates (23) can be converted to the benzyl bromide derivatives (24) by reaction with N-bromosuccinimide in a solvent (e.g. chloroform) under the influence of radical initiators (e.g. benzoyl peroxide) upon heating. Intermediates (24) can react with tert-butyl N-tert-butoxycarbosuitable solvent (e.g. dioxane or dichloromethane). Intermediates (26) can be converted to the urea derivatives (27) by reaction with a wide range of commercial carbamoyl chlorides under the influence of a base (e.g. triethylamine) in a suitable solvent (e.g. dichloromethane). The intermediates (27) can be converted to benzene-1,2-diamine derivatives (28) by desulphurisation with hydrogen gas under the influence of metal catalysts (e.g. Raney nickel) in a suitable solvent (e.g. methanol).

Scheme 6: Route 1 to Examples and Separation of Enantiomers

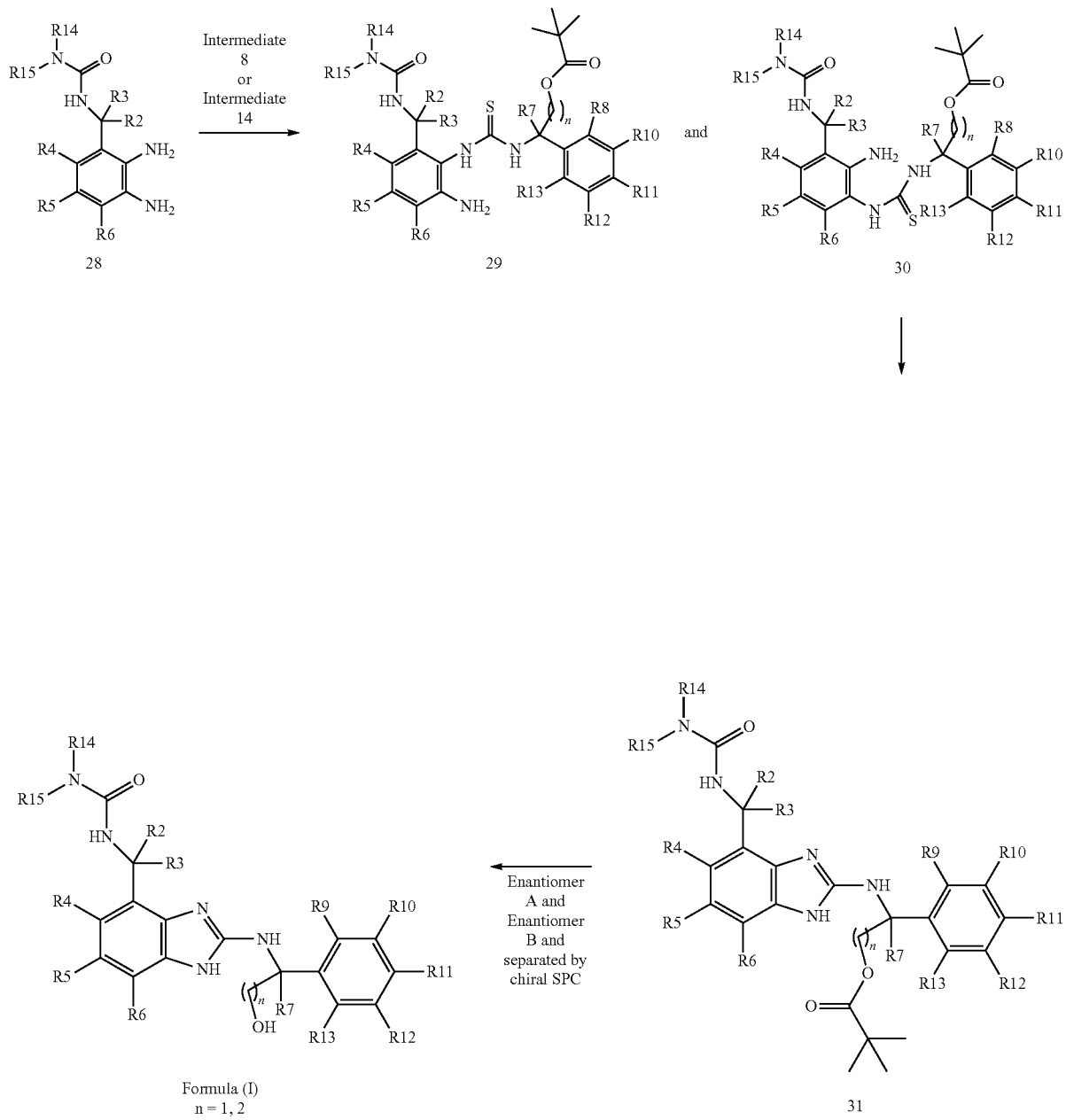

The benzene-1,2-diamine derivatives (28) can react with the isothiocyanates (8) or (14) in a suitable solvent (e.g. dichloromethane) to afford a mixture of the thiourea products (29) and (30). A wide range of other benzene-1,2-diamine derivatives are available commercially or can be readily prepared by well-established methods described in the literature (e.g. by nitration and subsequent reduction of commercial substituted benzene starting materials). The thiourea derivatives (29) and (30) can be converted to 2-aminobenzimidazole derivatives (31) by a ring forming reaction that occurs under the influence of iodoacetic acid and heating in a suitable solvent (such as methanol or acetonitrile). The cyclisation of (29) and (30) to afford (31) can also occur under the influence of mercury salts (e.g. mercuric oxide) with heating in a suitable solvent (e.g. acetonitrile). The 2-aminobenzimidazole ester derivatives (31) can be converted to compounds of Formula (I) by deprotection of the ester under the influence of a base (e.g. sodium hydroxide) in a suitable solvent (e.g. methanol).

The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

Scheme 7: Route to Examples and Separation of Enantiomers

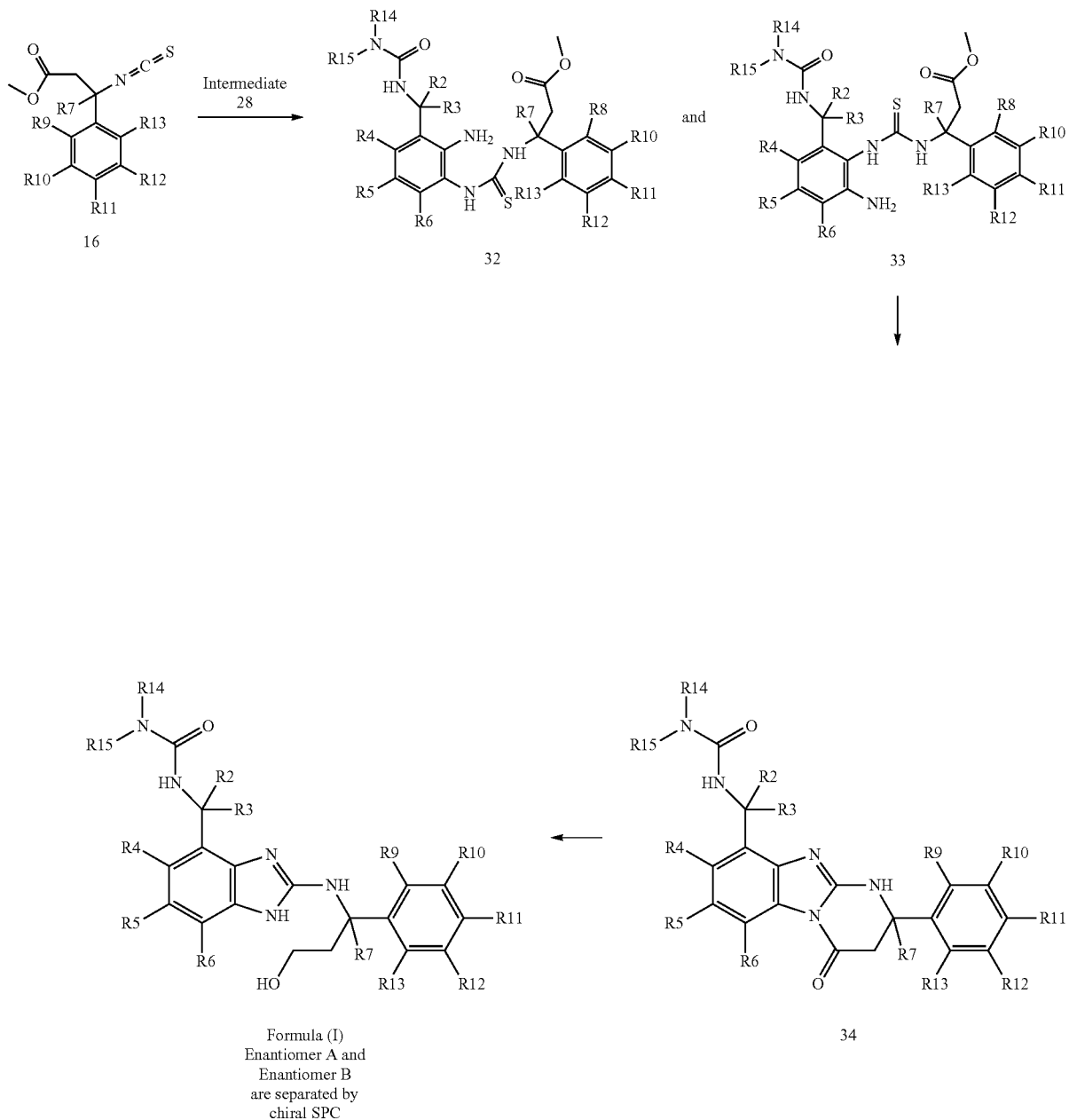

Formula (I)
Enantiomer A and
Enantiomer B
are separated by
chiral SPC

The benzene-1,2-diamine derivatives (28) can react with the isothiocyanates (16) in a suitable solvent (e.g. dichloromethane) to afford a mixture of the thiourea products (32) and (33). A wide range of other benzene-1,2-diamine derivatives are available commercially or can be readily prepared by well-established methods described in the literature (e.g. by nitration and subsequent reduction of commercial substituted benzene starting materials). The thiourea derivatives (32) and (33) can be converted to derivatives (34) by a ring forming reaction that occurs under the influence of iodoacetic acid and heating in a suitable solvent (such as methanol or acetonitrile). The cyclisation of (32) and (33) to afford (34) can also occur under the influence of mercury salts (e.g. mercuric oxide) with heating in suitable solvents (e.g. acetonitrile, methanol). The derivatives (34) can be converted to compounds of Formula (I) by reduction under the influence of a hydride reducing agent (e.g. sodium borohydride) with heating in a suitable solvent (e.g. tetrahydrofuran).

The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

Scheme 8: Route to Examples and Separation of Enantiomers
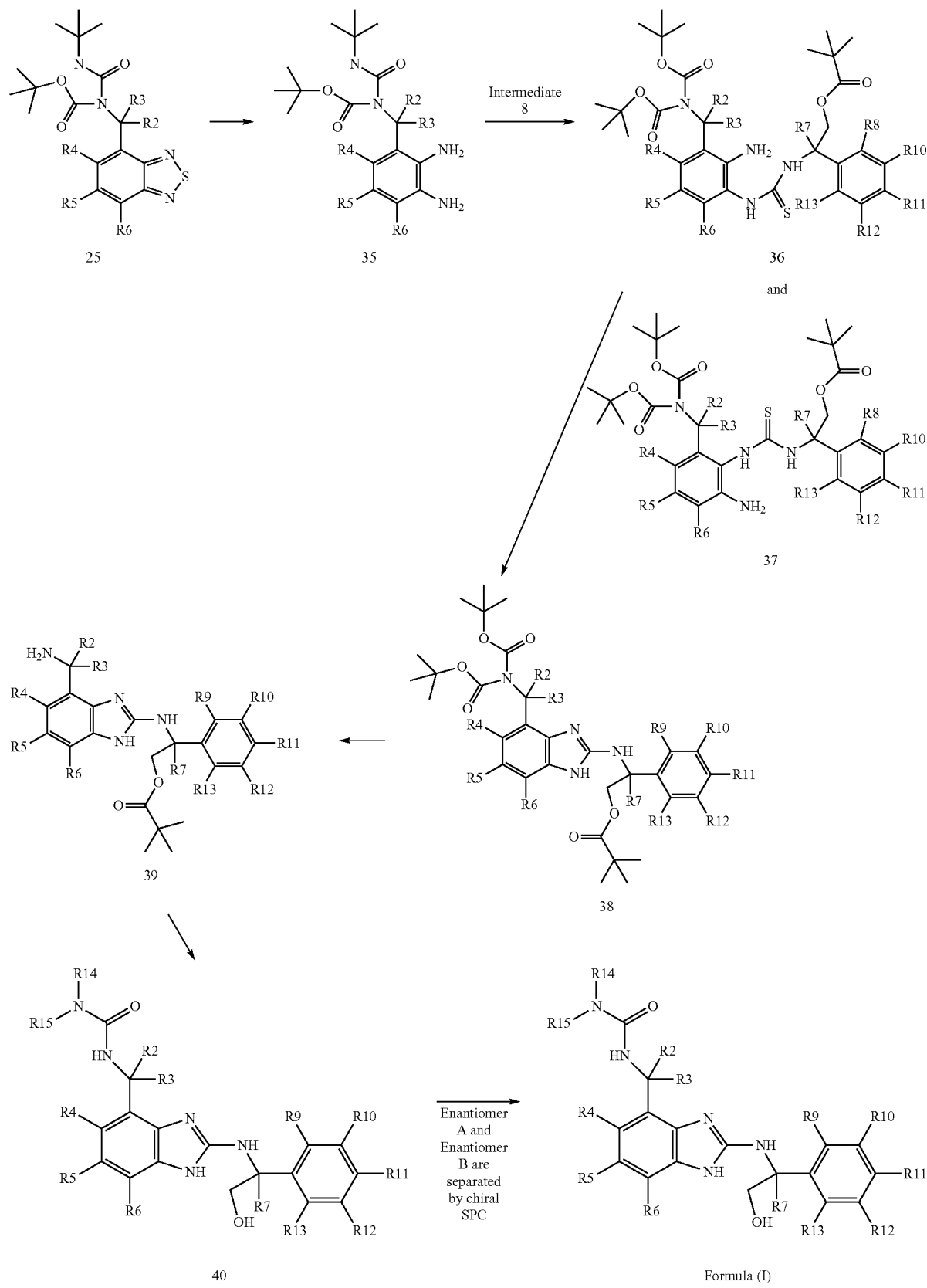

The intermediates (25) can be converted to the benzene-1,2-diamine derivatives (35) by desulphurisation with hydrogen gas under the influence of metal catalysts (e.g. Raney nickel) in a suitable solvent (e.g. methanol). Derivatives (35) can react with the isothiocyanates (8) in suitable solvents (e.g. dichloromethane, acetonitrile) to afford a mixture of the thiourea products (36) and (37). The thiourea derivatives (36) and (37) can be converted to 2-aminobenzimidazole derivatives (38) by a ring forming reaction that occurs under the influence of iodoacetic acid and heating in a suitable solvent (such as methanol or acetonitrile). The cyclisation of (36) and (37) to afford aminobenzimidazole derivatives (38) can also occur under the influence of mercury salts (e.g. mercuric oxide) with heating in a suitable solvent (e.g. acetonitrile, methanol). Intermediates (38) can be deprotected to the amine derivatives (39) by treatment with an acid (e.g. hydrochloric acid or trifluoroacetic acid) in a suitable solvent (e.g. dioxane or dichloromethane). Intermediates (39) can be converted to the urea derivatives (40) by reaction with a wide range of commercial carbamoyl chlorides or isocyanates under the influence of a base (e.g. triethylamine) in a suitable solvent (e.g. dichloromethane). The 2-aminobenzimidazole ester derivatives (40) can be converted to compounds of Formula (I) by deprotection of the ester under the influence of a base (e.g. sodium hydroxide) in a suitable solvent (e.g. ethanol). The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

Scheme 9: Route 4 to Examples

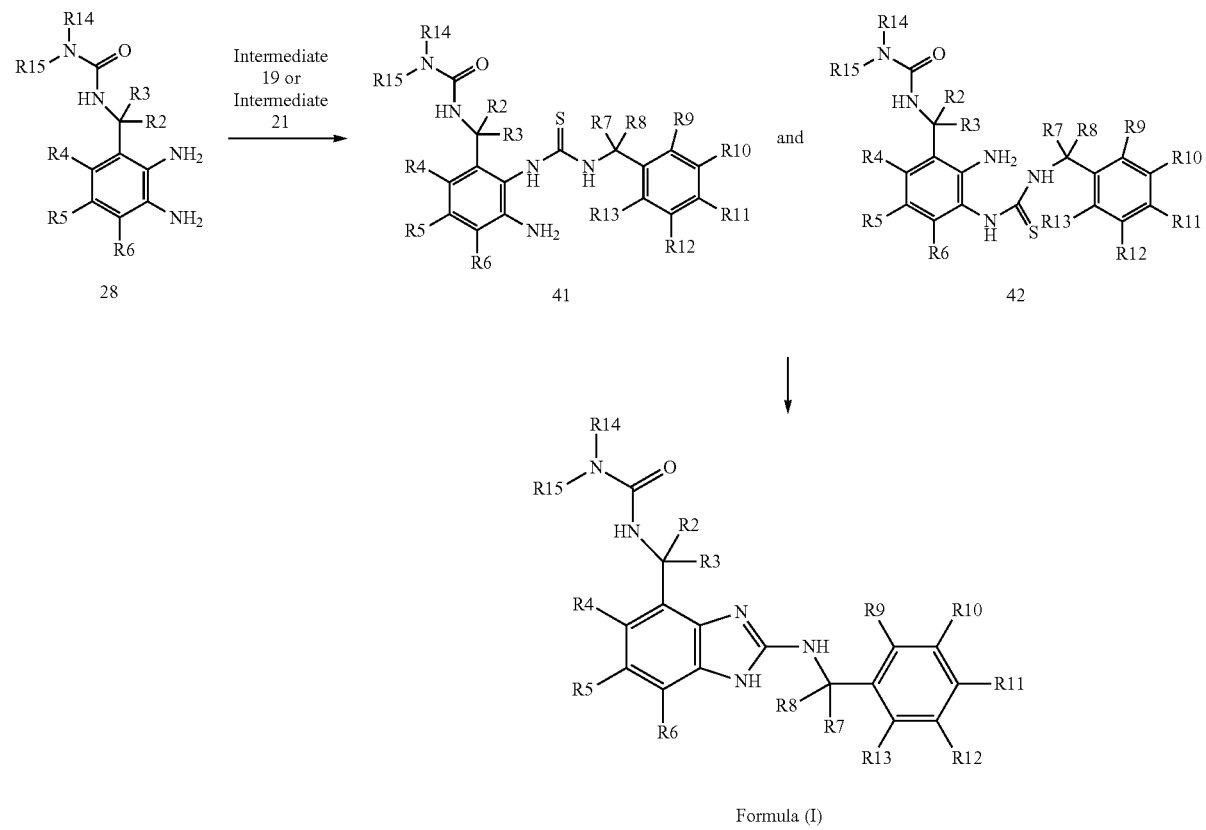

Formula (I)

The benzene-1,2-diamine derivatives (28) can react with the isothiocyanates (19) or (21) in a suitable solvent (e.g. dichloromethane) to afford a mixture of the thiourea products (41) and (42). The thiourea derivatives (41) and (42) can be converted to 2-aminobenzimidazole derivatives of Formula (I) by a ring forming reaction that occurs under the influence of iodoacetic acid and heating in a suitable solvent (such as methanol or acetonitrile). The cyclisation of (41) and (42) to afford derivatives of Formula (I) can also occur under the influence of mercury salts (e.g. mercuric oxide) with heating in a suitable solvent (e.g. acetonitrile, methanol). The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

The skilled person will understand that it may be necessary to adjust or change the order of steps in the processes described above, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldiphenylsilyl or trimethylsilyl), AcO(acetoxy), 2,2-dimethylpropanoate, TBS(t-butyldimethylsilyl), TMS(trimethylsilyl), PMB (β-methoxybenzyl), and tetrahydropyranyl. Suitable proteting groups for carboxylic acid include ($C_1$-$C_6$)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)$NH_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The compound of formula (I) have at least one asymmetric center, and may have further asymmetric centres and it is intended that any optical isomers (i.e. enantiomers or diastereomers), in the form of separated, pure or partially purified optical isomers and any mixtures thereof including racemic mixtures, i.e. a mixture of stereoisomeres, are included within the scope of the invention. In particular, the carbon atom of formula (I) wherein the 4 valence bonds are linked to R7, R8, NH, phenyl and is an asymmetric center giving rise to two optical isomers, an R form and an S form. In one embodiment, the compounds of the present invention have the S form. In another embodiment, the compounds of the present invention have the R form. In a further embodiment, the compounds of the present invention are a racemic mixture.

In this context it is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, the compound of the general formula I of the present invention has a benzimidazole structure which exists in tautomeric forms, and as used herein all tautomers are comprised by the compound of formula I although only one is shown.

Tautomers of formula (I) are:

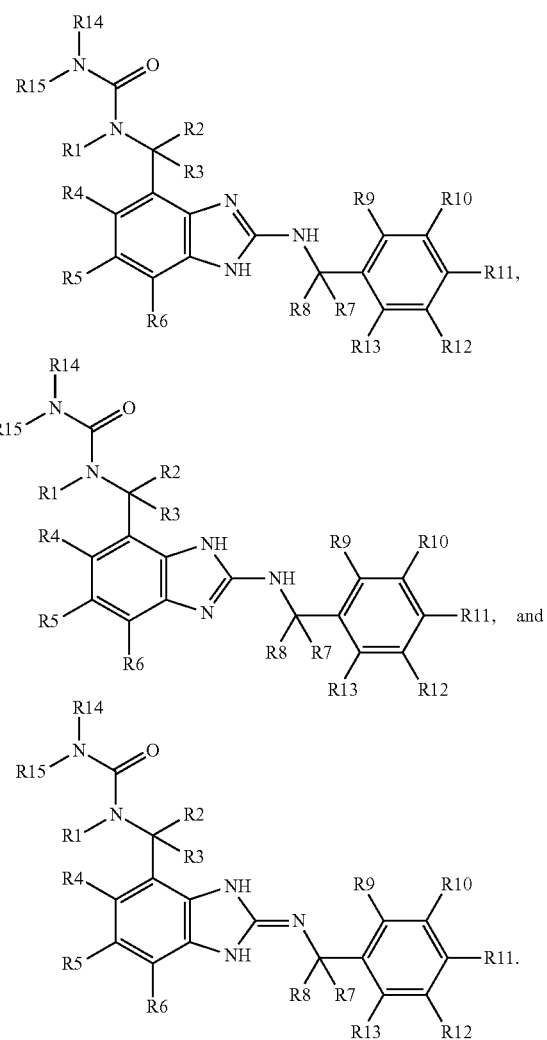

The benzimidazole tautomers of formula I above means that the hydrogen switches back and forth from one nitrogen to the other and that the double bond consequently switches back and forth between the nitrogen and carbon attachment point to the NHgroup. Further, when a structure is presented with a benzimidazole either as part of a general structure or as individual specified compounds it is to be understood as the benzimidazole covers all tautomers, thus although only one tautomer is shown it includes all.

Whenever a "compound of formula (I)" is used herein it means the compound of formula (I) in any form include the free form or as a salt thereof, such as a pharmaceutically acceptable salt thereof, unless otherwise indicated herein or clearly contradicted by context.

Whenever substituents are disclosed as R1-R15 it means that each and every consecutive possibility is disclosed, for instance R2-R4 means R2, R3 and R4, and e.g. R9-R13 means R9, R10, R11, R12 and R13. In a still further embodiment the compound I is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "free form" as used herein means a compound of formula (I) which is a free base or free acid, as the case may be, and which is not in any salt form.

The term "$C_{1-x}$ alkyl" as used herein means an alkyl group containing 1 to x carbon atoms, e.g. $C_{1-3}$, $C_{1-4}$, $C_{1-5}$ or $C_{1-6}$, such as methyl, ethyl, propyl, butyl, pentyl or hexyl, and also includes branched $C_{3-6}$ alkyl, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl. When Cl-x alkyl, such as $C_{1-6}$alkyl, is substituted with a group, such as halogen, such as a F, it means that such F, e.g. 3 F are attached to one carbon ($CF_3$) or two carbons ($CF_2$—CF) or even three carbons (CF—CF—CF).

The term "$C_{1-x}$ alkylene" as used herein means an alkylene group containing 1 to x carbon atoms, e.g. $C_{1-3}$, $C_{1-4}$, $C_{1-5}$ or $C_{1-6}$, such as methylene, ethylene, propylene, butylene, pentylene or hexylene, and also includes branched $C_{3-6}$ alkylene, such as isopropylene, isobutylene, tert-butylene, isopentylene, 3-methylbutylene, 2,2-dimethylpropylene, n-hexylene, 2-methylpentylene, 2,2-dimethylbutylene, 2,3-dimethylbutylene.

The term "Cl-x alkoxy" or "O—$C_{1-x}$ alkyl" (used interchangeable) as used herein means one oxygen atom covalently linked to an alkyl group containing 1 to x carbon atoms, e.g. $C_{1-5}$ or $C_{1-6}$, such as methoxy, ethoxy, n-propoxy, iso-propoxy, n-butyloxy, n-pentyloxy, or n-hexyloxy.

The term "$C_{1-x}$ alkylthio" or "S—$C_{1-x}$ alkyl" (used interchangeable) as used herein means one sulphur atom covalently linked to an alkyl group containing 1 to x carbon atoms, e.g. $C_{1-5}$ or $C_{1-6}$, such as methylthio, ethylthio, n-propylthio.

The term "$C_{3-4}$ cycloalkyl" as used herein means a cyclic alkyl group containing 3-4 carbon atoms, such as cyclopropyl or cyclobutyl.

The term "CN" as used herein means a cyano or nitril (C and N linked by triple bond).

The term "$C_{1-6}$ alkyl substituted with at least one halogen" as used herein means one or more halogen atoms as defined herein linked to one or more carbon atoms of the $C_{1-6}$ alkyl as defined herein, such as $CHFCF_3$ or $CF_3$.

The term "$C_{1-6}$ alkoxy substituted with at least one halogen" as used herein means one or more halogen atoms as defined herein linked to one or more carbon atoms of the $C_{1-6}$ alkoxy as defined herein, such as $OCH_2CHF_2$ or $OCF_3$.

The term "$C_{1-4}$ alkyl substituted with one OH" as used herein means one OH groups linked via the oxygen to one or more carbon atoms of the $C_{1-4}$ alkyl as defined herein, such as $CH_2OH$, $CH_2CH_2OH$, or $CHOHCH_3$.

The term "$C_{1-4}$ alkyl substituted with one $OC_{1-3}$ alkyl" as used herein means one or more $OC_{1-3}$ alkyl groups linked via the oxygen to one or more carbon atoms of the $C_{1-4}$ alkyl as defined herein, such as $CH_2OCH_3$, or $CH_2CH_2OCH_3$.

The term "halogen" as used herein means an atom selected from Chloro (Cl), Flouro (F), Iodo (I) and Bromo (Br).

The term "a 5 or 6-membered aromatic heterocycle comprising at least one nitrogen atom and optionally 1 oxygen atom and optionally 1 sulphur atom" as used herein means a chemically stable mono aromatic ring system containing at least one nitrogen, and preferably from 1 to 3 N, and no more than 5 carbon atoms, 1 oxygen atom may be included and/or 1 sulphur atom, such as including but not limited to pyrrolyl, imidazolyl, pyrazolyl, oxazolyl, isoxazolyl, thiazolyl, isothiazolyl, triazolyl, furazanyl, oxadiazolyl, thiadiazolyl, tetrazolyl, pyrimidinyl, pyridinyl, diazinyl, pyridazinyl, triazinyl, and tetrazinyl.

The term "a 4-6 membered non-aromatic heterocycle containing 1-2 nitrogen atoms, optionally 1 oxygen atom, and optionally 1 sulphur atom" as used herein means a monocyclic ring system with 1 or 2 nitrogen atoms and optionally 1 oxygen and optionally one sulphur atom forming a saturated or unsaturated 4, 5 or 6-membered ring system, such as azetidinyl, pyrrolidinyl, piperidinyl, piperazinyl, morpholinyl, thiomorpholinyl, pyrazolidinyl, isothiazolidinyl and isoxazolidinyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a pharmaceutically acceptable salt" as used herein is used to specify that the salt is suitable for use in the human or animal body. An example list of pharmaceutically acceptable salts can be found in the Handbook of Pharmaceutical Salts: Properties, Selection and Use, P. H. Stahl and C. G. Wermuth, editors, Weinheim/Zurich:Wiley-VCH/VHCA, 2002. A pharmaceutically acceptable salt of a compound of Formula (I) includes such salts that may be formed within the human or animal body after administration of said compound to said human or animal body.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient. Typically, the present invention relates to a pharmaceutical composition comprising the compound of formula (I) and a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures Automated Patch Clamping Automated whole cell patch-clamp recordings were performed using a QPatch 16 HT system and single-hole Qplates (Biolin Scientific, Sophion, Denmark) on HEK-293 cells stably expressing the human SK3 channel (hK$_{Ca}$2.3). Cells were cultured and prepared for experiments using normal cell culturing procedures. A total of 4-5 million cells were used per experiment. The Qpatch automatically generates giga sealing, whole-cell formation, compound application and recording of current. hK$_{Ca}$2.3 currents were recorded in symmetrical K$^+$ solutions, with an intracellular solution consisting of in mM: KCl 108; KOH/EGTA (ethylene glycol-bis(2-aminoethylether)-N,N,N',N'-tetraacetic acid) 31.25/10; CaCl$_2$) 8.1; MgCl$_2$ 1.2; HEPES (2-[4-(2-hydroxyethyl)piperazin-1-yl]ethanesulfonic acid) 10; KOH 15, pH adjusted to pH=7.2 with HCl. The free calcium concentration was calculated to 400 nM. The extracellular solution consisted of in mM: KCl 150; CaCl$_2$) 0.1; MgCl$_2$ 3; HEPES 10; Glucose 10, pH=7.4 with KOH. The cells were held at 0 mV and hK$_{Ca}$2.3 currents were elicited by a linear voltage ramp from −80 mV to +80 mV (200 ms in duration) applied every 5th second. The compound application protocol consisted of 12 recording periods lasting from 50-200 s: 1) Baseline recordings in extracellular solution; 2) Application of the positive control N-methyl bicuculline (100 µM), which is characterized by full efficacy, fast on- and off-rate; 3-4) Wash-out; 5-9) Increasing concentrations of test compound to establish an IC50 value; 10-11) Wash-out; 12) positive control with compound NS8593 (N-[(1R)-1,2,3,4-tetrahydro-1-naphthalenyl]-1H-benzimidazol-2-amine) (1 µM). Data were sampled at 10 kHz, 4th order Bessel filter, cut-off frequency 3 kHz. Currents were compensated for run-down. Potency was quantified as the concentration needed to inhibit half of the SK channel activity and reported as an IC50 value. All effects of compounds of the present invention as tested were normalized to the observed inhibitory effect of N-methyl bicuculline.

Results

The examples described are potent inhibitors of the SK3 channel and have shown the following IC50 in the Automated patch clamping assay described above: Examples: 1, 1b, 2, 2a, 2b, 3, 3a, 3b, 4, 4a, 4b, 5, 5a, 5b, 6, 6a, 6b, 7, 7a, 7b, 8, 8a, 8b, 9, 9b, 10, 10a, 10b, 11, 11a, 12, 12a, 12b, 13, 13a, 13b, 14, 14a, 14b, 15, 15a, 15b, 16, 16a, 16b, 17, 17a, 18, 18a, 18b, 19, 19a, 20, 20a and 21b all have an IC50 below 1 □M.
Examples: 1a, 9a, 11b, 17b, 19b, 20b, 21 and 21a all have an IC50 below 3 QM.

Materials and Methods

Commercial reagents were used without further purification unless otherwise stated. Analytical TLC was performed on silica gel 60-F254 (Merck) with detection by fluorescence and by immersion in a KMnO$_4$ solution [KMnO$_4$ solution recipe: Dissolve 1.5 g KMnO$_4$, 10 g K2CO3, and 1.25 mL 10% NaOH in 200 mL of water] followed by charring. Purification of compound was carried out by column chromatography on silica gel (60-120 mesh, Swambe Chemicals, India). NMR spectra such as $^1$H, $^{13}$C and 2D COSY were recorded with Bruker AV 400 MHz spectrometer (400 MHz for $^1$H, 100 MHz for $^{13}$C) at ambient temperature by using deuterated DMSO-d6, CDCl$_3$, CD$_3$CO$_2$D (AcOH-d4) or CD$_3$OD as a solvent for NMR. Chemical shifts are reported in δ parts per million (ppm). ESI-MS was recorded on Agilent LC1200 series MS single quadrupole 6130 mass spectrometer.

Abbreviations Used in Experimental Section:

BOP=(Benzotriazol-1-yloxy)tris(dimethylamino)phosphonium hexafluorophosphate

PyBOP=(Benzotriazol-1-yloxy)tripyrrolidinophosphonium hexafluorophosphate

EDC.HCl=N-(3-Dimethylaminopropyl)-N'-ethylcarbodiimide hydrochloride

HBTU=N,N,N',N'-Tetramethyl-O(1H-benzotriazol-1-yl) uronium hexafluorophosphate.

DCM=Dichloromethane; DMF=N,N-Dimethylformamide; TEA=Triethylamine

TFA=Trifluoroacetic acid; Boc-anhydride=Di-tert-butyl dicarbonate; Boc=Di-tert-butyl; Piv=2,2-dimethylpropanoate; THF=Tetrahydrofuran; t-BuOH=2-Methylpropan-2-ol; DEA=Diethylamine; DIEA=Ethylbis(propan-2-yl)amine; IPA=Propan-2-ol; Pd/C=Palladium on Carbon; RT=Ambient Temperature; MeOH=Methanol.

Grace Flash Chromatography System:

The Grace REVELERIS® Prep Purification System was used to perform sample purification by flash chromatography, using Flash Cartridges pre-packed with silica: Columns Used:

Hi-Purit Flash Columns Silica (Normal Phase);

12 g, 60 A, max pressure 350 psi (24 bar), 24 g, 60 A, max pressure 350 psi (24 bar), 40 g, 60 A, max pressure 350 psi (24 bar), 80 g, 60 A, max pressure 350 psi (24 bar).

Solvents: Hexane, EtOAc, CHCl3 and MeOH.

Example 1: Preparation of 1-((2-((1-hydroxy-2-(3-(trifluoromethyl) phenyl) propan-2-yl) amino)-1H-benzo[d]imidazol-4-yl) methyl)-3-methylurea

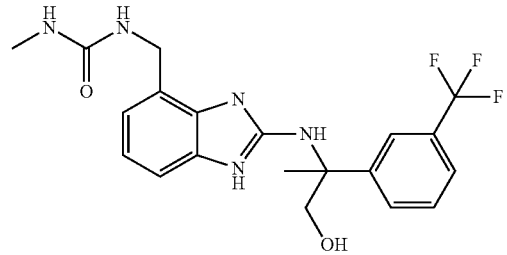 [SMILES: CNC(=O)NCc1cccc2nc(NC(C)(CO)c3cccc(C(F)(F)F)c3)[nH]c12]

Example 1, Step 1: Preparation of 5-methyl-5-(3-(trifluoromethyl) phenyl) imidazolidine-2,4-dione

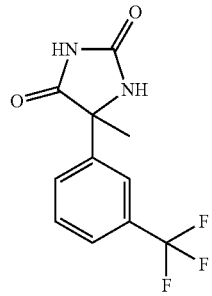 [SMILES: CC1(c2cccc(C(F)(F)F)c2)NC(=O)NC1=O]

To a stirred solution of 3-trifluoromethyl acetophenone (commercially available) (45.00 g, 239.00 mmol) in a mixture of solvents ethanol/water (1: 1, 1000 mL) was added ammonium carbonate (115.00 g, 1200.00 mmol) followed by potassium cyanide (18.70 g, 287.00 mmol) and the mixture was stirred at 60° C. for 16 h. The reaction mass was poured into ice-cold water (1500 mL) and it was stirred for 30 min. The solid formed was filtered off and dried to afford 5-methyl-5-(3-(trifluoromethyl) phenyl) imidazolidine-2,4-dione (61.00 g) as an off-white solid, it was used in the next step without further any purification.

$^1$H NMR (400 MHz, DMSO-$d_6$: $D_2O$) δ 7.78 (d, 1H, J=7.70 Hz), 7.72 (d, 2H, J=8.90 Hz), 7.65 (t, 1H, J=7.70 Hz), 1.69 (s, 3H); MS: m/z 259 (M+1).

Example 1, Step 2: Preparation of 2-amino-2-(3-(trifluoromethyl) phenyl) propanoic acid

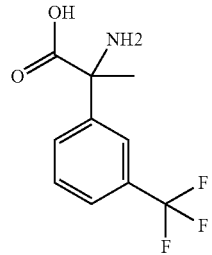 [SMILES: CC(N)(C(=O)O)c1cccc(C(F)(F)F)c1]

5-methyl-5-(3-(trifluoromethyl) phenyl) imidazolidine-2,4-dione (from Example 1, Step 1) (110.00 g, 426.00 mmol) was added to 10% aqueous sodium hydroxide solution (600 mL) and the mixture was refluxed for 48 h. The reaction mixture was neutralized (adjusted pH=7) with 6.0 N HCl (250 mL), the solid that formed was filtered and dried to afford 2-amino-2-(3-(trifluoromethyl) phenyl) propanoic acid (100.00 g) as a white solid, which was used in the next step without further any purification.

$^1$H NMR (400 MHz, DMSO-$d_6$: $D_2O$) δ 7.85 (s, 1H), 7.79 (d, 1H, J=8.00 Hz), 7.65 (d, 1H, J=7.60 Hz), 7.60 (t, 1H, J=7.60 Hz), 1.68 (s, 3H); MS: m/z 234.1 (M+1).

Example 1, Step 3: Preparation of 2-((tert-butoxycarbonyl) amino)-2-(3-(trifluoromethyl) phenyl) propanoic acid

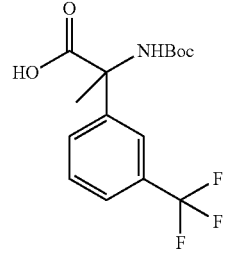 [SMILES: CC(C)(C)OC(=O)NC(C)(C(=O)O)c1cccc(C(F)(F)F)c1]

To a suspension of 2-amino-2-(3-(trifluoromethyl) phenyl) propanoic acid (from Example 1, Step 2) (100.00 g, 429.00 mmol) in a mixture of tetrahydrofuran:water (1: 1, 1400 mL) was added sodium bicarbonate (216.00 g, 2570.00 mmol) followed by di-tert-butyl dicarbonate (148.00 mL, d=0.95 g/cm$^3$, 643.00 mmol) and the whole mixture was stirred at ambient temperature for 72 h. The reaction mixture was diluted with water (1000 mL) and extracted with ethyl acetate (4×2000 mL). The combined organic layer was dried over sodium sulphate, filtered and concentrated to afford 2-((tert-butoxycarbonyl) amino)-2-(3-(trifluoromethyl) phenyl) propanoic acid (140.00 g) as a yellowish gum, which was used in the next step without further any purification.

$^1$H NMR (400 MHz, DMSO-$d_6$: $D_2O$) δ 7.64 (s, 1H), 7.57 (s, 1H), 7.47 (d, 2H, J=4.40 Hz), 1.47 (s, 3H), 1.35 (s, 9H); MS: m/z 234.1 [(M+1)-Boc].

Example 1, Step 4: Preparation of tert-butyl N-{1-hydroxy-2-[3-(trifluoromethyl)phenyl]propan-2-yl}carbamate

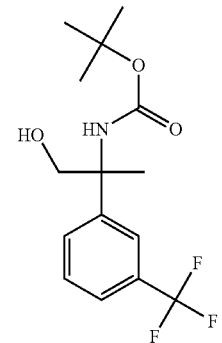 [SMILES: CC(C)(C)OC(=O)NC(C)(CO)c1cccc(C(F)(F)F)c1]

To a solution of 2-((tert-butoxycarbonyl) amino)-2-(3-(trifluoromethyl) phenyl) propanoic acid (from Example 1, Step 3) (140.00 g, 378.00 mmol) in dry tetrahydrofuran (1000 mL) was added triethyl amine (158.00 mL, d=0.726 g/cm$^3$, 1130.00 mmol) followed by isobutyl chloroformate (68.80 mL, d=1.053 g/cm$^3$, 529.00 mmol) at 0° C. and stirred at same temperature for 4 h. The solid that formed was filtered off at 0° C. and the residue was washed with dry tetrahydrofuran (400 mL). The combined filtrate was added to a cooled mixture of sodium borohydride (85.80 g, 2270.00 mmol) in water (200 mL). The reaction mass was slowly warmed to ambient temperature and stirred for 30 h. The reaction mass was quenched with ice cold water (1000 mL), extracted with ethyl acetate (4×2000 mL), and the combined organic layer was washed with brine (250 mL), dried over sodium sulphate, filtered and concentrated to afford crude (200 g) of a yellowish liquid. The liquid was purified by flash chromatography using 60-120 silica gel and the product was eluted with 30-35% ethyl acetate in petroleum ether to afford tert-butyl N-{1-hydroxy-2-[3-(trifluoromethyl)phenyl]propan-2-yl}carbamate (63.00 g) as a colorless liquid.

$^1$H NMR (400 MHz, DMSO-$d_6$) δ 7.61 (t, 2H, J=6.80 Hz), 7.57 (s, 1H), 7.53 (t, 1H, J=7.20 Hz), 6.92 (bs, 1H), 4.98 (t, 1H, J=5.20 Hz), 3.50 (d, 2H, J=6.00 Hz), 1.59 (s, 3H), 1.35 (s, 9H);

MS: m/z 221.2 [(M+1)-Boc].

Example 1, Step 5: Preparation of 2-{[(tert-butoxy)carbonyl]amino}-2-[3-(trifluoromethyl)phenyl]propyl 2,2-dimethylpropanoate

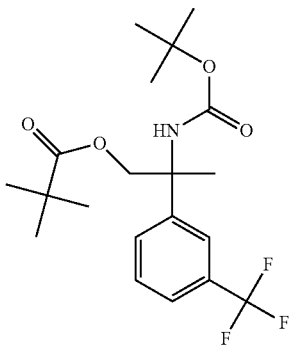 [SMILES: CC(C)(C)OC(=O)NC(C)(COC(=O)C(C)(C)C)c1cccc(C(F)(F)F)c1]

To a solution of tert-butyl N-[2-hydroxy-1-methyl-1-[3-(trifluoromethyl) phenyl]ethyl] carbamate (from Example 1, Step 4) (63.00 g, 197.00 mmol) in dry dichloromethane (800 mL) under nitrogen atmosphere was added triethyl amine (96.2 mL, d=0.726 g/cm$^3$, 691.00 mmol) followed by pivaloyl chloride (36.40 mL, d=0.985 g/cm$^3$, 296.00 mmol) at 0° C. dropwise and the whole reaction mixture was stirred at ambient temperature for 36 h. The reaction mixture was quenched with ice cold water (500 mL) and extracted with dichloromethane (4×1000 mL). The combined organic layer was dried over sodium sulphate, filtered and concentrated to afford a brown liquid (110.00 g), which was purified by flash chromatography using 60-120 silica gel and the product eluted with 20% ethyl acetate in hexane to afford 2-{[(tert-butoxy)carbonyl]amino}-2-[3-(trifluoromethyl)phenyl]propyl2,2-dimethylpropanoate (70.00 g) as a yellowish liquid.

$^1$H NMR (400 MHz, DMSO-$d_6$: $D_2O$) δ 7.61 (d, 2H, J=6.80 Hz), 7.55 (t, 1H, J=7.60 Hz), 7.51 (s, 1H), 4.26 (q, 2H, J=10.40 Hz), 1.52 (s, 3H), 1.35 (s, 9H), 1.05 (s, 9H);

MS: m/z 305.2 [(M+1)-Boc].

Example 1, Step 6: Preparation of 2-amino-2-[3-(trifluoromethyl)phenyl]propyl 2,2-dimethylpropanoate hydrochloride

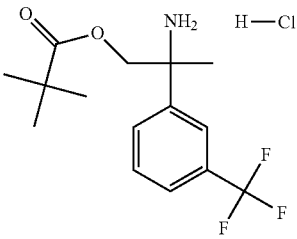

To a solution of 2-{[(tert-butoxy)carbonyl]amino}-2-[3-(trifluoromethyl)phenyl]propyl 2,2-dimethylpropanoate (from Example 1, Step 5) (70.00 g, 174.00 mmol) in dry dichloromethane (700 mL) under nitrogen atmosphere was added 4M HCl in dioxane solution (127.00 mL, 521.00 mmol) dropwise at 0° C. and the reaction mixture was stirred at ambient temperature for 16 h. The reaction mixture was concentrated under high vacuum to afford 2-amino-2-[3-(trifluoromethyl)phenyl]propyl 2,2-dimethylpropanoate hydrochloride (60.00 g) as a yellowish gum, which was used in the next step without further any purification.

$^1$H NMR (400 MHz, DMSO-$d_6$: $D_2O$) δ 7.88 (s, 1H), 7.84 (d, 1H, J=8.00 Hz), 7.79 (d, 11H, J=7.60 Hz), 7.71 (t, 11H, J=7.60 Hz), 4.49 (d, 11H, J=12.00 Hz), 4.27 (d, 11H, J=12.00 Hz), 1.72 (s, 3H), 1.01 (s, 9H);

MS: m/z 304.1 [(M+1)–HCl].

Example 1, Step 7: Preparation of 2-isothiocyanato-2-[3-(trifluoromethyl)phenyl]propyl 2,2-dimethylpropanoate

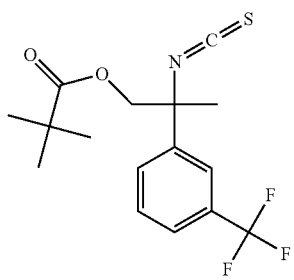 [SMILES: CC(C)(C)C(=O)OCC(C)(N=C=S)c1cccc(C(F)(F)F)c1]

To a solution of 2-amino-2-[3-(trifluoromethyl)phenyl] propyl 2,2-dimethylpropanoate hydrochloride (from Example 1, Step 6) (40.00 g, 118.00 mmol) in dry dichloromethane (500 mL) was added 10% aq. sodium bicarbonate solution (500 mL) at 0° C. After 15 min, thiophosgene (14.40 mL, d=1.5 g/cm$^3$, 188.00 mmol) was added and allowed to stir at same temperature for 1 h. The reaction mass was extracted with dichloromethane (3×1000 mL) and the combined organic layer was dried over anhydrous sodium sulphate, filtered and concentrated to afford a yellow liquid (75.00 g), which was purified by column chromatography using 60-120 mesh silica gel and 5% ethyl acetate in hexane as eluent to afford 2-isothiocyanato-2-[3-(trifluoromethyl)phenyl]propyl 2,2-dimethylpropanoate (44.00 g) as a yellow liquid.

¹H NMR (400 MHz, DMSO-d₆) δ 7.85 (s, 1H), 7.81 (d, 1H, J=7.20 Hz), 7.76 (d, 1H, J=7.60 Hz), 7.69 (t, 1H, J=8.40 Hz), 4.51 (q, 2H, J=15.20 Hz), 1.83 (s, 3H), 1.35 (s, 9H); MS: m/z 344.0 (M-1).

Example 1, Step 8: Preparation of 4-methylbenzo[c] [1, 2,5] thiadiazole

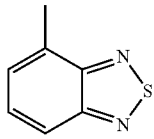

To a solution of 3-methylbenzene-1,2-diamine (commercially available) (330.00 g, 2700.00 mmol) in dry pyridine (1800 mL) was added thionyl chloride (500.00 mL, d=1.64 g/cm³, 6750.00 mmol) dropwise over a period of 60 min at 0° C. During this addition the internal temperature was kept below 45° C. and then the reaction mass was stirred at ambient temperature for 3 h. The reaction mixture was quenched with conc. hydrochloric acid (1300 mL) by dropwise addition until the pH of the reaction adjusted to 2-3, during this stage internal temperature was kept below 65° C. The reaction mass was diluted with water (1500 mL) and ethyl acetate (2000 mL) and stirred for 2 h. Then it was filtered through a celite bed and the organic layer was separated and then the aqueous layer was extracted further with ethyl acetate (3×1500 mL). The combined organic layer was washed with brine solution (300 mL), dried over sodium sulphate, filtered and concentrated to afford 4-methylbenzo[c] [1,2,5] thiadiazole (380.00 g) as a brown liquid, which was used in the next step without any further purification.

¹H NMR (400 MHz, DMSO-d₆) δ 7.90 (d, 1H, J=8.80 Hz), 7.61 (t, 1H, J=8.80 Hz), 7.51 (d, 1H, J=6.80 Hz), 2.69 (s, 3H);
MS: m/z 151.2 (M+1).

Example 1, Step 9: Preparation of 4(bromomethyl) benzo[c] [1, 2, 5] thiadiazole

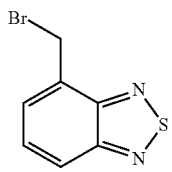

To a stirred solution of 4-methylbenzo[c] [1,2,5] thiadiazole (from Example 1, Step 8) (100.00 g, 666.00 mmol) under nitrogen atmosphere in dry chloroform (1200 mL) was added benzoyl peroxide (3.23 g, 13.30 mmol) followed by N-bromosuccinimide (118.00 g, 666.00 mmol) and the reaction mixture was refluxed for 28 h. The reaction mass was cooled and the succinimide precipitate was removed by filtration. The filtrate was concentrated to afford a brown semi solid (170.00 g) which was taken in methanol (1000 mL) and stirred for 30 min. The solid was filtered, dried under high-vacuum to afford 4-(bromomethyl) benzo[c] [1, 2,5] thiadiazole (110.00 g) as a yellow solid, which was used in the next step without further purification.

¹H NMR (400 MHz, DMSO-d₆) δ 8.09 (d, 1H, J=8.60 Hz), 7.87 (d, 1H, J=8.80 Hz), 7.71 (t, 1H, J=8.40 Hz), 5.13 (s, 2H);
MS: Molecular ion not observed.

Example 1, Step 10: Preparation of tert-butyl N-[(2,1,3-benzothiadiazol-4-yl)methyl]-N-[(tert-butoxy)carbonyl]carbamate

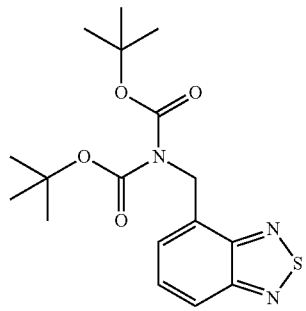 [SMILES: CC(C)(C)OC(=O)N(Cc1cccc2nsnc12)C(=O)OC(C)(C)C]

To a solution of 4-(bromomethyl) benzo[c] [1,2,5] thiadiazole (from Example 1, Step 9) (300.00 g, 1310.00 mmol) under nitrogen atmosphere in dry tetrahydrofuran (2500 mL) was added potassium carbonate (543.00 g, 3930.00 mmol) followed by tert-butyl N-tert-butoxycarbonyl carbamate (427.00 g, 1960 mmol) and the mixture was stirred at 70° C. for 48 h. The reaction mass was filtered to remove the inorganic solids and the filtrate was concentrated. The residue was dissolved in water (1500 mL) and then it was extracted with ethyl acetate (5×3000 mL). The combined organic layer was washed with brine, dried over sodium sulphate, filtered and concentrated to afford tert-butyl N-[(2,1,3-benzothiadiazol-4-yl)methyl]-N-[(tert-butoxy)carbonyl] carbamate (350.00 g) as an off-white solid, which was used in the next step without further purification.

¹H NMR (400 MHz, DMSO-d₆) δ 7.99 (d, 1H, J=8.80 Hz), 7.31 (t, 1H, J=8.00 Hz), 7.34 (d, 1H, J=6.80 Hz), 5.21 (s, 2H), 1.39 (s, 18H);
MS: m/z 166.2 [(M+1)-2xBoc].

Example 1, Step 11: Preparation of 2,1,3-benzothiadiazol-4-ylmethanamine hydrochloride

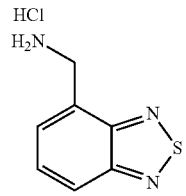

To a solution of tert-butyl N-[(2,1,3-benzothiadiazol-4-yl)methyl]-N-[(tert-butoxy)carbonyl]carbamate (from Example 1, Step 10) (650.00 g, 1780.00 mmol) in dichloromethane (2400 mL) was added 4 M hydrochloric acid in 1,4 dioxane (2223.00 mL, 8890.00 mmol) at 0° C. and stirred at ambient temperature for 75 h. The reaction mass was concentrated under reduced pressure to afford a yellow solid (370.00 g), which was triturated with hexane (2×1000 mL), filtered and dried to afford 2,1,3-benzothiadiazol-4- ylmethanamine hydrochloride (340.00 g) as a white solid, which was used in the next step without further purification.

¹H NMR (400 MHz, DMSO-d₆) δ 8.94 (bs, 3H), 8.10 (d, 1H, J=8.80 Hz), 7.91 (t, 1H, J=6.40 Hz), 7.79 (d, 1H, J=6.80 Hz), 4.52 (s, 2H);

MS: m/z 166.1 [(M+1)–HCl].

Example 1, Step 12: Preparation of 1-(benzo[c] [1, 2, 5] thiadiazol-4-ylmethyl)-3-methylurea

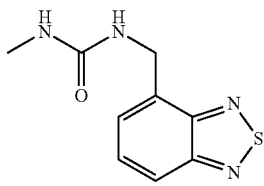

To a solution of 2,1,3-benzothiadiazol-4-ylmethanamine hydrochloride (from Example 1, Step 11) (6.00 g, 29.80 mmol) under nitrogen atmosphere in dry dichloromethane (100 mL) was added triethylamine (12.40 mL, d: 0.726 g/cm³, 89.30 mmol) followed by N-methylcarbamoyl chloride (4.17 g, 44.60 mmol) at 0° C. and then stirred at room temperature for 1 h. The reaction mass was quenched with ice cold water (75 mL) and the aqueous layer was extracted with dichloromethane (4×500 mL). The combined organic layer was dried over sodium sulphate, filtered and concentrated to afford 1-(benzo[c] [1, 2, 5] thiadiazol-4-ylmethyl)-3-methylurea (4.20 g) as a yellow gum, which was used in the next step without further purification.

¹H NMR (400 MHz, DMSO-d₆: D₂O) δ 7.94 (d, 1H, J=8.80 Hz), 7.68 (t, 1H, J=7.84 Hz), 7.47 (d, 1H, J=6.84 Hz), 4.68 (s, 2H), 2.57 (s, 3H);

MS: m/z 223.0 (M+1).

Example 1, Step 13: Preparation of 1-(2, 3-diaminobenzyl)-3-methylurea

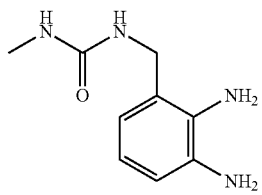

To a de-gassed solution of 1-(benzo[c] [1, 2, 5] thiadiazol-4-ylmethyl)-3-methylurea (from Example 1, Step 12) (5.00 g, 22.00 mmol) in dry methanol (150 mL) was added Raney nickel (10.00 g, 200% w/w, pre-washed five times with dry methanol) and the resultant reaction mixture was stirred under a hydrogen atmosphere at bladder pressure (Approx. 1.5 kg/cm²) at ambient temperature for 24 h. The reaction mixture was filtered through a celite bed and the bed was washed with methanol (3×1000 mL). The combined filtrates were concentrated to afford 1-(2, 3-diaminobenzyl)-3-methylurea (3.50 g) as a brown solid, which used in the next step without further purification.

¹H NMR (400 MHz, DMSO-d₆: D₂O) δ 6.48 (d, 1H, J=7.20 Hz), 6.37 (t, 1H, J=7.20 Hz), 6.32 (d, 1H, J=7.32 Hz), 4.03 (s, 2H), 2.54 (s, 3H);

MS: m/z 195.1 (M+1).

Example 1, Step 14: Preparation of 2-{[(2-amino-6-{[(methylcarbamoyl)amino]methyl}phenyl)carbamothioyl]amino}-2-[3-(trifluoromethyl)phenyl]propyl 2,2-dimethylpropanoate and 2-{[(2-amino-3-{[(methylcarbamoyl)amino]methyl}phenyl)carbamothioyl]amino}-2-[3-(trifluoromethyl)phenyl]propyl 2,2-dimethylpropanoate (mixture of regio isomers)

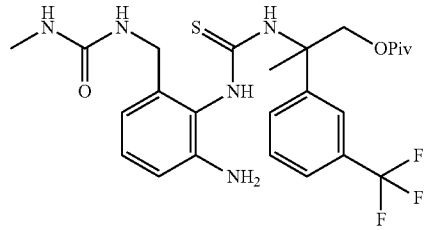

AND

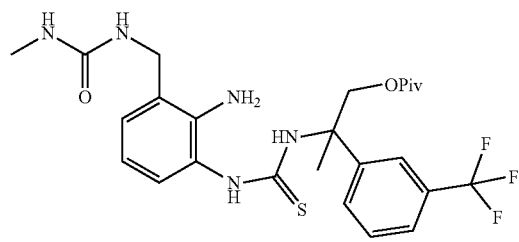

To a solution 1-(2, 3-diaminobenzyl)-3-methylurea (from Example 1, Step 13) (7.00 g, 36.00 mmol) in a mixture of solvents acetonitrile:methanol (4:1, 120 mL) was added 2-isothiocyanato-2-[3-(trifluoromethyl)phenyl]propyl 2,2-dimethylpropanoate (from Example 1, Step 7) (14.33 g, 43.00 mmol) and the mixture was stirred at ambient temperature for 16 h. The reaction mass was concentrated to afford a brown gum (20.00 g). This was purified by flash column chromatography using 230-300 silica gel and the product was eluted with 40-45% ethyl acetate in hexane to afford 2-{[(2-amino-6-{[(methylcarbamoyl)amino]methyl}phenyl)carbamothioyl]amino}-2-[3-(trifluoromethyl)phenyl]propyl 2,2-dimethylpropanoate and 2-{[(2-amino-3-{[(methylcarbamoyl)amino]methyl}phenyl)carbamothioyl]amino}-2-[3-(trifluoromethyl)phenyl]propyl 2,2-dimethylpropanoate (as a mixture of regio isomers) (16.00 g) as a brown solid, which was used in the next step without further purification.

MS: m/z 540.1 (M+1).

Example 1, Step 15: Preparation of 2-[(4-{[(methylcarbamoyl)amino]methyl}-1H-1,3-benzodiazol-2-yl)amino]-2-[3-(trifluoromethyl)phenyl]propyl 2,2-dimethylpropanoate

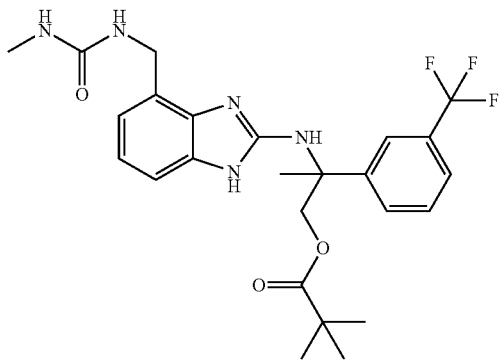

To a solution of 2-{[(2-amino-6-{[(methylcarbamoyl)amino]methyl}phenyl)carbamothioyl]amino}-2-[3-(trifluoromethyl)phenyl]propyl 2,2-dimethylpropanoate and 2-{[(2-amino-3-{[(methylcarbamoyl)amino]methyl}phenyl)carbamothioyl]amino}-2-[3-(trifluoromethyl)phenyl]propyl 2,2-dimethylpropanoate (as a mixture of regio isomers) (from Example 1, Step 14) (16.00 g, 30.00 mmol) in methanol (160 mL) was added iodoacetic acid (6.62 g, 36.00 mmol) and the mixture was stirred at 65° C. for 2 h. The reaction mass was concentrated to remove the solvent and the residue was dissolved in 10% aqueous sodium bicarbonate solution (150 mL) and extracted with ethyl acetate (3×1000 mL). The combined organic extracts were dried over sodium sulphate, filtered and concentrated to afford a brown gum (15.00 g). It was purified by Grace chromatography using 120.00 g pre-packed flash cartridge filled with normal phase silica gel 60° A, 40-63 μm and the product eluted with 2-4% methanol in chloroform to afford 2-[(4-{[(methylcarbamoyl)amino]methyl}-1H-1,3-benzodiazol-2-yl)amino]-2-[3-(trifluoromethyl)phenyl]propyl 2,2-dimethylpropanoate (12.50 g) as a yellow solid.

$^1$H NMR (400 MHz, AcOH-d$_4$) δ 7.92 (s, 1H), 7.90 (d, 1H, J=7.60 Hz), 7.72 (d, 1H, J=8.00 Hz), 7.65 (t, 1H, J=7.60 Hz), 7.35 (d, 1H, J=8.00 Hz), 7.18 (t, 1H, J=8.00 Hz), 7.10 (d, 1H, J=7.60 Hz), 4.65 (d, 1H, J=11.60 Hz), 4.56 (d, 1H, J=11.60 Hz), 4.41 (d, 2H, J=6.80 Hz), 2.70 (s, 3H), 2.05 (s, 3H), 1.16 (s, 9H);

MS: m/z 506.2 (M+1).

Example 1: Preparation of 1-((2-((1-hydroxy-2-(3-(trifluoromethyl) phenyl) propan-2-yl) amino)-1H-benzo[d]imidazol-4-yl) methyl)-3-methylurea

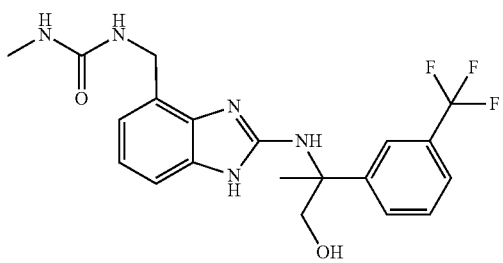 [SMILES: CNC(=O)NCc1cccc2[nH]c(NC(C)(CO)c3cccc(C(F)(F)F)c3)nc12]

To a solution of 2-[(4-{[(methylcarbamoyl)amino]methyl}-1H-1,3-benzodiazol-2-yl)amino]-2-[3-(trifluoromethyl)phenyl]propyl 2,2-dimethylpropanoate (from Example 1, Step 15) (0.130 g, 0.257 mmol) in ethanol (10 mL) was added sodium hydroxide pellets (0.031 g, 0.771 mmol) and the mixture was stirred at ambient temperature for 2 h. The reaction mass was concentrated and the residue was diluted with 10% aq. sodium bicarbonate solution (15 mL) and it was extracted with ethyl acetate (3×50 mL). The combined organic layer was dried over sodium sulphate, filtered and concentrated to afford a brown gum (0.110 g), which was purified by column chromatography on silica gel (60° A, 40-63 μm) and the product eluted with 3-5% methanol in chloroform to afford 1-((2-((1-hydroxy-2-(3-(trifluoromethyl) phenyl) propan-2-yl) amino)-1H-benzo[d]imidazol-4-yl) methyl)-3-methylurea (0.040 g) as a yellow solid.

$^1$H NMR (400 MHz, AcOH-d$_4$) δ 7.87 (s, 1H), 7.84 (d, 1H, J=8.40 Hz), 7.68 (d, 1H, J=8.00 Hz), 7.60 (t, 1H, J=8.00 Hz), 7.31 (d, 1H, J=7.20 Hz), 7.17 (t, 1H, J=7.60 Hz), 7.12 (d, 1H, J=6.80 Hz), 4.46 (q, 2H, J=15.20 Hz), 4.29 (d, 1H, J=12.00 Hz), 4.07 (d, 1H, J=12.00 Hz), 2.69 (s, 3H), 1.88 (s, 3H);

MS: m/z 422.1 (M+1).

Example 1, 15a: (+) 2-[(4-{[(methylcarbamoyl)amino]methyl}-1H-1,3-benzodiazol-2-yl)amino]-2-[3-(trifluoromethyl)phenyl]propyl 2,2-dimethylpropanoate and 15b: (−) 2-[(4-{[(methylcarbamoyl)amino]methyl}-1H-1,3-benzodiazol-2-yl)amino]-2-[3-(trifluoromethyl)phenyl]propyl 2,2-dimethylpropanoate 2-[(4-{[(methylcarbamoyl)amino]methyl}-1H-1,3-benzodiazol-2-yl)amino]-2-[3-(trifluoromethyl)phenyl]propyl 2,2-dimethylpropanoate (from Example 1, Step 15) was separated into its two enantiomers by chiral SFC chromatography using the method: Column: Chiral Pak OX—H; Flow rate: 3.0 mL/min; Co-Solvent: 20%; Co-solvent Name: 0.5% diethyl amine in isopropyl alcohol; injected Volume: 15.0 μL; outlet pressure: 100 bar; Temperature: 35° C. to obtain the two enantiomers 15a and 15b.

The (+) enantiomer 15a was the first to elute off the column.

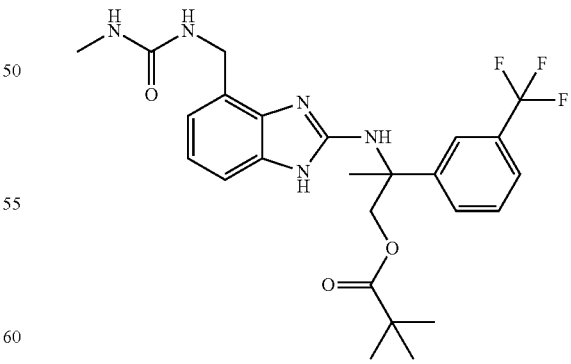

Fraction-1 was eluted first from the SFC column and it was concentrated to afford (+) 2-[(4-{[(methylcarbamoyl)amino]methyl}-1H-1,3-benzodiazol-2-yl)amino]-2-[3-(trifluoromethyl)phenyl]propyl 2,2-dimethylpropanoate (0.270 g) with 100% ee as a yellow solid.

The (−) enantiomer 15 b was the second to elute off the column.

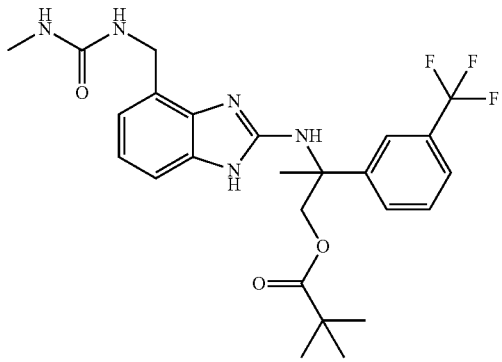

Fraction-2 was eluted second from the SFC column and it was concentrated to afford (−) 2-[(4-{[(methylcarbamoyl)amino]methyl}-1H-1,3-benzodiazol-2-yl)amino]-2-[3-(trifluoromethyl)phenyl]propyl 2,2-dimethylpropanoate (0.300 g) with 100% ee as a yellow solid.

Example 1a: Preparation of (+)-1-((2-((1-hydroxy-2-(3-(trifluoromethyl) phenyl) propan-2-yl) amino)-1H-benzo[d] imidazol-4-yl) methyl)-3-methylurea

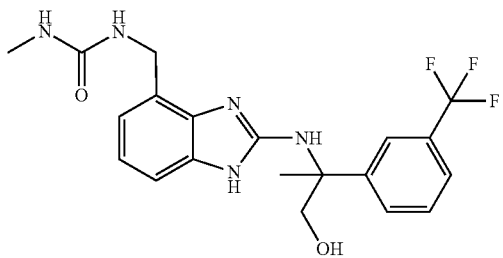 [SMILES: CNC(=O)NCc1cccc2[nH]c(NC(C)(CO)c3cccc(C(F)(F)F)c3)nc12]

To a solution of (+) 2-[(4-{[(methylcarbamoyl)amino] methyl}-1H-1,3-benzodiazol-2-yl)amino]-2-[3-(trifluoromethyl)phenyl]propyl 2,2-dimethylpropanoate (from Step 15, Compound 15a, Fraction 1) (0.300 g, 0.593 mmol) in ethanol (15 mL) was added sodium hydroxide (0.071 g, 2.00 mmol) pellets and it was stirred at ambient temperature for 2 h. The reaction mass was concentrated and the residue was diluted with water (20 mL) and extracted with ethyl acetate (3×75 mL). The combined organic layer was dried over sodium sulphate, filtered and concentrated to afford (+)-1-((2-((1-hydroxy-2-(3-(trifluoromethyl) phenyl) propan-2-yl) amino)-1H-benzo[d] imidazol-4-yl) methyl)-3-methylurea (Isomer a, 0.180 g) as a yellow solid.

$^1$H NMR (400 MHz, AcOH-d$_4$): S 7.86 (s, 1H), 7.83 (d, 1H, J=8.00 Hz), 7.67 (d, 1H, J=7.76 Hz), 7.59 (t, 1H, J=7.76 Hz), 7.30 (d, 1H, J=7.76 Hz), 7.17 (t, 1H, J=7.80 Hz), 7.11 (d, 1H, J=7.36 Hz), 4.45 (q, 2H, J=15.24 Hz), 4.28 (d, 1H, J=12.00 Hz), 4.06 (d, 1H, J=11.96 Hz), 2.68 (s, 3H), 1.87 (s, 3H);

MS: m/z 422.2 (M+1);

[α] D $^{22.3}$ (+) 12.00 (MeOH, c=0.1).

Example 1b: Preparation of (−)-1-((2-((1-hydroxy-2-(3-(trifluoromethyl) phenyl) propan-2-yl) amino)-1H-benzo[d] imidazol-4-yl) methyl)-3-methylurea

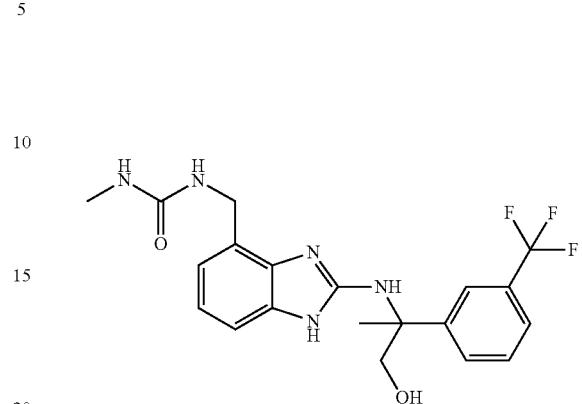

To a solution of (−) 2-[(4-{[(methylcarbamoyl)amino] methyl}-1H-1,3-benzodiazol-2-yl)amino]-2-[3-(trifluoromethyl)phenyl]propyl 2,2-dimethylpropanoate (from Step 15, Compound 15b, Fraction 2) (0.270 g, 0.534 mmol) in ethanol (15 mL) was added sodium hydroxide pellets (0.071 g, 2.00 mmol) and it was stirred at ambient temperature for 2 h. The reaction mass was concentrated and the residue was diluted with water (20 mL) and extracted with ethyl acetate (3×75 mL). The combined organic layer had dried over sodium sulphate, filtered and concentrated to afford (−)-1-((2-((1-hydroxy-2-(3-(trifluoromethyl) phenyl) propan-2-yl) amino)-1H-benzo[d] imidazol-4-yl) methyl)-3-methylurea (Isomer b, 0.175 g) as a yellow solid.

$^1$H NMR (400 MHz, AcOH-d$_4$) δ 7.86 (s, 1H), 7.83 (d, 1H, J=7.96 Hz), 7.67 (d, 1H, J=7.64 Hz), 7.59 (t, 1H, J=7.72 Hz), 7.30 (d, 1H, J=7.88 Hz), 7.16 (t, 1H, J=7.84 Hz), 7.11 (d, 1H, J=7.52 Hz), 4.45 (q, 2H, J=15.20 Hz), 4.28 (d, 1H, J=11.92 Hz), 4.06 (d, 1H, J=11.92 Hz), 2.68 (s, 3H), 1.87 (s, 3H);

MS: m/z 422.2 (M+1);

[α] D $^{22.5}$ (−) 12.00 (MeOH, c=0.1).

Example 2: Preparation of 3-((2-((1-hydroxy-2-(3-(trifluoromethyl) phenyl) propan-2-yl) amino)-1H-benzo[d]imidazol-4-yl) methyl)-1, 1-dimethylurea

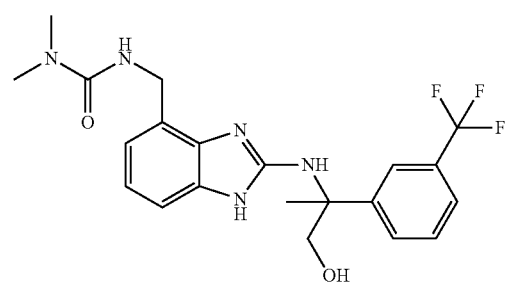 [SMILES: CN(C)C(=O)NCc1cccc2[nH]c(NC(C)(CO)c3cccc(C(F)(F)F)c3)nc12]

Example 2, Step 1: Preparation of 3-(benzo[c] [1, 2, 5] thiadiazol-4-ylmethyl)-1, 1-dimethylurea

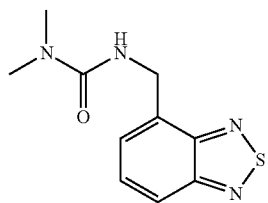 [SMILES: CN(C)C(=O)NCc1cccc2nsnc12]

To a solution of 2, 1, 3-benzothiadiazol-4-ylmethanamine hydrochloride (from Example 1, Step 11) (10.00 g, 49.6 mmol) under nitrogen atmosphere in dry dichloromethane (100 mL) cooled at 0° C., was added triethyl amine (17.30 mL, d: 0.726 g/cm$^3$, 124.00 mmol) followed by N, N-dimethyl carbamoyl chloride (6.85 mL, d: 1.168 g/cm$^3$, 74.40 mmol) and the mixture was then stirred at room temperature for 2 h. The above reaction mass was quenched with ice cold water (50 mL) and the aqueous layer was extracted with dichloromethane (3×50 mL). The combined organic layer was dried over sodium sulphate, filtered and concentrated to afford a yellow gum (12.00 g). This was purified by chromatography on a Grace instrument using 120.0 g pre-packed cartridge filled with 60-120 silica gel and the product was eluted with 8% methanol in chloroform to afford 3-(benzo[c][1,2,5] thiadiazol-4-ylmethyl)-1,1-dimethylurea (6.00 g) as a colourless gum, which was used in the next step without further purification.

$^1$H NMR (400 MHz, DMSO-d$_6$) δ 7.95 (d, 1H, J=8.70 Hz), 7.70 (t, 1H, J=7.58 Hz), 7.47 (d, 1H, J=6.80 Hz), 7.01 (t, 1H, J=5.44 Hz), 4.74 (d, 2H, J=5.60 Hz), 2.87 (s, 6H); MS: m/z 237.2 (M+1).

Example 2, Step 2: Preparation of 3-(2, 3-diaminobenzyl)-1, 1-dimethylurea

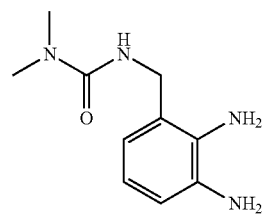

To a de-gassed solution of 3-(2, 1, 3-benzothiadiazol-4-ylmethyl)-1, 1-dimethyl-urea (from Example 2, Step 1) (9.00 g, 38.1 mmol) in dry methanol (1000 mL) was added Raney nickel (18.00 g, 200% w/w, pre-washed five times with dry methanol) and the resultant reaction mixture was stirred under a hydrogen atmosphere under bladder pressure (Approx. 1.5 kg/cm$^2$) at ambient temperature for 24 h. The reaction mixture was filtered through a celite bed and the bed was washed with methanol (3×1000 mL). The combined filtrates were concentrated to afford 3-(2, 3-diaminobenzyl)-1, 1-dimethylurea (6.00 g) as a brown solid, which used in the next step without further purification.

$^1$H NMR (400 MHz, DMSO-d$_6$) δ 6.63 (bs, 1H), 6.45 (s, 1H), 6.40 (s, 1H), 6.34 (d, 1H, J=6.40 Hz), 4.62 (bs, 2H), 4.37 (bs, 2H), 4.09 (bs, 2H), 2.80 (s, 6H); MS: m/z 209.2 (M+1).

Example 2, Step 3: Preparation of 2-{[(2-amino-6-{[(dimethylcarbamoyl)amino]methyl}phenyl)carbamothioyl]amino}-2-[3-(trifluoromethyl)phenyl]propyl 2,2-dimethylpropanoate and 2-{[(2-amino-3-{[(dimethylcarbamoyl)amino]methyl}phenyl)carbamothioyl]amino}-2-[3-(trifluoromethyl)phenyl]propyl 2,2-dimethylpropanoate (Mixture of Regio isomers)

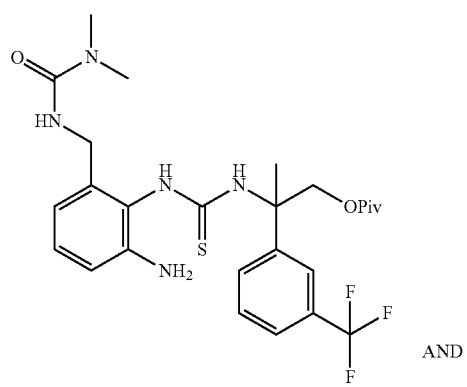

AND

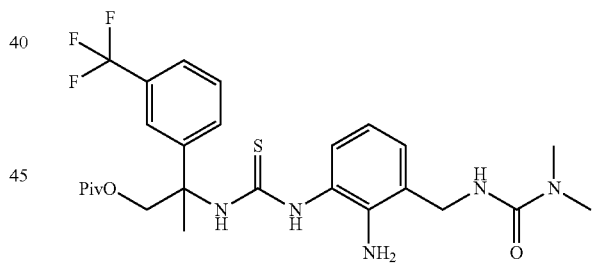

To a stirred solution of 3-(2, 3-diaminobenzyl)-1, 1-dimethylurea (from Example 2, Step 2) (0.600 g, 2.88 mmol) in acetonitrile (10 mL) was added [2-isothiocyanato-2-[3-(trifluoromethyl) phenyl] propyl] 2, 2-dimethylpropanoate (from Example 1, Step 7) (0.995 g, 2.88 mmol) and stirred at room temperature for 16 h. The reaction mixture was concentrated to afford 2-{[(2-amino-6-{[(dimethylcarbamoyl)amino]methyl}phenyl)carbamothioyl]amino}-2-[3-(trifluoromethyl)phenyl]propyl 2,2-dimethylpropanoate and 2-{[(2-amino-3-{[(dimethylcarbamoyl)amino]methyl}phenyl)carbamothioyl]amino}-2-[3-(trifluoromethyl)phenyl]propyl 2,2-dimethylpropanoate (as a 1:1 mixture of regioisomers) as a yellowish gum (1.50 g), which was used in the next step without further purification.

MS: m/z 554.3 (M+1).

Example 2, Step 4: Preparation of 2-[(4-{[(dimethylcarbamoyl)amino]methyl}-1H-1,3-benzodiazol-2-yl)amino]-2-[3-(trifluoromethyl)phenyl]propyl 2,2-dimethylpropanoate

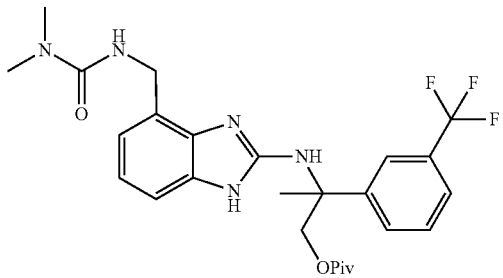

To a mixture of 2-{[(2-amino-6-{[(dimethylcarbamoyl)amino]methyl}phenyl)carbamothioyl]amino}-2-[3-(trifluoromethyl)phenyl]propyl 2,2-dimethylpropanoate and 2-{[(2-amino-3-{[(dimethylcarbamoyl)amino]methyl}phenyl)carbamothioyl]amino}-2-[3-(trifluoromethyl)phenyl]propyl 2,2-dimethylpropanoate (as a 1:1 mixture of regioisomers) (from Example 2, Step 3) (1.50 g, 2.71 mmol) in methanol (20 mL) was added iodoacetic acid (1.01 g, 5.42 mmol) and the reaction mixture was heated at 65° C. for 2 h. The reaction mixture was concentrated and the residue was dissolved in dichloromethane (100 mL), washed with 10% aqueous sodium bicarbonate solution (2×10 mL), the organic layer was dried over sodium sulphate, filtered and concentrated to afford a reddish gum (1.40 g). This was purified by flash column chromatography using 230-400 silica gel and the product was eluted with 70% ethyl acetate in petroleum ether to afford 2-[(4-{[(dimethylcarbamoyl)amino]methyl}-1H-1,3-benzodiazol-2-yl)amino]-2-[3-(trifluoromethyl)phenyl]propyl 2,2-dimethylpropanoate (0.450 g) as an off-white solid.

$^1$H NMR (400 MHz, DMSO-$d_6$) δ 10.57 (s, 1H), 7.87 (s, 2H), 7.59-7.56 (m, 2H), 7.33 (s, 1H), 6.96 (s, 2H), 6.80-6.75 (m, 2H), 4.54 (s, 2H), 4.29 (s, 2H), 2.81 (s, 3H), 2.67 (s, 3H), 1.85 (s, 3H), 1.03 (s, 9H);

MS: m/z 520.2 (M+1).

Example 2: Preparation of 3-((2-((1-hydroxy-2-(3-(trifluoromethyl) phenyl) propan-2-yl) amino)-1H-benzo[d]imidazol-4-yl) methyl)-1, 1-dimethylurea

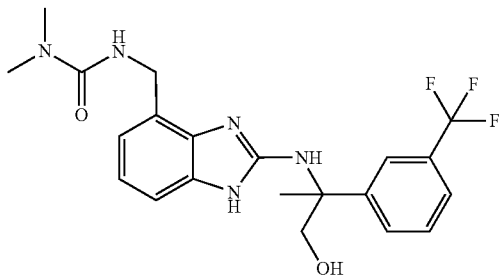 [SMILES: CN(C)C(=O)NCc1cccc2[nH]c(NC(C)(CO)c3cccc(C(F)(F)F)c3)nc12]

To a solution of 2-[(4-{[(dimethylcarbamoyl)amino]methyl}-1H-1,3-benzodiazol-2-yl)amino]-2-[3-(trifluoromethyl)phenyl]propyl 2,2-dimethylpropanoate (from Example 2, Step 4) (0.450 g, 0.866 mmol) in ethanol (10 mL) was added sodium hydroxide pellets (0.346 g, 8.66 mmol) and stirred at room temperature for 0.5 h. The reaction mixture was concentrated and the residue was dissolved in water (30 mL) and extracted with ethyl acetate (3×150 mL), the combined organic layer was dried over sodium sulphate, filtered and concentrated to afford crude a brown gum (0.370 g), which was purified by preparative HPLC to afford 3-((2-((1-hydroxy-2-(3-(trifluoromethyl) phenyl) propan-2-yl) amino)-1H-benzo[d]imidazol-4-yl) methyl)-1,1-dimethylurea (0.260 g) as an off-white solid.

$^1$H NMR (400 MHz, AcOH-$d_4$) δ 7.85 (t, 2H, J=7.60 Hz), 7.67 (d, 1H, J=7.60 Hz), 7.60 (t, 1H, J=7.60 Hz), 7.34 (d, 1H, J=7.20 Hz), 7.17 (t, 1H, J=8.00 Hz), 7.10 (d, 1H, J=6.80 Hz), 4.51 (d, 1H, J=14.80 Hz), 4.40 (d, 1H, J=15.20 Hz), 4.25 (d, 1H, J=11.60 Hz), 4.06 (d, 1H, J=11.60 Hz), 2.86 (s, 6H), 1.90 (s, 3H);

MS: m/z 436.2 (M+1).

The above product was resolved into its two enantiomers by Chiral SFC using the method; Column: Chiral Pak OX—H; Flow rate: 3.0 mL/min, Co-Solvent: 30%; Co-solvent Name: 0.5% isopropyl amine in isopropyl alcohol; injected Volume: 15.0 pIL; Out let pressure: 100 bar; Temperature: 35° C. to obtain the two enantiomers 2a and bb.

Example 2a: (+)-3-((2-((1-hydroxy-2-(3-(trifluoromethyl) phenyl) propan-2-yl) amino)-1H-benzo[d]imidazol-4-yl) methyl)-1, 1-dimethylurea The (+) enantiomer was the first to elute off the column.

$^1$H NMR (400 MHz, AcOH-$d_4$) δ 7.85 (t, 2H, J=7.60 Hz), 7.67 (d, 1H, J=7.60 Hz), 7.60 (t, 1H, J=7.60 Hz), 7.34 (d, 1H, J=7.20 Hz), 7.17 (t, 1H, J=8.00 Hz), 7.10 (d, 1H, J=6.80 Hz), 4.51 (d, 1H, J=14.80 Hz), 4.40 (d, 1H, J=15.20 Hz), 4.25 (d, 1H, J=11.60 Hz), 4.06 (d, 1H, J=11.60 Hz), 2.86 (s, 6H), 1.90 (s, 3H);

MS: m/z 436.2 (M+1);

$[α]D^{22.4}$ (+) 44.0 (MeOH, c=0.1).

Example 2b: (−)-3-((2-((1-hydroxy-2-(3-(trifluoromethyl) phenyl) propan-2-yl) amino)-1H-benzo[d]imidazol-4-yl) methyl)-1, 1-dimethylurea The (−) enantiomer was the second to elute off the column.

$^1$H NMR (400 MHz, AcOH-$d_4$) δ 7.85 (t, 2H, J=7.60 Hz), 7.67 (d, 1H, J=7.60 Hz), 7.60 (t, 1H, J=7.60 Hz), 7.34 (d, 1H, J=7.20 Hz), 7.17 (t, 1H, J=8.00 Hz), 7.10 (d, 1H, J=6.80 Hz), 4.51 (d, 1H, J=14.80 Hz), 4.40 (d, 1H, J=15.20 Hz), 4.25 (d, 1H, J=11.60 Hz), 4.06 (d, 1H, J=11.60 Hz), 2.86 (s, 6H), 1.90 (s, 3H);

MS: m/z 436.2 (M+1);

$[α]D^{22.5}$ (−) 20.0 (MeOH, c=0.1).

Example 3: Preparation of 1-((2-((1-methoxy-2-(3-(trifluoromethyl) phenyl) propan-2-yl) amino)-1H-benzo[d]imidazol-4-yl) methyl)-3-methylurea

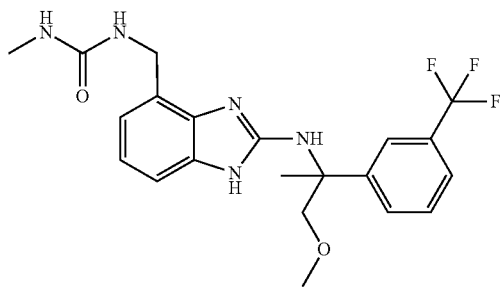 [SMILES: CNC(=O)NCc1cccc2[nH]c(NC(C)(COC)c3cccc(C(F)(F)F)c3)nc12]

Example 3, Step 1: Preparation of tert-butyl N-{1-methoxy-2-[3-(trifluoromethyl)phenyl]propan-2-yl}carbamate

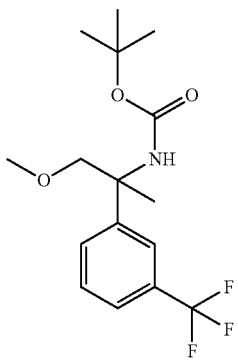 [SMILES: COCC(C)(NC(=O)OC(C)(C)C)c1cccc(C(F)(F)F)c1]

To a stirred solution of tert-butyl N-(1-hydroxy-2-(3-(trifluoromethyl) phenyl) propan-2-yl) carbamate (from Example 1, Step 4) (5.00 g, 15.70 mmol) in acetonitrile (75 mL) was added silver oxide (11.1 g, 78.30 mmol) followed by methyl iodide (6.00 mL, 95 mmol) and stirred at room temperature in the absence of light for 48 h. The reaction mixture was filtered and concentrated to afford a brown gum (5.20 g), which was purified by flash column chromatography over 230-400 silica gel and the product was eluted with 30% ethyl acetate in petroleum ether to afford tert-butyl N-{1-methoxy-2-[3-(trifluoromethyl)phenyl]propan-2-yl}carbamate (2.50 g) as a brown gum.

$^1$H NMR (400 MHz, DMSO-$d_6$) δ 7.65-7.53 (m, 4H), 7.12 (s, 1H), 3.55-3.47 (m, 2H), 3.23 (s, 3H), 1.58 (s, 3H), 1.34 (s, 9H);

MS: m/z 234.1 [(M+1)-Boc].

Example 3, Step 2: 1-methoxy-2-(3-(trifluoromethyl) phenyl) propan-2-amine hydrochloride

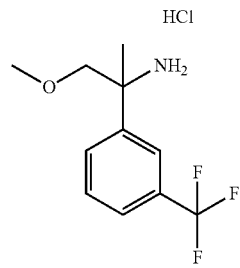 [SMILES: Cl ; COCC(C)(N)c1cccc(C(F)(F)F)c1]

To a stirred solution of tert-butyl N-{1-methoxy-2-[3-(trifluoromethyl)phenyl]propan-2-yl}carbamate (from Example 3, Step 1) (2.50 g, 7.50 mmol) in dichloromethane (30 mL) was added 4.0 M HCl in dioxane (2 mL) at 0° C. and the reaction mixture was slowly warmed to room temperature and stirred for 2 h. The reaction mixture was concentrated to afford 1-methoxy-2-(3-(trifluoromethyl) phenyl) propan-2-amine hydrochloride (1.80 g) as a brown gum, which was used in the next step without further purification.

$^1$H NMR (400 MHz, DMSO-$d_6$) δ 8.74 (s, 2H), 7.87-7.71 (m, 3H), 3.76 (d, 1H, J=10.00 Hz), 3.65 (d, 1H, J=10.00 Hz), 3.57 (d, 2H, J=2.40 Hz), 3.35 (s, 3H), 1.62 (s, 3H);

MS: m/z 234.1 (M+1).

Example 3, Step 3: 1-(2-isothiocyanato-1-methoxy-propan-2-yl)-3-(trifluoromethyl) benzene

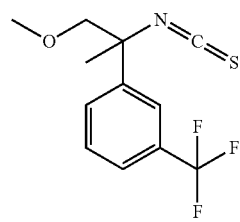 [SMILES: COCC(C)(N=C=S)c1cccc(C(F)(F)F)c1]

To a stirred solution of 1-methoxy-2-(3-(trifluoromethyl) phenyl) propan-2-amine hydrochloride (from Example 3, Step 2) (1.70 g, 7.29 mmol) in dichloromethane (15 mL) was added 10% sodium bicarbonate solution followed by thiophosgene (0.55 mL, 7.29 mmol) at 0° C. and the reaction mixture was slowly warmed to room temperature and stirred for 2 h. The reaction mixture was diluted with dichloromethane (100 mL), the organic layer was separated and dried over sodium sulphate, filtered and concentrated to afford a brown gum (2.00 g), which was purified by flash column chromatography over 230-400 silica gel and the product was eluted with 20% ethyl acetate in petroleum ether to afford 1-(2-isothiocyanato-1-methoxypropan-2-yl)-3-(trifluoromethyl) benzene (0.700 g) as an off-white gum.

$^1$H NMR (400 MHz, DMSO-$d_6$) δ 7.82-7.74 (m, 3H), 7.70-7.67 (m, 1H), 3.76 (s, 2H), 3.33 (s, 3H), 1.77 (s, 3H);

Example 3, Step 4: 1-(3-amino-2-(3-(1-methoxy-2-(3-(trifluoromethyl) phenyl) propan-2-yl) thioureido)benzyl)-3-methylurea and 1-(2-amino-3-(3-(1-methoxy-2-(3-(trifluoromethyl) phenyl)propan-2-yl) thioureido) benzyl)-3-methylurea (mixture of Regioisomers)

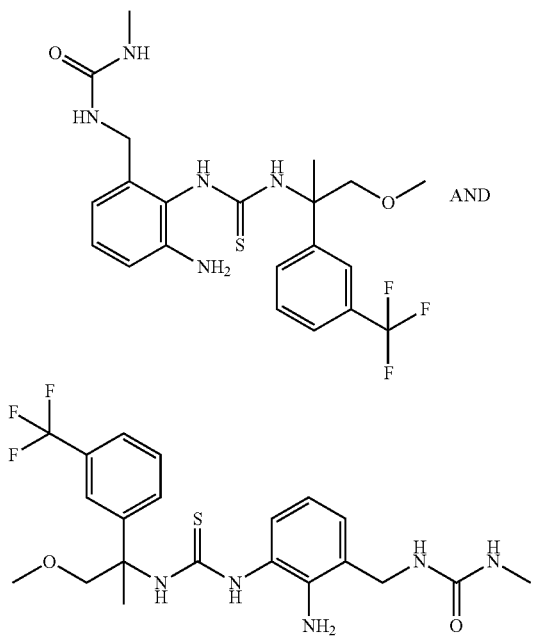

To a stirred solution of 1-(2, 3-diaminobenzyl)-3-methylurea (from Example 1, Step 13) (0.494 g, 2.54 mmol) in dichloromethane (20 mL) was added 1-(2-isothiocyanato-1-methoxypropan-2-yl)-3-(trifluoromethyl) benzene (from Example 3, Step 3) (0.700 g, 2.54 mmol) and stirred at room temperature for 16 h. The reaction mixture was concentrated to afford 1-(3-amino-2-(3-(1-methoxy-2-(3-(trifluoromethyl) phenyl) propan-2-yl) thioureido) benzyl)-3-methylurea and 1-(2-amino-3-(3-(1-methoxy-2-(3-(trifluoromethyl) phenyl) propan-2-yl) thioureido) benzyl)-3-methylurea (as a 1:1 mixture of regioisomers) (1.00 g) as a brown gum, which was used in the next step without further purification.

MS: m/z 470.2 (M+1).

Example 3: Preparation of 1-((2-((1-methoxy-2-(3-(trifluoromethyl) phenyl) propan-2-yl) amino)-1H-benzo[d]imidazol-4-yl) methyl)-3-methylurea

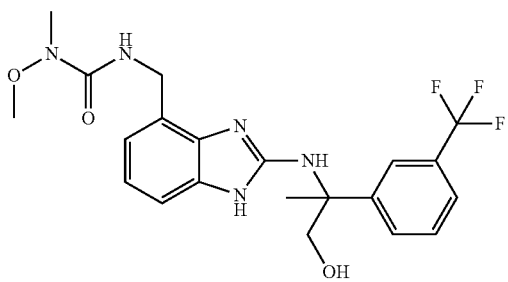 [SMILES: CON(C)C(=O)NCc1cccc2[nH]c(NC(C)(CO)c3cccc(C(F)(F)F)c3)nc12]

To a solution of 1-(3-amino-2-(3-(1-methoxy-2-(3-(trifluoromethyl) phenyl) propan-2-yl) thioureido)benzyl)-3-methylurea and 1-(2-amino-3-(3-(1-methoxy-2-(3-(trifluoromethyl) phenyl) propan-2-yl) thioureido) benzyl)-3-methylurea (as a 1:1 mixture of regioisomers) (from Example 3, Step 4) (1.00 g, 2.13 mmol) in methanol (20 mL) was added iodoacetic acid (0.594 g, 3.19 mmol) and heated at 65° C. for 3 h. The reaction mixture was concentrated and the residue was dissolved in ethyl acetate (100 mL), washed with 10% aqueous sodium bicarbonate solution (2×20 mL), dried over sodium sulphate, filtered and concentrated to afford a brown gum (0.900 g). This was purified by flash column chromatography over 230-400 silica gel and the product was eluted with 50% ethyl acetate in petroleum ether to afford 1-((2-((1-methoxy-2-(3-(trifluoromethyl)phenyl)propan-2-yl)amino)-1H-benzo[d]imidazol-4-yl) methyl)-3-methylurea (0.45 g) as an off-white solid.

$^1$H NMR (400 MHz, AcOH-d$_4$) δ 7.85-7.82 (m, 2H), 7.69 (d, 1H, J=7.20 Hz), 7.61 (t, 1H, J=7.60 Hz, 1H), 7.30 (d, 1H, J=7.60 Hz), 7.20-7.14 (m, 2H), 4.47 (d, 2H, J=10.00 Hz), 4.02 (d, 1H, J=10.40 Hz), 3.84 (d, 1H, J=10.00 Hz), 3.48 (s, 3H), 2.71 (s, 3H), 1.91 (s, 3H);

MS: m/z 436.2 (M+1).

The above product was resolved into its two enantiomers by Chiral SFC using the method; Column: Chiral Pak OX—H; Flow rate: 3.0 mL/min, Co-Solvent: 40%; Co-solvent Name: 0.5% isopropyl amine in isopropyl alcohol; injected Volume: 10.0 μL; Out let pressure: 100 bar; Temperature: 35° C. to obtain the two enantiomers 3a and 3b.

Example 3a: (+)-1-((2-((1-methoxy-2-(3-(trifluoromethyl) phenyl) propan-2-yl) amino)-1H-benzo[d] imidazol-4-yl) methyl)-3-methylurea The (+) enantiomer was the first to elute off the column.

$^1$H NMR (400 MHz, AcOH-d$_4$) δ 7.85-7.82 (m, 2H), 7.69 (d, 1H, J=7.20 Hz), 7.61 (t, 1H, J=7.60 Hz), 7.30 (d, 1H, J=7.60 Hz), 7.20-7.14 (m, 2H), 4.47 (d, 2H, J=10.00 Hz), 4.02 (d, 1H, J=10.40 Hz), 3.84 (d, 1H, J=10.00 Hz), 3.48 (s, 3H), 2.71 (s, 3H), 1.91 (s, 3H);

MS: m/z 436.2 (M+1);

[α]D $^{22.4}$ (+) 13.59 (MeOH, c=0.1).

Example 3b: (−)-1-((2-((1-methoxy-2-(3-(trifluoromethyl) phenyl) propan-2-yl) amino)-1H-benzo[d] imidazol-4-yl) methyl)-3-methylurea The (−) enantiomer was the second to elute off the column.

$^1$H NMR (400 MHz, AcOH-d$_4$) δ 7.85-7.82 (m, 2H), 7.69 (d, 1H, J=7.20 Hz), 7.61 (t, 1H, J=7.60 Hz), 7.30 (d, 1H, J=7.60 Hz), 7.20-7.14 (m, 2H), 4.47 (d, 2H, J=10.00 Hz), 4.02 (d, 1H, J=10.40 Hz), 3.84 (d, 1H, J=10.00 Hz), 3.48 (s, 3H), 2.71 (s, 3H), 1.91 (s, 3H);

MS: m/z 436.2 (M+1);

[α]D $^{23.5}$ (−) 12.60 (MeOH, c=0.1).

Example 4: Preparation of 1-{[2-({1-hydroxy-2-[3-(trifluoromethyl)phenyl]propan-2-yl}amino)-1H-1,3-benzodiazol-4-yl]methyl}-3-methoxy-3-methylurea

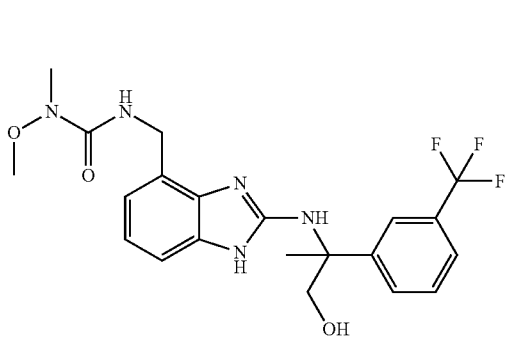 [SMILES: CON(C)C(=O)NCc1cccc2[nH]c(NC(C)(CO)c3cccc(C(F)(F)F)c3)nc12]

Example 4, Step 1: Preparation of 3-(benzo[c] [1, 2, 5] thiadiazol-4-ylmethyl)-1-methoxy-1-methyl-urea

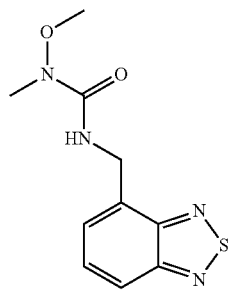 [SMILES: CON(C)C(=O)NCc1cccc2nsnc12]

To a stirred solution of solution of benzo[c] [1, 2, 5] thiadiazol-4-ylmethanamine hydrochloride (from Example 1, Step 11) (20.00 g, 99.20 mmol) in dichloromethane (200 mL) had added trimethylamine (42.5 mL, d=0.724 gm/cm³, 305.00 mmol) and the reaction mixture was stirred for 5 min. Then N-methoxy-N-methyl-carbamoyl chloride (12.91 mL, 129.00 mmol) was added drop-wise to the reaction mixture at 0° C. over a period of 5 min and the mixture was slowly warmed to room temperature and stirred for 2 h. The reaction was quenched with ice-cold water (100 mL), the organic phase was separated, and the aqueous phase was further extracted with dichloromethane (3×500 mL). The combined organic layer was dried over sodium sulphate, filtered and concentrated to afford a colorless gum (25.00 g), which was purified by flash column chromatography over 230-400 silica gel and the product was eluted with 45% ethyl acetate in petroleum ether to afford 3-(benzo[c] [1,2,5] thiadiazol-4-ylmethyl)-1-methoxy-1-methylurea (15.00 g) as a colorless gum.

¹H NMR (400 MHz, DMSO-d₆) δ 7.98 (dd, 1H, J=8.80, 0.80 Hz), 7.89 (t, 1H, J=6.00 Hz), 7.72 (q, 1H, J=6.80 Hz), 7.47 (dd, 1H, J=7.00, 0.80 Hz), 4.77 (d, 2H, J=6.00 Hz), 3.67 (s, 3H), 3.00 (s, 3H);

MS: m/z 253.0 (M+1).

Example 4, Step 2: Preparation of 3-(2, 3-diaminobenzyl)-1-methoxy-1-methylurea

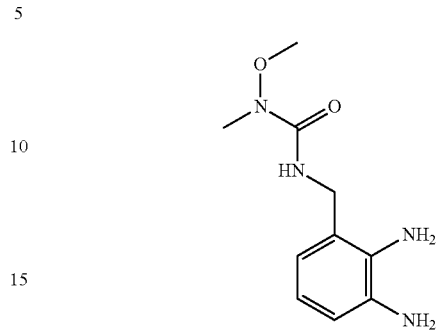

To a stirred solution of 3-(2,1,3-benzothiadiazol-4-ylmethyl)-1-methoxy-1-methyl-urea (from Example 4, Step 1) (15.00 g, 59.50 mmol) in methanol (450 mL) was added Raney nickel (45.00 g, 300% wt/wt) and the reaction mixture was hydrogenated at 1.5 kg/cm² using a bladder at room temperature for 4 h. The reaction mixture was filtered through a celite bed, and the filtrate was concentrated to afford a yellow solid (13.00 g). This was purified by flash column chromatography over 230-400 silica gel and the product was eluted with 100% ethyl acetate to afford 3-(2, 3-diaminobenzyl)-1-methoxy-1-methylurea (7.00 g) as a yellow solid.

¹H NMR (400 MHz, DMSO-d₆) δ 7.53-7.49 (m, 1H), 6.47 (dd, 1H, J=7.40, 1.60 Hz), 6.42 (dd, 1H, J=7.40, 1.20 Hz), 6.34 (t, 1H, J=7.60 Hz), 4.52 (s, 2H), 4.42 (s, 2H), 4.09 (d, 2H, J=6.4 Hz), 3.58 (s, 3H), 2.95 (s, 3H);

MS: m/z 225.2 (M+1).

Example 4, Step 3: Preparation of 2-({[2-amino-6-({[methoxy(methyl)carbamoyl]amino}methyl)phenyl]carbamothioyl}amino)-2-[3-(trifluoromethyl)phenyl]propyl 2,2-dimethylpropanoate and 2-({[2-amino-3-({[methoxy(methyl)carbamoyl]amino}methyl)phenyl]carbamothioyl}amino)-2-[3-(trifluoromethyl)phenyl]propyl 2,2-dimethylpropanoate (mixture of Regioisomers)

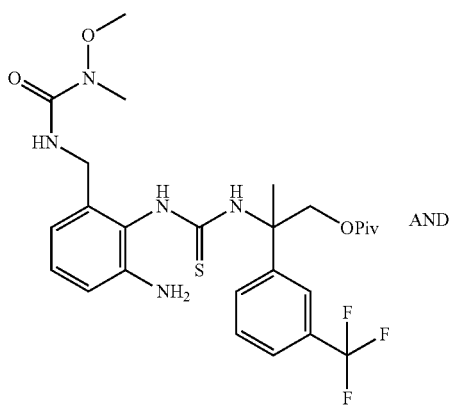

AND

-continued

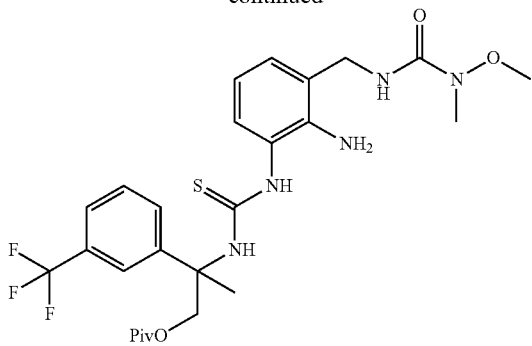

To a stirred solution of 3-[(2, 3-diaminophenyl) methyl]-1-methoxy-1-methyl-urea (Example 4, Step 2) (0.390 g, 1.74 mmol) in acetonitrile (6 mL) was added [2-isothiocyanato-2-[3-(trifluoromethyl) phenyl] propyl] 2, 2-dimethylpropanoate (from Example 1, Step 7) (0.6 g, 1.74 mmol) and the mixture was stirred at room temperature for 24 h. The reaction mixture was concentrated to afford 2-({[2-amino-6-({[methoxy(methyl)carbamoyl]amino}methyl)phenyl]carbamothioyl}amino)-2-[3-(trifluoromethyl)phenyl]propyl 2,2-dimethylpropanoate and 2-({[2-amino-3-({[methoxy(methyl)carbamoyl]amino}methyl)phenyl]carbamothioyl}amino)-2-[3-(trifluoromethyl)phenyl]propyl 2,2-dimethylpropanoate (as a 1:1 mixture of regioisomers) (0.980 g) as a yellowish gum, which was used in the next step without further purification.

MS: m/z 570.2 (M+1).

Example 4, Step 4: Preparation of 2-{[4-({[methoxy(methyl)carbamoyl]amino}methyl)-1H-1,3-benzodiazol-2-yl]amino}-2-[3-(trifluoromethyl)phenyl]propyl 2,2-dimethylpropanoate

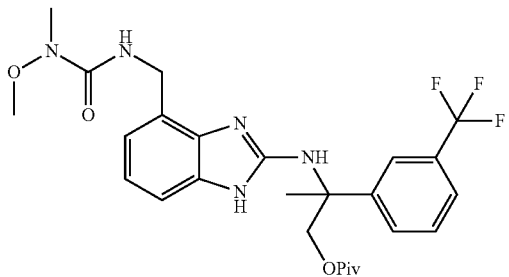

To a solution of 2-({[2-amino-6-({[methoxy(methyl)carbamoyl]amino}methyl)phenyl]carbamothioyl}amino)-2-[3-(trifluoromethyl)phenyl]propyl 2,2-dimethylpropanoate and 2-({[2-amino-3-({[methoxy(methyl)carbamoyl]amino}methyl)phenyl]carbamothioyl}amino)-2-[3-(trifluoromethyl)phenyl]propyl 2,2-dimethylpropanoate (as a 1:1 mixture of regioisomers) (from Example 4, Step 3) (0.98 g, 1.72 mmol) in methanol (10 mL) was added iodoacetic acid (0.64 g, 3.40 mmol) and the reaction mixture was stirred at room temperature for 1.5 h. The reaction mixture was concentrated and the residue was dissolved in dichloromethane (100 mL), washed with 10% aqueous sodium bicarbonate solution (2×10 mL), dried over sodium sulphate, filtered and concentrated to afford a reddish gum (0.90 g). This was purified by flash column chromatography over 230-400 silica gel and the product was eluted with 2% methanol in dichloromethane to afford 2-{[4-({[methoxy(methyl)carbamoyl]amino}methyl)-1H-1,3-benzodiazol-2-yl]amino}-2-[3-(trifluoromethyl)phenyl]propyl 2,2-dimethylpropanoate (0.700 g) as a reddish gum.

$^1$H NMR (400 MHz, DMSO-d$_6$: D$_2$O) δ 7.76 (s, 2H), 7.58 (t, 2H, J=7.60 Hz), 7.03 (s, 1H), 6.90-6.80 (m, 2H), 4.52 (s, 2H), 4.29 (s, 2H), 3.52 (s, 3H), 2,93 (s, 3H), 1.83 (s, 3H), 0.99 (s, 9H);

MS: m/z 536.6 (M+1).

Example 4: Preparation of 1-{[2-({1-hydroxy-2-[3-(trifluoromethyl)phenyl]propan-2-yl}amino)-1H-1,3-benzodiazol-4-yl]methyl}-3-methoxy-3-methylurea

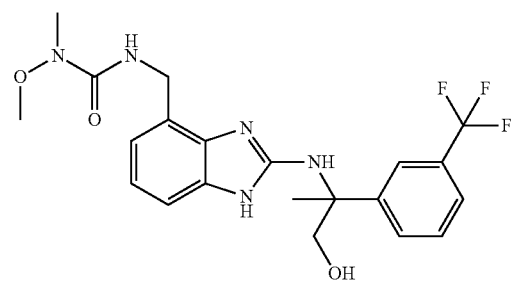 [SMILES: CON(C)C(=O)NCc1cccc2[nH]c(NC(C)(CO)c3cccc(C(F)(F)F)c3)nc12]

To a solution of [2-[[4-[[[methoxy(methyl)carbamoyl]amino] methyl]-1H-benzimidazol-2-yl] amino]-2-[3-(trifluoromethyl) phenyl] propyl] 2,2-dimethylpropanoate (from Example 4, Step 4) (0.70 g, 1.31 mmol) in methanol (25 mL) had added 0.5 N sodium hydroxide solution in methanol (10.50 ml, 5.23 mmol) and stirred at room temperature for 1 h. The reaction mixture was quenched with 1.5 N hydrochloride solution (3 mL) and concentrated under reduced pressure at 30° C. to afford a brown gum (0.600 g). This was purified by preparative HPLC using 0.1% TFA in acetonitrile: water to afford 1-{[2-({1-hydroxy-2-[3-(trifluoromethyl)phenyl]propan-2-yl}amino)-1H-1,3-benzodiazol-4-yl]methyl}-3-methoxy-3-methylurea (0.410 g) as an off-white solid.

$^1$H NMR (400 MHz, AcOH-d$_4$) δ 7.87 (s, 1H), 7.84 (d, 1H, J=7.60 Hz), 7.67 (d, 1H, J=8.00 Hz), 7.60 (t, 1H, J=7.60 Hz), 7.36 (d, 1H, J=8.00 Hz), 7.19 (t, 1H, J=7.60 Hz), 7.13 (d, 1H, J=7.20 Hz), 4.45 (q, 2H, J=15.20 Hz), 4.26 (d, 1H, J=12.00 Hz), 4.06 (d, 1H, J=11.60 Hz), 3.60 (s, 3H), 3.02 (s, 3H), 1.89 (s, 3H);

MS: m/z 452.2 (M+1).

The above product was resolved into its two enantiomers by Chiral SFC using the method; Column: Lux C$_4$; Flow rate: 3.0 mL/min, Co-Solvent: 30%; Co-solvent Name: 0.5% isopropyl amine in isopropyl alcohol; injected Volume: 15.0 µL; Out let pressure: 100 bar; Temperature: 35° C. to obtain the two enantiomers 4a and 4b.

Example 4a: (+)-3-((2-((1-hydroxy-2-(3-(trifluoromethyl)phenyl)propan-2-yl)amino)-1H-benzo[d]imidazol-4-yl)methyl)-1-methoxy-1-methylurea The (+) enantiomer was the first to elute off the column.
$^1$H NMR (400 MHz, AcOH-d$_4$) δ 7.87 (s, 1H), 7.84 (d, 1H, J=7.60 Hz), 7.67 (d, 1H, J=8.00 Hz), 7.60 (t, 1H, J=7.60 Hz), 7.36 (d, 1H, J=8.00 Hz), 7.19 (t, 1H, J=7.60 Hz), 7.13 (d, 1H, J=7.20 Hz), 4.45 (q, 2H, J=15.20 Hz), 4.26 (d, 1H, J=12.00 Hz), 4.06 (d, 1H, J=11.60 Hz), 3.60 (s, 3H), 3.02 (s, 3H), 1.89 (s, 3H);

MS: m/z 452.2 (M+1);
[α]D $^{25.0}$ (+) 15.40 (MeOH, c=1.0).

Example 4b: (−)-3-((2-((1-hydroxy-2-(3-(trifluoromethyl)phenyl)propan-2-yl)amino)-1H-benzo[d]imidazol-4-yl)methyl)-1-methoxy-1-methylurea The (−) enantiomer was the second to elute off the column.
$^1$H NMR (400 MHz, AcOH-d$_4$) δ 7.87 (s, 1H), 7.84 (d, 1H, J=7.60 Hz), 7.67 (d, 1H, J=8.00 Hz), 7.60 (t, 1H, J=7.60 Hz), 7.36 (d, 1H, J=8.00 Hz), 7.19 (t, 1H, J=7.60 Hz), 7.13 (d, 1H, J=7.20 Hz), 4.45 (q, 2H, J=15.20 Hz), 4.26 (d, 1H, J=12.00 Hz), 4.06 (d, 1H, J=11.60 Hz), 3.60 (s, 3H), 3.02 (s, 3H), 1.89 (s, 3H);
MS: m/z 452.2 (M+1);
[α]D $^{252}$ (−) 16.20 (MeOH, c=1.0).

Example 5: Preparation of 1-ethyl-3-((2-((1-hydroxy-2-(3-(trifluoromethyl) phenyl) propan-2-yl) amino)-1H-benzo[d]imidazol-4-yl) methyl)-1-methylurea

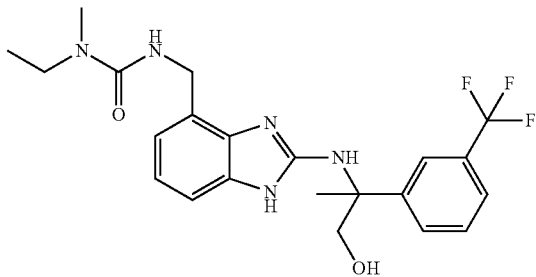 [SMILES: CCN(C)C(=O)NCc1cccc2[nH]c(NC(C)(CO)c3cccc(C(F)(F)F)c3)nc12]

Example 5, Step 1: Preparation of 3-(benzo[c] [1,2,5] thiadiazol-4-ylmethyl)-1-ethyl-1-methylurea

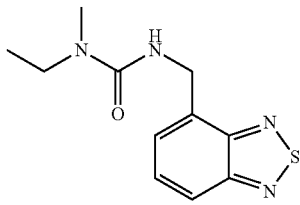 [SMILES: CCN(C)C(=O)NCc1cccc2nsnc12]

To a solution of 2, 1, 3-benzothiadiazol-4-ylmethanamine hydrochloride (from Example 1, Step 11) (25.00 g, 124.00 mmol) under a nitrogen atmosphere in dry dichloromethane (800 mL) cooled at 0° C., was added triethylamine (52.00 mL, d: 0.726 g/cm$^3$, 372.00 mmol) followed by N-Ethyl-N-methyl-carbamoyl chloride (20.50 mL, d: 1.11 g/cm$^3$, 186.00 mmol) and the mixture was then stirred at room temperature for 2 h. The above reaction mixture was quenched with ice cold water (200 mL) and the aqueous layer was extracted with dichloromethane (3×1000 mL). The combined organic layer was dried over sodium sulphate, filtered and concentrated to afford a yellow gum (31.00 g). This was purified by chromatography using a Grace instrument using 220.0 g pre-packed flash cartridge filled with normal phase silica gel 60° A, 40-63 μm and the product was eluted with 26% ethyl acetate in petroleum ether to afford 3-(benzo[c] [1,2,5] thiadiazol-4-ylmethyl)-1-ethyl-1-methylurea (27.00 g) as a yellow gum.
$^1$H NMR (400 MHz, DMSO-d$_6$; D$_2$O) δ 7.94 (d, 1H, J=8.80 Hz), 7.67 (d, 1H, J=6.80 Hz), 7.42 (dd, 1H, J=7.20, 1.20 Hz), 4.72 (s, 2H), 3.25 (d, 2H, J=7.20 Hz), 2.83 (s, 3H), 1.02 (t, 3H, J=7.20 Hz);
MS: m/z 251.1 (M+1).

Example 5, Step 2: Preparation of 3-(2, 3-diaminobenzyl)-1-ethyl-1-methylurea

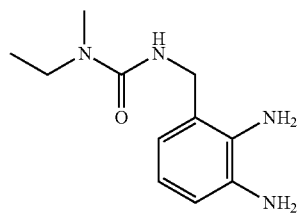 [SMILES: CCN(C)C(=O)NCc1cccc(N)c1N]

To a de-gassed solution of 3-(benzo[c] [1,2,5] thiadiazol-4-ylmethyl)-1-ethyl-1-methylurea (from Example 5, Step 1) (27.00 g, 108.00 mmol) in dry methanol (1500 mL) was added Raney nickel (54.00 g, 200% w/w, pre-washed five times with dry methanol) and the resultant reaction mixture was stirred under a hydrogen atmosphere at bladder pressure (approx. 1.5 kg/cm$^2$) at ambient temperature for 24 h. The reaction mixture was filtered over a celite bed and the bed was washed with methanol (3×2500 mL). The combined filtrates were concentrated to afford 3-(2, 3-diaminobenzyl)-1-ethyl-1-methylurea (22.00 g) as a dark-green solid, which was used in the next step without further purification.
$^1$H NMR (400 MHz, DMSO-d$_6$: D$_2$O) δ 6.45 (d, 1H, J=7.42 Hz), 6.40 (d, 1H, J=7.24 Hz), 7.33 (t, 1H, J=7.50 Hz), 4.07 (s, 2H), 3.20 (d, 2H, J=7.00 Hz), 2.75 (s, 3H), 0.97 (t, 3H, J=7.00 Hz);
MS: m/z 223.3 (M+1).

Example 5, Step 3: Preparation of 2-({[2-amino-6-({[ethyl(methyl)carbamoyl]amino}methyl)phenyl]carbamothioyl}amino)-2-[3-(trifluoromethyl)phenyl]propyl 2,2-dimethylpropanoate and 2-({[2-amino-3-({[ethyl(methyl)carbamoyl]amino}methyl)phenyl]carbamothioyl}amino)-2-[3-(trifluoromethyl)phenyl]propyl 2,2-dimethylpropanoate (Mixture of Regioisomers)

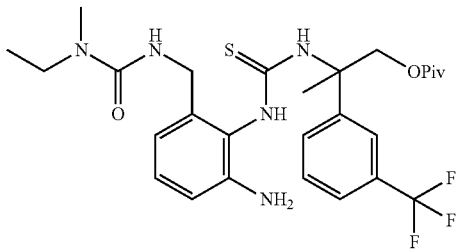

-continued

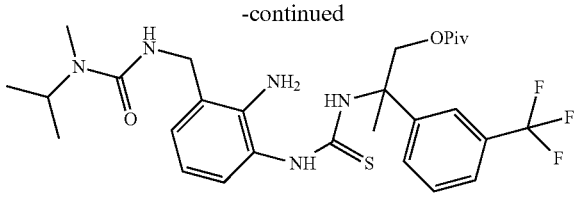

To a solution of 3-(2, 3-diaminobenzyl)-1-ethyl-1-methylurea (from Example 5, Step 2) (9.00 g, 40.40 mmol) in a mixture of solvents dichloromethane:methanol (4:1, 200 mL) was added 2-isothiocyanato-2-[3-(trifluoromethyl)phenyl]propyl 2,2-dimethylpropanoate (from Example 1, Step 7) (14.00 g, 40.50 mmol) and the mixture was stirred at ambient temperature for 48 h. The reaction mass was concentrated to afford a brown gum (23.00 g), which was purified by chromatography on a Grace instrument using 120.0 g pre-packed flash cartridge filled with normal phase silica gel 60° A, 40-63 μm and the product was eluted with 5% methanol in chloroform to afford 2-({[2-amino-6-({[ethyl(methyl)carbamoyl]amino}methyl)phenyl]carbamothioyl}amino)-2-[3-(trifluoromethyl)phenyl]propyl 2,2-dimethylpropanoate and 2-({[2-amino-3-({[ethyl(methyl)carbamoyl]amino}methyl)phenyl]carbamothioyl}amino)-2-[3-(trifluoromethyl)phenyl]propyl 2,2-dimethylpropanoate (as a 4:1 mixture of regioisomers) (17.00 g) as a yellow solid.

MS: m/z 568.3 (M+1).

Example 5, Step 4: Preparation of 2-{[4-({[ethyl(methyl)carbamoyl]amino}methyl)-1H-1,3-benzodiazol-2-yl]amino}-2-[3-(trifluoromethyl)phenyl]propyl 2,2-dimethylpropanoate

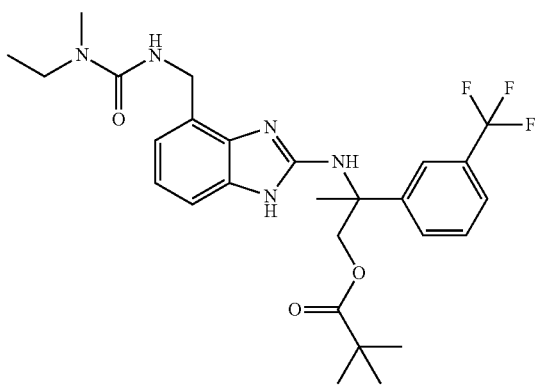 [SMILES: CCN(C)C(=O)NCc1cccc2[nH]c(NC(C)(COC(=O)C(C)(C)C)c3cccc(C(F)(F)F)c3)nc12]

Starting with 2-({[2-amino-6-({[ethyl(methyl)carbamoyl]amino}methyl)phenyl]carbamothioyl}amino)-2-[3-(trifluoromethyl)phenyl]propyl 2,2-dimethylpropanoate and 2-({[2-amino-3-({[ethyl(methyl)carbamoyl]amino}methyl)phenyl]carbamothioyl}amino)-2-[3-(trifluoromethyl)phenyl]propyl 2,2-dimethylpropanoate (as a 4:1 mixture of regioisomers) (from Example 5 step 3) the procedure described in Example 1 step 15 was used to afford the product 2-{[4-({[ethyl(methyl)carbamoyl]amino}methyl)-1H-1,3-benzodiazol-2-yl]amino}-2-[3-(trifluoromethyl)phenyl]propyl 2,2-dimethylpropanoate (11.50 g) as an off-white solid.

$^1$H NMR (400 MHz, DMSO-d$_6$: D$_2$O) δ 7.82 (s, 1H), 7.77 (d, 1H, J=8.00 Hz), 7.57 (d, 2H, J=11.20 Hz), 6.97 (d, 1H, J=10.40 Hz), 6.79 (t, 1H, J=9.60 Hz), 6.73 (t, 1H, J=11.60 Hz), 4.49 (d, 2H, J=11.20 Hz), 4.28 (s, 2H), 3.23 (t, 1H, J=9.60 Hz), 3.14 (t, 1H, J=4.80 Hz), 2.77 (s, 3H), 1.89 (s, 3H), 1.01 (s, 9H), 0.96 (t, 3H, J=9.20 Hz);

MS: m/z 534.2 (M+1).

Example 5: Preparation of 1-ethyl-3-((2-((1-hydroxy-2-(3-(trifluoromethyl) phenyl) propan-2-yl) amino)-1H-benzo[d]imidazol-4-yl) methyl)-1-methylurea

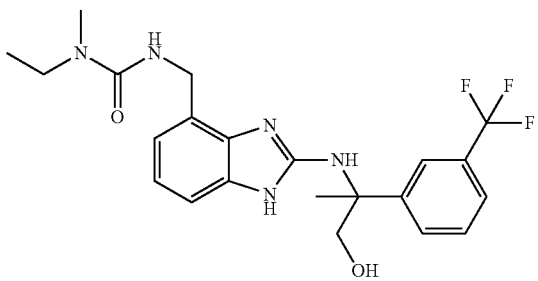 [SMILES: CCN(C)C(=O)NCc1cccc2[nH]c(NC(C)(CO)c3cccc(C(F)(F)F)c3)nc12]

To a solution of 2-{[4-({[ethyl(methyl)carbamoyl]amino}methyl)-1H-1,3-benzodiazol-2-yl]amino}-2-[3-(trifluoromethyl)phenyl]propyl 2,2-dimethylpropanoate (from Example 5, Step 4) (10.00 g, 18.70 mmol) in methanol (200 mL) solvent was added sodium hydroxide pellets (2.25 g, 56.20 mmol) and the mixture was stirred at ambient temperature for 2 h. The reaction mass was concentrated to remove the solvent methanol and the residue was dissolved with water (100 mL) and it had extracted with ethyl acetate (4×500 mL). The combined organic layer was washed with brine (100 mL), dried over sodium sulphate, filtered and concentrated to afford a brown gum (9.00 g). This purified by chromatography on a Grace instrument using 220.0 g pre-packed flash cartridge filled with normal phase silica gel 60° A, 40-63 μm and the product was eluted with 5-7% methanol in chloroform to afford 1-ethyl-3-((2-((1-hydroxy-2-(3-(trifluoromethyl) phenyl) propan-2-yl) amino)-1H-benzo[d]imidazol-4-yl) methyl)-1-methylurea (8.00 g) as an off-white solid.

$^1$H NMR (400 MHz, AcOH-d$_4$) δ 7.87 (s, 1H), 7.84 (d, 1H, J=8.00 Hz), 7.67 (d, 1H, J=7.60 Hz), 7.60 (t, 1H, J=8.00 Hz), 7.33 (d, 1H, J=8.00 Hz), 7.17 (t, 1H, J=8.00 Hz), 7.11 (d, 1H, J=7.20 Hz), 4.46 (q, 2H, J=15.20 Hz), 4.25 (d, 1H, J=12.00 Hz), 4.06 (d, 1H, J=12.00 Hz), 3.27 (d, 2H, J=7.20 Hz), 2.87 (s, 3H), 1.91 (s, 3H), 1.08 (t, 3H, J=6.80 Hz);

MS: m/z 450.1 (M+1).

The above product was resolved into its two enantiomers by Chiral SFC using the method; Column: Chiralcel OX—H; Flow rate: 3.0 mL/min, Co-Solvent: 30%; Co-solvent Name: 0.5% isopropyl amine in isopropyl alcohol; injected Volume: 15.0 μL; Out let pressure: 100 bar; Temperature: 35° C. to obtain the two enantiomers 5a and 5b.

Example 5a: (+)-1-ethyl-3-((2-((1-hydroxy-2-(3-(trifluoromethyl) phenyl) propan-2-yl) amino)-1H-benzo[d] imidazol-4-yl) methyl)-1-methylurea The (+) enantiomer was the first to elute-off the column.

$^1$H NMR (400 MHz, AcOH-d$_4$) δ 7.87 (s, 1H), 7.82 (d, 1H, J=8.00 Hz), 7.67 (d, 1H, J=7.60 Hz), 7.60 (t, 1H, J=7.60 Hz), 7.33 (d, 1H, J=7.60 Hz), 7.17 (t, 1H, J=7.60 Hz), 7.10 (d, 1H, J=7.20 Hz), 4.48 (q, 2H, J=15.20 Hz), 4.24 (d, 1H,

J=12.00 Hz), 4.06 (d, 1H, J=11.60 Hz), 3.27 (d, 2H, J=7.20 Hz), 2.84 (s, 3H), 1.90 (s, 3H), 1.08 (t, 3H, J=7.20 Hz);
MS: m/z 450.3 (M+1);
[α] D $^{23.8}$ (+) 71.16 (MeOH, c=1.0).

Example 5b: (−)-1-ethyl-3-((2-((1-hydroxy-2-(3-(trifluoromethyl) phenyl) propan-2-yl) amino)-1H-benzo [d] imidazol-4-yl) methyl)-1-methylurea The (−) enantiomer was the second to elute-off the column.
$^1$H NMR (400 MHz, AcOH-d$_4$) δ 7.87 (s, 1H), 7.84 (d, 1H, J=7.60 Hz), 7.67 (d, 1H, J=7.60 Hz), 7.58 (t, 1H, J=7.60 Hz), 7.33 (d, 1H, J=7.60 Hz), 7.17 (t, 1H, J=7.60 Hz), 7.10 (d, 1H, J=7.60 Hz), 4.50 (q, 2H, J=14.80 Hz), 4.23 (d, 1H, J=12.00 Hz), 4.06 (d, 1H, J=11.60 Hz), 3.27 (d, 2H, J=6.80 Hz), 2.84 (s, 3H), 1.90 (s, 3H), 1.08 (t, 3H, J=7.20 Hz);
MS: m/z 450.3 (M+1);
[α] D $^{23.7}$ (−) 61.12 (MeOH, c=1.0).

Example 6: Preparation of 3-((5-fluoro-2-((1-hydroxy-2-(3-(trifluoromethyl) phenyl) propan-2-yl) amino)-1H-benzo[d]imidazol-4-yl) methyl)-1, 1-dimethylurea

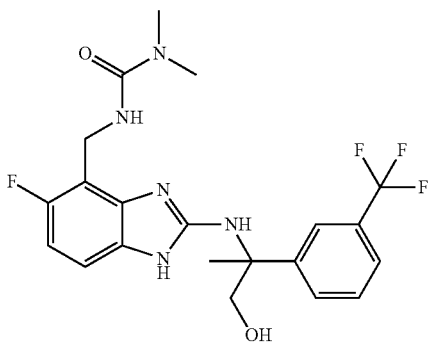 [SMILES: CN(C)C(=O)NCc1c(F)ccc2[nH]c(NC(C)(CO)c3cccc(C(F)(F)F)c3)nc12]

Example 6, Step 1: Preparation of 5-fluoro-4-methylbenzo[c] [1, 2, 5] thiadiazole

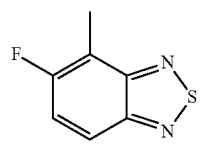

To a solution of 4-fluoro-3-methylbenzene-1, 2-diamine (commercially available) (4.00 g, 28.50 mmol) in dry pyridine (24 mL) was added thionyl chloride (5.00 mL, d=1.64 g/cm$^3$, 68.50 mmol) drop wise over a period of 60 min at 0° C., during this addition the internal temperature was kept below 45° C. and then the reaction mixture was stirred at ambient temperature for 3 h. The reaction mixture was quenched with con. hydrochloric acid (30 mL) by dropwise addition until the pH of the reaction adjusted to 2-3, during this stage internal temperature was kept below 65° C. The reaction mixture was diluted with water (100 mL) and ethyl acetate (200 mL) and stirred for 2 h. Then it was filtered through a celite bed and the organic layer was separated and the aqueous layer was extracted further with ethyl acetate (3×500 mL). The combined organic layer was washed with brine solution (50 mL), dried over sodium sulphate, filtered and concentrated to afford 5-fluoro-4-methylbenzo[c] [1,2, 5]thiadiazole (4.50 g) as a brown liquid, which was used in the next step without further purification.
$^1$H NMR (400 MHz, DMSO-d$_6$) δ 7.82 (d, 1H, J=4.80 Hz), 7.43 (t, 1H, J=9.60 Hz), 2.65 (s, 3H);
MS: m/z 169.0 (M+1).

Example 6, Step 2: Preparation of 4-(bromomethyl)-5-fluorobenzo[c] [1, 2, 5]thiadiazole

To a stirred solution of 5-fluoro-4-methylbenzo[c] [1,2,5] thiadiazole (from Example 6, Step 1) (4.50 g, 26.80 mmol) under a nitrogen atmosphere in dry chloroform (100 mL) was added benzyl peroxide (0.130 g, 0.535 mmol) followed by N-bromosuccinimide (5.24 g, 29.40 mmol) and the reaction mixture was refluxed for 16 h. The reaction mass was cooled and the succinimide solid was removed by filtration. The filtrate was concentrated to afford a brown semi solid (7.00 g). Crystallization in ethyl acetate (50 mL) was carried out and the solid that formed was filtered, dried under high-vacuum to afford 4-(bromomethyl)-5-fluorobenzo[c] [1, 2, 5] thiadiazole (3.50 g) as a yellow solid, which was used in the next step without further purification.
$^1$H NMR (400 MHz, DMSO-d$_6$) δ 8.00 (d, 1H, J=9.52 Hz), 7.47 (t, 1H, J=9.40 Hz), 5.00 (s, 2H);

Example 6, Step 3: Preparation of tert-butyl N-[(tert-butoxy)carbonyl]-N-[(5-fluoro-2,1,3-benzothiadiazol)ethyl]carbamate

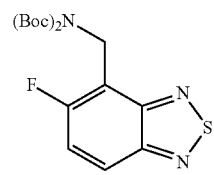

To a solution of 4-(bromomethyl)-5-fluorobenzo[c] [1,2, 5] thiadiazole (from Example 6, Step 2) (2.50 g, 10.10 mmol) under nitrogen atmosphere in dry tetrahydrofuran (50 mL) was added potassium carbonate (7.00 g, 50.60 mmol) followed by tert-butyl N-tert-butoxycarbonyl carbamate (commercially available) (2.20 g, 10.10 mmol) and the mixture was stirred at 70° C. for 24 h. The reaction mass was filtered to remove the inorganic solids and the filtrate was concentrated. The residue was dissolved in water (50 mL) and extracted with ethyl acetate (3×250 mL). The combined organic layer was washed with brine (30 mL), dried over sodium sulphate, filtered and concentrated to afford a yellow solid (4.00 g). This was purified by chromatography on a Grace instrument using 40.0 g pre-packed flash cartridge filled with normal phase silica gel 60° A, 40-63 μm and the product was eluted with 1-2% ethyl acetate in hexane to afford tert-butyl N-[(tert-butoxy)carbonyl]-N-[(5-fluoro-2,1, 3-benzothiadiazol-4-yl)methyl]carbamate (3.80 g) as an off-white solid.

$^1$H NMR (400 MHz, DMSO-$d_6$) δ 8.10 (d, 1H, J=9.52 Hz), 7.72 (t, 1H, J=10.32 Hz), 5.22 (s, 2H), 1.35 (s, 18H); MS: m/z 283.0 [(M+1)-Boc].

Example 6, Step 4: Preparation of (5-fluorobenzo[c] [1, 2, 5] thiadiazol-4-yl) methanamine hydrochloride

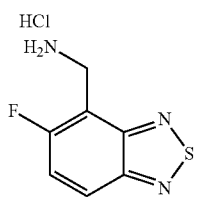 [SMILES: Cl ; NCc1c(F)ccc2nsnc12]

To a solution of tert-butyl N-[(tert-butoxy)carbonyl]-N-[(5-fluoro-2,1,3-benzothiadiazol-4-yl)methyl]carbamate (from Example 6, Step 3) (4.40 g, 11.50 mmol) in dichloromethane (100 mL) was added 4 M hydrochloric acid in 1,4 dioxane (14.50 mL, 57.5 mmol) at 0° C. and then stirred at ambient temperature for 16 h. The reaction mass was concentrated under reduced pressure to afford a yellow solid (3.00 g). This was triturated with hexane (2×100 mL), the supernatant layer was decanted and dried to afford (5-fluorobenzo[c] [1, 2, 5] thiadiazol-4-yl) methanamine hydrochloride (2.50 g) as a white solid, which was used in the next step without further purification.

$^1$H NMR (400 MHz, DMSO-$d_6$: $D_2O$) δ 8.20 (d, 1H, J=12.00 Hz), 7.77 (t, 1H, J=8.00 Hz), 4.47 (s, 2H); MS: m/z 184.1 [(M+1)–HCl].

Example 6, Step 5: Preparation of 3-((5-fluorobenzo[c] [1, 2, 5] thiadiazol-4-yl)methyl)-1, 1-dimethylurea

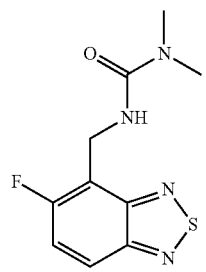 [SMILES: CN(C)C(=O)NCc1c(F)ccc2nsnc12]

To a solution of afford (5-fluorobenzo[c] [1,2,5] thiadiazol-4-yl) methanamine hydrochloride (from Example 6, Step 4) (2.00 g, 9.10 mmol) under nitrogen atmosphere in dry dichloromethane (50 mL) at 0° C., was added triethylamine (3.81 mL, d: 0.726 g/cm$^3$, 27.30 mmol) followed by N, N-dimethyl carbamoyl chloride (commercially available) (1.26 mL, d: 1.168 g/cm$^3$, 13.70 mmol) and the mixture was then stirred at room temperature for 2 h. The reaction mass was quenched with ice cold water (50 mL) and the aqueous layer was extracted with dichloromethane (3×200 mL). The combined organic layer was dried over sodium sulphate, filtered and concentrated to afford a yellow gum (2.50 g). This purified by chromatography on Grace instrument using 40.0 g pre-packed flash cartridge filled with normal phase silica gel 60° A, 40-63 μm and the product was eluted with 5-8% methanol in chloroform to afford 3-((5-fluorobenzo[c] [1,2,5] thiadiazol-4-yl) methyl)-1,1-dimethylurea (1.50 g) as a pale yellow liquid.

$^1$H NMR (400 MHz, DMSO-$d_6$: $D_2O$) δ 8.04 (d, 1H, J=9.60 Hz), 7.66 (t, 1H, J=9.60 Hz), 4.68 (s, 2H), 2.74 (s, 6H);
MS: m/z 255.0 (M+1).

Example 6, Step 6: Preparation of 3-(2, 3-diamino-6-fluorobenzyl)-1, 1-dimethylurea

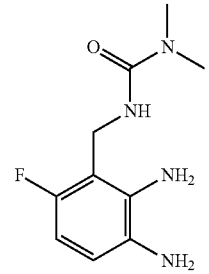

To a de-gassed solution of 3-((5-fluorobenzo[c] [1,2,5] thiadiazol-4-yl) methyl)-1,1-dimethylurea (from Example 6, Step 5) (1.50 g, 5.90 mmol) in dry methanol (60 mL) was added Raney nickel (3.00 g, 200% w/w, pre-washed five times with dry methanol) and the resultant reaction mixture was stirred under a hydrogen atmosphere at bladder pressure (Approx. 1.5 kg/cm$^2$) at ambient temperature for 16 h. Then the reaction mixture was filtered through a celite bed and the bed was washed with methanol (3×200 mL). The combined filtrates were concentrated to afford 3-(2, 3-diamino-6-fluorobenzyl)-1, 1-dimethylurea (1.20 g) as a dark green solid, which was used in the next step without further purification.

1H NMR (400 MHz, CD$_3$OD) δ 6.59 (t, 1H, J=7.80 Hz), 6.27 (t. 1H, J=9.20 Hz), 4.36 (s, 2H), 2.85 (s, 6H);
MS: m/z 227.2 (M+1).

Example 6, Step 7: Preparation of 2-{[(6-amino-2-{[(dimethylcarbamoyl)amino]methyl}-3-fluorophenyl)carbamothioyl]amino}-2-[3-(trifluoromethyl) phenyl]propyl 2,2-dimethylpropanoate and 2-{[(2-amino-3-{[(dimethylcarbamoyl)amino]methyl}-4-fluorophenyl)carbamothioyl]amino}-2-[3-(trifluoromethyl)phenyl]propyl 2,2-dimethylpropanoate. (Mixture of Regioisomers)

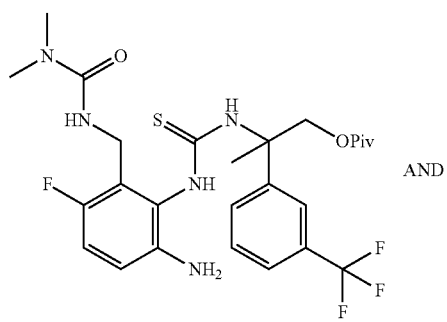

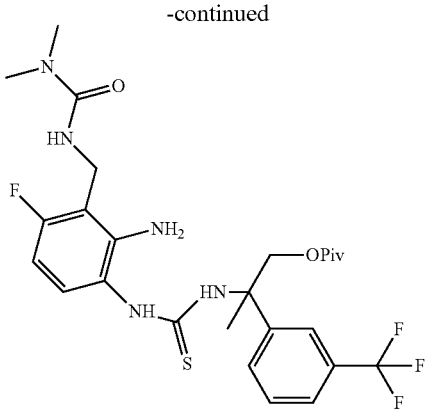

To a solution 3-(2, 3-diamino-6-fluorobenzyl)-1, 1-dimethylurea (from Example 6, Step 6) (0.270 g, 1.19 mmol) in a mixture of solvents dichloromethane:methanol (4:1, 20 mL) was added 2-isothiocyanato-2-[3-(trifluoromethyl)phenyl]propyl 2,2-dimethylpropanoate (from Example 1, Step 7) (0.412 g, 1.19 mmol) and the mixture was stirred at ambient temperature for 48 h. The reaction mass was concentrated to afford a brown gum (0.682). Which was purified by chromatography on a Grace instrument using 24.0 g pre-packed flash cartridge filled with normal phase silica gel 60° A, 40-63 μm and the product was eluted with 80-85% ethyl acetate in hexane to afford 2-{[(6-amino-2-{[(dimethylcarbamoyl)amino]methyl}-3-fluorophenyl)carbamothioyl]amino}-2-[3-(trifluoromethyl)phenyl]propyl 2,2-dimethylpropanoate and 2-{[(2-amino-3-{[(dimethylcarbamoyl)amino]methyl}-4-fluorophenyl)carbamothioyl]amino}-2-[3-(trifluoromethyl)phenyl]propyl 2,2-dimethylpropanoate (as a 1: 1 mixture of regioisomers) (0.460 g) as a yellow solid.

MS: m/z 572.2 (M+1).

Example 6, Step 8: Preparation of 2-[(4-{[(dimethylcarbamoyl)amino]methyl}-5-fluoro-1H-1,3-benzodiazol-2-yl)amino]-2-[3-(trifluoromethyl)phenyl]propyl 2,2-dimethylpropanoate

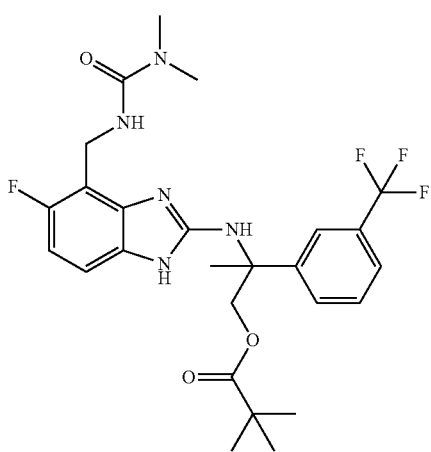 [SMILES: CN(C)C(=O)NCc1c(F)ccc2[nH]c(NC(C)(COC(=O)C(C)(C)C)c3cccc(C(F)(F)F)c3)nc12]

To a solution of 2-{[(6-amino-2-{[(dimethylcarbamoyl)amino]methyl}-3-fluorophenyl)carbamothioyl]amino}-2-[3-(trifluoromethyl)phenyl]propyl 2,2-dimethylpropanoate and 2-{[(2-amino-3-{[(dimethylcarbamoyl)amino]methyl}-4-fluorophenyl)carbamothioyl]amino}-2-[3-(trifluoromethyl)phenyl]propyl 2,2-dimethylpropanoate (as a 1: 1 mixture of regioisomers) (from Example 6, Step 7) (0.460 g, 0.805 mmol) under nitrogen atmosphere in dry methanol (20 mL) was added iodoacetic acid (0.195 g, 1.05 mmol) and the mixture was stirred at 70° C. for 1 h. The reaction mass was concentrated to remove the methanol solvent and the residue was diluted with 10% aqueous sodium bicarbonate solution (30 mL), and extracted with ethyl acetate (3×150 mL). The combined organic layer was washed with brine solution (30 mL), dried over sodium sulphate, filtered and concentrated to afford a brown gum (0.450 g). It was purified by chromatography on a Grace instrument using 24.0 g pre-packed flash cartridge filled with normal phase silica gel 60° A, 40-63 μm and the product was eluted with 3-5% methanol in chloroform to afford 2-[(4-{[(dimethylcarbamoyl)amino]methyl}-5-fluoro-1H-1,3-benzodiazol-2-yl)amino]-2-[3-(trifluoromethyl)phenyl]propyl 2,2-dimethylpropanoate (0.380 g) as an off-white solid.

1H NMR (400 MHz, DMSO-$d_6$) δ 10.69 (s, 1H), 7.78 (s, 2H), 7.61 (t, 1H, J=10.80 Hz), 7.54 (d, 1H, J=10.00 Hz), 7.50 (s, 11H), 7.00 (d, 11H, J=10.80 Hz), 6.92 (d, 11H, J=6.00 Hz), 6.65 (t, 1H, J=15.20 Hz), 4.57 (q, 2H, J=8.00 Hz), 4.35 (t, 2H, J=13.20 Hz), 2.82 (s, 6H), 1.83 (s, 3H), 1.02 (s, 9H);

MS: m/z 538.3 (M+1).

Example 6: Preparation of 3-((5-fluoro-2-((1-hydroxy-2-(3-(trifluoromethyl) phenyl) propan-2-yl) amino)-1H-benzo[d]imidazol-4-yl) methyl)-1, 1-dimethylurea

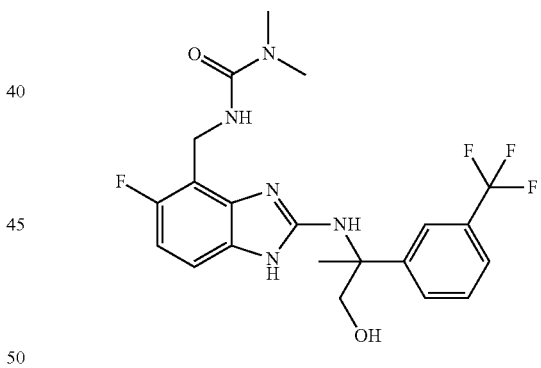

To a solution of 2-[(4-{[(dimethylcarbamoyl)amino]methyl}-5-fluoro-1H-1,3-benzodiazol-2-yl)amino]-2-[3-(trifluoromethyl)phenyl]propyl 2,2-dimethylpropanoate (from Example 6, Step 8) (0.160 g, 0.298 mmol) in methanol (10 mL) was added sodium hydroxide pellets (0.060 g, 1.49 mmol) and the mixture was stirred at ambient temperature for 1 h. The reaction mixture was concentrated to remove the solvent methanol and the residue was dissolved with water (20 mL) and extracted with ethyl acetate (4×50 mL). The combined organic layer was washed with brine (20 mL), dried over sodium sulphate, filtered and concentrated to afford a brown gum (0.140 g). This was purified by chromatography on a Grace instrument using 12.0 g pre-packed flash cartridge filled with normal phase silica gel 60° A, 40-63 μm and the product was eluted with 5-8% methanol in chloroform to afford 3-((5-fluoro-2-((1-hydroxy-2-(3-(trifluoromethyl) phenyl) propan-2-yl) amino)-1H-benzo[d]imidazol-4-yl) methyl)-1, 1-dimethylurea (0.090 g) as an off-white solid.

$^1$H NMR (400 MHz, AcOH-d$_4$) δ 7.88 (s, 1H), 7.83 (d, 1H, J=7.84 Hz), 7.67 (d, 1H, J=7.72 Hz), 7.61 (d, 11H, J=7.76 Hz), 7.34 (d, 1H, J=7.32 Hz), 6.98 (t, 1H, J=9.92 Hz), 4.48 (s, 2H), 4.22 (d, 1H, J=11.84 Hz), 4.03 (d, 1H, J=11.90 Hz), 2.85 (s, 6H), 1.91 (s, 3H);

MS: m/z 454.1 (M+1).

The above product was resolved into its two enantiomers by Chiral SFC using the method; Column: RR-Whelk-01; Flow rate: 3.0 mL/min, Co-Solvent: 40%; Co-solvent Name: 0.5% isopropyl amine in isopropyl alcohol; injected Volume: 7.0 μL; Out let pressure: 100 bar; Temperature: 35° C. to obtain the two enantiomers 6a and 6b.

Example 6a: (+)-3-((5-fluoro-2-((1-hydroxy-2-(3-(trifluoromethyl) phenyl) propan-2-yl) amino)-1H-benzo[d] imidazol-4-yl) methyl)-1, 1-dimethylurea The (+) enantiomer was the first to elute-off the column.

$^1$H NMR (400 MHz, AcOH-d$_4$) δ 7.88 (s, 1H), 7.83 (d, 1H, J=8.08 Hz), 7.67 (d, 1H, J=7.72 Hz), 7.60 (d, 1H, J=8.00 Hz), 7.32 (d, 1H, J=8.00 Hz), 6.98 (t, 1H, J=10.24 Hz), 4.48 (s, 2H), 4.23 (d, 1H, J=12.04 Hz), 4.03 (d, 1H, J=11.90 Hz), 2.84 (s, 6H), 1.91 (s, 3H);

MS: m/z 454.2 (M+1);

[α] D $^{21.2}$ (+) 18.40 (MeOH, c=0.5).

Example 6b: (−)-3-((5-fluoro-2-((1-hydroxy-2-(3-(trifluoromethyl) phenyl) propan-2-yl) amino)-1H-benzo[d] imidazol-4-yl) methyl)-1, 1-dimethylurea The (−) enantiomer was the second to elute-off the column.

$^1$H NMR (400 MHz, AcOH-d$_4$) δ 7.88 (s, 1H), 7.83 (d, 1H, J=8.04 Hz), 7.67 (d, 1H, J=7.84 Hz), 7.60 (t, 1H, J=7.90 Hz), 7.34 (d, 1H, J=8.80 Hz), 6.98 (t, 1H, J=10.28 Hz), 4.48 (s, 2H), 4.22 (d, 1H, J=11.90 Hz), 4.04 (d, 1H, J=11.80 Hz), 2.85 (s, 6H), 1.91 (s, 3H);

MS: m/z 454.2 (M+1);

[α] D $^{21.3}$ (−) 14.80 (MeOH, c=0.5).

Example 7: Preparation of 1-cyclopropyl-3-((2-((1-hydroxy-2-(3-(trifluoromethyl) phenyl) propan-2-yl) amino)-1H-benzo[d]imidazol-4-yl) methyl) urea

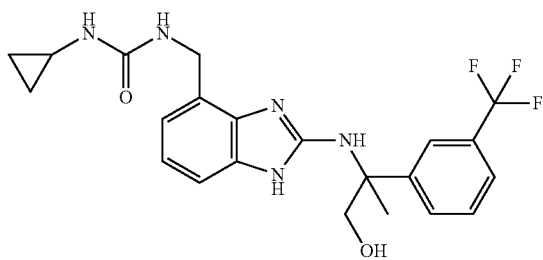 [SMILES: CC(CO)(Nc1nc2c(CNC(=O)NC3CC3)cccc2[nH]1)c1cccc(C(F)(F)F)c1]

Example 7, Step 1: Preparation of 1-(benzo[c] [1, 2, 5] thiadiazol-4-ylmethyl)-3-cyclopropyl urea

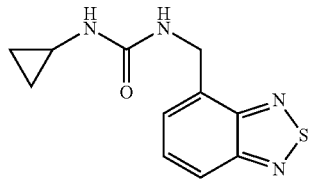 [SMILES: O=C(NCc1cccc2nsnc12)NC1CC1]

To a solution of 2,1,3-benzothiadiazol-4-ylmethanamine hydrochloride (from Example 1, Step 11) (5.00 g, 24.80 mmol) under nitrogen atmosphere in dry dichloromethane (100 mL), cooled to at 0° C., was added triethylamine (10.40 mL, d: 0.726 g/cm$^3$, 74.40 mmol) followed by isocyanato-cyclopropane (2.90 g, 34.80 mmol) and the mixture was then stirred at room temperature for 1 h. The reaction mass was diluted with ice cold water (50 mL) and the precipitate that formed was filtered and washed with dichloromethane (50 mL). The solid was dried under vacuum to afford 1-(benzo[c] [1, 2, 5] thiadiazol-4-ylmethyl)-3-cyclopropyl urea (3.80 g) as an off-white solid, which was used in the next step without further purification.

$^1$H NMR (400 MHz, DMSO-d$_6$) δ 7.96 (d, 1H, J=8.80 Hz), 7.70 (t, 1H, J=8.80 Hz), 7.48 (d, 1H, J=6.80 Hz), 6.59 (s, 1H), 6.40 (s, 1H), 4.72 (d, 2H, J=5.60 Hz), 2.46 (q, 1H, J=3.60 Hz), 0.59 (q, 2H, J=6.40 Hz), 0.37 (t, 2H, J=7.60 Hz);

MS: m/z 249.1 (M+1).

Example 7, Step 2: Preparation of 1-cyclopropyl-3-(2, 3-diaminobenzyl) urea

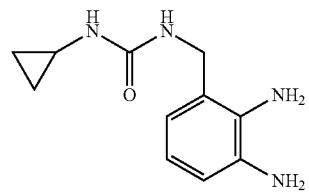 [SMILES: Nc1cccc(CNC(=O)NC2CC2)c1N]

To a de-gassed solution of 1-(benzo[c] [1, 2, 5] thiadiazol-4-ylmethyl)-3-cyclopropyl urea (from Example 7, Step 1) (3.80 g, 15.30 mmol) in dry methanol (150 mL) was added Raney nickel (7.60 g, 200% w/w, pre-washed five times with dry methanol) and the resultant reaction mixture was stirred under a hydrogen atmosphere at bladder pressure (Approx. 1.5 kg/cm$^2$) at ambient temperature for 24 h. Then the reaction mixture was filtered over a celite bed and the bed was washed with methanol (3×1000 mL). The combined filtrates were concentrated to afford 1-cyclopropyl-3-(2, 3-diaminobenzyl) urea (3.20 g) as a brown solid, which was used in the next step without further purification.

$^1$H NMR (400 MHz, CD$_3$OD) δ 6.69 (d, 1H, J=7.28 Hz), 6.63 (t, 1H, J=6.60 Hz), 6.57 (d, 1H, J=7.48 Hz), 4.29 (s, 2H), 2.47 (s, 1H), 0.69 (d, 2H, J=5.20 Hz), 0.46 (s, 2H);

MS: m/z 221.2 (M+1).

Example 7, Step 3: Preparation of 2-{[(2-amino-3-{[(cyclopropylcarbamoyl)amino]methyl}phenyl)carbamothioyl]amino}-2-[3-(trifluoromethyl)phenyl]propyl 2,2-dimethylpropanoate and 2-{[(2-amino-6-{[(cyclopropylcarbamoyl)amino]methyl}phenyl)carbamothioyl]amino}-2-[3-(trifluoromethyl)phenyl]propyl 2,2-dimethylpropanoate (Mixture of regioisomers)

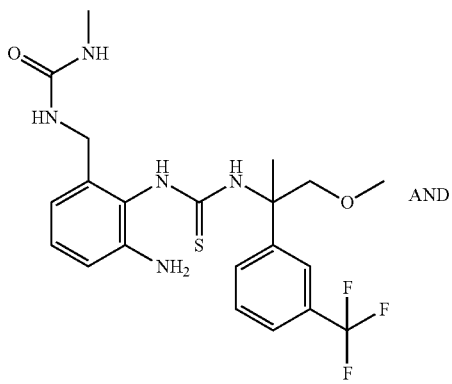

AND

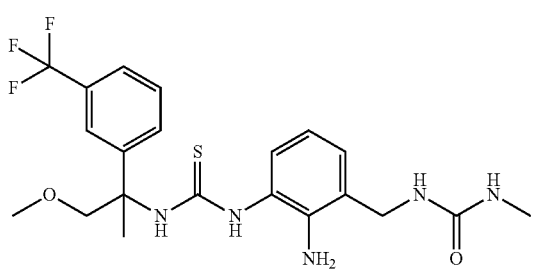

A solution of 1-cyclopropyl-3-(2, 3-diaminobenzyl) urea (from Example 7, Step 2) (0.250 g, 1.13 mmol) and 2-isothiocyanato-2-[3-(trifluoromethyl)phenyl]propyl 2,2-dimethylpropanoate (from Example 1, Step 7) (0.390 g, 1.13 mmol) in a mixture of solvents dichloromethane:methanol (4:1, 10.0 mL) was stirred at ambient temperature for 16 h. The reaction mass was concentrated to afford 2-{[(2-amino-3-{[(cyclopropylcarbamoyl)amino]methyl}phenyl)carbamothioyl]amino}-2-[3-(trifluoromethyl)phenyl]propyl 2,2-dimethylpropanoate and 2-{[(2-amino-6-{[(cyclopropylcarbamoyl)amino]methyl}phenyl)carbamothioyl]amino}-2-[3-(trifluoromethyl)phenyl]propyl 2,2-dimethylpropanoate (as a 1:1 mixture of region-isomers) (0.700 g) as a brown gum, which was used in the next step without any further purification.

MS: m/z 566.2 (M+1).

Example 7, Step 4: Preparation of 2-[(4-{[(cyclopropylcarbamoyl)amino]methyl}-1H-1,3-benzodiazol-2-yl)amino]-2-[3-(trifluoromethyl)phenyl]propyl 2,2-dimethylpropanoate

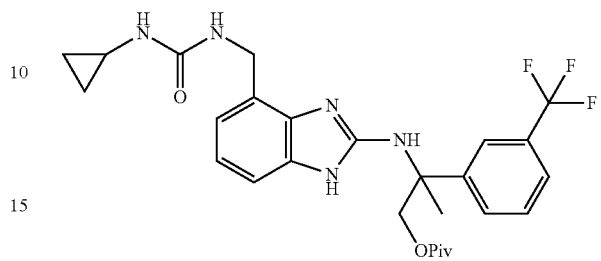

To a solution of 2-{[(2-amino-3-{[(cyclopropylcarbamoyl)amino]methyl}phenyl)carbamothioyl]amino}-2-[3-(trifluoromethyl)phenyl]propyl 2,2-dimethylpropanoate and 2-{[(2-amino-6-{[(cyclopropylcarbamoyl)amino]methyl}phenyl)carbamothioyl]amino}-2-[3-(trifluoromethyl)phenyl]propyl 2,2-dimethylpropanoate (as a 1:1 mixture of region-isomers) (from Example 7, Step 3) (0.500 g, 0.884 mmol) in methanol (20.0 mL) was added iodoacetic acid (0.329 g, 1.768 mmol) and stirred at 70° C. for 2 h. The reaction was concentrated and the residue was diluted with 10% aqueous sodium bicarbonate solution (30 mL) and the aqueous layer was extracted with ethyl acetate (3×150 mL). The combined organic layer was washed with brine (30 mL), dried over sodium sulphate, filtered and concentrated to afford 2-[(4-{[(cyclopropylcarbamoyl)amino]methyl}-1H-1,3-benzodiazol-2-yl)amino]-2-[3-(trifluoromethyl)phenyl]propyl 2,2-dimethylpropanoate (0.450 g) as a brown gum, which was used in the next step without any further purification.

MS: m/z 532.1 (M+1).

Example 7: Preparation of 1-cyclopropyl-3-((2-((1-hydroxy-2-(3-(trifluoromethyl) phenyl)propan-2-yl)amino)-1H-benzo[d]imidazol-4-yl) methyl) urea

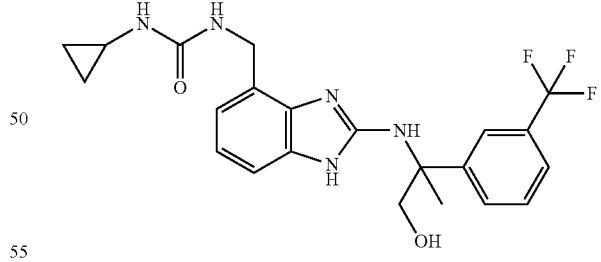

To a stirred solution of 2-[(4-{[(cyclopropylcarbamoyl)amino]methyl}-1H-1,3-benzodiazol-2-yl)amino]-2-[3-(trifluoromethyl)phenyl]propyl 2,2-dimethylpropanoate (from Example 7, Step 4) (0.450 g, 0.845 mmol) in methanol (10 mL) was added sodium hydroxide pellets (0.170 g, 4.23 mmol) and the mixture was stirred at ambient temperature for 1 h. The reaction mass was concentrated and the residue was diluted with water (30.0 mL). The aqueous layer was extracted with ethyl acetate (3×70.0 mL) and the combined organic layer was washed with brine (30.0 mL), dried over sodium sulphate, filtered and concentrated to afford (0.350 g) of a dark brown gum. This was purified by preparatory HPLC to afford 1-cyclopropyl-3-((2-((1-hydroxy-2-(3-(trifluoromethyl) phenyl) propan-2-yl) amino)-1H-benzo[d]imidazol-4-yl) methyl) urea (0.210 g) as a brown gum.

$^1$H NMR (400 MHz, AcOH-d$_4$) δ 7.84 (t, 2H, J=8.08 Hz), 7.68 (d, 1H, J=7.80 Hz), 7.61 (t, 1H, J=7.64 Hz), 7.35 (d, 1H, J=8.00 Hz), 7.21-7.15 (m, 2H), 4.52 (d, 2H, J=15.44 Hz), 4.31 (d, 1H, J=11.96 Hz), 4.09 (d, 1H, J=12.00 Hz), 2.41 (d, 1H, J=3.28 Hz), 1.88 (s, 3H), 0.72 (t, 2H, J=1.72 Hz), 0.53-0.50 (m, 2H);

MS: m/z 448.1 (M+1).

The above product was resolved into its two enantiomers by Chiral SFC using the method; Column: (S, S) WHELK-01; Flow rate: 3.0 mL/min, Co-Solvent: 30%; Co-solvent Name: 0.5% isopropyl amine in isopropyl alcohol; injected Volume: 12.0 µL; Out let pressure: 100 bar; Temperature: 35° C. to obtain the two enantiomers 7a and 7b.

Example 7a: (−)-1-cyclopropyl-3-((2-((1-hydroxy-2-(3-(trifluoromethyl)phenyl)propan-2-yl) amino)-1H-benzo[d]imidazol-4-yl)methyl)urea The (−) enantiomer had the first to elute off the column.
$^1$H NMR (400 MHz, AcOH-d$_4$) δ 7.81 (s, 1H), 7.82 (d, 1H, J=8.00 Hz), 7.67 (d, 1H, J=7.60 Hz), 7.60 (t, 1H, J=8.00 Hz), 7.33 (d, 1H, J=8.00 Hz), 7.21-7.13 (m, 2H), 4.51 (t, 2H, J=16.80 Hz), 4.29 (d, 1H, J=12.00 Hz), 4.08 (d, 1H, J=12.00 Hz), 2.41 (t, 1H, J=3.20 Hz), 1.87 (s, 3H), 0.71 (q, 2H, J=4.80 Hz), 0.51 (q, 2H, J=7.20 Hz);

MS: m/z 448.2 (M+1);
[α] D $^{22.5}$ (−)$_{16.80}$ (MeOH, c=1.0).

Example 7b: (+)-1-cyclopropyl-3-((2-((1-hydroxy-2-(3-(trifluoromethyl) phenyl) propan-2-yl) amino)-1H-benzo[d]imidazol-4-yl) methyl) urea The (+) enantiomer had the second elute off the column.
$^1$H NMR (400 MHz, AcOH-d$_4$) δ 7.86 (s, 1H), 7.82 (d, 1H, J=7.60 Hz), 7.67 (d, 1H, J=7.60 Hz), 7.60 (t, 1H, J=7.60 Hz), 7.32 (d, 1H, J=8.00 Hz), 7.21-7.13 (m, 2H), 4.51 (d, 2H, J=1.60 Hz), 4.29 (d, 1H, J=12.00 Hz), 4.08 (d, 1H, J=12.00 Hz), 2.41 (q, 1H, J=3.60 Hz), 1.87 (s, 3H), 0.72 (q, 2H, J=2.00 Hz), 0.52 (t, 2H, J=2.40 Hz);

MS: m/z 448.2 (M+1);
[α] D $^{22.5}$ (+) 15.47 (MeOH, c=1.0).

Example 8: Preparation of N-((2-((1-hydroxy-2-(3-(trifluoromethyl) phenyl) propan-2-yl) amino)-1H-benzo[d]imidazol-4-yl) methyl) azetidine-1-carboxamide

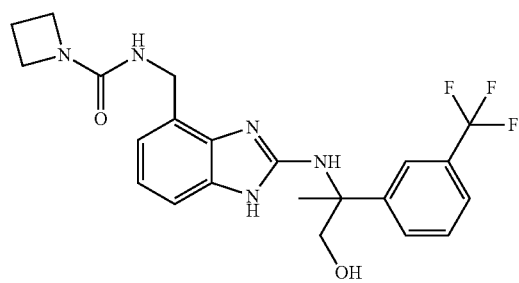 [SMILES: CC(CO)(Nc1nc2c(CNC(=O)N3CCC3)cccc2[nH]1)c1cccc(C(F)(F)F)c1]

Example 8, Step 1: Preparation of N-(benzo[c] [1,2,5] thiadiazol-4-ylmethyl) azetidine-1-carboxamide

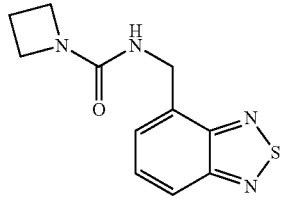 [SMILES: O=C(NCc1cccc2nsnc12)N1CCC1]

To a solution of benzo[c] [1, 2, 5] thiadiazol-4-ylmethanamine (from Example 1, Step 11, free base) (50.00 g, 303.00 mmol) in dry dichloromethane (850 mL) was added triethylamine (127.00 mL, d=0.726 g/cm$^2$, 908.00 mmol) at 0° C. and then stirred for 15 min. 4-Nitro-phenylchloroformate (90.00 g, 272.00 mmol) was added and the reaction was allowed to stir at the same temperature for 2 h. The complete consumption of starting material with the formation of new non-polar intermediate spot was confirmed by TLC. Then azetidine hydrochloride (28.00 g, 300.00 mmol) was added followed by triethylamine (38.00 mL, d=0.726 g/cm$^2$, 272.00 mmol) and then the reaction was allowed to stir at ambient temperature for 16 h. The reaction mixture was diluted with aq. sodium hydroxide solution (300 mL), extracted with dichloromethane (5×1000 mL). The combined organic extracts were dried over anhydrous sodium sulphate, filtered and evaporated to afford a yellow solid (68.00 g). This was purified by chromatography on a Grace instrument using a 330.0 g pre-packed flash cartridge filled with normal phase silica gel 60° A, 40-63 µm and the product was eluted with 10% ethyl acetate in petroleum ether to afford yellow solid. The solid was washed (to remove by-product 4-nitro phenol) with 15% ethyl acetate in petroleum ether (3×300 mL) stirred for 30 min, filtered and dried under vacuum to afford N-(benzo[c] [1,2,5]thiadiazol-4-ylmethyl) azetidine-1-carboxamide (15.0 gm) as an off white solid.

1H NMR (400 MHz, DMSO-d$_6$: D$_2$O) δ 7.94 (d, 1H, J=6.80 Hz), 7.70 (t, 1H, J=7.60 Hz), 7.48 (d, 1H, J=7.20 Hz), 4.68 (d, 2H, J=5.20 Hz), 3.87 (t, 4H, J=7.60 Hz), 2.20-2.13 (m, 2H);

MS: m/z 249.0 (M+1).

Example 8, Step 2: Preparation of N-(2, 3-diaminobenzyl) azetidine-1-carboxamide

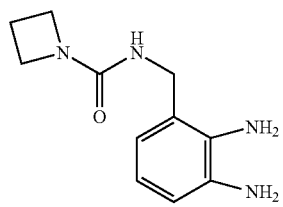 [SMILES: Nc1cccc(CNC(=O)N2CCC2)c1N]

To a de-gassed solution of N-(benzo[c] [1,2,5] thiadiazol-4-ylmethyl) azetidine-1-carboxamide (from Example 8, Step 1) (15.00 g, 60.40 mmol) in dry methanol (1200 mL) was added Raney nickel (30.0 g, 200% w/w, pre-washed five times with dry methanol) and the resultant reaction mixture was stirred under a hydrogen atmosphere at bladder pressure (Approx. 1.5 kg/cm²) at ambient temperature for 48 h. The reaction mixture was filtered through a celite bed and the bed was washed with methanol (3×2000 mL). The combined filtrates were concentrated to afford N-(2, 3-diaminobenzyl) azetidine-1-carboxamide (12.50 g) as a brown solid, which was used in the next step without further purification.

$^1$H NMR (400 MHz, DMSO-$d_6$: $D_2O$) δ 6.46 (d, 1H, J=7.24 Hz), 6.38 (d, 1H, J=6.84 Hz), 6.34 (t, 1H, J=7.40 Hz), 4.02 (d, 2H, J=4.52 Hz), 3.77 (t, 4H, J=7.40 Hz), 2.14-2.07 (m, 2H);

MS: m/z 221.1 (M+1).

Example 8, Step 3: Preparation of 2-{[(2-amino-6-{[(azetidine-1-carbonyl)amino]methyl}phenyl)carbamothioyl]amino}-2-[3-(trifluoromethyl)phenyl]propyl 2,2-dimethylpropanoate and 2-{[(2-amino-3-{[(azetidine-1-carbonyl)amino]methyl}phenyl)carbamothioyl]amino}-2-[3-(trifluoromethyl)phenyl]propyl 2,2-dimethylpropanoate (Mixture of regioisomers)

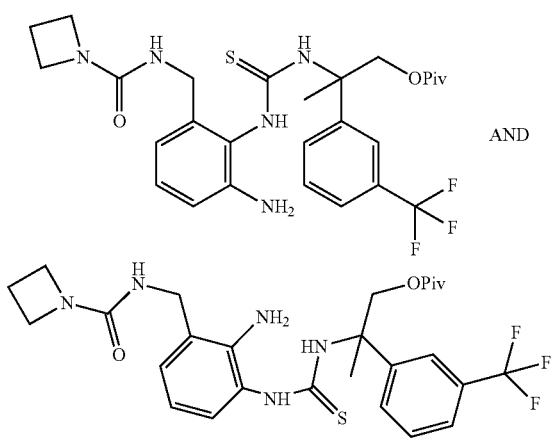

AND

To a solution of N-(2, 3-diaminobenzyl) azetidine-1-carboxamide (from Example 8, Step 2) (0.500 g, 2.00 mmol) in a mixture of solvents dichloromethane/methanol (4:1; mL) was added 2-isothiocyanato-2-[3-(trifluoromethyl)phenyl]propyl 2,2-dimethylpropanoate (from Example 1, Step 7) (1.69 g, 5.00 mmol) and the mixture was stirred at ambient temperature for 4 days. The reaction mass was concentrated to afford a brown gum (1.300 g). This was purified by chromatography on a Grace instrument using 40.0 g pre-packed flash cartridge filled with normal phase silica gel 60° A, 40-63 μm and the product was eluted with 2-3% methanol in chloroform to afford 2-{[(2-amino-6-{[(azetidine-1-carbonyl)amino]methyl}phenyl)carbamothioyl]amino}-2-[3-(trifluoromethyl)phenyl]propyl 2,2-dimethylpropanoate and 2-{[(2-amino-3-{[(azetidine-1-carbonyl)amino]methyl}phenyl)carbamothioyl]amino}-2-[3-(trifluoromethyl)phenyl]propyl 2,2-dimethylpropanoate (as a 1:1 mixture of regioisomers) (0.200 g) as a yellow solid.

MS: m/z 566.3 (M+1).

Example 8, Step 4: Preparation of 2-[(4-{[(azetidine-1-carbonyl)amino]methyl}-1H-1,3-benzodiazol-2-yl)amino]-2-[3-(trifluoromethyl)phenyl]propyl 2,2-dimethylpropanoate

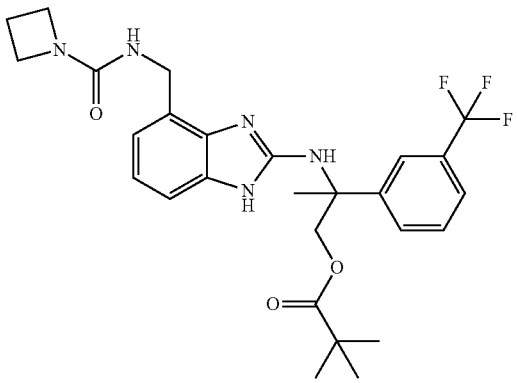 [SMILES: CC(C)(C)C(=O)OCC(C)(Nc1nc2c(CNC(=O)N3CCC3)cccc2[nH]1)c1cccc(C(F)(F)F)c1]

To a solution of 2-{[(2-amino-6-{[(azetidine-1-carbonyl)amino]methyl}phenyl)carbamothioyl]amino}-2-[3-(trifluoromethyl)phenyl]propyl 2,2-dimethylpropanoate and 2-{[(2-amino-3-{[(azetidine-1-carbonyl)amino]methyl}phenyl)carbamothioyl]amino}-2-[3-(trifluoromethyl)phenyl]propyl 2,2-dimethylpropanoate (as a 1:1 mixture of regioisomers) (from Example 8, Step 3) (0.900 g, 0.999 mmol) under nitrogen atmosphere in dry methanol (30 mL) was added iodoacetic acid (0.372 g, 2.00 mmol) and the mixture had stirred at 70° C. for 1 h. The reaction mass was concentrated to remove the methanol solvent and the residue was diluted with 10% aqueous sodium bicarbonate solution (30 mL) and extracted with ethyl acetate (3×150 mL). The combined organic layer was washed with brine solution (30 mL), dried over sodium sulphate, filtered and concentrated to afford a brown gum (0.540 g). This was purified by chromatography on a Grace instrument using 24.0 g pre-packed flash cartridge filled with normal phase silica gel 60° A, 40-63 μm and the product was eluted with 1-2% methanol in chloroform to afford 2-[(4-{[(azetidine-1-carbonyl)amino]methyl}-1H-1,3-benzodiazol-2-yl)amino]-2-[3-(trifluoromethyl)phenyl]propyl 2,2-dimethylpropanoate (0.430 g) as a yellow solid.

$^1$H NMR (400 MHz, AcOH-$d_4$) δ 7.92 (s, 1H), 7.89 (d, 1H, J=7.72 Hz), 7.72 (d, 1H, J=7.48 Hz), 7.64 (t, 1H, J=7.68 Hz), 7.31 (d, 1H, J=7.80 Hz), 7.17 (t, 1H, J=7.84 Hz), 7.10 (d, 1H, J=7.32 Hz), 4.65 (d, 1H, J=11.52 Hz), 4.57 (d, 1H, J=11.52 Hz), 4.40 (q, 2H, J=15.04 Hz), 3.96 (t, 4H, J=7.28 Hz), 2.25 (q, 2H, J=7.44 Hz), 2.05 (s, 3H), 1.16 (s, 9H);

MS: m/z 532.3 (M+1).

Example 8: Preparation of N-((2-((1-hydroxy-2-(3-(trifluoromethyl) phenyl) propan-2-yl) amino)-1H-benzo[d]imidazol-4-yl) methyl) azetidine-1-carboxamide

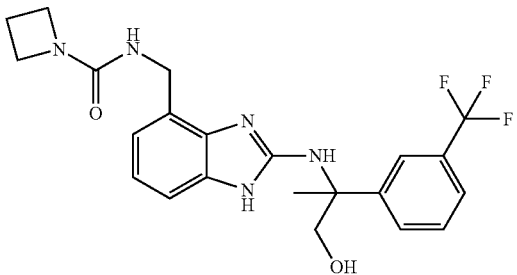 [SMILES: CC(CO)(Nc1nc2c(CNC(=O)N3CCC3)cccc2[nH]1)c1cccc(C(F)(F)F)c1]

To a solution of 2-[(4-{[(azetidine-1-carbonyl)amino]methyl}-1H-1,3-benzodiazol-2-yl)amino]-2-[3-(trifluoromethyl)phenyl]propyl 2,2-dimethylpropanoate (from Example 8, Step 4) (0.410 g, 0.756 mmol) in methanol (30 mL) solvent was added sodium hydroxide pellets (0.756 g, 19.00 mmol) and the mixture was stirred at ambient temperature for 3 h. The reaction mass was concentrated to remove the solvent methanol and the residue was dissolved with water (25 mL) and extracted with ethyl acetate (3×125 mL). The combined organic layer was washed with brine (30 mL), dried over sodium sulphate, filtered and concentrated to afford a brown gum (0.350 g). This was purified by chromatography on a Grace instrument using 24.0 g prepacked flash cartridge filled with normal phase silica gel 60° A, 40-63 μm and the product was eluted at 8% methanol in chloroform to afford N-((2-((1-hydroxy-2-(3-(trifluoromethyl) phenyl) propan-2-yl) amino)-1H-benzo[d] imidazol-4-yl) methyl) azetidine-1-carboxamide (0.320 g) as an off-white solid.

$^1$H NMR (400 MHz, CD$_3$OD) δ 7.82 (s, 1H), 7.79 (d, 1H, J=7.88 Hz), 7.69 (d, 1H, J=7.76 Hz), 7.64 (t, 1H, J=7.56 Hz), 7.27 (d, 1H, J=7.84 Hz), 7.21 (t, 1H, J=7.88 Hz), 7.14 (d, 1H, J=7.40 Hz), 4.35 (s, 2H), 4.01-3.88 (m, 6H), 2.25 (q, 2H, J=7.44 Hz), 1.90 (s, 3H);

MS: m/z 448.2 (M+1).

The above product was resolved into its two enantiomers by Chiral SFC using the method; Column: Lux-A1; Flow rate: 3.0 mL/min, Co-Solvent: 20%; Co-solvent Name: 0.5% Isopropyl amine in isopropyl alcohol; injected Volume: 15.0 μL; Out let pressure: 100 bar; Temperature: 35° C. to obtain the two enantiomers 8a and 8b.

Example 8a: (−)-N-((2-((1-hydroxy-2-(3-(trifluoromethyl) phenyl) propan-2-yl) amino)-1H-benzo[d]imidazol-4-yl) methyl) azetidine-1-carboxamide The (−) enantiomer was the first to elute off the column.

$^1$H NMR (400 MHz, AcOH-d$_4$) δ 7.87 (s, 1H), 7.84 (d, 1H, J=8.00 Hz), 7.68 (d, 1H, J=7.60 Hz), 7.61 (t, 1H, J=7.60 Hz), 7.33 (d, 1H, J=8.00 Hz), 7.17 (t, 1H, J=8.00 Hz), 7.11 (d, 1H, J=7.20 Hz), 4.45 (q, 2H, J=15.20 Hz), 4.33 (d, 1H, J=12.00 Hz), 4.09 (d, 1H, J=12.00 Hz), 4.00-3.91 (m, 4H), 2.24 (t, 2H, J=7.20 Hz), 1.87 (s, 3H);

MS: m/z 448.2 (M+1);

[α] D $^{22.0}$ (−) 38.46 (MeOH, c=0.104).

Example 8b: (+)-N-((2-((1-hydroxy-2-(3-(trifluoromethyl) phenyl) propan-2-yl) amino)-1H-benzo[d] imidazol-4-yl) methyl) azetidine-1-carboxamide The (+) enantiomer was the second to elute off the column.

$^1$H NMR (400 MHz, AcOH-d$_4$) δ 7.87 (s, 1H), 7.84 (d, 1H, J=8.40 Hz), 7.68 (d, 1H, J=8.00 Hz), 7.61 (t, 1H, J=7.60 Hz), 7.33 (d, 1H, J=8.40 Hz), 7.17 (t, 1H, J=7.60 Hz), 7.11 (d, 1H, J=7.60 Hz), 4.45 (q, 2H, J=15.20 Hz), 4.33 (d, 1H, J=12.40 Hz), 4.09 (d, 1H, J=12.00 Hz), 4.00-3.93 (m, 4H), 2.24 (t, 2H, J=7.20 Hz), 1.87 (s, 3H);

MS: m/z 448.2 (M+1);

[α] D $^{22.3}$ (+) 34.62 (MeOH, c=0.104).

Example 9: Preparation of 3-ethyl-1-{[2-({1-hydroxy-2-[3-(trifluoromethyl)phenyl]propan-2-yl}amino)-1H-1,3-benzodiazol-4-yl]methyl}urea

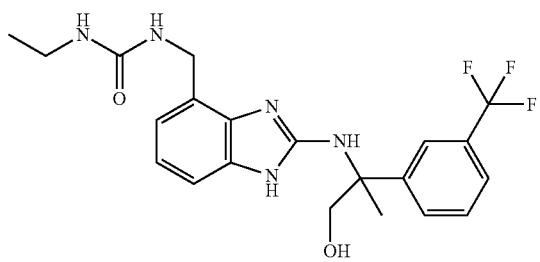 [SMILES: CCNC(=O)NCc1cccc2[nH]c(NC(C)(CO)c3cccc(C(F)(F)F)c3)nc12]

Example 9, Step 1: Preparation of tert-butyl N-[(tert-butoxy)carbonyl]-N-[(2,3-diaminophenyl)methyl]carbamate

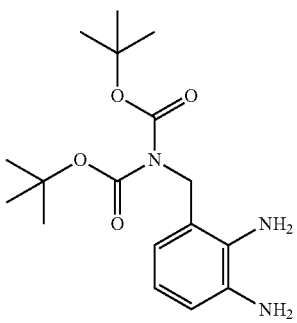 [SMILES: CC(C)(C)OC(=O)N(Cc1cccc(N)c1N)C(=O)OC(C)(C)C]

To a stirred solution of tert-butyl N-[(2,1,3-benzothiadiazol-4-yl)methyl]-N-[(tert-butoxy)carbonyl]carbamate (from Example 1, Step 10) (20.00 g, 55.00 mmol) in dry methanol (1000 mL) was added Raney nickel (40.00 g, 200% w/w, pre-washed five times with dry methanol) and the mixture was hydrogenated using balloon pressure at ambient temperature for 24 h. The above reaction mass was filtered through a celite bed and washed with methanol (5×500 ml). The combined filtrate was concentrated to afford tert-butyl N-[(tert-butoxy)carbonyl]-N-[(2,3-diaminophenyl)methyl]carbamate (14.00 g) as a dark green gum, which was used in the next step without further purification.

¹H NMR (400 MHz, DMSO-d₆: D₂O) δ 6.46 (d, 1H, J=7.20 Hz), 6.36 (t, 1H, J=7.60 Hz), 6.25 (d, 1H, J=7.20 Hz), 4.51 (s, 2H), 1.39 (s, 18H);

MS: m/z 238.2 [(M+1)-Boc].

Example 9, Step 2: Preparation of 2-({[2-amino-6-({bis[(tert-butoxy)carbonyl]amino}methyl)phenyl]carbamothioyl}amino)-2-[3-(trifluoromethyl)phenyl]propyl 2,2-dimethylpropanoate and 2-({[2-amino-3-({bis[(tert-butoxy)carbonyl]amino}methyl)phenyl]carbamothioyl}amino)-2-[3-(trifluoromethyl)phenyl]propyl 2,2-dimethylpropanoate (Mixture of regioisomers)

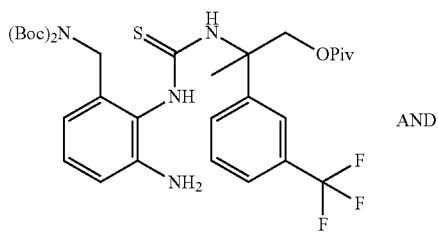

AND

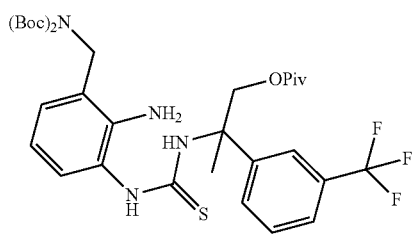

To a solution of tert-butyl N-[(tert-butoxy)carbonyl]-N-[(2,3-diaminophenyl)methyl]carbamate (from Example 9, Step 1) (2.44 g, 7.00 mmol) in a mixture of solvents acetonitrile:methanol (4:1, 16 mL) was added 2-isothiocyanato-2-[3-(trifluoromethyl)phenyl]propyl 2,2-dimethylpropanoate (from Example 1, Step 7) (2.50 g, 7.00 mmol) and the mixture was stirred at ambient temperature for 48 h. The reaction mass was concentrated to afford 2-({[2-amino-6-({bis[(tert-butoxy)carbonyl]amino}methyl)phenyl]carbamothioyl}amino)-2-[3-(trifluoromethyl)phenyl]propyl 2,2-dimethylpropanoate and 2-({[2-amino-3-({bis[(tert-butoxy)carbonyl]amino}methyl)phenyl]carbamothioyl}amino)-2-[3-(trifluoromethyl)phenyl]propyl 2,2-dimethylpropanoate (as a 3:2 mixture of regioisomers) (4.90 g) as a brown gum, which used in the next step without further purification.

MS: m/z 683.3 (M+1).

Example 9, Step 3: Preparation of 2-{[4-({bis[(tert-butoxy)carbonyl]amino}methyl)-1H-1,3-benzodiazol-2-yl]amino}-2-[3-(trifluoromethyl)phenyl]propyl 2,2-dimethylpropanoate

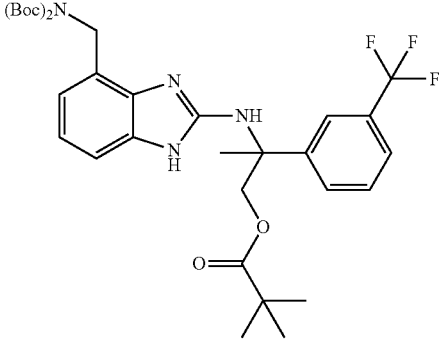

To a solution of 2-({[2-amino-6-({bis[(tert-butoxy)carbonyl]amino}methyl)phenyl]carbamothioyl}amino)-2-[3-(trifluoromethyl)phenyl]propyl 2,2-dimethylpropanoate and 2-({[2-amino-3-({bis[(tert-butoxy)carbonyl]amino}methyl)phenyl]carbamothioyl}amino)-2-[3-(trifluoromethyl)phenyl]propyl 2,2-dimethylpropanoate (as a 3:2 mixture of regioisomers) (from Example 9, Step 2) (4.90 g, 7.00 mmol) in methanol (50 mL) was added mercuric oxide (2.52 g, 11.00 mmol) followed by elemental sulphur (0.116 g, 4.00 mmol) and the whole mixture was stirred at 65° C. for 3 h. The reaction mass was filtered through a celite bed and washed with methanol (3×500 mL). The combined filtrate was concentrated to afford a brown liquid (4.70 g) which was purified by gravity column chromatography using 60-120 silica gel, and the product eluted with 5-8% ethyl acetate in hexane to afford 2-{[4-({bis[(tert-butoxy)carbonyl]amino}methyl)-1H-1,3-benzodiazol-2-yl]amino}-2-[3-(trifluoromethyl)phenyl]propyl 2,2-dimethylpropanoate (2.80 g) as a yellow solid.

¹H NMR (400 MHz, DMSO-d₆: D₂O) δ 7.75 (d, 2H, J=5.20 Hz), 7.56 (dd, 2H, J=7.60, 1.60 Hz), 6.98 (d, 1H, J=8.00 Hz), 6.82 (t, 1H, J=7.60 Hz), 6.59 (t, 1H, J=7.60 Hz), 4.75 (s, 2H), 4.57 (d, 2H, J=7.60 Hz), 1.82 (s, 3H), 1.39 (s, 18H), 1.02 (s, 9H);

MS: m/z 649.3 (M+1).

Example 9, Step 4: Preparation of 2-{[4-(aminomethyl)-1H-1,3-benzodiazol-2-yl]amino}-2-[3-(trifluoromethyl)phenyl]propyl 2,2-dimethylpropanoate

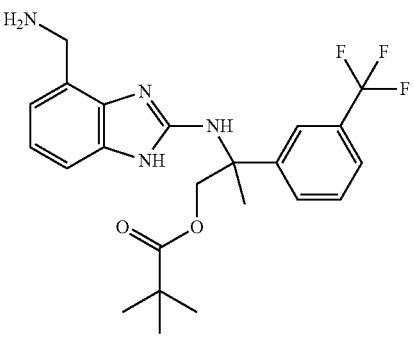 [SMILES: CC(C)(C)C(=O)OCC(C)(Nc1nc2c(CN)cccc2[nH]1)c1cccc(C(F)(F)F)c1]

To a solution of 2-{[4-({bis[(tert-butoxy)carbonyl]amino}methyl)-1H-1,3-benzodiazol-2-yl]amino}-2-[3-(trifluoromethyl)phenyl]propyl 2,2-dimethylpropanoate (from Example 9, Step 3) (0.800 g, 1.00 mmol) in dichloromethane (25 mL) was added 4M HCl in dioxane (0.925 mL, 4.00 mmol) at 0° C. and the reaction mass was stirred at ambient temperature for 16 h. The reaction mass was concentrated and the residue was diluted with 10% aqueous sodium bicarbonate solution (20 mL). The aqueous layer was extracted with ethyl acetate (3×150 mL), the combined organic layer was dried over sodium sulphate, filtered and concentrated to afford a brown gum (0.70 g). This was purified by preparative HPLC to afford 2-{[4-(aminomethyl)-1H-1,3-benzodiazol-2-yl]amino}-2-[3-(trifluoromethyl)phenyl]propyl 2,2-dimethylpropanoate, isolated as the trifluoroacetate acid salt, (0.400 g) as an off-white solid.

$^1$H NMR (400 MHz, AcOH-d$_4$) δ 7.87 (d, 2H, J=8.40 Hz), 7.73 (d, 1H, J=8.00 Hz), 7.65 (t, 1H, J=8.00 Hz), 7.44 (dd, 1H, J=2.00 Hz), 7.28 (d, 1H, J=1.60 Hz), 7.27 (s, 1H), 4.57 (s, 2H), 4.54 (t, 2H, J=5.20 Hz), 1.82 (s, 3H), 1.18 (s, 9H); MS: m/z 449.2 [(M+1)].

Example 9, Step 5: Preparation of 2-[(4-{[(ethylcarbamoyl)amino]methyl}-1H-1,3-benzodiazol-2-yl)amino]-2-[3-(trifluoromethyl)phenyl]propyl 2,2-dimethylpropanoate

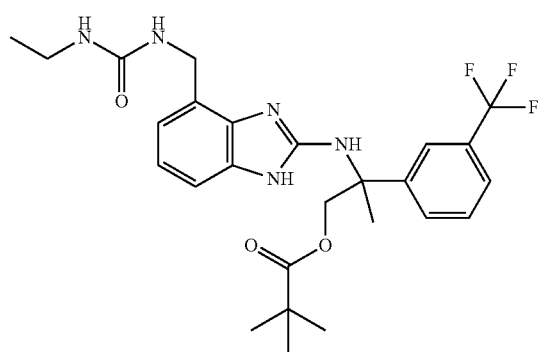 [SMILES: CCNC(=O)NCc1cccc2[nH]c(NC(C)(COC(=O)C(C)(C)C)c3cccc(C(F)(F)F)c3)nc12]

To a solution of 2-{[4-(aminomethyl)-1H-1,3-benzodiazol-2-yl]amino}-2-[3-(trifluoromethyl)phenyl]propyl 2,2-dimethylpropanoate; trifluoroacetic acid (from Example 9, Step 4) (0.700 g, 1.00 mmol) in dry dichloromethane (30 mL) was added triethylamine (7.97 mL, d=0.724 g/cm$^3$, 6.00 mmol) followed by ethyl isocyanate (0.154 g, 2.00 mmol) and the mixture was stirred at ambient temperature for 16 h. The reaction mass was concentrated and the residue diluted with 10% aq. sodium bicarbonate solution (30 mL) and extracted with ethyl acetate (3×100 mL). The combined organic layer was dried over sodium sulphate, filtered and concentrated to afford a brown gum (0.915 g), which was purified by preparative HPLC to afford 2-[(4-{[(ethylcarbamoyl)amino]methyl}-1H-1,3-benzodiazol-2-yl)amino]-2-[3-(trifluoromethyl)phenyl]propyl 2,2-dimethylpropanoate, isolated as the trifluoroacetate salt, (0.350 g) as a yellow solid.

$^1$H NMR (400 MHz, DMSO-d$_6$: D$_2$O) δ 7.81 (d, 2H, J=10.40 Hz), 7.73 (d, 1H, J=7.60 Hz), 7.65 (t, 1H, J=8.00 Hz), 7.27 (d, 1H, J=8.00 Hz), 7.18 (t, 1H, J=7.60 Hz), 7.10 (d, 1H, J=7.20 Hz), 4.48 (q, 2H, J=12.00 Hz), 4.21 (s, 2H), 2.97 (q, 2H, J=7.20 Hz), 1.91 (s, 3H), 1.02 (s, 9H), 0.96 (t, 3H, J=7.20 Hz);

MS: m/z 520.1 [(M+1)].

Example 9: Preparation of 3-ethyl-1-{[2-({1-hydroxy-2-[3-(trifluoromethyl)phenyl]propan-2-yl}amino)-1H-1,3-benzodiazol-4-yl]methyl}urea

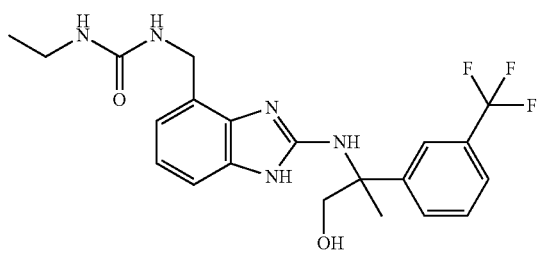 [SMILES: CCNC(=O)NCc1cccc2[nH]c(NC(C)(CO)c3cccc(C(F)(F)F)c3)nc12]

To a solution of 2-[(4-{[(ethylcarbamoyl)amino]methyl}-1H-1,3-benzodiazol-2-yl)amino]-2-[3-(trifluoromethyl)phenyl]propyl 2,2-dimethylpropanoate; trifluoroacetic acid (from Example 9, Step 5) (0.300 g, 0.470 mmol) in ethanol (10 mL) was added sodium hydroxide pellets (0.057 g, 1.41 mmol) and the mixture was stirred at ambient temperature for 4 h. The reaction mass was concentrated and the residue diluted with 10% aq. sodium bicarbonate solution (15 mL) and extracted with ethyl acetate (3×50 mL). The combined organic layer was dried over sodium sulphate, filtered and concentrated to afford a brown gum (0.320 g). This was purified by preparative HPLC to afford 3-ethyl-1-{[2-({1-hydroxy-2-[3-(trifluoromethyl)phenyl]propan-2-yl}amino)-1H-1,3-benzodiazol-4-yl]methyl}urea, isolated at the trifluoroacetate salt, (0.040 g) as a yellow solid.

$^1$H NMR (400 MHz, AcOH-d$_4$) δ 7.87 (s, 1H), 7.84 (d, 1H, J=7.60 Hz), 7.68 (d, 1H, J=7.60 Hz), 7.61 (t, 1H, J=8.00 Hz), 7.30 (d, 1H, J=7.60 Hz), 7.19 (d, 1H, J=7.60 Hz), 7.15 (t, 1H, J=6.40 Hz), 4.47 (q, 2H, J=15.20 Hz); 4.29 (d, 1H, J=12.00 Hz), 4.08 (d, 1H, J=11.60 Hz), 3.13 (q, 2H, J=6.80 Hz), 1.90 (s, 3H), 1.11 (t, 3H, J=7.20 Hz);

MS: m/z 436.3 [(M+1)].

2-[(4-{[(ethylcarbamoyl)amino]methyl}-1H-1,3-benzodiazol-2-yl)amino]-2-[3-(trifluoromethyl)phenyl]propyl 2,2-dimethylpropanoate; trifluoroacetic acid (from Example 9, Step 5) was resolved into its two enantiomers by Chiral SFC using the method: Column: Chiral Pak OX—H; Flow rate: 3.0 mL/min; Co-Solvent: 30%; Co-solvent Name: 0.5% isopropyl amine in isopropyl alcohol; injected Volume: 15.0 μL; out let pressure: 100 bar; Temperature: 40° C. to obtain the two enantiomers shown in steps 5a and 5b.

Example 9, 5a: 2-[(4-{[(ethylcarbamoyl)amino]
methyl}-1H-1,3-benzodiazol-2-yl)amino]-2-[3-(trif-
luoromethyl)phenyl]propyl 2,2-dimethylpropanoate,
Enantiomer 1

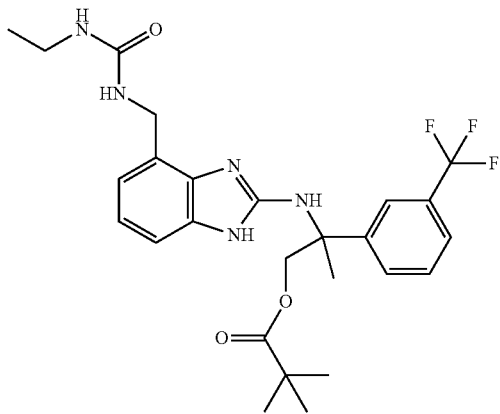 [SMILES: CCNC(=O)NCc1cccc2[nH]c(NC(C)(COC(=O)C(C)(C)C)c3cccc(C(F)(F)F)c3)nc12]

Fraction-1 eluted first from the SFC column and it was
concentrated to afford Enantiomer 1 (0.120 g) with 100% ee,
isolated as the trifluoroacetate salt, as a yellow solid Example 9, 5b: 2-[(4-{[(ethylcarbamoyl)amino]
methyl}-1H-1,3-benzodiazol-2-yl)amino]-2-[3-(trif-
luoromethyl)phenyl]propyl 2,2-dimethylpropanoate,
Enantiomer 2

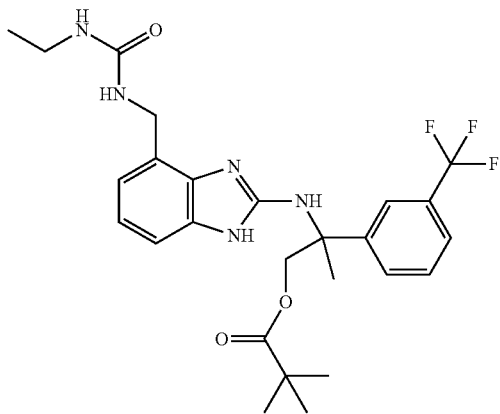 [SMILES: CCNC(=O)NCc1cccc2[nH]c(NC(C)(COC(=O)C(C)(C)C)c3cccc(C(F)(F)F)c3)nc12]

Fraction-2 eluted second from the SFC column and it had
concentrated to afford Enantiomer 2 (0.120 g) with 100% ee,
isolated as the trifluoroacetate salt, as a yellow solid.

Example 9a: Preparation of (+)-1-ethyl-3-((2-((1-
hydroxy-2-(3-(trifluoromethyl) phenyl) propan-2-yl)
amino)-1H-benzo[d]imidazol-4-yl) methyl) urea

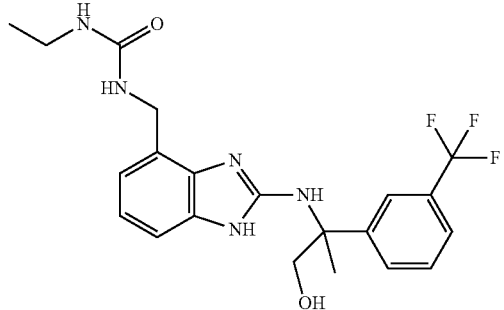 [SMILES: CCNC(=O)NCc1cccc2[nH]c(NC(C)(CO)c3cccc(C(F)(F)F)c3)nc12]

To a solution of 2-[(4-{[(ethylcarbamoyl)amino]methyl}-
1H-1,3-benzodiazol-2-yl)amino]-2-[3-(trifluoromethyl)phe-
nyl]propyl 2,2-dimethylpropanoate; trifluoroacetic acid
(from Step 5, Fraction 1) (0.150 g, 0.24 mmol) in ethanol (5
mL) was added sodium hydroxide (0.077 g, 1.92 mmol)
pellets and it was stirred at ambient temperature for 2 h. The
reaction mass was concentrated and the residue was diluted
with water (20 mL) and extracted with ethyl acetate (3×50
mL). The combined organic layer was dried over sodium
sulphate, filtered and concentrated to afford (+)-1-ethyl-3-
((2-((1-hydroxy-2-(3-(trifluoromethyl) phenyl) propan-2-yl)
amino)-1H-benzo[d]imidazol-4-yl) methyl) urea (0.080 g)
as a yellow solid.

$^1$H NMR (400 MHz, AcOH-$d_4$) δ 7.87 (s, 1H), 7.83 (d,
1H, J=8.00 Hz), 7.68 (d, 1H, J=7.60 Hz), 7.60 (t, 1H, J=7.60
Hz), 7.31 (d, 1H, J=7.20 Hz), 7.17 (t, 1H, J=7.60 Hz), 7.12
(d, 1H, J=6.80 Hz), 4.46 (q, 2H, J=15.20 Hz), 4.27 (d, 1H,
J=12.00 Hz), 4.07 (d, 1H, J=12.00 Hz), 3.12 (q, 2H, J=7.20
Hz), 1.89 (s, 3H), 1.10 (t, 3H, J=7.20 Hz);

MS: m/z 436.3 (M+1);

[α] D $^{22.5}$ (+) 57.48, (MeOH, c=1.0).

Example 9b: Preparation of (−)-1-ethyl-3-((2-((1-
hydroxy-2-(3-(trifluoromethyl)phenyl) propan-2-yl)
amino)-1H-benzo[d]imidazol-4-yl)methyl)urea

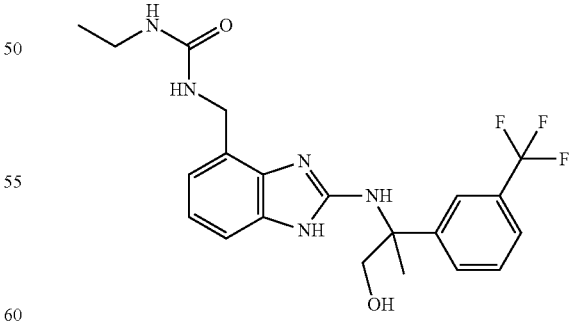

To a solution of 2-[(4-{[(ethylcarbamoyl)amino]methyl}-
1H-1,3-benzodiazol-2-yl)amino]-2-[3-(trifluoromethyl)phe-
nyl]propyl 2,2-dimethylpropanoate; trifluoroacetic acid,
Enantiomer 2 (from Step 5, Fraction 2) (0.150 g, 0.24 mmol)
in ethanol (5 mL) was added sodium hydroxide (0.077 g,
1.92 mmol) pellets and it was stirred at ambient temperature for 2 h. The reaction mass was concentrated and the residue diluted with water (20 mL) and extracted with ethyl acetate (3×50 mL). The combined organic layer was dried over sodium sulphate, filtered and concentrated to afford (−)-1-ethyl-3-((2-((1-hydroxy-2-(3-(trifluoromethyl)phenyl) propan-2-yl)amino)-1H-benzo[d]imidazol-4-yl)methyl)urea (0.090 g) as a yellow solid.

¹H NMR (400 MHz, AcOH-d₄) δ 7.87 (s, 1H), 7.83 (d, 1H, J=8.00 Hz), 7.68 (d, 1H, J=7.60 Hz), 7.60 (t, 1H, J=7.60 Hz), 7.31 (d, 1H, J=8.00 Hz), 7.18 (d, 1H, J=7.60 Hz), 7.13 (t, 1H, J=6.80 Hz), 4.46 (q, 2H, J=15.20 Hz), 4.27 (d, 1H, J=12.00 Hz), 4.07 (d, 1H, J=12.00 Hz), 3.12 (q, 2H, J=7.20 Hz), 1.89 (s, 3H), 1.11 (t, 3H, J=7.20 Hz);

MS: m/z 436.3 (M+1);

[α] D $^{22.6}$ (−) 59.68 (MeOH, c=1.0).

Example 10: Preparation of 1-((2-((1-hydroxy-2-(3-(trifluoromethyl) phenyl) butan-2-yl) amino)-1H-benzo[d]imidazol-4-yl) methyl)-3-methylurea

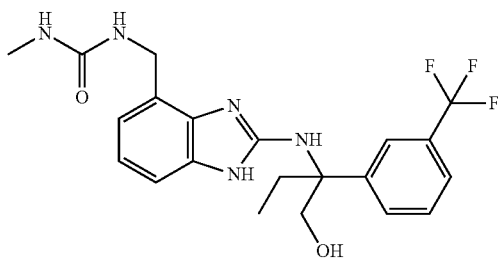 [SMILES: CCC(CO)(Nc1nc2c(CNC(=O)NC)cccc2[nH]1)c1cccc(C(F)(F)F)c1]

Example 10, Step 1: Preparation of 5-ethyl-5-(3-(trifluoromethyl) phenyl) imidazolidine-2, 4-dione

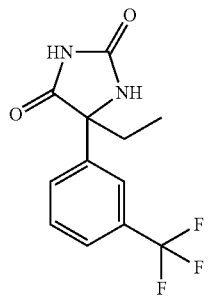 [SMILES: CCC1(c2cccc(C(F)(F)F)c2)NC(=O)NC1=O]

To a stirred solution of 1-(3-(trifluoromethyl) phenyl) propan-1-one (commercially available) (45.00 g, 223.00 mmol) in a mixture of solvents ethanol/water (1:1, 1000 mL) was added ammonium carbonate (107.00 g, 1110.00 mmol) followed by potassium cyanide (17.10 g, 263.00 mmol) and the mixture was stirred at 60° C. for 16 h. The reaction mass was poured into ice-cold water (1500 mL) and stirred for 30 min. The solid that formed was filtered off and dried to afford 5-ethyl-5-(3-(trifluoromethyl) phenyl) imidazolidine-2, 4-dione (55.00 g) as an off-white solid, which was used in the next step without further purification.

¹H NMR (400 MHz, DMSO-d₆: D₂O) δ 7.78 (d, 1H, J=7.68 Hz), 7.75 (s, 1H), 7.68 (d, 1H, J=7.84 Hz), 7.63 (t, 1H, J=7.76 Hz), 2.08 (q, 1H, J=7.20 Hz), 1.90 (q, 1H, J=7.32 Hz), 0.78 (t, 3H, J=7.24 Hz);

MS: m/z 271.1 (M−1).

Example 10, Step 2: Preparation of 2-amino-2-(3-(trifluoromethyl) phenyl) butanoic acid

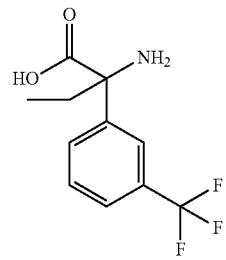 [SMILES: CCC(N)(C(=O)O)c1cccc(C(F)(F)F)c1]

5-ethyl-5-(3-(trifluoromethyl) phenyl) imidazolidine-2, 4-dione (from Example 10, Step 1) (55.00 g, 202.00 mmol) was taken up into 10% aqueous sodium hydroxide solution (350 mL) and the mixture had refluxed for 48 h. The reaction mixture was neutralized (adjusted pH=7) with 6.0 N HCl (200 mL), and the solid that formed was filtered and dried to afford 2-amino-2-(3-(trifluoromethyl) phenyl) butanoic acid (31.00 g) as a white solid, which was used in the next step without further purification.

1H NMR (400 MHz, DMSO-d₆: D₂O) δ 7.86 (s, 1H), 7.80 (d, 1H, J=7.60 Hz), 7.62 (d, 1H, J=7.60 Hz), 7.57 (t, 1H, J=7.60 Hz), 2.14-2.08 (m, 2H), 0.81 (t, 3H, J=7.60 Hz);

MS: m/z 248.2 (M+1).

Example 10, Step 3: Preparation of 2-amino-2-(3-(trifluoromethyl) phenyl) butan-1-ol

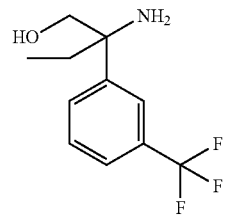 [SMILES: CCC(N)(CO)c1cccc(C(F)(F)F)c1]

To a solution of 2-amino-2-(3-(trifluoromethyl) phenyl) butanoic acid (from Example 10, Step 2) (40.00 g, 162.00 mmol) in dry tetrahydrofuran (1200 mL) was added a 2M solution of lithium aluminum hydride in tetrahydrofuran (202.00 mL, 405.00 mmol) at 0° C. and the reaction mass was slowly warmed to ambient temperature and stirred for 3 h. The reaction mixture was cooled to 0° C. and it was quenched with dropwise addition of ethyl acetate (120 mL) and stirred for 30 min. Then finally quenched with saturated solution of ammonium chloride dropwise (150 mL) and stirred for 15 min at 0° C. The precipitate obtained was separated by filtration and the filtrate had concentrated under reduced pressure to afford a yellow gum (40.00 g). This was diluted with 10% sodium hydroxide solution (100 mL) and extracted with ethyl acetate (4×1000 mL). The combined organic layer was dried over anhydrous sodium sulphate, filtered and concentrated to afford 2-amino-2-(3-(trifluoromethyl) phenyl) butan-1-ol (18.50 g) as a yellow oil, which was used in the next step without further purification.

¹H NMR (400 MHz, DMSO-d₆) δ 7.85 (s, 1H), 7.75 (d, 1H, J=6.00 Hz), 7.53 (d, 2H, J=6.40 Hz), 4.76 (t, 1H, J=5.60 Hz), 3.54 (dd, 2H, J=10.20, 5.60 Hz), 1.84 (s, 2H), 1.75 (q, 1H, J=7.60 Hz), 1.62 (q, 1H, J=6.80 Hz), 0.61 (t, 3H, J=7.60 Hz);

MS: m/z 234.1 (M+1).

Example 10, Step 4: Preparation of tert-butyl N-{1-hydroxy-2-[3-(trifluoromethyl)phenyl]butan-2-yl}carbamate

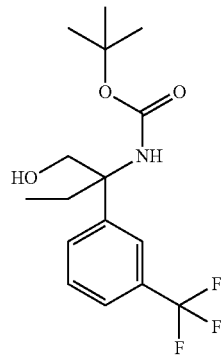 [SMILES: CCC(CO)(NC(=O)OC(C)(C)C)c1cccc(C(F)(F)F)c1]

To a suspension of 2-amino-2-(3-(trifluoromethyl) phenyl) butan-1-ol (from Example 10, Step 3) (18.50 g, 51.60 mmol) in a mixture of solvents dichloromethane:1, 4-dioxane (4:1, 500 mL) was added di-tert-butyl dicarbonate (13.50 mL, d: 0.950 g/cm³, 61.90 mmol) dropwise at 0° C. and the mixture was stirred at ambient temperature for 48 h. The reaction mixture was diluted with water (200 mL) and extracted with ethyl acetate (4×1000 mL). The combined organic layer was dried over sodium sulphate, filtered and concentrated to afford a yellow gum (18.00 g). This was purified by chromatography on a Grace instrument using 220.0 g pre-packed flash cartridge filled with normal phase silica gel 60° A, 40-63 μm and the product eluted with 25-30% ethyl acetate in hexane to afford tert-butyl N-{1-hydroxy-2-[3-(trifluoromethyl)phenyl]butan-2-yl}carbamate (11.50 g) as a colourless gum.

¹H NMR (400 MHz, DMSO-d₆: D₂O) δ 7.58 (s, 1H), 7.56 (d, 2H, J=2.16 Hz), 7.53 (t, 1H, J=6.32 Hz), 3.61 (t, 2H, J=12.40 Hz), 1.97 (q, 2H, J=7.64 Hz), 1.46 (s, 9H), 0.61 (t, 3H, J=7.60 Hz);

MS: m/z 234.2 [(M+1)-Boc].

Example 10, Step 5: Preparation of 2-{[(tert-butoxy)carbonyl]amino}-2-[3-(trifluoromethyl)phenyl]butyl 2,2-dimethylpropanoate

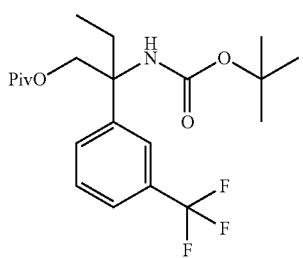

To a solution of tert-butyl N-{1-hydroxy-2-[3-(trifluoromethyl)phenyl]butan-2-yl}carbamate (from Example 10, Step 4) (11.50 g, 34.50 mmol) in dry dichloromethane (300 mL) under a nitrogen atmosphere was added triethylamine (31.30 mL, d=0.726 g/cm³, 224.00 mmol) followed by pivaloyl chloride (12.70 mL, d=0.985 g/cm³, 103.00 mmol) at 0° C. dropwise and the whole reaction mixture was then stirred at ambient temperature for 48 h. The reaction mixture was quenched with ice-cold water (100 mL) and extracted with dichloromethane (4×500 mL). The combined organic layer was dried over sodium sulphate, filtered and concentrated to afford a brown gum (15.00 g). This was purified by chromatography on a Grace instrument using 120.0 g pre-packed flash cartridge filled with normal phase silica gel 60° A, 40-63 μm and the product eluted with 15-20% ethyl acetate in hexane to afford 2-{[(tert-butoxy)carbonyl]amino}-2-[3-(trifluoromethyl)phenyl]butyl 2,2-dimethylpropanoate (10.00 g) as a colourless gum.

1H NMR (400 MHz, DMSO-d₆: D₂O) δ 7.61 (s, 1H), 7.59 (d, 2H, J=7.52 Hz), 7.58 (t, 1H, J=7.00 Hz), 4.38 (q, 2H, J=14.40 Hz), 1.95 (q, 2H, J=7.28 Hz), 1.39 (s, 9H), 1.11 (s, 9H), 1.09 (t, 3H, J=6.08 Hz);

MS: m/z 318.2 [(M+1)-Boc].

Example 10, Step 6: Preparation of 2-amino-2-[3-(trifluoromethyl)phenyl]butyl 2,2-dimethylpropanoate hydrochloride

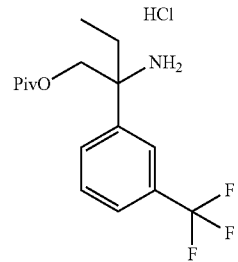

To a solution of 2-{[(tert-butoxy)carbonyl]amino}-2-[3-(trifluoromethyl)phenyl]butyl 2,2-dimethylpropanoate (from Example 10, Step 5) (10.00 g, 24.00 mmol) in dry dichloromethane (300 mL) under a nitrogen atmosphere was added 4M HCl in dioxane solution (15.00 mL, 59.90 mmol) dropwise at 0° C. and the reaction mixture was stirred at ambient temperature for 16 h. The reaction mixture was concentrated and the residue triturated with hexane (3×250 mL). The supernatant layer was decanted and the solid dried to afford 2-amino-2-[3-(trifluoromethyl)phenyl]butyl 2,2-dimethylpropanoate hydrochloride (8.50 g) as a colourless gum, which was used in the next step without further purification.

¹H NMR (400 MHz, DMSO-d₆: D₂O) δ 7.74 (s, 1H), 7.68 (d, 2H, J=13.60 Hz), 7.56 (t, 1H, J=8.84 Hz), 4.56 (d, 1H, J=12.08 Hz), 4.22 (d, 1H, J=12.12 Hz), 2.17-1.97 (m, 2H), 1.02 (s, 9H), 0.78 (t, 3H, J=7.36 Hz);

MS: m/z 318.2 [(M+1)-HCl].

Example 10, Step 7: Preparation of 2-isothiocyanato-2-[3-(trifluoromethyl)phenyl]butyl 2,2-dimethylpropanoate

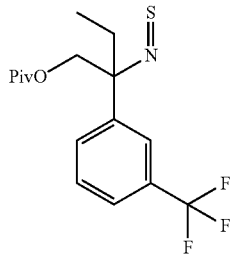

To a solution of 2-amino-2-[3-(trifluoromethyl)phenyl] butyl 2,2-dimethylpropanoate hydrochloride (from Example 10, Step 6) (8.50 g, 24.00 mmol) in dry dichloromethane (300 mL) was added 10% aqueous sodium bicarbonate solution (300 mL) at 0° C. After 30 min, to this solution thiophosgene (11.00 mL, d=1.5 g/cm$^3$, 144.00 mmol) was added and allowed to stir at same temperature for 1 h. The reaction mass was extracted with dichloromethane (3×500 mL) and the combined organic layer was dried over anhydrous sodium sulphate, filtered, and concentrated to afford crude a yellow liquid (9.00 g). This was purified by chromatography on a Grace instrument using 60.0 g pre-packed flash cartridge filled with normal phase silica gel 60° A, 40-63 μm and the product eluted with 5-10% ethyl acetate in hexane to afford 2-isothiocyanato-2-[3-(trifluoromethyl)phenyl]butyl 2,2-dimethylpropanoate (6.50 g) as a yellow liquid.

$^1$H NMR (400 MHz, DMSO-d$_6$) δ 7.62 (s, 1H), 7.59 (d, 2H, J=7.16 Hz), 7.56 (t, 1H, J=7.76 Hz), 4.39 (d, 2H, J=4.04 Hz), 2.21 (q, 1H, J=7.20 Hz), 2.07 (q, 1H, J=6.96 Hz), 1.16 (s, 9H), 0.91 (t, 3H, J=7.12 Hz);

Example 10, Step 8: Preparation of 2-{[(2-amino-6-{[(methylcarbamoyl)amino]methyl}phenyl)carbamothioyl]amino}-2-[3-(trifluoromethyl)phenyl]butyl 2,2-dimethylpropanoate and 2-{[(2-amino-3-{[(methylcarbamoyl)amino]methyl}phenyl)carbamothioyl]amino}-2-[3-trifluoromethyl)phenyl]butyl 2,2-dimethylpropanoate (mixture of regioisomers)

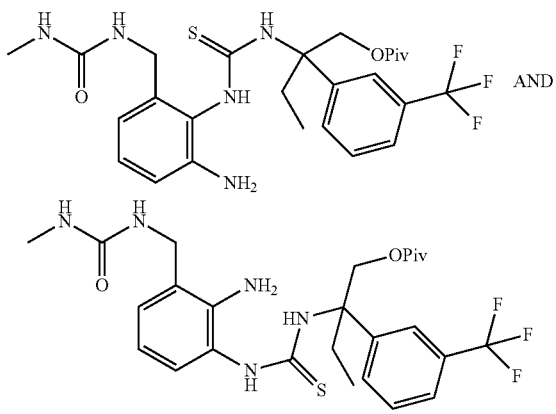

To a solution 1-(2, 3-diaminobenzyl)-3-methylurea (from Example 1, Step 13) (0.200 g, 10.00 mmol) in a mixture of solvents dichloromethane/methanol (4:1, 20 mL) was added 2-isothiocyanato-2-[3-(trifluoromethyl)phenyl]butyl 2,2-dimethylpropanoate (from Example 10, Step 7) (0.598 g, 20.00 mmol) and the mixture was stirred at ambient temperature for 24 h. The reaction mass was concentrated to afford a brown gum (0.600 g). This was purified by chromatography on a Grace instrument using 24.0 g pre-packed flash cartridge filled with normal phase silica gel 60° A, 40-63 μm and the product was eluted with 2-3% methanol in chloroform to afford 2-{[(2-amino-6-{[(methylcarbamoyl)amino]methyl}phenyl)carbamothioyl]amino}-2-[3-(trifluoromethyl)phenyl]butyl 2,2-dimethylpropanoate and 2-{[(2-amino-3-{[(methylcarbamoyl)amino]methyl}phenyl)carbamothioyl]amino}-2-[3-(trifluoromethyl)phenyl]butyl 2,2-dimethylpropanoate (as a 4:1 mixture of regioisomers) (0.200 g) as a yellow solid.

MS: m/z 554.3 (M+1).

Example 10, Step 9: Preparation of 2-[(4-{[(methylcarbamoyl)amino]methyl}-1H-1,3-benzodiazol-2-yl)amino]-2-[3-(trifluoromethyl)phenyl]butyl2,2-dimethylpropanoate

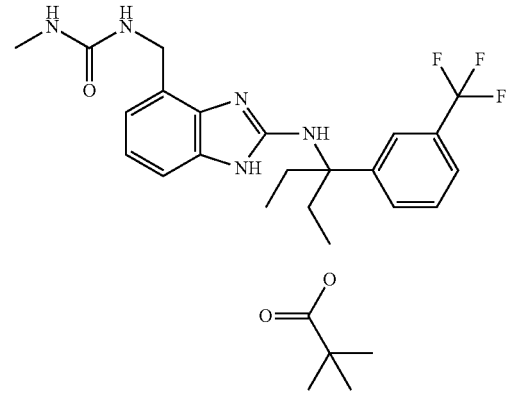

To a solution of 2-{[(2-amino-6-{[(methylcarbamoyl)amino]methyl}phenyl)carbamothioyl]amino}-2-[3-(trifluoromethyl)phenyl]butyl 2,2-dimethylpropanoate and 2-{[(2-amino-3-{[(methylcarbamoyl)amino]methyl}phenyl)carbamothioyl]amino}-2-[3-(trifluoromethyl)phenyl]butyl 2,2-dimethylpropanoate (as a 4:1 mixture of regioisomers) (from Example 10, Step 8) (0.550 g, 0.993 mmol) under a nitrogen atmosphere in dry methanol (30 mL) was added iodoacetic acid (0.369 g, 1.99 mmol) and refluxed for 1 h. The reaction mass was concentrated to remove the methanol solvent and the residue was diluted with 10% aqueous sodium bicarbonate solution (30 mL) and extracted with ethyl acetate (3×150 mL). The combined organic layer was washed with brine solution (30 mL), dried over sodium sulphate, filtered and concentrated to a brown gum (0.550 g). This was purified by chromatography on a Grace instrument using 24.0 g pre-packed flash cartridge filled with normal phase silica gel 60° A, 40-63 μm and the product was eluted with 1-2% methanol in chloroform to afford 2-[(4-{[(methylcarbamoyl)amino]methyl}-1H-1,3-benzodiazol-2-yl)amino]-2-[3-(trifluoromethyl)phenyl]butyl 2,2-dimethylpropanoate (0.400 g) as a yellow solid.

$^1$H NMR (400 MHz, DMSO-d$_6$: D$_2$O) δ 7.72 (s, 2H), 7.57 (d, 2H, J=11.32 Hz), 6.98 (s, 1H), 6.83 (d, 1H, J=7.44 Hz), 6.76 (t, 1H, J=7.32 Hz), 4.66 (t, 2H, J=7.52 Hz), 4.25 (q, 2H, J=12.88 Hz), 2.58 (d, 2H, J=16.04 Hz), 2.22 (s, 3H), 1.00 (s, 9H), 0.77 (t, 3H, J=4.40 Hz);
MS: m/z 520.1 (M+1).

Example 10: Preparation of 1-((2-((1-hydroxy-2-(3-(trifluoromethyl) phenyl) butan-2-yl) amino)-1H-benzo[d]imidazol-4-yl) methyl)-3-methylurea

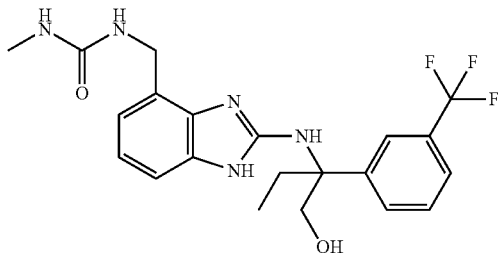 [SMILES: CCC(CO)(Nc1nc2c(CNC(=O)NC)cccc2[nH]1)c1cccc(C(F)(F)F)c1]

To a solution of 2-[(4-{[(methylcarbamoyl)amino] methyl}-1H-1,3-benzodiazol-2-yl)amino]-2-[3-(trifluoromethyl)phenyl]butyl 2,2-dimethylpropanoate (from Example 10, Step 9) (0.600 g, 0.958 mmol) in methanol (30 mL) solvent was added sodium hydroxide pellets (0.948 g, 24.00 mmol) and the mixture was stirred at ambient temperature for 3 h. The reaction mass was concentrated to remove the solvent methanol and the residue was dissolved with water (30 mL) and extracted with ethyl acetate (3×100 mL). The combined organic layer was washed with brine (25 mL), dried over sodium sulphate, filtered and concentrated to afford a brown gum (0.420 g). This was purified by chromatography on a Grace instrument using 24.0 g pre-packed flash cartridge filled with normal phase silica gel 60° A, 40-63 μm and the product was eluted with 8% methanol in chloroform to afford 1-((2-((1-hydroxy-2-(3-(trifluoromethyl) phenyl) butan-2-yl) amino)-1H-benzo[d]imidazol-4-yl) methyl)-3-methylurea (0.370 g) as an off-white solid.

$^1$H NMR (400 MHz, AcOH-d$_4$) δ 7.81 (s, 1H), 7.77 (d, 1H, J=7.80 Hz, 1H), 7.67 (d, 1H, J=7.92 Hz), 7.60 (t, 1H, J=7.84 Hz), 7.28 (d, 1H, J=7.48 Hz), 7.16 (t, 1H, J=7.56 Hz), 7.12 (d, 1H, J=6.24 Hz), 4.54 (q, 2H, J=15.36 Hz), 4.42 (d, 1H, J=15.28 Hz), 4.27 (d, 1H, J=12.24 Hz), 2.70 (s, 3H), 2.21-2.05 (m, 2H), 0.90 (t, 3H, J=8.32 Hz);
MS: m/z 436.2 (M+1).

The above product was resolved into its two enantiomers by Chiral SFC using the method; Column: Lux-Al; Flow rate: 3.0 mL/min, Co-Solvent: 20%; Co-solvent Name: 0.5% di-ethyl amine in isopropyl alcohol; injected Volume: 15.0 μL; Out let pressure: 100 bar; Temperature: 40° C. to obtain the two enantiomers 10a and 10b.

Example 10a: (−)-1-((2-((1-hydroxy-2-(3-(trifluoromethyl) phenyl) butan-2-yl) amino)-1H-benzo[d]imidazol-4-yl) methyl)-3-methylurea The (−) enantiomer was the first to elute off the column.
$^1$H NMR (400 MHz, AcOH-d$_4$) δ 7.81 (s, 1H), 7.77 (d, 1H, J=7.88 Hz), 7.67 (d, 1H, J=7.88 Hz), 7.60 (t, 1H, J=7.76 Hz), 7.27 (d, 1H, J=7.60 Hz), 7.16 (t, 1H, J=7.60 Hz), 7.12 (d, 1H, J=7.52 Hz), 4.54 (q, 2H, J=15.28 Hz), 4.42 (d, 1H, J=15.32 Hz), 4.27 (d, 1H, J=12.24 Hz), 2.70 (s, 3H), 2.20-2.11 (m, 2H), 0.91 (t, 3H, J=8.32 Hz);
MS: m/z 436.3 (M+1);
[α] D $^{24.6}$ (−) 29.60 (MeOH, c=0.5).

Example 10b: (+)-1-((2-((1-hydroxy-2-(3-(trifluoromethyl) phenyl) butan-2-yl) amino)-1H-benzo[d]imidazol-4-yl) methyl)-3-methylurea The (+) enantiomer was the second to elute off the column.
$^1$H NMR (400 MHz, AcOH-d$_4$) δ 7.81 (s, 1H), 7.77 (d, 1H, J=8.04 Hz), 7.67 (d, 1H, J=7.24 Hz), 7.60 (t, 1H, J=7.44 Hz), 7.27 (d, 1H, J=7.36 Hz), 7.17 (t, 1H, J=7.52 Hz), 7.12 (d, 1H, J=7.52 Hz), 4.54 (q, 2H, J=15.64 Hz), 4.42 (d, 1H, J=15.32 Hz), 4.27 (d, 1H, J=12.00 Hz), 2.70 (s, 3H), 2.19-2.11 (m, 2H), 0.91 (t, 3H, J=8.32 Hz);
MS: m/z 436.1 (M+1);
[α] D $^{24.6}$ (+) 24.80 (MeOH, c=0.5).

Example 11: Preparation of 3-((2-((2-(3-chlorophenyl)-1-hydroxypropan-2-yl) amino)-1H-benzo[d]imidazol-4-yl) methyl)-1-methoxy-1-methylurea

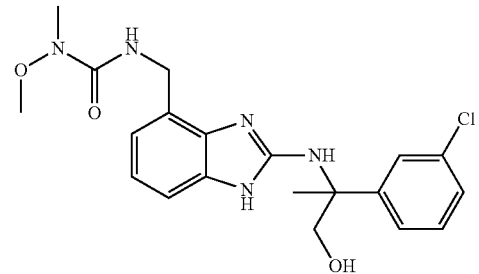 [SMILES: CON(C)C(=O)NCc1cccc2[nH]c(NC(C)(CO)c3cccc(Cl)c3)nc12]

Example 11, Step 1: Preparation of 5-(3-chlorophenyl)-5-methylimidazolidine-2,4-dione

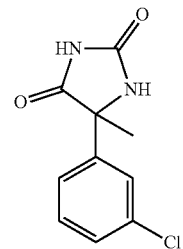

To a stirred solution of 1-(3-chlorophenyl) ethan-1-one (commercially available) (120.00 g, 776.00 mmol) in a mixture of solvents ethanol/water (1:1, 2400 mL) was added ammonium carbonate (448.00 g, 4660.00 mmol) followed by potassium cyanide (45.60 g, 931.00 mmol) and the mixture was stirred at 60° C. for 16 h. The reaction mass was poured into ice-cold water (1500 mL) and it was stirred for 30 min. The solid that formed was filtered off and dried to afford 5-(3-chlorophenyl)-5-methylimidazolidine-2,4-dione (160.00 g) as an off-white solid, which was used in the next step without further purification.

$^1$H NMR (400 MHz, DMSO-d$_6$) δ 10.87 (bs, 1H), 8.63 (s, 1H), 7.50 (d, 1H, J=1.60 Hz), 7.47 (d, 1H, J=4.80 Hz), 7.45 (t, 1H, J=2.40 Hz), 7.42 (dd, 1H, J=2.40 Hz), 1.65 (s, 3H);
MS: m/z 225.2 (M+1).

Example 11, Step 2: Preparation of 2-amino-2-(3-chlorophenyl) propanoic acid

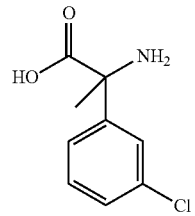

5-(3-chlorophenyl)-5-methylimidazolidine-2,4-dione (from Example 11, Step 1) (160.00 g, 712.00 mmol) was taken into 10% aqueous sodium hydroxide solution (1200 mL) and the mixture was stirred at 110° C. for 72 h. The reaction mixture was neutralized (adjusted pH=7) with 6.0 N HCl (500 mL), and the solid that formed was filtered and dried to afford 2-amino-2-(3-chlorophenyl) propanoic acid (205.00 g) as a white solid, which was used in the next step without further purification.

$^1$H NMR (400 MHz, DMSO-$d_6$: $D_2O$) δ 7.56 (s, 1H), 7.46 (d, 1H, J=7.60 Hz), 7.37 (t, 1H, J=7.60 Hz), 7.35 (d, 1H, J=7.60 Hz), 1.65 (s, 3H);

MS: m/z 200.1 (M+1).

Example 11, Step 3: Preparation of 2-((tert-butoxycarbonyl) amino)-2-(3-chlorophenyl) propanoic acid

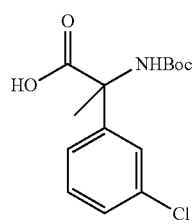

To a suspension of 2-amino-2-(3-chlorophenyl) propanoic acid (from Example 11, Step 2) (286.00 g, 1430.00 mmol) in a mixture of solvents tetrahydrofuran:water (1:1, 5000 mL) was added sodium bicarbonate (842.00 g, 10000.00 mmol) followed by di-tert-butyl dicarbonate (658.00 mL, d: 0.950 g/cm$^3$, 2870.00 mmol) and the whole mixture was stirred at ambient temperature for 15 days. The reaction mixture was diluted with water (2000 mL) and extracted with ethyl acetate (4×5000 mL). The combined organic layer was dried over sodium sulphate, filtered and concentrated to afford 2-((tert-butoxycarbonyl) amino)-2-(3-chlorophenyl) propanoic acid (410.00 g) as a colourless gum, which was used in the next step without further purification.

$^1$H NMR (400 MHz, DMSO-$d_6$) δ 7.23 (dd, 2H, J=6.40 Hz), 7.16 (t, 2H, J=6.40 Hz), 1.70 (s, 3H), 1.34 (s, 9H);

MS: m/z 199.9 [(M+1)-Boc].

Example 11, Step 4: Preparation of tert-butyl N-[2-(3-chlorophenyl)-1-hydroxypropan-2-yl]carbamate

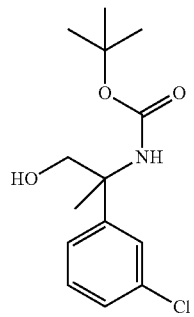 [SMILES: CC(C)(C)OC(=O)NC(C)(CO)c1cccc(Cl)c1]

To a solution of 2-((tert-butoxycarbonyl) amino)-2-(3-chlorophenyl) propanoic acid (from Example 11, Step 3) (250.00 g, 834.00 mmol) in dry tetrahydrofuran (2000 mL) was added triethylamine (349.00 mL, d=0.726 g/cm$^3$, 2500.00 mmol) followed by isobutyl chloroformate (130.00 mL, d=1.053 g/cm$^3$, 1080.00 mmol) at 0° C. and stirred at same temperature for 4 h. The solid that formed was filtered off at 0° C. and the residue was washed with tetrahydrofuran (400 mL). The combined filtrate was added to a cooled mixture of sodium borohydride (221.00 g, 5840.00 mmol) in water (500 mL). The reaction mass was slowly warmed to ambient temperature and stirred for 48 h. The reaction mass was quenched with ice cold water (1000 mL) and extracted with ethyl acetate (4×5000 mL). The combined organic layer was washed with brine (300 mL), dried over sodium sulphate, filtered and concentrated to afford a yellowish liquid (250.00 g), which was purified by gravity column chromatography using 60-120 silica gel and the product was eluted with 30-35% ethyl acetate in petroleum ether to afford tert-butyl (2-(3-chlorophenyl)-1-hydroxypropan-2-yl)carbamate (95.00 g) as a colorless liquid.

1H NMR (400 MHz, DMSO-$d_6$: $D_2O$) δ 7.34 (s, 1H), 7.32 (d, 1H, J=7.60 Hz), 7.28 (t, 1H, J=7.40 Hz), 7.25 (d, 1H, J=7.20 Hz), 3.57 (d, 2H, J=6.40 Hz), 1.52 (s, 3H), 1.34 (s, 9H);

MS: m/z 186.1 [(M+1)-Boc].

Example 11, Step 5: Preparation of 2-{[(tert-butoxy)carbonyl]amino}-2-(3-chlorophenyl)propyl 2,2-dimethylpropanoate

To a solution of tert-butyl (2-(3-chlorophenyl)-1-hydroxypropan-2-yl)carbamate (from Example 11, Step 4) (170.00 g, 595.00 mmol) in dry dichloromethane (1500 mL) under a nitrogen atmosphere was added triethyl amine (250.00 mL, d=0.726 g/cm$^3$, 1780.00 mmol) followed by pivaloyl chloride (145.50 mL, d=0.985 g/cm$^3$, 1190.00 mmol) at 0° C. dropwise and the whole reaction mixture was stirred at ambient temperature for 48 h. The reaction mixture was quenched with ice cold water (1000 mL) and extracted with dichloromethane (4×2500 mL). The combined organic layer was dried over sodium sulphate, filtered and concentrated to afford a brown liquid (200.00 g). This was purified by chromatography on a Grace instrument using 330.0 g pre-packed flash cartridge with 60-120 silica gel and the product eluted with 20% ethyl acetate in hexane to afford 2-{[(tert-butoxy)carbonyl]amino}-2-(3-chlorophenyl)propyl 2,2-dimethylpropanoate (218.00 g) as a yellowish liquid.

$^1$H NMR (400 MHz, DMSO-$d_6$: $D_2O$) δ 7.35 (d, 1H, J=8.00 Hz), 7.32 (s, 1H), 7.30 (d, 1H, J=7.20 Hz), 7.28 (t, 1H, J=6.80 Hz), 4.30 (d, 1H, J=10.40 Hz), 4.21 (d, 1H, J=10.80 Hz), 1.50 (s, 3H), 1.31 (s, 9H), 1.10 (s, 9H);

MS: m/z 271.8 [(M+1)-Boc].

Example 11, Step 6: Preparation of 2-amino-2-(3-chlorophenyl)propyl 2,2-dimethylpropanoate hydrochloride

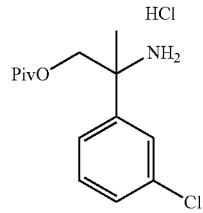

To a solution of 2-{[(tert-butoxy)carbonyl]amino}-2-(3-chlorophenyl)propyl 2,2-dimethylpropanoate (from Example 11, Step 5) (218.00 g, 589.00 mmol) in dry dichloromethane (1200 mL) under a nitrogen atmosphere was added 4M HCl in dioxane solution (442.00 mL, 1770.00 mmol) dropwise at 0° C. and then the reaction mixture was stirred at ambient temperature for 16 h. The reaction mixture was concentrated under high vacuum to afford 2-amino-2-(3-chlorophenyl)propyl 2,2-dimethylpropanoate hydrochloride (180.00 g) as a yellowish gum, which was used in the next step without further purification.

$^1$H NMR (400 MHz, DMSO-$d_6$: $D_2O$) δ 7.64 (s, 1H), 7.51-7.47 (m, 3H), 4.44 (d, 1H, J=11.60 Hz), 4.26 (d, 1H, J=11.60 Hz), 1.69 (s, 3H), 1.04 (s, 9H);

MS: m/z 270.1 [(M+1)-HCl].

Example 11, Step 7: Preparation of 2-(3-chlorophenyl)-2-isothiocyanatopropyl 2,2-dimethylpropanoate

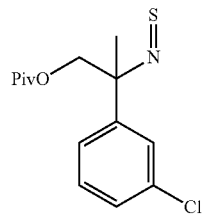

To a solution of 2-amino-2-(3-chlorophenyl)propyl 2,2-dimethylpropanoate hydrochloride (from Example 11, Step 6) (90.00 g, 294.00 mmol) in dry dichloromethane (900 mL) was added 10% aqueous sodium bicarbonate solution (900 mL) at 0° C. After 30 min, thiophosgene (33.80 mL, d=1.5 g/cm$^3$, 441.00 mmol) was added and allowed to stir at the same temperature for 1 h. The reaction mass was extracted with dichloromethane (3×2000 mL) and the combined organic layer was dried over anhydrous sodium sulphate, filtered, and concentrated to afford a yellow liquid (95.00 g), which was purified by gravity column chromatography over 60-120 mesh silica gel using 3-5% ethyl acetate in hexane as eluent to afford 2-(3-chlorophenyl)-2-isothiocyanatopropyl 2,2-dimethylpropanoate (75.00 g) as a yellow liquid.

$^1$H NMR (400 MHz, DMSO-$d_6$) δ 7.55 (s, 1H), 7.55-7.45 (m, 3H), 4.45 (dd, 2H, J=11.20 Hz), 1.79 (s, 3H), 1.11 (s, 9H);

Example 11, Step 8: Preparation of 2-({[2-amino-6-({[methoxy(methyl)carbamoyl]amino}methyl)phenyl]carbamothioyl}amino)-2-(3-chlorophenyl)propyl 2,2-dimethylpropanoate and 2-({[2-amino-3-({[methoxy(methyl)carbamoyl]amino}methyl)phenyl]carbamothioyl}amino)-2-(3-chlorophenyl)propyl 2,2-dimethylpropanoate (mixture of regioisomers)

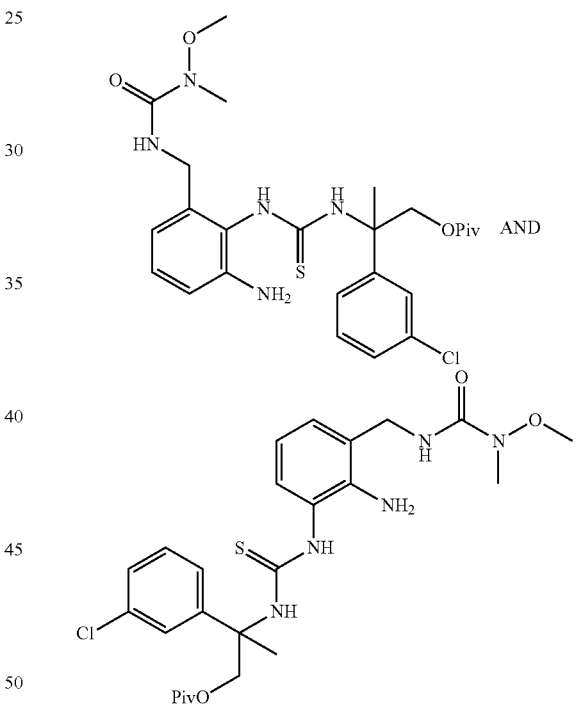

To a stirred solution of 3-[(2, 3-diaminophenyl) methyl]-1-methoxy-1-methyl-urea (from Example 4, Step 2) (0.21 g, 0.936 mmol) in acetonitrile (4 mL) was added 2-(3-chlorophenyl)-2-isothiocyanatopropyl 2,2-dimethylpropanoate (from Example 11, Step 7) (0.35 g, 1.12 mmol) and stirred at room temperature for 48 h. The reaction mixture was concentrated to afford 2-({[2-amino-6-({[methoxy(methyl)carbamoyl]amino}methyl)phenyl]carbamothioyl}amino)-2-(3-chlorophenyl)propyl 2,2-dimethylpropanoate and 2-({[2-amino-3-({[methoxy(methyl)carbamoyl]amino}methyl)phenyl]carbamothioyl}amino)-2-(3-chlorophenyl)propyl 2,2-dimethylpropanoate (as a mixture 4:1 of regioisomers) (0.560 g) as a brown gum which was used in the next step without further purification.

MS: m/z 537.2 (M+1).

Example 11, Step 9: Preparation of 2-(3-chlorophenyl)-2-{[4-({[methoxy(methyl)carbamoyl]amino}methyl)-1H-1,3-benzodiazol-2-yl]amino}propyl 2,2-dimethylpropanoate

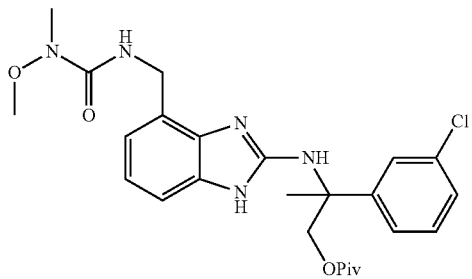

To a solution of 2-({[2-amino-6-({[methoxy(methyl)carbamoyl]amino}methyl)phenyl]carbamothioyl}amino)-2-(3-chlorophenyl)propyl 2,2-dimethylpropanoate and 2-({[2-amino-3-({[methoxy(methyl)carbamoyl]amino}methyl)phenyl]carbamothioyl}amino)-2-(3-chlorophenyl)propyl 2,2-dimethylpropanoate (as a mixture 4:1 of regioisomers) (from Example 11, Step 8) (0.56 g, 1.04 mmol) in methanol (6 mL) was added iodoacetic acid (0.388 g, 2.09 mmol) and stirred at room temperature for 1.5 h. The reaction mixture was concentrated and the residue was dissolved in dichloromethane (100 mL), washed with 10% aqueous sodium bicarbonate solution (2×10 mL). The organic layer was dried over sodium sulphate, filtered and concentrated to afford a reddish gum (0.500 g), which was purified by flash column chromatography over 230-400 silica gel and the product was eluted with 2% methanol in dichloromethane as eluent to afford 2-(3-chlorophenyl)-2-{[4-({[methoxy(methyl)carbamoyl]amino}methyl)-1H-1,3-benzodiazol-2-yl]amino}propyl 2,2-dimethylpropanoate (0.350 g) as a brown gum.

1H NMR (400 MHz, DMSO-d$_6$: D$_2$O) δ 7.51 (s, 1H), 7.42 (s, 3H), 7.26 (d, 1H, J=7.84 Hz), 7.20 (t, 1H, J=7.80 Hz), 7.13 (d, 1H, J=7.04 Hz), 4.49 (d, 1H, J=11.44 Hz), 4.39 (d, 1H, J=11.44 Hz), 4.30 (s, 2H), 3.53 (s, 3H), 2.92 (s, 3H), 1.83 (s, 3H), 1.04 (s, 9H);

MS: m/z 502.3/504.2 (M+1).

Example 11: Preparation of 3-((2-((2-(3-chlorophenyl)-1-hydroxypropan-2-yl) amino)-1H-benzo[d]imidazol-4-yl) methyl)-1-methoxy-1-methylurea

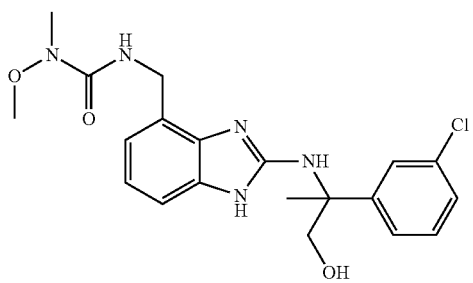 [SMILES: CON(C)C(=O)NCc1cccc2[nH]c(NC(C)(CO)c3cccc(Cl)c3)nc12]

To a stirred solution of 2-(3-chlorophenyl)-2-{[4-({[methoxy(methyl)carbamoyl]amino}methyl)-1H-1,3-benzodiazol-2-yl]amino}propyl 2,2-dimethylpropanoate (from Example 11, Step 9) (0.350 g, 0.697 mmol) in methanol (30 mL) was added 0.5 N sodium hydroxide solution in methanol (5.58 ml, 2.79 mmol) and stirred at room temperature for 1 h. The reaction mixture was quenched with 1.5 N hydrochloride solution (2 mL) and concentrated under reduced pressure at 30° C. to afford a brown gum (0.300 g). This was purified by preparative HPLC using 0.1% TFA in acetonitrile:water to afford 3-((2-((2-(3-chlorophenyl)-1-hydroxypropan-2-yl) amino)-1H-benzo[d]imidazol-4-yl) methyl)-1-methoxy-1-methylurea (0.230 g) as an off-white solid.

$^1$H NMR (400 MHz, AcOH-d$_4$) δ 7.58 (s, 1H), 7.49 (d, 1H, J=7.32 Hz), 7.41-7.35 (m, 3H), 7.20-7.12 (m, 2H), 4.48 (d, 2H, J=5.88 Hz), 4.22 (d, 1H, J=11.92 Hz), 4.02 (d, 1H, J=12.00 Hz), 3.61 (s, 3H), 3.05 (s, 3H), 1.85 (s, 3H);

MS: m/z 418.1/420.2 (M+1).

The above product was resolved into its two enantiomers by Chiral SFC using the method; Column: Lux C$_4$; Flow rate: 3.0 mL/min, Co-Solvent: 30%; Co-solvent Name: 0.5% isopropyl amine in isopropyl alcohol; injected Volume: 15.0 µL; Out let pressure: 100 bar; Temperature: 35° C. to obtain the two enantiomers 11a and 11b.

Example 11a: (−)-3-((2-((2-(3-chlorophenyl)-1-hydroxypropan-2-yl)amino)-1H-benzo[d] imidazol-4-yl)methyl)-1-methoxy-1-methylurea The (−) enantiomer was the first to elute off the column.

$^1$H NMR (400 MHz, AcOH-d$_4$) δ 7.58 (s, 1H), 7.49 (d, 1H, J=7.32 Hz), 7.41-7.35 (m, 3H), 7.20-7.12 (m, 2H), 4.48 (d, 2H, J=5.88 Hz), 4.22 (d, 1H, J=11.92 Hz), 4.02 (d, 1H, J=12.00 Hz), 3.61 (s, 3H), 3.05 (s, 3H), 1.85 (s, 3H);

MS: m/z 418.1/420.2 (M+1);

[α]D $^{23.2}$ (−) 11.52 (MeOH, c=1.0).

Example 11b: (+)-3-((2-((2-(3-chlorophenyl)-1-hydroxypropan-2-yl)amino)-1H-benzo[d] imidazol-4-yl)methyl)-1-methoxy-1-methylurea The (+) enantiomer was the second to elute off the column.

$^1$H NMR (400 MHz, AcOH-d$_4$) δ 7.58 (s, 1H), 7.49 (d, 1H, J=7.32 Hz), 7.41-7.35 (m, 3H), 7.20-7.12 (m, 2H), 4.48 (d, 2H, J=5.88 Hz), 4.22 (d, 1H, J=11.92 Hz), 4.02 (d, 1H, J=12.00 Hz), 3.61 (s, 3H), 3.05 (s, 3H), 1.85 (s, 3H);

MS: m/z 418.1/420.2 (M+1);

[α]D $^{25.9}$ (+) 11.04 (MeOH, c=1.0).

Example 12: Preparation of 1-[[2-[[1-(3-chloro-4-fluoro-phenyl)-2-hydroxy-1-methyl-ethyl] amino]-1H-benzimidazol-4-yl] methyl]-3-methyl-urea

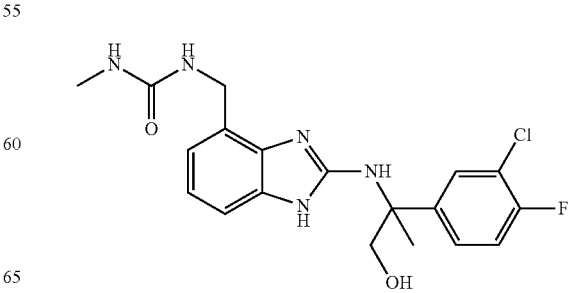

Example 12, Step 1: Preparation of [2-(3-chloro-4-fluoro-phenyl)-2-[[4-[(methyl carbamoyl amino) methyl]-1H-benzimidazol-2-yl] amino] propyl] 2,2-dimethyl propanoate

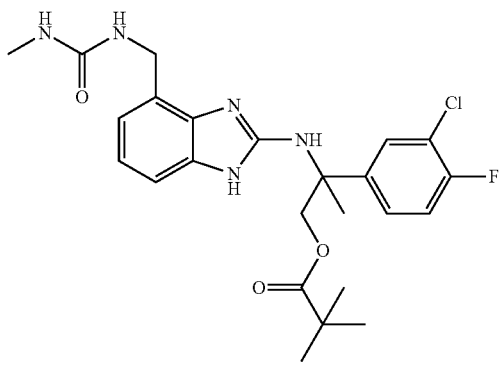 [SMILES: CNC(=O)NCc1cccc2[nH]c(NC(C)(COC(=O)C(C)(C)C)c3ccc(F)c(Cl)c3)nc12]

Starting with 1-(3-chloro-4-fluorophenyl)ethan-1-one in place of 1-[3-(trifluoromethyl)phenyl]ethan-1-one, the method described in Example 1, Steps 1 to 15 was used to afford [2-(3-chloro-4-fluoro-phenyl)-2-[[4-[(methylcarbamoylamino) methyl]-1H-benzimidazol-2-yl] amino] propyl] 2, 2-dimethyl propanoate (0.69 g) as an off-white solid, which was used in the next step without further purification.

$^1$H NMR (400 MHz, DMSO-$d_6$) δ 7.68 (s, 1H), 7.49-7.47 (m, 1H), 7.41-7.34 (m, 1H), 7.10 (bs, 1H), 7.00 (bs, 2H), 5.97 (bs, 1H), 4.47 (q, 2H, J=10.80 Hz), 4.25 (t, 2H, J=8.40 Hz), 3.74 (s, 3H), 1.83 (s, 3H), 1.06 (s, 9H);

MS: m/z 490.2 (M+1).

Example 12: Preparation of 1-[[2-[[1-(3-chloro-4-fluoro-phenyl)-2-hydroxy-1-methyl-ethyl] amino]-1H-benzimidazol-4-yl] methyl]-3-methyl-urea

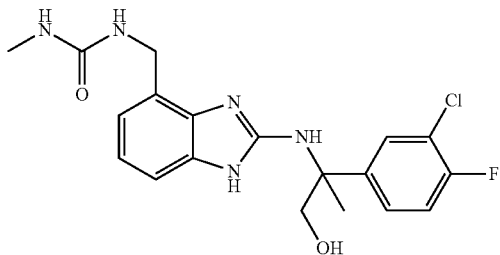 [SMILES: CNC(=O)NCc1cccc2[nH]c(NC(C)(CO)c3ccc(F)c(Cl)c3)nc12]

To a stirred solution of [2-(3-chloro-4-fluoro-phenyl)-2-[[4-[(methylcarbamoylamino) methyl]-1H-benzimidazol-2-yl] amino] propyl] 2,2-dimethylpropanoate (from Example 12, Step 1) (0.69 g, 1.41 mmol) in methanol (50.0 mL) was added sodium hydroxide pellets (0.39 g, 9.86 mmol) and the reaction mixture was stirred at ambient temperature for 1 h. The reaction mass was concentrated and the residue diluted with water (30 mL). The aqueous layer was extracted with ethyl acetate (3×70 mL) and the combined organic layer was washed with water (30 mL) followed by brine solution (30 mL), dried over sodium sulphate, filtered and concentrated to afford 1-[[2-[[1-(3-chloro-4-fluoro-phenyl)-2-hydroxy-1-methyl-ethyl] amino]-1H-benzimidazol-4-yl]methyl]-3-methyl-urea (0.49 g) as a pale yellow solid.

$^1$H NMR (400 MHz, DMSO-$d_6$) δ 10.62 (s, 1H), 7.69-7.67 (m, 1H), 7.53-7.50 (m, 1H), 7.33 (d, 1H, J=7.80 Hz), 7.25 (t, 1H, J=8.80 Hz), 7.18 (t, 1H, J=7.80 Hz), 7.11 (d, 1H, J=7.48 Hz), 6.47 (bs, 1H), 6.13 (d, 1H, J=5.40 Hz), 5.87 (d, 1H, J=4.56 Hz), 4.51 (d, 1H, J=15.24 Hz), 4.42 (d, 1H, J=15.24 Hz), 4.18-4.12 (m, 1H), 4.01 (d, 1H, J=11.92 Hz), 2.72 (s, 3H), 1.84 (s, 3H);

MS: m/z 406.1 (M+1).

The above product was resolved into its two enantiomers by Chiral SFC using the below method; Column: Lux $C_4$; Flow rate: 4.0 mL/min, Co-Solvent: 40%; Co-solvent Name: 0.5% isopropyl amine in isopropyl alcohol; injected Volume: 10.0 µL; Out let pressure: 100 bar; Temperature: 35° C. to obtain the two enantiomers 12a and 12b.

Example 12a: (−)-1-((2-((2-(3-chloro-4-fluorophenyl)-1-hydroxypropan-2-yl)amino)-1H-benzo[d]imidazol-4-yl)methyl)-3-methylurea The (−) enantiomer was the first to elute-off the column.

$^1$H NMR (400 MHz, AcOH-$d_4$) δ 7.69-7.67 (m, 1H), 7.54-7.50 (m, 1H), 7.33 (d, 1H, J=7.84 Hz), 7.25 (t, 1H, J=8.80 Hz), 7.18 (t, 1H, J=7.84 Hz), 7.12 (d, 1H, J=7.24 Hz), 4.51 (d, 1H, J=15.28 Hz), 4.42 (d, 1H, J=15.32 Hz), 4.19 (d, 1H, J=11.92 Hz), 4.01 (d, 1H, J=11.92 Hz), 2.72 (s, 3H), 1.84 (s, 3H);

MS: m/z 406.1 (M+1);

[α] D $^{22.5}$ (−) 7.31 (MeOH, c=1.0).

Example 12b: (+)-1-((2-((2-(3-chloro-4-fluorophenyl)-1-hydroxypropan-2-yl)amino)-1H-benzo[d]imidazol-4-yl)methyl)-3-methylurea The (+) enantiomer was the second elute off the column.

1H NMR (400 MHz, AcOH-$d_4$) δ 7.69-7.67 (m, 1H), 7.54-7.50 (m, 1H), 7.33 (d, 1H, J=7.88 Hz), 7.25 (t, 1H, J=8.80 Hz), 7.18 (t, 1H, J=7.84 Hz), 7.12 (d, 1H, J=7.36 Hz), 4.51 (d, 1H, J=15.28 Hz), 4.42 (d, 1H, J=15.16 Hz), 4.19 (d, 1H, J=11.92 Hz), 4.01 (d, 1H, J=11.92 Hz), 2.72 (s, 3H), 1.84 (s, 3H);

MS: m/z 406.2 (M+1);

[α] D $^{22.5}$ (+) 6.46 (MeOH, c=1.0).

Example 13: Preparation of 3-((2-((2-(3-chlorophenyl)-1-hydroxypropan-2-yl) amino)-1H-benzo[d]imidazol-4-yl)methyl)-1,1-dimethylurea

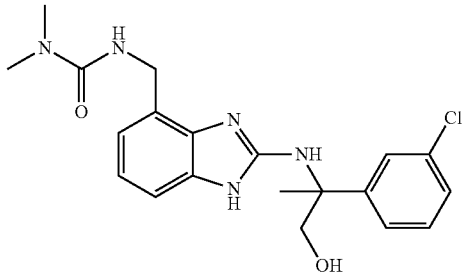 [SMILES: CN(C)C(=O)NCc1cccc2[nH]c(NC(C)(CO)c3cccc(Cl)c3)nc12]

Example 13, Step 1: Preparation of 2-{[(2-amino-6-{[(dimethylcarbamoyl)amino]methyl}phenyl)carbamothioyl]amino}-2-(3-chlorophenyl)propyl 2,2-dimethylpropanoate and 2-{[(2-amino-3-{[(dimethylcarbamoyl)amino]methyl}phenyl)carbamothioyl]amino}-2-(3-chlorophenyl)propyl 2,2-dimethylpropanoate (mixture of regioisomers)

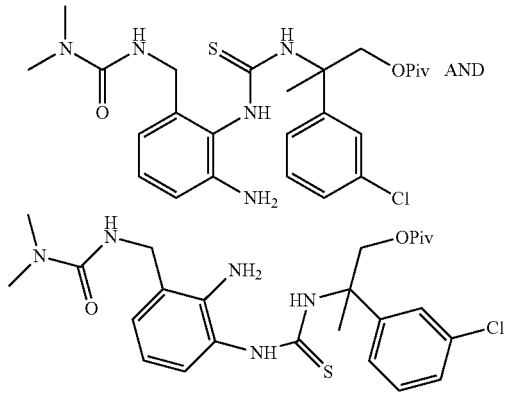

To a solution 3-(2, 3-diaminobenzyl)-1, 1-dimethylurea (Example 2, Step 2) (9.35 g, 44.90 mmol) in a mixture of solvents dichloromethane:methanol (4:1; 200 mL) was added 2-(3-chlorophenyl)-2-isothiocyanatopropyl 2,2-dimethylpropanoate (Example 11, Step 7) (14.00 g, 44.90 mmol) and the mixture was stirred at ambient temperature for 48 h. The reaction mass was concentrated to afford a brown gum (23.00 g). This was purified by chromatography on a Grace instrument using a 120.0 g pre-packed column with 60-120 silica gel, and the product was eluted by 75% ethyl acetate in hexane to afford 2-{[(2-amino-6-{[(dimethylcarbamoyl)amino]methyl}phenyl)carbamothioyl]amino}-2-(3-chlorophenyl)propyl 2,2-dimethylpropanoate and 2-{[(2-amino-3-{[(dimethylcarbamoyl)amino]methyl}phenyl)carbamothioyl]amino}-2-(3-chlorophenyl)propyl 2,2-dimethylpropanoate (as a 4:1 mixture of regioisomers) (17.00 g) as a yellow solid, which was used in the next step without further purification.

MS: m/z 521.2 (M+1).

Example 13, Step 2: Preparation of 2-(3-chlorophenyl)-2-[(4-{[(dimethylcarbamoyl)amino]methyl}-1H-1,3-benzodiazol-2-yl)amino]propyl 2,2-dimethylpropanoate

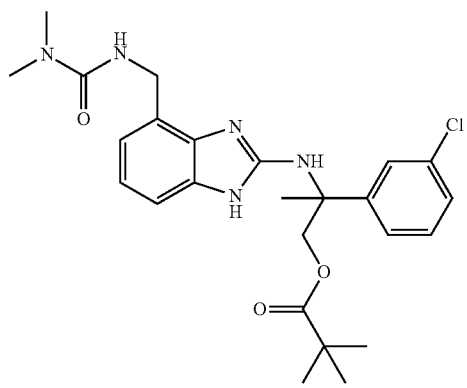 [SMILES: CN(C)C(=O)NCc1cccc2[nH]c(NC(C)(COC(=O)C(C)(C)C)c3cccc(Cl)c3)nc12]

To a solution of 2-{[(2-amino-6-{[(dimethylcarbamoyl)amino]methyl}phenyl)carbamothioyl]amino}-2-(3-chlorophenyl)propyl 2,2-dimethylpropanoate and 2-{[(2-amino-3-{[(dimethylcarbamoyl)amino]methyl}phenyl)carbamothioyl]amino}-2-(3-chlorophenyl)propyl 2,2-dimethylpropanoate (as a 4:1 mixture of regioisomers) (from Example 13, Step 1) (17.00 g, 32.70 mmol) under a nitrogen atmosphere in dry methanol (200 mL) was added iodoacetic acid (6.08 g, 32.70 mmol) and the mixture was stirred at 70° C. for 1 h. The above reaction mass was concentrated to remove the methanol solvent and the residue was diluted with 10% aqueous sodium bicarbonate solution (100 mL), and was extracted with ethyl acetate. The combined organic layer was washed with brine solution (100 mL), dried over sodium sulphate, filtered and concentrated to afford a brown gum (15.00 g). It was purified by chromatography on a Grace instrument using 80.0 g pre-packed cartridge filled with 60-120 silica gel column and the product was eluted with 5% methanol in chloroform to afford 2-(3-chlorophenyl)-2-[(4-{[(dimethylcarbamoyl)amino]methyl}-1H-1,3-benzodiazol-2-yl)amino]propyl 2,2-dimethylpropanoate (14.00 g) as a yellow solid.

$^1$H NMR (400 MHz, DMSO-$d_6$) δ 10.55 (s, 1H), 7.59 (s, 1H), 7.43 (d, 1H, J=7.60 Hz), 7.35 (t, 1H, J=7.60 Hz), 7.28 (d, 1H, J=7.60 Hz), 7.25 (s, 1H), 7.05 (bs, 1H), 6.97b (d, 1H, J=7.20 Hz), 6.79 (t, 1H, J=7.60 Hz), 6.73 (d, 1H, J=7.20 Hz), 4.52 (q, 2H, J=10.80 Hz), 4.29 (d, 2H, J=4.80 Hz), 2.82 (s, 6H), 1.80 (s, 3H), 1.02 (s, 9H);

MS: m/z 487.2 (M+1).

Example 13: Preparation of 3-((2-((2-(3-chlorophenyl)-1-hydroxypropan-2-yl) amino)-1H-benzo[d] imidazol-4-yl) methyl)-1, 1-dimethylurea

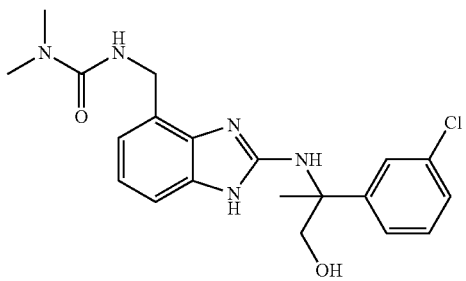 [SMILES: CN(C)C(=O)NCc1cccc2[nH]c(NC(C)(CO)c3cccc(Cl)c3)nc12]

To a solution of 2-(3-chlorophenyl)-2-[(4-{[(dimethylcarbamoyl)amino]methyl}-1H-1,3-benzodiazol-2-yl)amino]propyl 2,2-dimethylpropanoate (from Example 13, Step 2) (15.00 g, 30.90 mmol) in methanol (300 mL) solvent was added sodium hydroxide pellets (3.70 g, 92.60 mmol) and the mixture was stirred at ambient temperature for 1 h. The reaction mass was concentrated to remove the solvent methanol and the residue was dissolved with water (50 mL) extracted with ethyl acetate (4×300 mL). The combined organic layer was washed with brine (50 mL), dried over sodium sulphate, filtered and concentrated to afford a brown gum (12.40 g). This was purified by chromatography on a Grace instrument using 80.0 g pre-packed cartridge filled with 60-120 silica gel and the product was eluted with 8% methanol in chloroform to afford 3-((2-((2-(3-chlorophenyl)-1-hydroxypropan-2-yl) amino)-1H-benzo[d] imidazol-4-yl) methyl)-1,1-dimethylurea (12.00 g) as an off-white solid.

¹H NMR (400 MHz, AcOH-d₄) δ 7.59 (s, 1H), 7.50 (d, 1H, J=7.16 Hz), 7.38 (t, 1H, J=7.60 Hz), 7.33 (d, 2H, J=8.10 Hz), 7.18 (t, 1H, J=7.70 Hz), 7.11 (d, 1H, J=7.50 Hz), 4.47 (q, 2H, J=15.04 Hz), 4.20 (d, 1H, J=11.80 Hz), 4.00 (d, 1H, J=11.80 Hz), 2.87 (s, 6H), 1.85 (s, 3H);

MS: m/z 402.2 (M+1).

The above product was resolved into its two enantiomers by Chiral SFC using the method; Column: Chiralcel OX—H; Flow rate: 3 mL/min, Co-Solvent: 30%; Co-solvent Name: 0.5% isopropyl amine in isopropyl alcohol; injected Volume: 2.0 μL; out let pressure: 100 bar; Temperature: 35° C. to obtain the two enantiomers 13a and 13b.

Example 13a: (−)-3-((2-((2-(3-chlorophenyl)-1-hydroxypropan-2-yl) amino)-1H-benzo[d] imidazol-4-yl) methyl)-1, 1-dimethylurea The (−) enantiomer was the first to elute off the column.

¹H NMR (400 MHz, AcOH-d₄) δ 7.57 (s, 1H), 7.47 (d, 1H, J=7.60 Hz), 7.36 (t, 1H, J=7.60 Hz), 7.32 (d, 2H, J=7.20 Hz), 7.15 (t, 1H, J=8.00 Hz), 7.09 (d, 1H, J=7.20 Hz), 4.46 (q, 2H, J=14.80 Hz), 4.18 (d, 1H, J=12.00 Hz), 4.00 (d, 1H, J=12.00 Hz), 2.86 (s, 6H), 1.83 (s, 3H);

MS: m/z 402.2 (M+1);

[α] D $^{24.4}$ (−) 11.60 (MeOH, c=1.0).

Example 13b: (+)-3-((2-((2-(3-chlorophenyl)-1-hydroxypropan-2-yl) amino)-1H-benzo[d] imidazol-4-yl) methyl)-1, 1-dimethylurea The (+) enantiomer was the second to elute off the column.

¹H NMR (400 MHz, AcOH-d₄) δ 7.57 (s, 1H), 7.47 (d, 1H, J=7.60 Hz), 7.36 (t, 1H, J=7.60 Hz), 7.31 (d, 2H, J=7.20 Hz), 7.15 (t, 1H, J=8.00 Hz), 7.09 (d, 1H, J=6.80 Hz), 4.46 (q, 2H, J=15.20 Hz), 4.18 (d, 1H, J=11.60 Hz), 4.00 (d, 1H, J=11.80 Hz), 2.85 (s, 6H), 1.83 (s, 3H);

MS: m/z 402.2 (M+1);

[α] D $^{24.3}$ (+) 12.60 (MeOH, c=1.0).

Example 14: Preparation of 1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea

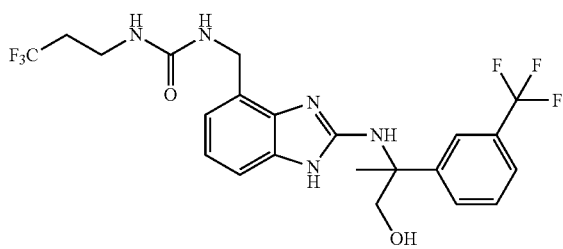 [SMILES: CC(CO)(Nc1nc2c(CNC(=O)NCCC(F)(F)F)cccc2[nH]1)c1cccc(C(F)(F)F)c1]

Example 14, Step 1: Preparation of 2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate

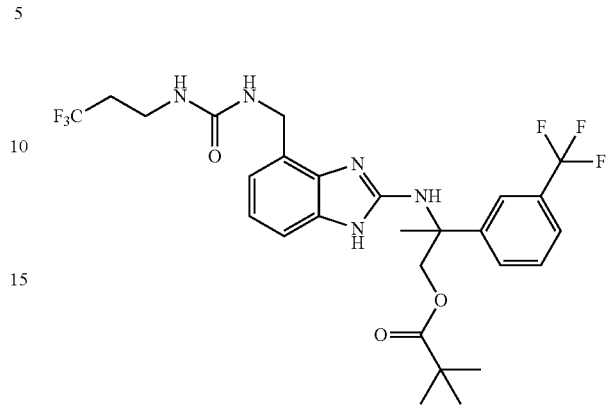

To a solution of 2-{[4-(aminomethyl)-1H-1,3-benzodiazol-2-yl]amino}-2-[3-(trifluoromethyl)phenyl]propyl 2,2-dimethylpropanoate; trifluoroacetic acid (from Example 9, Step 4) (1.00 g, 2.00 mmol) in dichloromethane (50 mL) was added triethyl amine (0.56 mL, d=0.726 g/cm³, 4.00 mmol) and the mixture was cooled to −78° C. Then 1, 1, 1-trifluoro-3-isocyanato-propane (0.310 g, 2.00 mmol) was added and the reaction was stirred at same temperature for 30 min. The reaction mixture was diluted with water (50 mL), extracted with dichloromethane (3×150 ML). The combined organic extracts were dried over anhydrous sodium sulphate, filtered and evaporated to afford a brown gum (1.00 g). This was purified by preparative HPLC to afford 2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate (0.650 g) as an off-white solid.

¹H NMR (400 MHz, DMSO-d₆: D₂O) δ 7.79 (s, 1H), 7.73 (d, 2H, J=7.70 Hz), 7.64 (t, 1H, J=8.00 Hz), 7.27 (d, 1H, J=7.84 Hz), 7.18 (t, 1H, J=7.70 Hz), 7.10 (d, 1H, J=7.52 Hz), 4.48 (q, 2H, J=11.40 Hz), 4.19 (d, 2H, J=5.04 Hz), 3.24 (dd, 2H, J=6.90 Hz), 2.35 (d, 2H, J=4.72 Hz), 1.89 (s, 3H), 1.03 (s, 9H);

MS: m/z 588.1 (M+1).

The above product was resolved into its two enantiomers by Chiral SFC using the method; Column: Chiralcel OX—H; Flow rate: 3.0 mL/min, Co-Solvent: 20%; Co-solvent d Name: 0.5% isopropyl amine in isopropyl alcohol; injected Volume: 15.0 μL; Out let pressure: 100 bar; Temperature: 35° C. to obtain the two enantiomers 14-1a and 14-1b.

Example 14-1a: (+)-2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate The (+) enantiomer was the first to elute off the column (Fraction 1).

MS: m/z 588.1 (M+1);

[α] D $^{26.0}$ (+) 14.00 (MeOH, c=1.0).

Example 14-1b: (−)-2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate The (−) enantiomer was the second to elute off the column (Fraction 2).

MS: m/z 588.1 (M+1);

[α] D $^{26.0}$ (−) 14.44 (MeOH, c=1.0).

Example 14: Preparation of 1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea

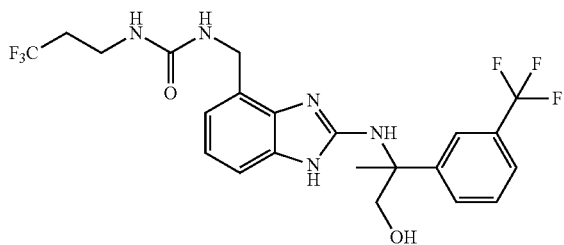 [SMILES: CC(CO)(Nc1nc2c(CNC(=O)NCCC(F)(F)F)cccc2[nH]1)c1cccc(C(F)(F)F)c1]

To a solution of 2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate (from Example 14, Step 1) (0.150 g, 0.255 mmol) in methanol (10 mL) was added sodium hydroxide pellets (0.051 g, 1.275 mmol) and the mixture was stirred at ambient temperature for 2 h. The reaction mass was concentrated and the residue diluted with 10% aqueous sodium bicarbonate solution (15 mL) and extracted with ethyl acetate (3×50 mL). The combined organic layer was dried over sodium sulphate, filtered and concentrated to afford a brown gum (0.130 g). This was purified by chromatography on a Grace instrument using 12.00 g pre-packed flash cartridge filled with normal phase silica gel 60° A, 40-63 μm and the product was eluted with 3-5% methanol in chloroform to afford 1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea (0.110 g) as an off-white solid.

$^1$H NMR (400 MHz, AcOH-d$_4$) δ 7.89 (s, 1H), 7.84 (d, 1H, J=8.00 Hz), 7.69 (d, 1H, J=7.80 Hz), 7.61 (t, 1H, J=7.90 Hz), 7.28 (d, 1H, J=7.52 Hz), 7.19 (t, 1H, J=7.60 Hz), 7.15 (d, 1H, J=7.52 Hz), 4.47 (q, 2H, J=15.32 Hz), 4.29 (d, 1H, J=12.00 Hz), 4.08 (d, 1H, J=12.00 Hz), 3.42 (d, 2H, J=4.40 Hz), 2.45-2.40 (m, 2H), 1.89 (s, 3H);

MS: m/z 504.2 (M+1).

Example 14a: Preparation of (−)-1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea

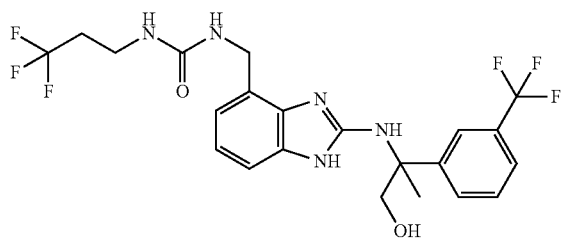 [SMILES: CC(CO)(Nc1nc2c(CNC(=O)NCCC(F)(F)F)cccc2[nH]1)c1cccc(C(F)(F)F)c1]

To a solution of (+)-2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate (from Example 14, Step 1, Compound 14-1a, Fraction 1) (0.250 g, 0.425 mmol) in methanol (20 mL) was added sodium hydroxide (0.085 g, 2.125 mmol) pellets and was stirred at ambient temperature for 2 h. The reaction mass was concentrated and the residue diluted with water (20 mL) and extracted with ethyl acetate (2×100 mL). The combined organic layer was dried over sodium sulphate, filtered and concentrated to afford a brown gum (0.214 g). This was purified by preparative HPLC to afford (−)-1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea (0.140 g) as an off-white solid.

$^1$H NMR (400 MHz, AcOH-d$_4$) δ 7.88 (s, 1H), 7.84 (d, 1H, J=7.90 Hz), 7.68 (d, 1H, J=7.90 Hz), 7.61 (t, 1H, J=7.80 Hz), 7.29 (d, 1H, J=7.00 Hz), 7.17 (t, 1H, J=7.64 Hz), 7.12 (d, 1H, J=6.72 Hz), 4.43 (q, 2H, J=15.40 Hz), 4.29 (d, 1H, J=11.92 Hz), 4.07 (d, 1H, J=12.00 Hz), 3.41 (t, 2H, J=7.00 Hz), 2.44-2.36 (m, 2H), 1.89 (s, 3H);

MS: m/z 504.2 (M+1);

[α] D $^{25.1}$ (−) 12.03 (MeOH, c=1.15).

Example 14b: Preparation of (+)-1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea

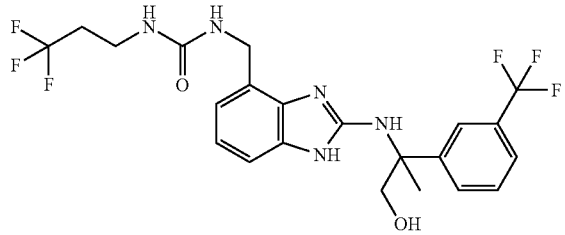 [SMILES: CC(CO)(Nc1nc2c(CNC(=O)NCCC(F)(F)F)cccc2[nH]1)c1cccc(C(F)(F)F)c1]

To a solution of (−)-2-[3-(trifluoromethyl)phenyl]-2-{[4-({[(3,3,3-trifluoropropyl)carbamoyl]amino}methyl)-1H-1,3-benzodiazol-2-yl]amino}propyl 2,2-dimethylpropanoate (from Example 14, Step 1, Compound 14-1b, Fraction 2) (0.250 g, 0.425 mmol) in methanol (20 mL) was added sodium hydroxide (0.085 g, 2.125 mmol) pellets and stirred at ambient temperature for 2 h. The reaction mass was concentrated and the residue was diluted with water (20 mL) and extracted with ethyl acetate (2×100 mL). The combined organic layer was dried over sodium sulphate, filtered and concentrated to afford a brown gum (0.214 g). This was purified by preparative HPLC to afford (+)-1-((2-((1-hydroxy-2-(3-(trifluoromethyl) phenyl) propan-2-yl) amino)-1H-benzo[d] imidazol-4-yl) methyl)-3-(3, 3, 3-trifluoropropyl) urea (0.160 g) as an off-white solid.

$^1$H NMR (400 MHz, AcOH-d$_4$) δ 7.89 (s, 1H), 7.84 (d, 1H, J=7.80 Hz), 7.68 (d, 1H, J=8.00 Hz), 7.61 (t, 1H, J=7.80 Hz), 7.29 (d, 1H, J=7.70 Hz), 7.18 (t, 1H, J=7.64 Hz), 7.12 (d, 1H, J=6.84 Hz), 4.43 (q, 2H, J=15.32 Hz), 4.28 (d, 1H, J=11.92 Hz), 4.07 (d, 1H, J=12.00 Hz), 3.41 (t, 2H, J=7.12 Hz), 2.43-2.36 (m, 2H), 1.89 (s, 3H);

MS: m/z 504.2 (M+1);

[α] D $^{25.2}$ (+) 14.73 (MeOH, c=1.20).

Example 15: Preparation of N-((2-((2-(3-chlorophenyl)-1-hydroxypropan-2-yl) amino)-1H-benzo[d]imidazol-4-yl) methyl) azetidine-1-carboxamide

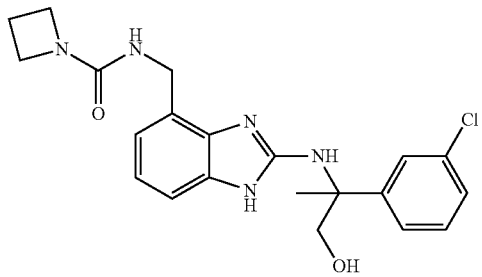 [SMILES: CC(CO)(Nc1nc2c(CNC(=O)N3CCC3)cccc2[nH]1)c1cccc(Cl)c1]

Example 15, Step 1: Preparation of 2-{[(2-amino-6-{[(azetidine-1-carbonyl)amino]methyl}phenyl)carbamothioyl]amino}-2-(3-chlorophenyl)propyl 2,2-dimethylpropanoate and 2-{[(2-amino-3-{[(azetidine-1-carbonyl)amino]methyl}phenyl)carbamothioyl]amino}-2-(3-chlorophenyl)propyl 2,2-dimethylpropanoate (mixture of regioisomers)

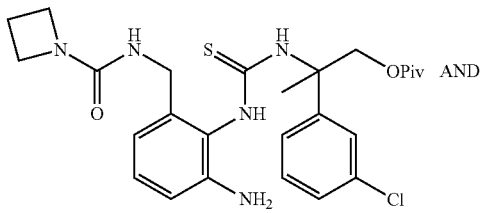

AND

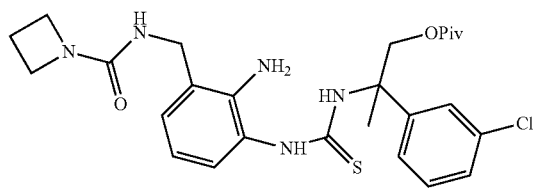

To a solution N-(2, 3-diaminobenzyl) azetidine-1-carboxamide (Example 8, Step 2) (0.60 g, 2.72 mmol) in dichloromethane (25 mL) was added 2-(3-chlorophenyl)-2-isothiocyanatopropyl 2,2-dimethylpropanoate (Example 11, Step 7) (0.813 g, 2.61 mmol) and the mixture was stirred at ambient temperature for 24 h. The reaction mass was concentrated to afford a brown gum (1.5 g). This was purified by chromatography on a Grace instrument using 24.0 g pre-packed flash cartridge filled with normal phase silica gel 60° A, 40-63 μm and the product was eluted with 65% ethyl acetate in hexane to afford 2-{[(2-amino-6-{[(azetidine-1-carbonyl)amino]methyl}phenyl)carbamothioyl]amino}-2-(3-chlorophenyl)propyl 2,2-dimethylpropanoate and 2-{[(2-amino-3-{[(azetidine-1-carbonyl)amino]methyl}phenyl)carbamothioyl]amino}-2-(3-chlorophenyl)propyl 2,2-dimethylpropanoate (as a 3:2 mixture of regioisomers) (0.90 g) as a yellow solid, which was used in the next step without further purification.

MS: m/z 533.2 (M+1).

Example 15, Step 2: Preparation of 2-[(4-{[(azetidine-1-carbonyl)amino]methyl}-1H-1,3-benzodiazol-2-yl)amino]-2-(3-chlorophenyl)propyl 2,2-dimethylpropanoate

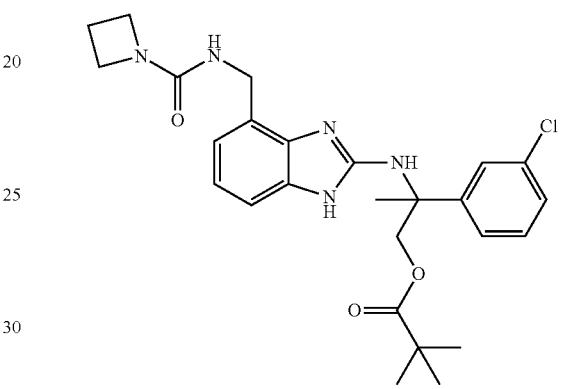

To a solution of 2-{[(2-amino-6-{[(azetidine-1-carbonyl)amino]methyl}phenyl)carbamothioyl]amino}-2-(3-chlorophenyl)propyl 2,2-dimethylpropanoate and 2-{[(2-amino-3-{[(azetidine-1-carbonyl)amino]methyl}phenyl)carbamothioyl]amino}-2-(3-chlorophenyl)propyl 2,2-dimethylpropanoate (as a 3:2 mixture of regioisomers) (from Example 15, Step 1) (0.90 g, 1.69 mmol) under a nitrogen atmosphere in dry methanol (20 mL) was added iodoacetic acid (0.799 g, 4.23 mmol) and the mixture was stirred at 70° C. for 1 h. The reaction mass was concentrated to remove the methanol solvent and the residue was diluted with 10% aqueous sodium bicarbonate solution (20 mL) and extracted with ethyl acetate (3×150 mL). The combined organic layer was washed with brine solution (20 mL), dried over sodium sulphate, filtered and concentrated to afford a brown gum (0.85 g). This was purified by chromatography on a Grace instrument using 24.0 g pre-packed flash cartridge filled with normal phase silica gel 60° A, 40-63 μm and the product was eluted with 90% ethyl acetate in petroleum ether to afford 2-[(4-{[(azetidine-1-carbonyl)amino]methyl}-1H-1,3-benzodiazol-2-yl)amino]-2-(3-chlorophenyl)propyl 2,2-dimethylpropanoate (0.83 g) as a yellow solid.

1H NMR (400 MHz, DMSO-$d_6$: $D_2O$) δ 7.45 (s, 1H), 7.40 (d, 1H, J=7.60 Hz), 7.34 (t, 1H, J=7.80 Hz), 7.27 (d, 1H, J=7.70 Hz), 6.97 (d, 1H, J=7.32 Hz), 6.81 (t, 1H, J=7.50 Hz), 6.73 (d, 1H, J=7.40 Hz), 4.50 (d, 2H, J=10.60 Hz), 4.43 (d, 2H, J=6.90 Hz), 4.02 (d, 2H, J=4.64 Hz), 3.78 (t, 2H, J=7.12 Hz), 2.11 (d, 2H, J=6.60 Hz), 1.81 (s, 3H), 1.02 (s, 9H);

MS: m/z 499.2 (M+1).

Example 15: Preparation of N-((2-((2-(3-chlorophenyl)-1-hydroxypropan-2-yl) amino)-1H-benzo[d]imidazol-4-yl) methyl) azetidine-1-carboxamide

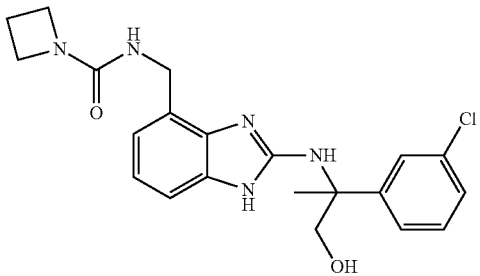 [SMILES: CC(CO)(Nc1nc2c(CNC(=O)N3CCC3)cccc2[nH]1)c1cccc(Cl)c1]

To a solution of 2-[(4-{[(azetidine-1-carbonyl)amino]methyl}-1H-1,3-benzodiazol-2-yl)amino]-2-(3-chlorophenyl)propyl 2,2-dimethylpropanoate (from Example 15, Step 2) (0.83 g, 1.67 mmol) in methanol (20 mL) solvent was added sodium hydroxide pellets (0.667 g, 1.67 mmol) and the mixture was stirred at ambient temperature for 3 h. The reaction mass was concentrated to remove the solvent methanol and the residue was dissolved with water (25 mL) and extracted with ethyl acetate (2×100 mL). The combined organic layer was washed with brine (20 mL), dried over sodium sulphate, filtered and concentrated to afford a brown gum (0.69 g). This was purified by chromatography on a Grace instrument using 24.0 g pre-packed flash cartridge filled with normal phase silica gel 60° A, 40-63 μm and the product was eluted with 8% methanol in chloroform to afford N-((2-((2-(3-chlorophenyl)-1-hydroxypropan-2-yl)amino)-1H-benzo[d]imidazol-4-yl) methyl) azetidine-1-carboxamide (0.65 g) as an off-white solid.

$^1$H NMR (400 MHz, AcOH-d$_4$) δ 7.57 (s, 1H), 7.48 (d, 1H, J=7.20 Hz), 7.39 (d, 1H, J=8.00 Hz), 7.36 (d, 1H, J=1.20 Hz), 7.32 (t, 1H, J=6.00 Hz), 7.16 (t, 1H, J=7.60 Hz), 7.10 (d, 1H, J=7.40 Hz), 4.52 (d, 1H, J=15.10 Hz), 4.38 (d, 1H, J=15.12 Hz), 4.27 (d, 1H, J=12.00 Hz), 4.02 (d, 1H, J=12.00 Hz), 3.96 (d, 4H, J=7.04 Hz), 2.24 (t, 2H, J=7.30 Hz), 1.85 (s, 3H);

MS: m/z 414.2 (M+1).

The above product was resolved into its two enantiomers by Chiral SFC using the method; Column: Chiral Pak OX—H; Flow rate: 3.0 mL/min, Co-Solvent: 30%; Co-solvent Name: 0.5% isopropyl amine in isopropyl alcohol; injected Volume: 7.0 μL; Out let pressure: 100 bar; Temperature: 35° C. to obtain the two enantiomers 15a and 15b.

Example 15a: (−)-(N-((2-((2-(3-chlorophenyl)-1-hydroxypropan-2-yl) amino)-1H-benzo[d]imidazol-4-yl) methyl) azetidine-1-carboxamide The (−) enantiomer was the first to elute off the column.

$^1$H NMR (400 MHz, AcOH-d$_4$) δ 7.56 (s, 1H), 7.46 (d, 1H, J=7.20 Hz), 7.39 (d, 1H, J=8.00 Hz), 7.36 (d, 1H, J=1.20 Hz), 7.32 (t, 1H, J=6.00 Hz), 7.14 (t, 1H, J=7.60 Hz), 7.08 (d, 1H, J=7.20 Hz), 4.48 (d, 1H, J=15.20 Hz), 4.37 (d, 1H, J=15.20 Hz), 4.26 (d, 1H, J=11.20 Hz), 4.02 (d, 1H, J=12.00 Hz), 3.96 (d, 4H, J=7.04 Hz), 2.21 (t, 2H, J=7.30 Hz), 1.79 (s, 3H);

MS: m/z 414.2 (M+1);

[α] D $^{22.2}$ (−) 18.40 (MeOH, c=1.0).

Example 15b: (+)-N-((2-((2-(3-chlorophenyl)-1-hydroxypropan-2-yl) amino)-1H-benzo [d]imidazol-4-yl) methyl) azetidine-1-carboxamide The (+) enantiomer was the second to elute-off the column.

$^1$H NMR (400 MHz, AcOH-d$_4$) δ 7.56 (s, 1H), 7.46 (d, 1H, J=7.20 Hz), 7.39 (d, 1H, J=8.00 Hz), 7.37 (t, 1H, J=8.40 Hz), 7.30 (d, 1H, J=7.60 Hz), 7.13 (t, 1H, J=7.60 Hz), 7.08 (d, 1H, J=7.60 Hz), 4.48 (d, 1H, J=15.20 Hz), 4.38 (d, 1H, J=15.60 Hz), 4.27 (d, 1H, J=12.40 Hz), 4.02 (d, 1H, J=12.40 Hz), 3.96 (d, 4H, J=7.04 Hz), 2.22 (t, 2H, J=7.60 Hz), 1.79 (s, 3H);

MS: m/z 414.2 (M+1);

[α] D $^{22.6}$ (+) 15.40 (MeOH, c=1.0).

Example 16: Preparation of 1-((2-((1-hydroxy-2-(3-(trifluoromethoxy)phenyl)propan-2-yl)amino)-1H-benzo[d]imidazol-4-yl)methyl)-3-methylurea

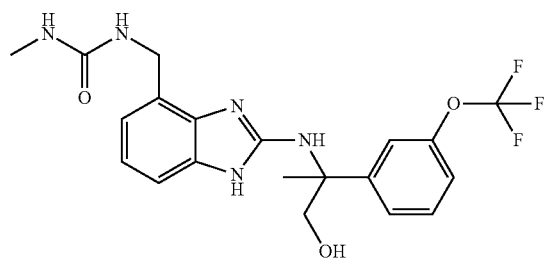 [SMILES: CNC(=O)NCc1cccc2[nH]c(NC(C)(CO)c3cccc(OC(F)(F)F)c3)nc12]

Example 16, Step 1: Preparation of 2-[(4-{[(methylcarbamoyl)amino]methyl}-1H-1,3-benzodiazol-2-yl)amino]-2-[3-(trifluoromethoxy)phenyl]propyl 2,2-dimethylpropanoate

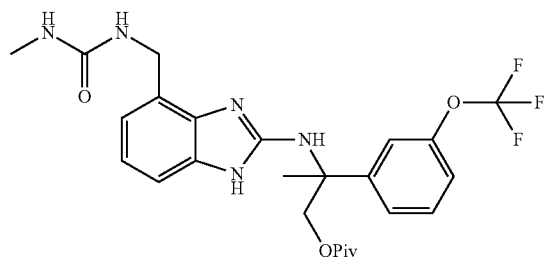

Starting with 1-[3-(trifluoromethoxy)phenyl]ethan-1-one in place of 1-[3-(trifluoromethyl)phenyl]ethan-1-one, the method described for Example 1, steps 1 to 15 was used to afford 2-[(4-{[(methylcarbamoyl)amino]methyl}-1H-1,3-benzodiazol-2-yl)amino]-2-[3-(trifluoromethoxy)phenyl]propyl 2,2-dimethylpropanoate (0.200 g) as a brown gum.

MS: m/z 522.1 (M+1).

Example 16: Preparation of 1-((2-((1-hydroxy-2-(3-(trifluoromethoxy) phenyl) propan-2-yl) amino)-1H-benzo [d]imidazol-4-yl) methyl)-3-methylurea

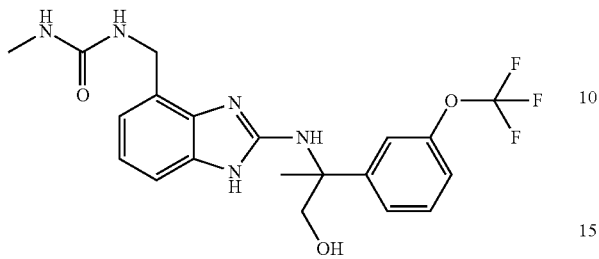

To a solution of 2-[(4-{[(methylcarbamoyl)amino]methyl}-1H-1,3-benzodiazol-2-yl)amino]-2-[3-(trifluoromethoxy)phenyl]propyl 2,2-dimethylpropanoate (from Example 16, Step 1) (0.120 g, 0.230 mmol) in methanol (10 mL) was added sodium hydroxide pellets (0.139 g, 3.45 mmol) and the mixture was stirred at ambient temperature for 1 h. The reaction mass was concentrated to remove the solvent methanol and the residue was dissolved with water (20 mL) and extracted with ethyl acetate (3×50 mL). The combined organic layer was washed with brine (10 mL), dried over sodium sulphate, filtered and concentrated to afford a brown gum (0.110 g). This was purified by chromatography on a Grace instrument using 12.0 g pre-packed flash cartridge filled with normal phase silica gel 60° A, 40-63 μm and the product was eluted with 3-5% methanol in chloroform to afford 1-((2-(((1-hydroxy-2-(3-(trifluoromethoxy)phenyl)propan-2-yl) amino)-1H-benzo [d]imidazol-4-yl) methyl)-3-methyl urea (0.04 g) as a brown solid.

$^1$H NMR (400 MHz, CD$_3$OD) δ 7.55 (d, 1H, J=7.60 Hz), 7.54 (s, 1H), 7.41 (s, 1H), 7.29 (t, 1H, J=7.20 Hz), 7.27 (d, 1H, J=7.80 Hz), 7.22 (t, 1H, J=7.60 Hz), 7.15 (d, 1H, J=7.60 Hz), 4.37 (s, 2H), 4.00 (d, 1H, J=11.20 Hz), 3.88 (d, 1H, J=11.60 Hz), 2.70 (s, 3H), 1.89 (s, 3H);

MS: m/z 438.1 (M+1).

The above product was resolved into its two enantiomers by Chiral SFC using the method; Column: Lux A1; Flow rate: 3.0 mL/min, Co-Solvent: 20%; Co-solvent Name: 0.5% isopropyl amine in isopropyl alcohol; injected Volume: 15.0 μL; Out let pressure: 100 bar; Temperature: 35° C. to obtain the two enantiomers 16a and 16b.

Example 16a: (−)-1-((2-((1-hydroxy-2-(3-(trifluoromethoxy) phenyl) propan-2-yl) amino)-1H-benzo [d] imidazol-4-yl) methyl)-3-methylurea The (−) enantiomer was the first to elute off the column.

$^1$H NMR (400 MHz, CD$_3$OD) δ 7.54 (d, 1H, J=7.32 Hz), 7.53 (s, 1H), 7.41 (s, 1H), 7.29 (dd, 1H, J=7.20 Hz), 7.26 (d, 1H), 7.21 (t, 1H, J=7.40 Hz), 7.14 (d, 1H, J=7.40 Hz), 4.36 (s, 2H), 3.98 (d, 1H, J=11.44 Hz), 3.87 (d, 1H, J=11.40 Hz), 2.69 (s, 3H), 1.88 (s, 3H);

MS: m/z 438.1 (M+1);

[α] D $^{20.5}$ (−) 16.67 (MeOH, c=0.60).

Example 16b: (+)-1-((2-((1-hydroxy-2-(3-(trifluoromethoxy) phenyl) propan-2-yl) amino)-1H-benzo [d] imidazol-4-yl) methyl)-3-methylurea The (+) enantiomer was the second to elute off the column.

$^1$H NMR (400 MHz, CD$_3$OD) δ 7.55 (d, 1H, J=7.20 Hz), 7.53 (s, 1H), 7.40 (s, 1H), 7.29 (t, 1H, J=7.20 Hz), 7.27 (d, 1H, J=8.32 Hz), 7.16 (t, 1H, J=7.64 Hz), 7.10 (d, 1H, J=7.32 Hz), 4.37 (s, 2H), 3.98 (d, 1H, J=11.50 Hz), 3.87 (d, 1H, J=11.32 Hz), 2.70 (s, 3H), 1.86 (s, 3H);

MS: m/z 438.1 (M+1);

[α] D $^{21.0}$ (+) 17.23, (MeOH, c=0.65).

Example 17: Preparation of 1-((2-((2-(3-chloro-4-fluorophenyl)-1-methoxypropan-2-yl) amino)-1H-benzo [d]imidazol-4-yl) methyl)-3-methylurea

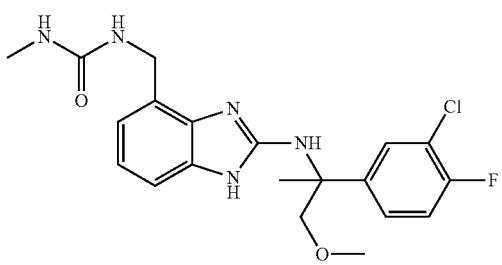 [SMILES: CNC(=O)NCc1cccc2[nH]c(NC(C)(COC)c3ccc(F)c(Cl)c3)nc12]

Example 17, Step 1: Preparation of 2-chloro-1-fluoro-4-(2-isothiocyanato-1-methoxypropan-2-yl) benzene

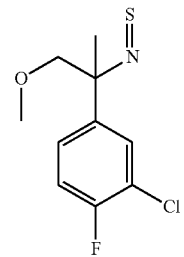

Starting with 1-(3-chloro-4-fluorophenyl)ethan-1-one in place of 1-[3-(trifluoromethyl)phenyl]ethan-1-one, the methods described in Example 1, Steps 1 to 4 and Example 3, Steps 1 to 3 were used to afford 2-chloro-1-fluoro-4-(2-isothiocyanato-1-methoxypropan-2-yl) benzene (3.50 g) as a yellow liquid.

$^1$H NMR (400 MHz, DMSO-d$_6$) δ 7.68-7.65 (m, 1H), 7.50 (d, 1H, J=7.50 Hz), 7.48-7.46 (m, 1H), 3.69 (s, 2H), 3.32 (s, 3H), 1.72 (s, 3H);

Example 17, Step 2: Preparation 1-(3-amino-2-(3-(2-(3-chloro-4-fluorophenyl)-1-methoxy propan-2-yl) thioureido) benzyl)-3-methylurea and 1-(2-amino-3-(3-(2-(3-chloro-4-fluoro phenyl)-1-methoxypropan-2-yl) thio ureido) benzyl)-3-methylurea (mixture of regioisomers)

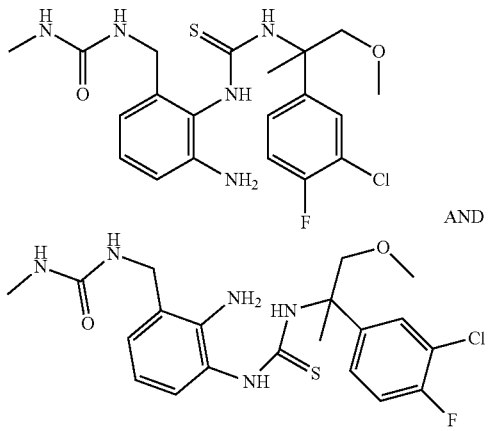

To a solution of 1-(2, 3-diaminobenzyl)-3-methylurea (from Example 1, Step 13) (0.200 g, 10.30 mmol) in dichloromethane (20 mL) was added 2-chloro-1-fluoro-4-(2-isothiocyanato-1-methoxypropan-2-yl) benzene (from Example 17, Step 1) (0.250 g, 9.63 mmol) and the mixture was stirred at ambient temperature for 48 h. The reaction mass was concentrated to afford a brown gum (0.440 g). This was purified by chromatography on a Grace instrument using 24.0 g pre-packed flash cartridge filled with normal phase silica gel 60° A, 40-63 µm and the product was eluted with 75% ethyl acetate in hexane to afford 1-(3-amino-2-(3-(2-(3-chloro-4-fluorophenyl)-1-methoxypropan-2-yl) thioureido)benzyl)-methyl urea and 1-(2-amino-3-(3-(2-(3-chloro-4-fluorophenyl)-1-methoxy propan-2-yl)thio ureido) benzyl)-3-methylurea (as a 4:1 mixture of regioisomers) (0.350 g) as a yellow solid.

MS: m/z 454.1 (M+1).

Example 17: Preparation of 1-((2-((2-(3-chloro-4-fluorophenyl)-1-methoxypropan-2-yl) amino)-1H-benzo [d]imidazol-4-yl) methyl)-3-methylurea

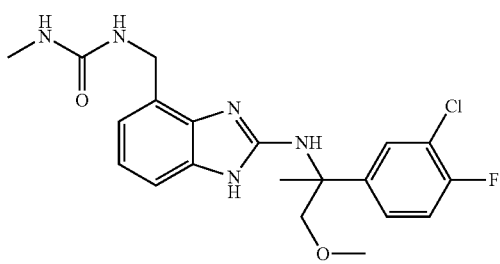 [SMILES: CNC(=O)NCc1cccc2[nH]c(NC(C)(COC)c3ccc(F)c(Cl)c3)nc12]

To a solution of 1-(3-amino-2-(3-(2-(3-chloro-4-fluorophenyl)-1-methoxypropan-2-yl) thioureido) benzyl)-methyl urea and 1-(2-amino-3-(3-(2-(3-chloro-4-fluorophenyl)-1-methoxypropan-2-yl) thio ureido) benzyl)-3-methylurea (4:1 mixture of regioisomers) (from Example 17, Step 2) (0.350 g, 7.71 mmol) under a nitrogen atmosphere in dry methanol (30 mL) was added iodoacetic acid (0.143 g, 7.71 mmol) and the mixture was stirred at 70° C. for 1 h. The reaction mass was concentrated to remove the methanol solvent and the residue was diluted with 10% Aqueous sodium bicarbonate solution (30 mL) and extracted with ethyl acetate (3×150 mL). The combined organic layer was washed with brine solution (30 mL), dried over sodium sulphate, filtered and concentrated to a brown gum (0.350 g). This was purified by chromatography on a Grace instrument using 24.0 g pre-packed flash cartridge filled with normal phase silica gel 60° A, 40-63 µm and the product was eluted with 5% methanol in chloroform to afford 1-((2-((2-(3-chloro-4-fluorophenyl)-1-methoxypropan-2-yl) amino)-1H-benzo [d]imidazol-4-yl) methyl)-3-methylurea (0.240 g) as a yellow solid.

$^1$H NMR (400 MHz, AcOH-$d_4$) δ 7.67 (d, 1H, J=6.84 Hz), 7.53-7.49 (m, 1H), 7.32 (d, 1H, J=7.72 Hz), 7.25 (t, 1H, J=8.84 Hz), 7.18 (t, 1H, J=7.70 Hz), 7.12 (d, 1H, J=7.12 Hz), 4.46 (q, 2H, J=15.32 Hz), 3.96 (d, 1H, J=10.00 Hz), 3.77 (d, 1H, J=10.00 Hz), 3.46 (s, 3H), 2.72 (s, 3H), 1.85 (s, 3H);

MS: m/z 420.2 (M+1).

The above product was resolved into its two enantiomers by Chiral SFC using the method; Column: Lux $C_4$; Flow rate: 3.0 mL/min, Co-Solvent: 40%; Co-solvent Name: 0.5% isopropyl amine in isopropyl alcohol; injected Volume: 4.0 µL; Out let pressure: 100 bar; Temperature: 35° C. to obtain the two enantiomers 17a and 17b.

Example 17a: (+)-1-((2-((2-(3-chloro-4-fluorophenyl)-1-methoxypropan-2-yl) amino)-1H-benzo[d] imidazol-4-yl) methyl)-3-methylurea The (+) enantiomer was the first to elute off the column.

$^1$H NMR (400 MHz, AcOH-$d_4$) δ 7.66 (d, 1H, J=6.52 Hz), 7.52 (t, 1H, J=4.40 Hz), 7.31 (d, 1H, J=7.80 Hz), 7.25 (t, 1H, J=8.80 Hz), 7.17 (t, 1H, J=7.60 Hz), 7.12 (d, 1H, J=7.50 Hz), 4.46 (q, 2H, J=15.30 Hz), 3.96 (d, 1H, J=10.00 Hz), 3.77 (d, 1H, J=10.00 Hz), 3.47 (s, 3H), 2.73 (s, 3H), 1.86 (s, 3H);

MS: m/z 420.1 (M+1);

[α] D $^{23.8}$ (+) 13.20 (MeOH, c=1.0).

Example 17b: (−)-1-((2-((2-(3-chloro-4-fluorophenyl)-1-methoxypropan-2-yl) amino)-1H-benzo[d] imidazol-4-yl) methyl)-3-methylurea The (−) enantiomer was the second to elute off the column.

1H NMR (400 MHz, AcOH-$d_4$) δ 7.66 (d, 1H, J=6.60 Hz), 7.52 (t, 1H, J=4.60 Hz), 7.32 (d, 1H, J=7.72 Hz), 7.25 (t, 1H, J=8.80 Hz), 7.18 (t, 1H, J=7.60 Hz), 7.12 (d, 1H, J=7.44 Hz), 4.47 (q, 2H, J=15.36 Hz), 3.97 (d, 1H, J=10.00 Hz), 3.77 (d, 1H, J=10.00 Hz), 3.47 (s, 3H), 2.73 (s, 3H), 1.86 (s, 3H);

MS: m/z 420.1 (M+1);

[α] D $^{23.8}$ (−) 11.36 (MeOH, c=1.0).

Example 18: Preparation of 3-((2-((2-(3-chlorophenyl)-1-hydroxypropan-2-yl) amino)-1H-benzo[d]imidazol-4-yl) methyl)-1-ethyl-1-methylurea

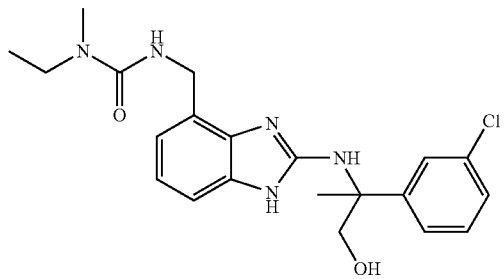 [SMILES: CCN(C)C(=O)NCc1cccc2[nH]c(NC(C)(CO)c3cccc(Cl)c3)nc12]

Example 18, Step 1: Preparation of 2-({[2-amino-6-({[ethyl(methyl)carbamoyl]amino}methyl)phenyl]carbamothioyl}amino)-2-(3-chlorophenyl)propyl 2,2-dimethylpropanoate and 2-({[2-amino-3-({[ethyl(methyl)carbamoyl]amino}methyl)phenyl]carbamothioyl}amino)-2-(3-chlorophenyl)propyl 2,2-dimethylpropanoate (mixture of regioisomers)

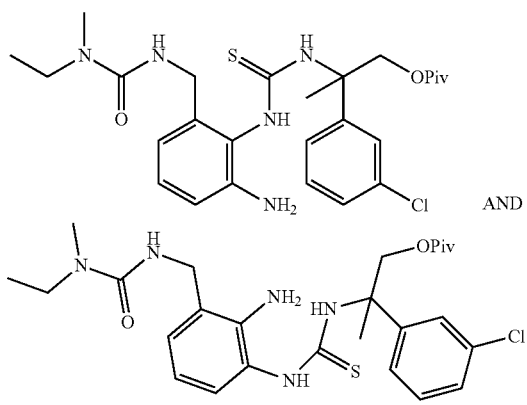

To a solution of 3-(2, 3-diaminobenzyl)-1-ethyl-1-methylurea (from Example 5, Step 2) (0.998 g, 4.49 mmol) in a mixture of solvents dichloromethane:methanol (4:1; 20 mL) was added 2-(3-chlorophenyl)-2-isothiocyanatopropyl 2,2-dimethylpropanoate (from Example 11, Step 7) (1.40 g, 4.49 mmol) and the mixture was stirred at ambient temperature for 16 h. The reaction mass was concentrated to afford a brown gum (2.40 g) which was purified by chromatography on a Grace instrument using 40.0 g pre-packed flash cartridge filled with normal phase silica gel 60° A, 40-63 μm and the product was eluted with 60-65% ethyl acetate in hexane to afford 2-({[2-amino-6-({[ethyl(methyl)carbamoyl]amino}methyl)phenyl]carbamothioyl}amino)-2-(3-chlorophenyl)propyl 2,2-dimethylpropanoate and 2-({[2-amino-3-({[ethyl(methyl)carbamoyl]amino}methyl)phenyl]carbamothioyl}amino)-2-(3-chlorophenyl)propyl 2,2-dimethylpropanoate (as a 4:1 mixture of regioisomers) (2.00 g) as a brown solid.

MS: m/z 535.1 (M+1).

Example 18, Step 2: Preparation of 2-(3-chlorophenyl)-2-{[4-({[ethyl(methyl)carbamoyl]amino}methyl)-1H-1,3-benzodiazol-2-yl]amino}propyl 2,2-dimethylpropanoate

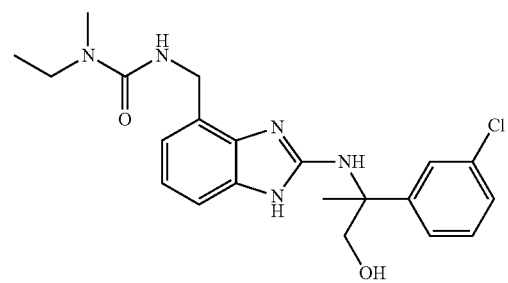 [SMILES: CCN(C)C(=O)NCc1cccc2[nH]c(NC(C)(CO)c3cccc(Cl)c3)nc12]

To a solution of 2-({[2-amino-6-({[ethyl(methyl)carbamoyl]amino}methyl)phenyl]carbamothioyl}amino)-2-(3-chlorophenyl)propyl 2,2-dimethylpropanoate and 2-({[2-amino-3-({[ethyl(methyl)carbamoyl]amino}methyl)phenyl]carbamothioyl}amino)-2-(3-chlorophenyl)propyl 2,2-dimethylpropanoate (as a 4:1 mixture of regioisomers) (from Example 18, Step 1) (2.00 g, 3.74 mmol) under a nitrogen atmosphere in dry methanol (30 mL) was added iodoacetic acid (1.39 g, 7.49 mmol) and the mixture was stirred at 70° C. for 1 h. The reaction mass was concentrated to remove the methanol solvent and the residue was diluted with 10% aqueous sodium bicarbonate solution (50 mL) and extracted with ethyl acetate (3×150 mL). The combined organic layer was washed with brine solution (50 mL), dried over sodium sulphate, filtered and concentrated to afford 2-(3-chlorophenyl)-2-{[4-({[ethyl(methyl)carbamoyl]amino}methyl)-1H-1,3-benzodiazol-2-yl]amino}propyl 2,2-dimethylpropanoate (1.90 g) as a brown gum, which was used in the next step without further any purification.

MS: m/z 501.2 (M+1).

Example 18: Preparation of 3-((2-((2-(3-chlorophenyl)-1-hydroxypropan-2-yl) amino)-1H-benzo[d]imidazol-4-yl) methyl)-1-ethyl-1-methylurea To a solution of 2-(3-chlorophenyl)-2-{[4-({[ethyl(methyl)carbamoyl]amino}methyl)-1H-1,3-benzodiazol-2-yl]amino}propyl 2,2-dimethylpropanoate (from Example 18, Step 2) (2.10 g, 4.20 mmol) in methanol (50 mL) solvent was added sodium hydroxide pellets (1.34 g, 3.36 mmol) and the mixture was stirred at ambient temperature for 1.5 h. The reaction mass was concentrated to remove the solvent methanol and the residue was dissolved with water (50 mL) and extracted with ethyl acetate (4×300 mL). The combined organic layer was washed with brine (30 mL), dried over sodium sulphate, filtered and concentrated to afford 3-((2-((2-(3-chlorophenyl)-1-hydroxy propan-2-yl) amino)-1H-benzo [d]imidazol-4-yl) methyl)-1-ethyl-1-methylurea (1.30 g) as an off-white solid, which was used in the next step without further purification.

$^1$H NMR (400 MHz, AcOH-d$_4$) δ 7.59 (s, 1H), 7.49 (t, 1H, J=7.34 Hz), 7.40 (d, 1H, J=8.00 Hz), 7.36 (d, 1H, J=7.60 Hz), 7.31 (d, 1H, =7.20 Hz), 7.18 (t, 1H, J=7.60 Hz), 7.14 (d, 1H, J=7.20 Hz), 4.50 (q, 2H, J=15.20 Hz), 4.22 (d, 1H, J=12.00 Hz), 4.03 (d, 1H, J=12.00 Hz), 3.30 (q, 2H, J=7.20 Hz), 2.85 (s, 3H), 1.86 (s, 3H), 1.10 (t, 3H, J=7.20 Hz);

MS: m/z 416.2 (M+1).

The above product was resolved into its two enantiomers by Chiral SFC using the method; Column: Chiral Pak OX—H; Flow rate: 3.0 mL/min, Co-Solvent: 30%; Co-solvent Name: 0.5% isopropyl amine in isopropyl alcohol; injected Volume: 15.0 μL; Out let pressure: 100 bar; Temperature: 35° C. to obtain the two enantiomers 18a and 18b.

Example 18a: (−)-3-((2-((2-(3-chlorophenyl)-1-hydroxypropan-2-yl) amino)-1H-benzo[d] imidazol-4-yl) methyl)-1-ethyl-1-methylurea The (−) enantiomer was the first to elute off the column.

$^1$H NMR (400 MHz, AcOH-d$_4$) δ 7.58 (s, 1H), 7.48 (t, 1H, J=7.40 Hz), 7.38 (d, 1H, J=8.00 Hz), 7.35 (d, 1H, J=7.40 Hz), 7.31 (d, 1H, J=8.40 Hz), 7.16 (t, 1H, J=7.60 Hz), 7.10 (d, 1H, J=7.20 Hz), 4.52 (d, 1H, J=14.80 Hz), 4.44 (d, 1H, J=14.80 Hz), 4.20 (d, 1H, J=12.00 Hz), 4.00 (d, 1H, J=12.00 Hz), 3.29 (q, 2H, J=7.20 Hz), 2.84 (s, 3H), 1.84 (s, 3H), 1.08 (t, 3H, J=7.20 Hz);

MS: m/z 416.2 (M+1);

[α] D $^{25.5}$ (−) 30.88 (MeOH, c=1.0).

Example 18b: (+)-3-((2-((2-(3-chlorophenyl)-1-hydroxypropan-2-yl) amino)-1H-benzo[d] imidazol-4-yl) methyl)-1-ethyl-1-methylurea The (+) enantiomer was the second to elute off the column.

$^1$H NMR (400 MHz, AcOH-d$_4$) δ 7.59 (s, 1H), 7.49 (t, 1H, J=7.60 Hz), 7.39 (d, 1H, J=8.00 Hz), 7.36 (d, 1H, J=7.30 Hz), 7.34 (d, 1H, J=7.60 Hz), 7.16 (t, 1H, J=8.00 Hz), 7.11 (d, 1H, J=7.20 Hz), 4.53 (d, 1H, J=14.80 Hz), 4.43 (d, 1H, J=15.20 Hz), 4.20 (d, 1H, J=12.00 Hz), 4.00 (d, 1H, J=12.00 Hz), 3.30 (q, 2H, J=7.20 Hz), 2.85 (s, 3H), 1.86 (s, 3H), 1.09 (t, 3H, J=7.20 Hz);

MS: m/z 416.2 (M+1);

[α] D $^{25.6}$ (+) 22.92 (MeOH, c=1.0).

Example 19: Preparation of N-[[2-[[1-(3-chlorophenyl)-2-hydroxy-1-methyl-ethyl] amino]-3H-benzimidazol-4-yl] methyl] isoxazolidine-2-carboxamide

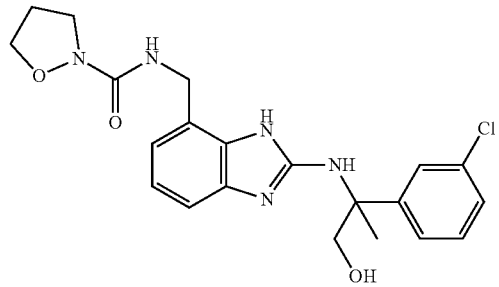 [SMILES: CC(CO)(Nc1nc2cccc(CNC(=O)N3CCCO3)c2[nH]1)c1cccc(Cl)c1]

Example 19, Step 1: Preparation of 2-({[2-amino-6-({bis[(tert-butoxy)carbonyl]amino}methyl)phenyl] carbamothioyl}amino)-2-(3-chlorophenyl)propyl 2,2-dimethylpropanoate and 2-({[2-amino-3-({bis[(tert-butoxy)carbonyl]amino}methyl)phenyl] carbamothioyl}amino)-2-(3-chlorophenyl)propyl 2,2-dimethylpropanoate (mixture of regioisomers)

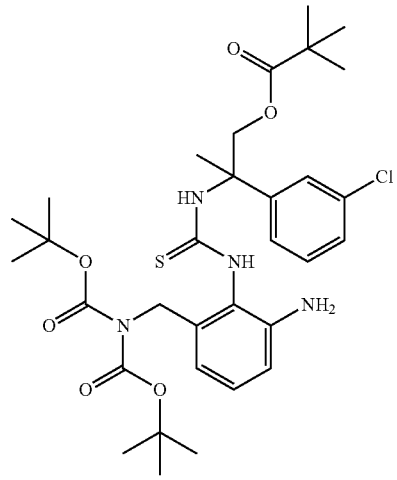

AND

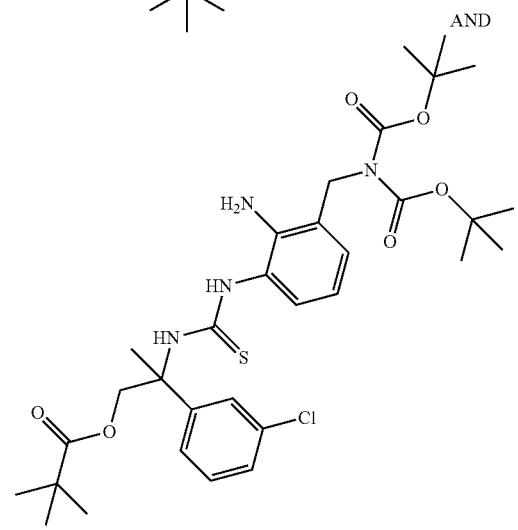

To a solution of tert-butyl N-tert-butoxycarbonyl-N-[(2,3-diaminophenyl) methyl]carbamate (from Example 9, Step 1) (1.0 g, 2.963 mmol) in a mixture of solvents methanol:dichloromethane (1:4; 5.00 ml) was added 2-(3-chlorophenyl)-2-isothiocyanatopropyl 2,2-dimethylpropanoate (from Example 11, Step 7) (0.924 g, 2.963 mmol) and the mixture was stirred at ambient temperature for 16 h. The reaction mass was concentrated to remove methanol and the crude product was purified by chromatography on a Grace instrument using 24.0 g pre-packed flash cartridge filled with normal phase silica gel 60° A, 40-63 μm and the product was eluted with 40-45% ethyl acetate in hexane to afford 2-({[2-amino-6-({bis[(tert-butoxy)carbonyl]amino}methyl)phenyl]carbamothioyl}amino)-2-(3-chlorophenyl)propyl 2,2-dimethylpropanoate and 2-({[2-amino-3-({bis[(tert-butoxy)carbonyl]amino}methyl)phenyl]carbamothioyl}amino)-2-(3-chlorophenyl)propyl 2,2-dimethylpropanoate (as a mixture of regioisomers) (1.30 g) as a brown solid.

MS: m/z 649.3 (M+1).

Example 19, Step 2: Preparation of 2-{[7-({bis[(tert-butoxy)carbonyl]amino}methyl)-1H-1,3-benzodiazol-2-yl]amino}-2-(3-chlorophenyl)propyl 2,2-dimethylpropanoate

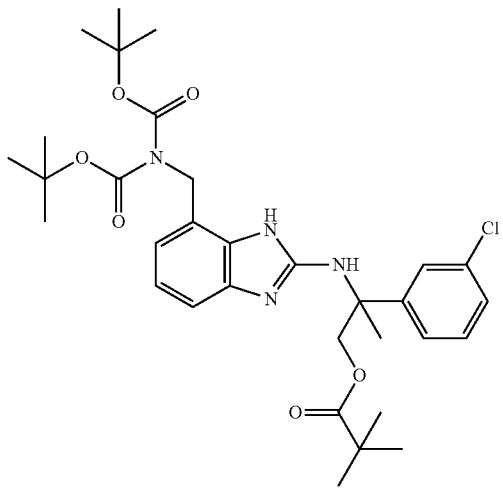 [SMILES: CC(C)(C)OC(=O)N(Cc1cccc2nc(NC(C)(COC(=O)C(C)(C)C)c3cccc(Cl)c3)[nH]c12)C(=O)OC(C)(C)C]

To a solution of 2-({[2-amino-6-({bis[(tert-butoxy)carbonyl]amino}methyl)phenyl]carbamothioyl}amino)-2-(3-chlorophenyl)propyl 2,2-dimethylpropanoate and 2-({[2-amino-3-({bis[(tert-butoxy)carbonyl]amino)methyl)phenyl]carbamothioyl}amino)-2-(3-chlorophenyl)propyl 2,2-dimethylpropanoate (as a mixture of regioisomers) (from Example 19, Step 1) (1.30 g, 2.00 mmol) in dry methanol (15 mL) was added iodoacetic acid (0.558 g, 3.003 mmol) and the mixture was stirred at 65° C. for 1.5 h. The reaction mass was concentrated to remove methanol and the residue was diluted with dichloromethane (100 mL) and washed with 10% sodium bicarbonate solution (2×50 mL). The organic layer was dried over anhydrous sodium sulphate, filtered, concentrated under reduced pressure to afford a brown gum (1.30 g). This was purified by chromatography on a Grace instrument using 40.0 g pre-packed flash cartridge filled with normal phase silica gel 60° A, 40-63 μm and the product was eluted with 50-55% ethyl acetate in hexane to afford 2-[7-({bis[(tert-butoxy)carbonyl]amino}methyl)-1H-1,3-benzodiazol-2-yl]amino}-2-(3-chlorophenyl)propyl 2,2-dimethylpropanoate (1.10 g) as a brown solid.

MS: m/z 615.2 (M+1).

Example 19, Step 3: Preparation of 2-{[7-(aminomethyl)-1H-1,3-benzodiazol-2-yl]amino}-2-(3-chlorophenyl)propyl 2,2-dimethylpropanoate; trifluoroacetic acid

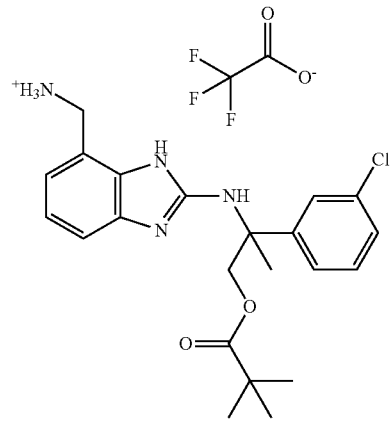 [SMILES: CC(C)(C)C(=O)OCC(C)(Nc1nc2cccc(C[NH3+])c2[nH]1)c1cccc(Cl)c1 ; O=C([O-])C(F)(F)F]

To a stirred solution of 2-{[7-({bis[(tert-butoxy)carbonyl]amino}methyl)-1H-1,3-benzodiazol-2-yl]amino}-2-(3-chlorophenyl)propyl 2,2-dimethylpropanoate (from Example 19, Step 2) (1.10 g, 1.79 mmol) in dichloromethane (30 mL) was added trifluoroacetic acid (0.41 mL, 5.36 mmol) at 0° C. and then stirred at ambient temperature for 16 h. The reaction mass was concentrated under reduced pressure to afford 2-{[7-(aminomethyl)-1H-1,3-benzodiazol-2-yl]amino}-2-(3-chlorophenyl)propyl 2,2-dimethylpropanoate; trifluoroacetic acid (1.60 g) as a brown gum, which was used in the next step without further purification.

MS: m/z 415.1 (M+1).

Example 19, Step 4: Preparation of 2-(3-chlorophenyl)-2-[(7-{[(1H-imidazole-1-carbonyl)amino]methyl}-1H-1,3-benzodiazol-2-yl)amino]propyl 2,2-dimethylpropanoate

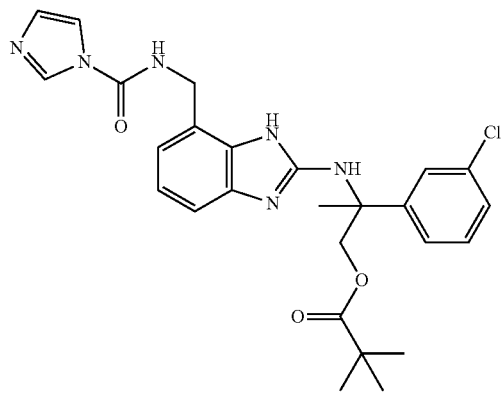 [SMILES: CC(C)(C)C(=O)OCC(C)(Nc1nc2cccc(CNC(=O)n3ccnc3)c2[nH]1)c1cccc(Cl)c1]

To a suspension of 2-{[7-(aminomethyl)-1H-1,3-benzodiazol-2-yl]amino}-2-(3-chlorophenyl)propyl 2,2-dimethylpropanoate; trifluoroacetic acid (from Example 19, Step 3) (1.00 g, 2.51 mmol) in dichloromethane (5 mL) was added triethylamine (1.05 mL, d=0.724 gm/cm³, 7.52 mmol) and the mixture was stirred at ambient temperature for 1 h. Then carbonyldiimidazole (0.610 g, 0.376 mmol) was added at 0° C. in portions and the reaction mixture stirred at ambient temperature for 16 h. The reaction mixture was quenched with water (30 mL) and extracted with dichloromethane (2×100 mL). The combined organic layer was dried over anhydrous sodium sulphate, filtered, concentrated under reduced pressure to afford 2-(3-chlorophenyl)-2-[(7-{[(1H-imidazole-1-carbonyl)amino]methyl}-1H-1,3-benzodiazol-2-yl)amino]propyl 2,2-dimethylpropanoate (0.70 g) as a brown gum, which was used in the next step without further purification.

MS: m/z 509.2 (M+1).

Example 19, Step 5: Preparation of 2-(3-chlorophenyl)-2-[(7-{[(1,2-oxazolidine-2-carbonyl)amino]methyl}-1H-1,3-benzodiazol-2-yl)amino]propyl 2,2-dimethylpropanoate

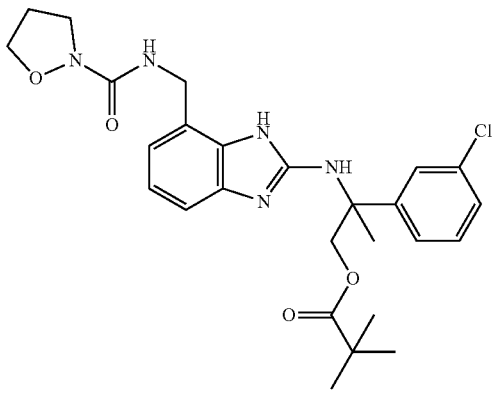 [SMILES: CC(C)(C)C(=O)OCC(C)(Nc1nc2cccc(CNC(=O)N3CCCO3)c2[nH]1)c1cccc(Cl)c1]

To a stirred solution of 2-(3-chlorophenyl)-2-[(7-{[(1H-imidazole-1-carbonyl)amino]methyl}-1H-1,3-benzodiazol-2-yl)amino]propyl 2,2-dimethylpropanoate (from Example 19, Step 4) (1.0 g, 1.97 mmol) in dry tetrahydrofuran (30 mL) was added 1,2-oxazolidine hydrochloride (0.431 g, 3.93 mmol) followed by potassium carbonate (0.816 g, 5.91 mmol) and mixture was stirred at 70° C. for 32 h. Then the reaction mixture was quenched with water (30 mL) and extracted with ethyl acetate (2×100 mL). The combined organic layer was dried over anhydrous sodium sulphate, filtered, concentrated under reduced pressure to afford 2-(3-chlorophenyl)-2-[(7-{[(1,2-oxazolidine-2-carbonyl)amino]methyl}-1H-1,3-benzodiazol-2-yl)amino]propyl 2,2-dimethylpropanoate (1.00 g) as a brown gum, which was used in the next step without further purification.

MS: m/z 514 (M+1).

Example 19: Preparation of N-[[2-[[1-(3-chlorophenyl)-2-hydroxy-1-methyl-ethyl]amino]-3H-benzimidazol-4-yl]methyl]isoxazolidine-2-carboxamide

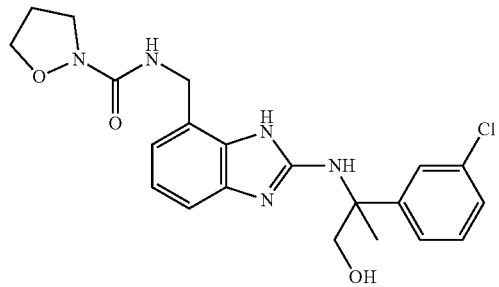 [SMILES: CC(CO)(Nc1nc2cccc(CNC(=O)N3CCCO3)c2[nH]1)c1cccc(Cl)c1]

To a solution of 2-(3-chlorophenyl)-2-[(7-{[(1,2-oxazolidine-2-carbonyl)amino]methyl}-1H-1,3-benzodiazol-2-yl)amino]propyl 2,2-dimethylpropanoate (from Example 19, Step 5) (1.2 g, 2.33 mmol) in methanol (10 mL) was added sodium hydroxide pellets (0.467 g, 11.7 mmol) at 0° C., and the reaction mixture was stirred at ambient temperature for 2 h. The reaction mixture was concentrated to remove methanol and the residue was diluted with dichloromethane (200 mL) and washed with water (2×30 mL). The combined organic layer was dried over anhydrous sodium sulphate, filtered and concentrated to afford a brown gum (0.580 g). This was purified by preparatory HPLC (ammonium acetate method) to afford N-[[2-[[1-(3-chlorophenyl)-2-hydroxy-1-methyl-ethyl]amino]-3H-benzimidazol-4-yl]methyl]isoxazolidine-2-carboxamide (0.450 g) as an off-white solid.

$^1$H NMR (400 MHz, AcOH-d$_4$) δ 7.59 (s, 1H), 7.50 (d, 1H, J=7.08 Hz), 7.40 (d, 1H, J=4.30 Hz), 7.36 (d, 1H, J=8.92 Hz), 7.34 (t, 1H, J=2.12 Hz), 7.18 (t, 1H J=7.52 Hz), 7.14 (d, 1H, J=1.00 Hz), 4.48 (d, 2H, J=4.32 Hz), 4.24 (d, 1H, J=11.96 Hz), 4.02 (d, 1H J=11.96 Hz), 3.85 (t, 2H, J=7.40 Hz), 3.60-3.56 (m, 2H), 2.24-2.16 (m, 2H), 1.84 (s, 3H);

MS: m/z 430.2 (M+1).

The above product was resolved into its two enantiomers by Chiral SFC using the method; Column: YMC Cellulose-SC; Flow rate: 3.0 mL/min, Co-Solvent: 40%; Co-solvent Name: 0.5% isopropyl amine in isopropyl alcohol; injected Volume: 7.0 µL; Out let pressure: 100 bar; Temperature: 35° C. to obtain the two enantiomers 19a and 19b.

Example 19a: (−)-N-((2-((2-(3-chlorophenyl)-1-hydroxypropan-2-yl)amino)-1H-benzo[d]imidazol-7-yl)methyl)isoxazolidine-2-carboxamide The (−) enantiomer was the first to elute off the column.
$^1$H NMR (400 MHz, AcOH-d$_4$) δ 7.59 (s, 1H), 7.50 (d, 1H, J=7.08 Hz), 7.40 (d, 1H, J=4.30 Hz), 7.37 (t, 1H, J=8.92 Hz), 7.34 (d, 1H, J=4.20 Hz), 7.19 (t, 1H, J=7.52 Hz), 7.14 (d, 1H, J=7.56 Hz), 4.47 (d, 2H, J=4.32 Hz), 4.24 (d, 1H, J=11.96 Hz), 4.02 (d, 1H, J=11.92 Hz), 3.85 (t, 2H, J=7.04 Hz), 3.56-3.60 (m, 2H), 2.20 (t, 2H, J=7.28 Hz), 1.84 (s, 3H);

MS: m/z 430.2 (M+1);

[α] D $^{22.2}$ (−) 14.40 (MeOH, c=1.0).

Example 19b: (+)-N-((2-((2-(3-chlorophenyl)-1-hydroxypropan-2-yl)amino)-1H-benzo[d]imidazol-7-yl)methyl)isoxazolidine-2-carboxamide The (+) enantiomer was the second to elute off the column.

1H NMR (400 MHz, AcOH-d$_4$) δ 7.59 (d, 1H, J=1.00 Hz), 7.50 (t, 1H, J=5.40 Hz), 7.39 (s, 1H), 7.37 (d, 1H, J=1.44 Hz), 7.34 (d, 1H, J=4.60 Hz), 7.19 (d, 1H, J=7.64 Hz), 7.15 (t, 1H, J=7.72 Hz), 4.47 (d, 2H, J=4.32 Hz), 4.24 (d, 1H, J=11.92 Hz), 4.02 (d, 1H, J=11.92 Hz), 3.85 (t, 2H, J=7.04 Hz), 3.56-3.60 (m, 2H), 2.20 (t, 2H, J=7.36 Hz), 1.84 (s, 3H);

MS: m/z 430.2 (M+1);

[α] D $^{22.3}$ (+) 17.0 (MeOH, c=1.0).

Example 20: Preparation of 1-((2-((4-hydroxy-2-(3-(trifluoromethyl) phenyl) butan-2-yl) amino)-1H-benzo[d]imidazol-4-yl) methyl)-3-methylurea

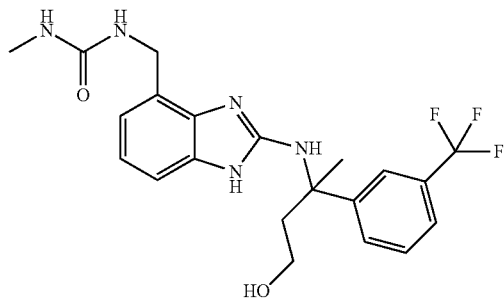 [SMILES: CNC(=O)NCc1cccc2[nH]c(NC(C)(CCO)c3cccc(C(F)(F)F)c3)nc12]

Example 20, Step 1: Preparation of (E)-2-methyl-N-(1-(3-(trifluoromethyl) phenyl) ethylidene) propane-2-sulfinamide

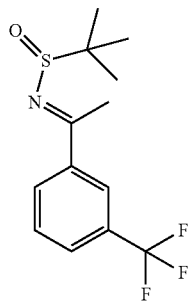 [SMILES: C/C(=N\S(=O)C(C)(C)C)c1cccc(C(F)(F)F)c1]

To a solution of 1-(3-(trifluoromethyl) phenyl) ethan-1-one (commercially available) (125.00 g, 664.00 mmol) under a nitrogen atmosphere in dry tetrahydrofuran (1500 mL) was added 2-methyl propane-2-sulfinamide (80.52 g, 664.00 mmol) followed by titanium (IV) ethoxide (278.60 mL, d=1.008 gm/mL, 1328.00 mmol) and the mixture was heated to 70° C. for 17 h. The reaction mass was diluted with brine solution (200 mL), filtered and the filtrate was evaporated to afford a yellowish gum (200.00 g). This was purified by gravity column chromatography using silica gel (60-120 mesh) and the product was eluted with 10% ethyl acetate in hexane to afford of (E)-2-methyl-N-(1-(3-(trifluoromethyl) phenyl)ethylidene)propane-2-sulfinamide (150.00 g) as a yellowish gum.

$^1$H NMR (400 MHz, CD$_3$OD) δ 8.25 (s, 1H), 8.23 (d, 1H, J=7.60 Hz), 7.88 (d, 1H, J=7.60 Hz), 7.72 (t, 1H, J=8.00 Hz), 2.84 (s, 3H), 1.35 (s, 9H);

MS: m/z 292.3 (M+1).

Example 20, Step 2: Preparation of methyl 3-[(2-methylpropane-2-sulfinyl)amino]-3-[3-(trifluoromethyl)phenyl]butanoate

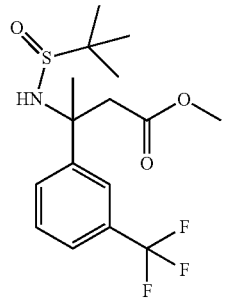 [SMILES: COC(=O)CC(C)(NS(=O)C(C)(C)C)c1cccc(C(F)(F)F)c1]

To a suspension of Zinc dust (269.30 g, 4.120 gm atom) in dry tetrahydrofuran (750 mL) was added copper (I) chloride (51.00, 515.00 mmol) and the mixture was stirred at 60° C. After 30 min, a solution of methyl 2-bromoacetate (122.00 mL, d=1.616 gm/mL, 1287.00 mmol) in dry tetrahydrofuran (500 mL) was added dropwise and then it was stirred for 30 min at the same temperature. A solution of (E)-2-methyl-N-(1-(3-(trifluoromethyl) phenyl) ethylidene) propane-2-sulfinamide (from Example 20, Step 1) (150.00 g, 515.00 mmol) in dry tetrahydrofuran (500 mL) was added dropwise at 0 to 5° C. and stirred at the same temperature for 1 h. The reaction mixture was quenched with saturated ammonium chloride solution (200 mL) and the solid that formed was filtered off and the filtrated was extracted with ethyl acetate (3×1000 mL). The combined organic extracts were dried over anhydrous sodium sulphate, filtered and evaporated to afford a brownish gum (250.00 g). This was purified by gravity column chromatography over 60-120 silica gel and the product was eluted at 70-75% ethyl acetate in hexane to afford methyl 3-[(2-methylpropane-2-sulfinyl)amino]-3-[3-(trifluoromethyl)phenyl]butanoate (135.00 g) as a yellowish gum.

$^1$H NMR (400 MHz, AcOH-d$_4$) δ 7.81 (d, 1H, J=7.6 Hz), 7.74 (d, 1H, J=8.00 Hz), 7.62 (d, 1H, J=7.60 Hz), 7.56 (t, 1H, J=8.00 Hz), 3.62 (s, 3H), 3.20 (q, 2H, J=16.40 Hz), 1.87 (s, 3H), 1.35 (s, 9H);

MS: m/z 366.2 (M+1).

Example 20, Step 3: Preparation of methyl 3-amino-3-(3-(trifluoromethyl)phenyl)butanoate hydrochloride

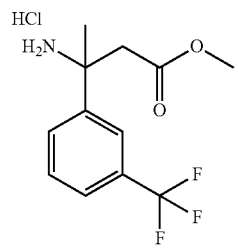

To a solution of methyl methyl 3-[(2-methylpropane-2-sulfinyl)amino]-3-[3-(trifluoromethyl)phenyl]butanoate (from Example 20, Step 2) (135.00 g, 369.00 mmol) in dioxane was added 4M HCl in dioxane (461.00 mL, 1845.00 mmol) at 0° C. and the mixture was stirred at ambient temperature for 3 h. The reaction mixture was evaporated to afford methyl 3-amino-3-(3-(trifluoromethyl)phenyl)butanoate hydrochloride (100.00 g) as a brownish gum, which was used in the next step without further purification.

$^1$H NMR (400 MHz, AcOH-d$_4$) δ 7.94 (s, 1H), 7.91 (d, J=8.80 Hz, 1H), 7.74 (d, J=7.60 Hz, 1H), 7.70 (t, J=7.60 Hz, 1H), 3.69 (s, 3H), 3.48 (s, 2H), 2.02 (s, 3H);

MS: m/z 262.2 [(M+1)-HCl].

Example 20, Step 4: Preparation of methyl 3-isothiocyanato-3-(3-(trifluoromethyl)phenyl)butanoate

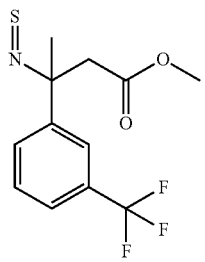 [SMILES: COC(=O)CC(C)(N=S)c1cccc(C(F)(F)F)c1]

To a solution of methyl 3-amino-3-(3-(trifluoromethyl)phenyl)butanoate hydrochloride (from Example 20, Step 3) (13.00 g, 50.00 mmol) in dry dichloromethane (150 mL) was added 10% aqueous sodium bicarbonate solution (150 mL) at 0° C. After 15 min, thiophosgene (5.72 mL, d=1.5 g/cm$^3$, 75.00 mmol) was added and allowed to stir at the same temperature for 1 h. The reaction mass was extracted with dichloromethane (3×250 mL) and the combined organic layer was dried over anhydrous sodium sulphate, filtered, and concentrated to afford a yellow liquid (30.00 g). This was purified by chromatography on a Grace instrument using 80.00 g pre-packed flash cartridge filled with normal phase silica gel 60° A, 40-63 μm and the product was eluted with 3-5% methanol in chloroform to afford methyl 3-isothiocyanato-3-(3-(trifluoromethyl)phenyl)butanoate (15.00 g) as a yellow liquid.

$^1$H NMR (400 MHz, DMSO-d$_6$) δ 7.83 (s, 1H), 7.81 (d, J=7.20 Hz, 1H), 7.72 (d, J=8.00 Hz, 1H), 7.66 (t, J=7.60 Hz, 1H), 3.53 (s, 3H), 3.30 (d, J=13.60 Hz, 2H), 1.86 (s, 3H);

MS: m/z 304.1 (M+1).

Example 20, Step 5: Preparation of methyl 3-(3-(2-amino-6-((3-methylureido)methyl)phenyl)thioureido)-3-(3-(trifluoromethyl)phenyl)butanoate and methyl 3-(3-(2-amino-3-((3-methylureido)methyl)phenyl)thioureido)-3-(3-(trifluoromethyl)phenyl)butanoate (mixture of regioisomers)

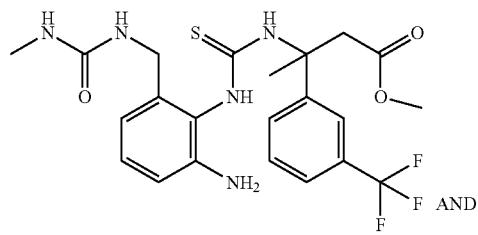
AND
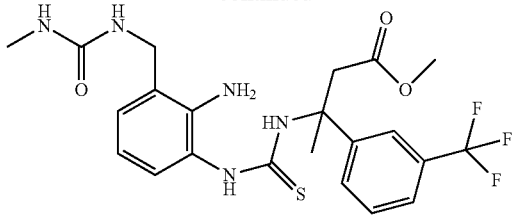

To a solution of 1-(2, 3-diaminobenzyl)-3-methylurea (from Example 1, Step 13) (0.800 g, 4.00 mmol) in a mixture of solvents acetonitrile:methanol (4:1; 16 mL) was added methyl 3-isothiocyanato-3-(3-(trifluoromethyl)phenyl)butanoate (from Example 20, Step 4) (1.249 g, 4.00 mmol) and the mixture was stirred at ambient temperature for 16 h. The reaction mass was concentrated to afford a yellow gum (2.05 g), which was purified by chromatography on a Grace instrument using 40.00 g pre-packed flash cartridge filled with normal phase silica gel 60° A, 40-63 μm and the product was eluted with 40-45% ethyl acetate in hexane to afford methyl 3-(3-(2-amino-6-((3-methylureido)methyl) phenyl)thioureido)-3-(3-(trifluoromethyl)phenyl)butanoate and methyl 3-(3-(2-amino-3-((3-methylureido)methyl)phenyl)thioureido)-3-(3-(trifluoromethyl)phenyl)butanoate (as a 7:3 mixture of regioisomers) (1.70 g) as a brown gum.

MS: m/z 498.2 (M+1).

Example 20, Step 6: Preparation of 1-methyl-3-((2-methyl-4-oxo-2-(3-(trifluoromethyl) phenyl)-1,2,3,4-tetrahydrobenzo [4,5] imidazo[1,2-a]pyrimidin-9-yl) methyl) urea

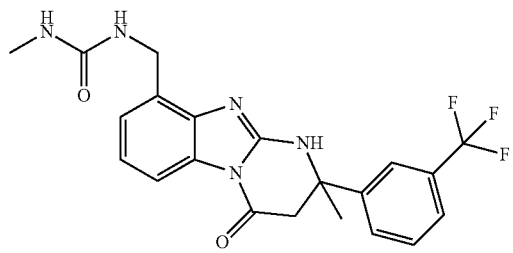 [SMILES: CNC(=O)NCc1cccc2c1nc1n2C(=O)CC(C)(c2cccc(C(F)(F)F)c2)N1]

To a solution of methyl 3-(3-(2-amino-6-((3-methylureido)methyl)phenyl)thioureido)-3-(3-(trifluoromethyl)phenyl)butanoate and methyl 3-(3-(2-amino-3-((3-methylureido)methyl)phenyl)thioureido)-3-(3-(trifluoromethyl) phenyl)butanoate (as a 7:3 mixture of regioisomers) (from Example 20, Step 5) (2.20 g, 4.42 mmol) in methanol (50 mL) was added mercuric oxide (1.92 g, 8.84 mmol) followed by elemental sulphur (0.071 g, 2.21 mmol) and the mixture was stirred at 65° C. for 3 h. The reaction mass was filtered through a celite bed and then washed with methanol (3×250 mL). The combined filtrate was concentrated to afford a brown liquid (1.91 g). This was purified by chromatography on a Grace instrument using 80.00 g pre-packed flash cartridge filled with normal phase silica gel 60° A, 40-63 μm and the product was eluted with 2-4% methanol in chloroform to afford 1-methyl-3-((2-methyl-4-oxo-2-(3-(trifluoromethyl) phenyl)-1,2,3,4-tetrahydrobenzo [4,5] imidazo[1,2-a] pyrimidin-9-yl) methyl) urea (1.70 g) as a yellow solid.

¹H NMR (400 MHz, DMSO-d₆: D₂O) δ 7.92 (s, 1H), 7.82 (d, 1H, J=7.20 Hz), 7.63 (d, 2H, J=7.60 Hz), 7.60 (t, 1H, J=7.20 Hz), 7.05 (d, 1H, J=6.80 Hz), 6.96 (t, 1H, J=8.00 Hz), 4.41 (s, 2H), 3.58 (d, 1H, J=16.40 Hz), 3.37 (d, 1H, J=12.40 Hz), 2.54 (s, 3H), 1.91 (s, 3H);

MS: m/z 432.2 (M+1).

Example 20: Preparation of 1-((2-((4-hydroxy-2-(3-(trifluoromethyl) phenyl) butan-2-yl) amino)-1H-benzo[d]imidazol-4-yl) methyl)-3-methylurea

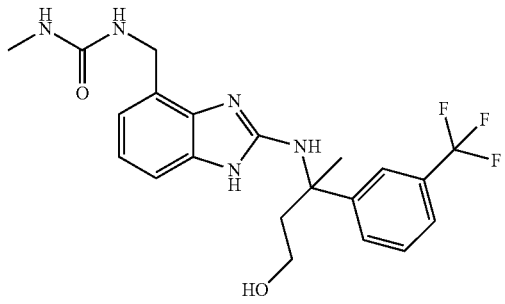 [SMILES: CNC(=O)NCc1cccc2[nH]c(NC(C)(CCO)c3cccc(C(F)(F)F)c3)nc12]

To a stirred solution of 1-methyl-3-((2-methyl-4-oxo-2-(3-(trifluoromethyl) phenyl)-1,2,3,4-tetrahydrobenzo [4,5] imidazo[1,2-a] pyrimidin-9-yl) methyl) urea (from Example 20, Step 6) (1.50 g, 3.00 mmol) under a nitrogen atmosphere in dry tetrahydrofuran, was added sodium borohydride (0.395 g, 10.00 mmol) at 0° C. then it was stirred at 50° C. for 12 h. The reaction mixture was quenched with saturated solution of sodium potassium tartrate in water (50 mL) and extracted with ethyl acetate (4×500 mL). The combined organic layer was washed with brine solution (30 mL), dried over sodium sulphate, filtered and concentrated to afford a brown gum (1.40 g). This was purified by preparative HPLC to afford 1-((2-((4-hydroxy-2-(3-(trifluoromethyl) phenyl) butan-2-yl) amino)-1H-benzo[d]imidazol-4-yl) methyl)-3-methylurea (0.400 g) as a brown solid.

¹H NMR (400 MHz, AcOH-d₄) δ 7.88 (s, 1H), 7.85 (d, 1H, J=7.60 Hz), 7.68 (d, 1H, J=7.56 Hz), 7.61 (t, 1H, J=7.76 Hz), 7.28 (d, 1H, J=7.96 Hz), 7.17 (t, 1H, J=8.00 Hz), 7.11 (d, 1H, J=7.44 Hz), 4.42 (s, 2H), 3.88-3.78 (m, 2H), 2.69 (s, 3H), 2.48-2.41 (m, 2H), 2.03 (s, 3H);

MS: m/z 436.2 (M+1).

The above product was resolved into its two enantiomers by Chiral SFC using the method; Column: Chiral Pak OX—H; Flow rate: 3.0 mL/min, Co-Solvent: 30%; Co-solvent Name: 0.5% Isopropyl amine in isopropyl alcohol; injected Volume: 15.0 µL; Out let pressure: 100 bar; Temperature: 40° C. to obtain the two enantiomers 20a and 20b.

Example 20a: (−)-1-((2-((4-hydroxy-2-(3-(trifluoromethyl)phenyl)butan-2-yl)amino)-1H-benzo[d]imidazol-4-yl)methyl)-3-methylurea The (−) enantiomer was the first to elute off the column.

¹H NMR (400 MHz, AcOH-d₄) δ 7.89 (s, 1H), 7.86 (d, 1H, J=7.60 Hz), 7.68 (d, 1H, J=8.00 Hz), 7.62 (t, 1H, J=7.60 Hz), 7.30 (d, 1H, J=8.00 Hz), 7.18 (t, 1H, J=7.60 Hz), 7.11 (d, 1H, J=7.20 Hz), 4.42 (s, 2H), 3.88-3.79 (m, 2H), 2.70 (s, 3H), 2.51-2.40 (m, 2H), 2.03 (s, 3H);

MS: m/z 436.2 (M+1);

[α] D $^{22.4}$ (−) 26.40 (MeOH, c=0.1).

Example 20b: (+)-1-((2-((4-hydroxy-2-(3-(trifluoromethyl)phenyl)butan-2-yl)amino)-1H-benzo[d]imidazol-4-yl)methyl)-3-methylurea The (+) enantiomer was the second to elute off the column.

¹H NMR (400 MHz, AcOH-d₄) δ 7.89 (s, 1H), 7.86 (d, 1H, J=8.00 Hz), 7.68 (d, 1H, J=8.00 Hz), 7.62 (t, 1H, J=7.60 Hz), 7.31 (d, 1H, J=8.00 Hz), 7.17 (t, 1H, J=8.00 Hz), 7.10 (d, 1H, J=7.60 Hz), 4.41 (s, 2H), 3.88-3.79 (m, 2H), 2.70 (s, 3H), 2.51-2.40 (m, 2H), 2.02 (s, 3H);

MS: m/z 436.2 (M+1);

[α] D $^{22.0}$ (+) 24.00 (MeOH, c=0.1).

Example 21: Preparation of N-((2-((1-hydroxy-2-(3-(trifluoromethyl) phenyl)

propan-2-yl) amino)-1H-benzo[d]imidazol-4-yl) methyl) morpholine-4-carboxamide

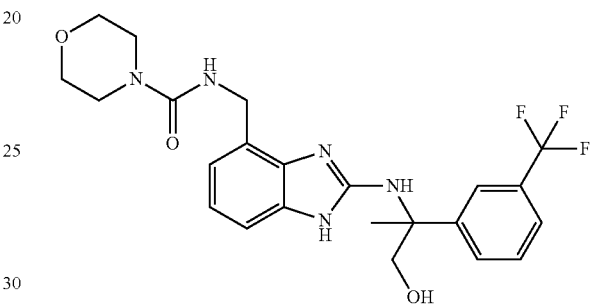

Example 21, Step 1: Preparation of N-(benzo[c] [1, 2,5] thiadiazol-4-ylmethyl) morpholine-4-carboxamide

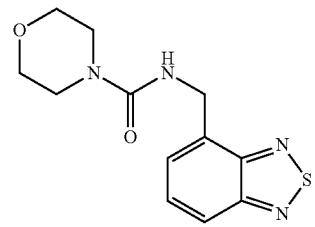 [SMILES: O=C(NCc1cccc2nsnc12)N1CCOCC1]

To a stirred solution of 2, 1, 3-benzothiadiazol-4-ylmethanamine; hydrochloride (from Example 1, Step 11) (13.00 g, 64.50 mmol) in dichloromethane (500 mL) was added triethylamine (27.00 mL, d: 0.726 g/cm³, 193.00 mmol) followed by morpholine-4-carbonyl chloride (9.05 mL, d=1.282 g/mL, 77.40 mmol) dropwise at 0° C. and the reaction mixture was stirred at ambient temperature for 2 h. The reaction mixture was quenched with ice-cold water (100 mL) and the aqueous layer was extracted with dichloromethane (4×750 mL). The combined organic layer was washed with brine (50 mL), dried over sodium sulphate, filtered and concentrated under reduced pressure to afford a yellow solid (18.00 g). The solid was triturated with n-Hexane (300 mL), the supernatant layer was discarded and the solid was dried to afford N-(benzo[c] [1, 2, 5]thiadiazol-4-ylmethyl) morpholine-4-carboxamide (14.5 g) as an off-white solid, which was used in the next step without further purification.

¹H NMR (400 MHz, DMSO-d₆: D₂O) δ 7.95 (d, 1H, J=8.76 Hz), 7.70 (t, 1H, J=8.72 Hz), 7.47 (d, 1H, J=6.72 Hz), 4.75 (s, 2H), 3.58 (t, 4H, J=4.92 Hz), 3.34 (t, 4H, J=4.60 Hz);

MS: m/z 279.1 (M+1).

Example 21, Step 2: Preparation of N-(2, 3-diaminobenzyl) morpholine-4-carboxamide

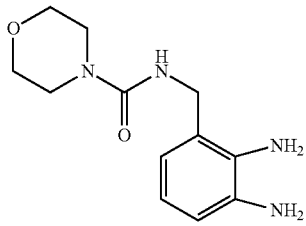 [SMILES: Nc1cccc(CNC(=O)N2CCOCC2)c1N]

To a de-gassed solution of N-(benzo[c] [1, 2, 5] thiadiazol-4-ylmethyl) morpholine-4-carboxamide (from Example 21, Step 1) (11.00 g, 39.50 mmol) in dry methanol (1000 mL) was added Raney nickel (22.00 g, 200% w/w, pre-washed five times with dry methanol) and the resultant reaction mixture was stirred under a hydrogen atmosphere at bladder pressure (Approx. 1.5 kg/cm$^2$) and at ambient temperature for 48 h. The reaction mixture was filtered through a celite bed and the bed was washed with methanol (3×2000 mL). The combined filtrates were concentrated to afford N-(2, 3-diaminobenzyl) morpholine-4-carboxamide (9.00 g) as a green solid, which was used in the next step without further purification.

$^1$H NMR (400 MHz, DMSO-d$_6$) δ 6.94 (t, 1H, J=5.20 Hz), 6.47 (d, 1H, J=7.20 Hz), 6.39 (t, 1H, J=12.00 Hz), 6.33 (d, 1H, J=7.20 Hz), 4.60 (s, 2H), 4.42 (s, 2H), 4.11 (d, 2H, J=5.20 Hz), 3.54 (t, 4H, J=4.00 Hz), 3.31 (t, 4H, J=4.40 Hz);

MS: m/z 251.2 (M+1).

Example 21, Step 3: Preparation of 2-{[(2-amino-6-{[(morpholine-4-carbonyl)amino]methyl}phenyl)carbamothioyl]amino}-2-[3-(trifluoromethyl)phenyl]propyl 2,2-dimethylpropanoate and 2-{[(2-amino-3-{[(morpholine-4-carbonyl)amino]methyl}phenyl)carbamothioyl]amino}-2-[3-(trifluoromethyl)phenyl]propyl 2,2-dimethylpropanoate (mixture of regioisomers)

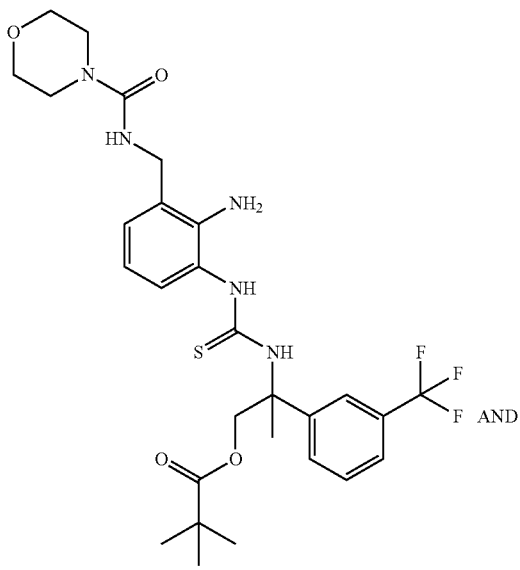

AND

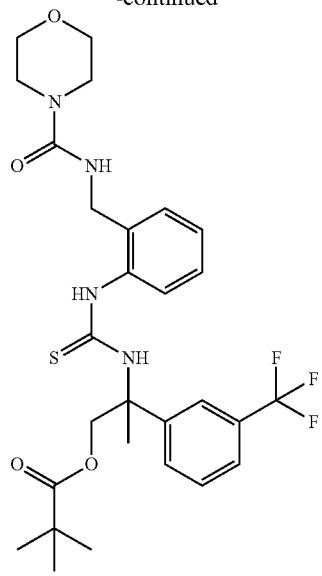

To a solution of N-(2, 3-diaminobenzyl) morpholine-4-carboxamide (from Example 21, Step 2) (0.22 g, 0.87 mmol) in a mixture of solvents dichloromethane:methanol (4:1; mL) was added 2-isothiocyanato-2-[3-(trifluoromethyl)phenyl]propyl 2,2-dimethylpropanoate (from Example 1, Step 7) (0.30 g, 0.87 mmol) and the mixture was stirred at ambient temperature for 26 h. The reaction mass was concentrated to afford a brown gum (0.53 g). This was purified by chromatography on a Grace instrument using 24.0 g pre-packed flash cartridge filled with normal phase silica gel 60° A, 40-63 μm and the product eluted with 60-70% ethyl acetate in hexane to afford 2-{[(2-amino-6-{[(morpholine-4-carbonyl)amino]methyl}phenyl)carbamothioyl]amino}-2-[3-(trifluoromethyl)phenyl]propyl 2,2-dimethylpropanoate and 2-{[(2-amino-3-{[(morpholine-4-carbonyl)amino]methyl}phenyl)carbamothioyl]amino}-2-[3-(trifluoromethyl)phenyl]propyl 2,2-dimethylpropanoate (as a 1:1 mixture of regioisomers) (0.25 g) as a brown gum.

MS: m/z 596.2 (M+1).

Example 21, Step 4: Preparation of 2-[(7-{[(morpholine-4-carbonyl)amino]methyl}-1H-1,3-benzodiazol-2-yl)amino]-2-[3-(trifluoromethyl)phenyl]propyl 2,2-dimethylpropanoate

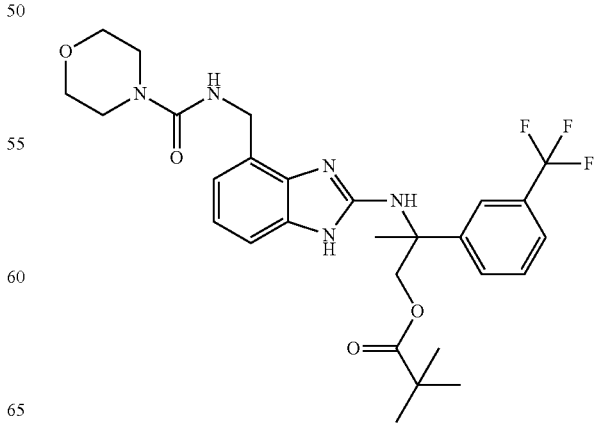

To a solution of 2-{[(2-amino-6-{[(morpholine-4-carbonyl)amino]methyl}phenyl)carbamothioyl]amino}-2-[3-(trifluoromethyl)phenyl]propyl 2,2-dimethylpropanoate and 2-{[(2-amino-3-{[(morpholine-4-carbonyl)amino]methyl}phenyl)carbamothioyl]amino}-2-[3-(trifluoromethyl)phenyl]propyl 2,2-dimethylpropanoate (as a 1:1 mixture of regioisomers) (from Example 21, Step 3) (1.60 g, 2.69 mmol) under a nitrogen atmosphere in dry methanol (20 mL) was added iodoacetic acid (0.50 g, 2.69 mmol) and the mixture was stirred at 70° C. for 1 h. The reaction mass was concentrated and the residue was poured into ice-cold water (100 mL). The aqueous layer was extracted with ethyl acetate (3×100 mL) and the combined organic layer was washed with saturated bicarbonate solution (30 mL), followed by brine (30 mL), dried over sodium sulphate, filtered and concentrated to afford 2-[(7-{[(morpholine-4-carbonyl)amino]methyl}-1H-1,3-benzodiazol-2-yl)amino]-2-[3-(trifluoromethyl)phenyl]propyl 2,2-dimethylpropanoate (1.20 g) as a brown solid.

1H NMR (400 MHz, DMSO-d$_6$: D$_2$O) δ 7.87 (d, 2H, J=12.80 Hz), 7.72 (d, 1H, J=8.00 Hz), 7.66 (t, 1H, J=7.60 Hz), 7.29 (d, 1H, J=8.00 Hz), 7.20 (t, 1H, J=7.60 Hz), 7.13 (d, 1H, J=7.60 Hz), 4.70 (d, 1H, J=11.60 Hz), 4.57 (d, 1H, J=11.60 Hz), 4.36 (d, 2H, J=6.40 Hz), 3.65 (s, 2H), 3.64-3.62 (m, 4H), 3.36 (d, 2H, J=5.20 Hz), 1.98 (s, 3H), 1.16 (s, 9H);

MS: m/z 562.2 (M+1).

Example 21: Preparation of N-((2-((1-hydroxy-2-(3-(trifluoromethyl) phenyl) propan-2-yl) amino)-1H-benzo[d]imidazol-4-yl) methyl) morpholine-4-carboxamide

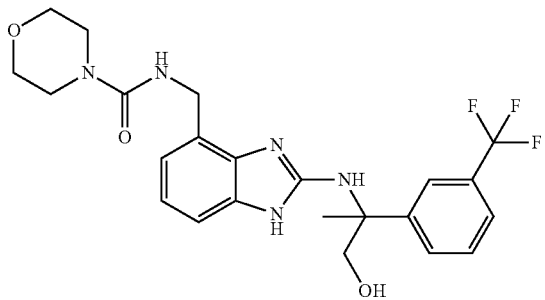 [SMILES: CC(CO)(Nc1nc2c(CNC(=O)N3CCOCC3)cccc2[nH]1)c1cccc(C(F)(F)F)c1]

To a stirred solution of 2-[(7-{[(morpholine-4-carbonyl)amino]methyl}-1H-1,3-benzodiazol-2-yl)amino]-2-[3-(trifluoromethyl)phenyl]propyl 2,2-dimethylpropanoate (from Example 21, Step 4) (1.00 g, 1.78 mmol) in methanol (20.0 mL) was added sodium hydroxide pellets (0.22 g, 5.34 mmol) and the mixture was stirred at ambient temperature for 1 h. The reaction mass was concentrated and the residue was diluted with water (50 mL). The aqueous layer was extracted with dichloromethane (3×100 mL) and the combined organic layer was washed with water (25 mL) followed by brine (20 mL), dried over sodium sulphate, filtered and concentrated to afford a brown gum (0.650 g). This was purified by preparative HPLC to afford N-((2-((1-hydroxy-2-(3-(trifluoromethyl) phenyl) propan-2-yl) amino)-1H-benzo[d]imidazol-4-yl) methyl) morpholine-4-carboxamide (0.450 g) as an off-white solid.

$^1$H NMR (400 MHz, AcOH-d$_4$) δ 7.88 (s, 1H), 7.85 (d, 1H, J=8.00 Hz), 7.68 (d, 1H, J=7.60 Hz), 7.61 (d, 1H, J=7.60 Hz), 7.34 (d, 1H, J=8.00 Hz), 7.17 (t, 1H, J=8.00 Hz), 7.11 (d, 1H, J=7.60 Hz), 4.45 (q, 2H, J=14.80 Hz), 4.23 (d, 1H, J=12.00 Hz), 4.06 (d, 1H, J=11.60 Hz), 3.69 (t, 4H, J=4.80 Hz), 3.35 (t, 4H, J=3.60 Hz), 1.90 (s, 3H);

MS: m/z 478.2 (M+1).

The above product was resolved into its two enantiomers by Chiral SFC using the method; Column: Chiralcel OX—H; Flow rate: 3.0 mL/min; Co-Solvent: 30%; Co-solvent Name: 0.5% isopropyl amine in isopropyl alcohol; injected Volume: 15.0 μL; Outlet pressure: 100 bar; Temperature: 35° C. to obtain the two enantiomers 21a and 21b.

Example 21a: (+)-N-((2-((1-hydroxy-2-(3-(trifluoromethyl) phenyl) propan-2-yl) amino)-1H-benzo[d]imidazol-4-yl) methyl) morpholine-4-carboxamide The (+) enantiomer was the first to elute off the column.
$^1$H NMR (400 MHz, CD$_3$OD): δ 7.78 (d, 2H, J=12.80 Hz), 7.58-7.52 (m, 2H), 7.11 (d, 1H, J=7.60 Hz), 6.96-6.88 (m, 2H), 4.47 (s, 2H), 3.99 (d, 1H, J=11.60 Hz), 3.85 (d, 1H, J=11.20 Hz), 3.64 (t, 4H, J=5.20 Hz), 3.36 (t, 4H, J=5.20 Hz), 1.78 (s, 3H);

MS: m/z 478.2 (M+1);
[α] D $^{22.5}$ (+) 19.8 (MeOH, c=1.0).

Example 21b: (−)-N-((2-((1-hydroxy-2-(3-(trifluoromethyl) phenyl) propan-2-yl) amino)-1H-benzo[d]imidazol-4-yl) methyl) morpholine-4-carboxamide The (−) enantiomer was the second to elute-off the column.
$^1$H NMR (400 MHz, CD$_3$OD): δ 7.78 (t, 2H, J=7.20 Hz), 7.55 (t, 2H, J=7.20 Hz), 7.11 (d, 1H, J=7.60 Hz), 6.94 (t, 1H, J=8.00 Hz), 6.89 (d, 1H, J=7.20 Hz), 4.47 (s, 2H), 3.99 (d, 1H, J=11.60 Hz), 3.85 (d, 1H, J=11.20 Hz), 3.64 (t, 4H, J=4.80 Hz), 3.36 (t, 4H, J=4.80 Hz), 1.78 (s, 3H);

MS: m/z 478.2 (M+1);
[α] D $^{22.5}$ (−) 19.12 (MeOH, c=1.0).

We claim:
1. A compound of formula (I)

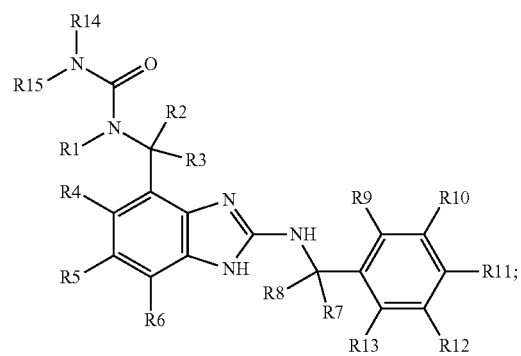

Wherein
R1 is selected from hydrogen and $C_{1-6}$ alkyl;
R2-R3 are independently a group selected from hydrogen and $C_{1-6}$ alkyl;
or R2 and R3 taken together with the carbon atom to which they are linked form a $C_{3-4}$ cycloalkyl;
R4-R6 are independently a group selected from hydrogen, halogen, and $C_{1-4}$ alkyl;
R7 is selected from the group consisting of hydrogen and $C_{1-4}$ alkyl, R8 is selected from the group consisting of $C_{1-6}$ alkyl, $C_{1-6}$ alkyl substituted with one OH, and $C_{1-6}$ alkyl substituted with one $OC_{1-3}$ alkyl, or R7 and R8 taken together with the carbon atom to which they are linked form a $C_{3-4}$ cycloalkyl;

R9-R13 are independently a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano;

R14 is selected from H, $C_{1-6}$ alkyl, or $C_{1-6}$ alkoxy;

R15 is selected from H, $C_{1-6}$ alkyl, $C_{1-6}$ alkyl substituted with at least one halogen, $C_{1-6}$ alkoxy, $C_{1-6}$ alkoxy substituted with at least one a halogen, or $C_{3-4}$ cycloalkyl;

or R14 and R15 taken together with the nitrogen atom to which they are linked form a 4-6 membered non-aromatic heterocycle containing 1-2 nitrogen atoms, optionally 1 oxygen atom, and optionally 1 sulphur atom, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen; or a pharmaceutically acceptable salt thereof.

2. The compound of claim 1 or a pharmaceutically acceptable salt thereof, wherein R1 is selected from hydrogen (H) and methyl.

3. The compound of claim 1 or a pharmaceutically acceptable salt thereof, wherein R2-R3 are independently a group selected from H and $C_{1-3}$ alkyl.

4. The compound of claim 1 or a pharmaceutically acceptable salt thereof, wherein R2-R3 are both H.

5. The compound of claim 1 or a pharmaceutically acceptable salt thereof, wherein R4-R6 are independently a group selected from H, F, and methyl.

6. The compound of claim 1 or a pharmaceutically acceptable salt thereof, wherein R7 is a group selected from H and $C_{1-3}$ alkyl.

7. The compound of claim 1 or a pharmaceutically acceptable salt thereof, wherein R8 is a group selected from $C_{1-4}$ alkyl substituted with one OH, and $C_{1-4}$ alkyl substituted with one $OC_{1-3}$ alkyl.

8. The compound of claim 1 or a pharmaceutically acceptable salt thereof, wherein R9-R13 are independently a group selected from H, halogen, $C_{1-6}$ alkyl substituted with at least one halogen, and $C_{1-6}$ alkoxy substituted with at least one halogen.

9. The compound of claim 1 (or a pharmaceutically acceptable salt thereof, wherein R9, R12 and R13 are all H, and R10-R11 are independently a group selected from H, halogen, $C_{1-6}$ alkyl substituted with at least one halogen, and $C_{1-6}$ alkoxy substituted with at least one halogen; provided that R10 and R11 are not both H.

10. The compound of claim 1 or a pharmaceutically acceptable salt thereof, wherein R14 is selected from H and $C_{1-6}$ alkyl.

11. The compound of claim 1 or a pharmaceutically acceptable salt thereof, wherein R15 is selected from H, $C_{1-6}$ alkyl, $C_{1-6}$ alkyl substituted with at least one halogen, $C_{1-6}$ alkoxy, $C_{1-6}$ alkoxy substituted with at least one halogen, or $C_{3-4}$ cycloalkyl.

12. The compound of claim 1 or a pharmaceutically acceptable salt thereof, wherein R14 and R15 taken together with the nitrogen atom to which they are linked form a 4-6 membered non-aromatic heterocycle containing 1 nitrogen atom and optionally 1 oxygen atom, optionally substituted with at least one halogen.

13. The compound of claim 1 selected from any one of:
1-((2-((1-hydroxy-2-(3-(trifluoromethyl) phenyl) propan-2-yl) amino)-1H-benzo[d]imidazol-4-yl) methyl)-3-methylurea,
(+)-1-((2-((1-hydroxy-2-(3-(trifluoromethyl) phenyl) propan-2-yl) amino)-1H-benzo[d]imidazol-4-yl) methyl)-3-methylurea,
(−)-1-((2-((1-hydroxy-2-(3-(trifluoromethyl) phenyl) propan-2-yl) amino)-1H-benzo[d]imidazol-4-yl) methyl)-3-methylurea,
3-((2-((1-hydroxy-2-(3-(trifluoromethyl) phenyl) propan-2-yl) amino)-1H-benzo[d]imidazol-4-yl) methyl)-1, 1-dimethylurea,
(+)-3-((2-((1-hydroxy-2-(3-(trifluoromethyl) phenyl) propan-2-yl) amino)-1H-benzo[d]imidazol-4-yl) methyl)-1, 1-dimethylurea,
(−)-3-((2-((1-hydroxy-2-(3-(trifluoromethyl) phenyl) propan-2-yl) amino)-1H-benzo[d]imidazol-4-yl) methyl)-1, 1-dimethylurea,
1-((2-((1-methoxy-2-(3-(trifluoromethyl) phenyl) propan-2-yl) amino)-1H-benzo[d]imidazol-4-yl) methyl)-3-methylurea,
(+)-1-((2-((1-methoxy-2-(3-(trifluoromethyl) phenyl) propan-2-yl) amino)-1H-benzo[d]imidazol-4-yl) methyl)-3-methylurea,
(−)-1-((2-((1-methoxy-2-(3-(trifluoromethyl) phenyl) propan-2-yl) amino)-1H-benzo[d]imidazol-4-yl) methyl)-3-methylurea,
1-{[2-({1-hydroxy-2-[3-(trifluoromethyl)phenyl]propan-2-yl}amino)-1H-1,3-benzodiazol-4-yl]methyl}-3-methoxy-3-methylurea,
(+)-3-((2-((1-hydroxy-2-(3-(trifluoromethyl)phenyl)propan-2-yl)amino)-1H-benzo[d]imidazol-4-yl)methyl)-1-methoxy-1-methylurea,
(−)-3-((2-((1-hydroxy-2-(3-(trifluoromethyl)phenyl)propan-2-yl)amino)-1H-benzo[d]imidazol-4-yl)methyl)-1-methoxy-1-methylurea,
1-ethyl-3-((2-((1-hydroxy-2-(3-(trifluoromethyl) phenyl) propan-2-yl) amino)-1H-benzo[d]imidazol-4-yl) methyl)-1-methylurea,
(+)-1-ethyl-3-((2-((1-hydroxy-2-(3-(trifluoromethyl) phenyl) propan-2-yl) amino)-1H-benzo[d] imidazol-4-yl) methyl)-1-methylurea,
(−)-1-ethyl-3-((2-((1-hydroxy-2-(3-(trifluoromethyl) phenyl) propan-2-yl) amino)-1H-benzo [d] imidazol-4-yl) methyl)-1-methylurea,
3-((5-fluoro-2-((1-hydroxy-2-(3-(trifluoromethyl) phenyl) propan-2-yl) amino)-1H-benzo[d]imidazol-4-yl) methyl)-1, 1-dimethylurea,
(+)-3-((5-fluoro-2-((1-hydroxy-2-(3-(trifluoromethyl) phenyl) propan-2-yl) amino)-1H-benzo[d] imidazol-4-yl) methyl)-1, 1-dimethylurea,
(−)-3-((5-fluoro-2-((1-hydroxy-2-(3-(trifluoromethyl) phenyl) propan-2-yl) amino)-1H-benzo[d] imidazol-4-yl) methyl)-1, 1-dimethylurea,
1-cyclopropyl-3-((2-((1-hydroxy-2-(3-(trifluoromethyl) phenyl) propan-2-yl) amino)-1H-benzo[d]imidazol-4-yl) methyl) urea,
(−)-1-cyclopropyl-3-((2-((1-hydroxy-2-(3-(trifluoromethyl)phenyl)propan-2-yl) amino)-1H-benzol[d]imidazol-4-yl)methyl)urea,
(+)-1-cyclopropyl-3-((2-((1-hydroxy-2-(3-(trifluoromethyl) phenyl) propan-2-yl) amino)-1H-benzo[d]imidazol-4-yl) methyl) urea,
N-((2-((1-hydroxy-2-(3-(trifluoromethyl) phenyl) propan-2-yl) amino)-1H-benzo[d]imidazol-4-yl) methyl) azetidine-1-carboxamide, (−)-N-((2-((1-hydroxy-2-(3-(trifluoromethyl) phenyl) propan-2-yl) amino)-1H-benzo[d]imidazol-4-yl) methyl) azetidine-1-carboxamide, (+)-N-((2-((1-hydroxy-2-(3-(trifluoromethyl) phenyl) propan-2-yl) amino)-1H-benzo[d]imidazol-4-yl) methyl) azetidine-1-carboxamide, 3-ethyl-1-{[2-({1-hydroxy-2-[3-(trifluoromethyl)phenyl] propan-2-yl}amino)-1H-1,3-benzodiazol-4-yl] methyl}urea, (+)-1-ethyl-3-((2-((1-hydroxy-2-(3-(trifluoromethyl) phenyl) propan-2-yl) amino)-1H-benzo[d]imidazol-4-yl) methyl) urea, (−)-1-ethyl-3-((2-((1-hydroxy-2-(3-(trifluoromethyl)phenyl) propan-2-yl)amino)-1H-benzo[d]imidazol-4-yl) methyl)urea, 1-((2-((1-hydroxy-2-(3-(trifluoromethyl) phenyl) butan-2-yl) amino)-1H-benzo[d]imidazol-4-yl) methyl)-3-methylurea, (−)-1-((2-((1-hydroxy-2-(3-(trifluoromethyl) phenyl) butan-2-yl) amino)-1H-benzo[d]imidazol-4-yl) methyl)-3-methylurea, (+)-1-((2-((1-hydroxy-2-(3-(trifluoromethyl) phenyl) butan-2-yl) amino)-1H-benzo[d]imidazol-4-yl) methyl)-3-methylurea, 3-((2-((2-(3-chlorophenyl)-1-hydroxypropan-2-yl) amino)-1H-benzo[d] imidazol-4-yl) methyl)-1-methoxy-1-methylurea, (−)-3-((2-((2-(3-chlorophenyl)-1-hydroxypropan-2-yl) amino)-1H-benzo[d] imidazol-4-yl)methyl)-1-methoxy-1-methylurea, (+)-3-((2-((2-(3-chlorophenyl)-1-hydroxypropan-2-yl) amino)-1H-benzo[d] imidazol-4-yl)methyl)-1-methoxy-1-methylurea, 1-[[2-[[1-(3-chloro-4-fluoro-phenyl)-2-hydroxy-1-methyl-ethyl]amino]-1H-benzimidazol-4-yl] methyl]-3-methyl-urea, (−)-1-((2-((2-(3-chloro-4-fluorophenyl)-1-hydroxypropan-2-yl)amino)-1H-benzo[d]imidazol-4-yl)methyl)-3-methylurea, (+)-1-((2-((2-(3-chloro-4-fluorophenyl)-1-hydroxypropan-2-yl)amino)-1H-benzo[d]imidazol-4-yl)methyl)-3-methylurea, 3-((2-((2-(3-chlorophenyl)-1-hydroxypropan-2-yl) amino)-1H-benzo[d]imidazol-4-yl) methyl)-1, 1-dimethylurea, (−)-3-((2-((2-(3-chlorophenyl)-1-hydroxypropan-2-yl) amino)-1H-benzo[d] imidazol-4-yl) methyl)-1, 1-dimethylurea, (+)-3-((2-((2-(3-chlorophenyl)-1-hydroxypropan-2-yl) amino)-1H-benzo[d] imidazol-4-yl) methyl)-1, 1-dimethylurea, 1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea, (−)-1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea, (+)-1-((2-((1-hydroxy-2-(3-(trifluoromethyl) phenyl) propan-2-yl) amino)-1H-benzo[d]imidazol-4-yl) methyl)-3-(3, 3, 3-trifluoropropyl) urea, N-((2-((2-(3-chlorophenyl)-1-hydroxypropan-2-yl) amino)-1H-benzo[d] imidazol-4-yl) methyl) azetidine-1-carboxamide, (−)-(N-((2-((2-(3-chlorophenyl)-1-hydroxypropan-2-yl) amino)-1H-benzo[d] imidazol-4-yl) methyl) azetidine-1-carboxamide, (+)-N-((2-((2-(3-chlorophenyl)-1-hydroxypropan-2-yl) amino)-1H-benzo[d]imidazol-4-yl) methyl) azetidine-1-carboxamide, 1-((2-((1-hydroxy-2-(3-(trifluoromethoxy)phenyl)propan-2-yl)amino)-1H-benzol[d]imidazol-4-yl)methyl)-3-methylurea, (−)-1-((2-((1-hydroxy-2-(3-(trifluoromethoxy) phenyl) propan-2-yl) amino)-1H-benzo[d]imidazol-4-yl) methyl)-3-methylurea, (+)-1-((2-((1-hydroxy-2-(3-(trifluoromethoxy) phenyl) propan-2-yl) amino)-1H-benzo[d]imidazol-4-yl) methyl)-3-methylurea, 1-((2-((2-(3-chloro-4-fluorophenyl)-1-methoxypropan-2-yl) amino)-1H-benzo [d]imidazol-4-yl) methyl)-3-methylurea, (+)-1-((2-((2-(3-chloro-4-fluorophenyl)-1-methoxypropan-2-yl) amino)-1H-benzo[d]imidazol-4-yl) methyl)-3-methylurea, (−)-1-((2-((2-(3-chloro-4-fluorophenyl)-1-methoxypropan-2-yl) amino)-1H-benzo[d]imidazol-4-yl) methyl)-3-methylurea, 3-((2-((2-(3-chlorophenyl)-1-hydroxypropan-2-yl) amino)-1H-benzo [d]imidazol-4-yl) methyl)-1-ethyl-1-methylurea, (−)-3-((2-((2-(3-chlorophenyl)-1-hydroxypropan-2-yl) amino)-1H-benzo[d] imidazol-4-yl) methyl)-1-ethyl-1-methylurea, (+)-3-((2-((2-(3-chlorophenyl)-1-hydroxypropan-2-yl) amino)-1H-benzo[d] imidazol-4-yl) methyl)-1-ethyl-1-methylurea, N-[[2-[[1-(3-chlorophenyl)-2-hydroxy-1-methyl-ethyl] amino]-3H-benzimidazol-4-yl]methyl] isoxazolidine-2-carboxamide, (−)-N-((2-((2-(3-chlorophenyl)-1-hydroxypropan-2-yl) amino)-1H-benzo[d] imidazol-7-yl) methyl) isoxazolidine-2-carboxamide, (+)-N-((2-((2-(3-chlorophenyl)-1-hydroxypropan-2-yl) amino)-1H-benzo[d] imidazol-7-yl) methyl) isoxazolidine-2-carboxamide, 1-((2-((4-hydroxy-2-(3-(trifluoromethyl) phenyl) butan-2-yl) amino)-1H-benzo[d]imidazol-4-yl) methyl)-3-methylurea, (−)-1-((2-((4-hydroxy-2-(3-(trifluoromethyl)phenyl)butan-2-yl)amino)-1H-benzo [d]imidazol-4-yl)methyl)-3-methylurea, (+)-1-((2-((4-hydroxy-2-(3-(trifluoromethyl)phenyl)butan-2-yl)amino)-1H-benzol[d]imidazol-4-yl)methyl)-3-methylurea, N-((2-((1-hydroxy-2-(3-(trifluoromethyl) phenyl) propan-2-yl) amino)-1H-benzo[d]imidazol-4-yl) methyl) morpholine-4-carboxamide, (+)-N-((2-((1-hydroxy-2-(3-(trifluoromethyl) phenyl) propan-2-yl) amino)-1H-benzo[d]imidazol-4-yl) methyl) morpholine-4-carboxamide, and (−)-N-((2-((1-hydroxy-2-(3-(trifluoromethyl) phenyl) propan-2-yl) amino)-1H-benzo[d]imidazol-4-yl) methyl) morpholine-4-carboxamide; or a pharmaceutically acceptable salt thereof.

14. A pharmaceutical composition comprising the compound of claim 1 optionally a pharmaceutically acceptable additive.

* * * * *